United States Patent
Aram et al.

(10) Patent No.: US 8,357,166 B2
(45) Date of Patent: Jan. 22, 2013

(54) CUSTOMIZED PATIENT-SPECIFIC INSTRUMENTATION AND METHOD FOR PERFORMING A BONE RE-CUT

(75) Inventors: Luke J. Aram, Warsaw, IN (US); Daniel D. Auger, Fort Wayne, IN (US); Bryan Rose, South Whitley, IN (US); Richard Beech, Houston, TX (US)

(73) Assignee: DePuy Products, Inc., Warsaw, IN (US)

( * ) Notice: Subject to any disclaimer, the term of this patent is extended or adjusted under 35 U.S.C. 154(b) by 1108 days.

(21) Appl. No.: 12/240,985

(22) Filed: Sep. 29, 2008

(65) Prior Publication Data

US 2009/0088759 A1    Apr. 2, 2009

Related U.S. Application Data

(60) Provisional application No. 60/976,447, filed on Sep. 30, 2007, provisional application No. 60/976,448, filed on Sep. 30, 2007, provisional application No. 60/976,451, filed on Sep. 30, 2007, provisional application No. 60/976,444, filed on Sep. 30, 2007, provisional application No. 60/976,446, filed on Sep. 30, 2007.

(51) Int. Cl.
*A61B 17/15* (2006.01)
(52) U.S. Cl. .......................... 606/88; 606/87
(58) Field of Classification Search .............. 606/79, 606/86 R, 87–89, 96–98
See application file for complete search history.

(56) References Cited

U.S. PATENT DOCUMENTS

| | | |
|---|---|---|
| 2,702,550 A | 2/1955 | Rowe |
| 3,229,372 A | 1/1966 | Quashnock et al. |
| 3,298,410 A | 1/1967 | Noboru |
| 3,624,747 A | 11/1971 | McKnight et al. |
| 3,685,720 A | 8/1972 | Brady |
| 3,698,017 A | 10/1972 | Scales et al. |
| 3,774,244 A | 11/1973 | Walker |
| 3,840,904 A | 10/1974 | Tronzo |
| 3,869,731 A | 3/1975 | Waugh et al. |
| 3,901,298 A | 8/1975 | Eby |
| 3,903,549 A | 9/1975 | Deyerle |
| 3,920,022 A | 11/1975 | Pastor |
| 3,941,127 A | 3/1976 | Froning |
| 3,965,950 A | 6/1976 | MacDonald |
| 3,994,287 A | 11/1976 | Turp et al. |
| 4,055,862 A | 11/1977 | Farling |
| 4,081,866 A | 4/1978 | Upshaw et al. |
| 4,085,466 A | 4/1978 | Goodfellow et al. |
| 4,140,161 A | 2/1979 | Russo et al. |
| 4,197,886 A | 4/1980 | MacDonald |

(Continued)

FOREIGN PATENT DOCUMENTS
CA    2447694 A1    12/2002
(Continued)

OTHER PUBLICATIONS

PCT Search Report for Application PCT/US2008/078143 (17 pages).

(Continued)

*Primary Examiner* — Kevin T Truong
*Assistant Examiner* — Larry E Waggle, Jr.
(74) *Attorney, Agent, or Firm* — Barnes & Thornburg LLP

(57) ABSTRACT

A number of orthopedic surgical instruments are also disclosed. A method, apparatus, and system for fabricating such instruments are also disclosed.

11 Claims, 112 Drawing Sheets

U.S. PATENT DOCUMENTS

| | | |
|---|---|---|
| 4,311,145 A | 1/1982 | Esty et al. |
| 4,349,018 A | 9/1982 | Chambers |
| 4,373,709 A | 2/1983 | Whitt |
| 4,386,609 A | 6/1983 | Mongeon |
| 4,400,833 A | 8/1983 | Kurland |
| 4,436,684 A | 3/1984 | White |
| D273,895 S | 5/1984 | Kenna |
| D274,091 S | 5/1984 | Kenna |
| 4,475,549 A | 10/1984 | Oh |
| 4,501,269 A | 2/1985 | Bagby |
| 4,506,393 A | 3/1985 | Murphy |
| 4,509,518 A | 4/1985 | McGarry et al. |
| 4,534,365 A | 8/1985 | Bonetta et al. |
| 4,545,375 A | 10/1985 | Cline |
| 4,562,598 A | 1/1986 | Kranz |
| 4,565,192 A | 1/1986 | Shapiro |
| 4,567,886 A | 2/1986 | Peterson |
| 4,574,794 A | 3/1986 | Cooke et al. |
| 4,621,630 A | 11/1986 | Kenna |
| 4,632,111 A | 12/1986 | Roche |
| 4,641,648 A | 2/1987 | Shapiro |
| 4,646,729 A | 3/1987 | Kenna et al. |
| 4,662,372 A | 5/1987 | Sharkany et al. |
| 4,663,720 A | 5/1987 | Duret et al. |
| 4,695,283 A | 9/1987 | Aldinger |
| 4,703,751 A | 11/1987 | Pohl |
| 4,704,686 A | 11/1987 | Aldinger |
| 4,711,233 A | 12/1987 | Brown |
| 4,718,413 A | 1/1988 | Johnson |
| 4,718,916 A | 1/1988 | Morscher |
| 4,719,907 A | 1/1988 | Banko et al. |
| 4,721,104 A | 1/1988 | Kaufman et al. |
| 4,739,751 A | 4/1988 | Sapega et al. |
| 4,787,383 A | 11/1988 | Kenna |
| 4,791,934 A | 12/1988 | Brunnett |
| 4,800,874 A | 1/1989 | David et al. |
| 4,822,365 A | 4/1989 | Walker et al. |
| 4,834,080 A | 5/1989 | Brown |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |
| 4,860,735 A | 8/1989 | Davey et al. |
| 4,888,022 A | 12/1989 | Huebsch |
| 4,893,619 A | 1/1990 | Dale et al. |
| 4,896,663 A | 1/1990 | Vandewalls |
| 4,911,721 A | 3/1990 | Andergaten 3 et al. |
| 4,927,422 A | 5/1990 | Engelhardt |
| 4,935,023 A | 6/1990 | Whiteside et al. |
| 4,936,852 A | 6/1990 | Kent et al. |
| 4,936,862 A | 6/1990 | Walker et al. |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen, III et al. |
| 4,979,957 A | 12/1990 | Hodorek |
| 4,985,037 A | 1/1991 | Petersen |
| 5,002,579 A | 3/1991 | Copf et al. |
| 5,007,912 A | 4/1991 | Albrektsson et al. |
| 5,007,936 A | 4/1991 | Woolson |
| 5,015,247 A | 5/1991 | Michelson |
| 5,030,221 A | 7/1991 | Buechel et al. |
| 5,032,132 A | 7/1991 | Matsen, III et al. |
| 5,035,700 A | 7/1991 | Kenna |
| 5,041,117 A | 8/1991 | Engelhardt |
| 5,053,037 A | 10/1991 | Lackey |
| 5,053,039 A | 10/1991 | Hofmann et al. |
| 5,060,678 A | 10/1991 | Bauman et al. |
| 5,061,286 A | 10/1991 | Lyle |
| 5,062,843 A | 11/1991 | Mahony, III |
| 5,084,050 A | 1/1992 | Draenert |
| 5,086,401 A | 2/1992 | Glassman et al. |
| 5,092,869 A | 3/1992 | Waldron |
| 5,098,383 A | 3/1992 | Hemmy et al. |
| 5,098,436 A | 3/1992 | Ferrante et al. |
| 5,098,437 A | 3/1992 | Kashuba et al. |
| 5,100,689 A | 3/1992 | Goldberg et al. |
| 5,111,987 A | 5/1992 | Moeinzadeh et al. |
| 5,122,144 A | 6/1992 | Bert et al. |
| 5,123,906 A | 6/1992 | Kelman |
| 5,129,908 A | 7/1992 | Petersen |
| 5,129,909 A | 7/1992 | Sutherland |
| 5,133,660 A | 7/1992 | Fenick |
| 5,133,760 A | 7/1992 | Petersen et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |
| 5,186,174 A | 2/1993 | Schlondorff et al. |
| 5,192,327 A | 3/1993 | Brantigan |
| 5,197,488 A | 3/1993 | Kovacevic |
| 5,197,971 A | 3/1993 | Bonutti |
| 5,197,987 A | 3/1993 | Koch et al. |
| 5,207,680 A | 5/1993 | Dietz et al. |
| 5,207,692 A | 5/1993 | Kraus et al. |
| 5,211,165 A | 5/1993 | Dumoulin et al. |
| 5,217,463 A | 6/1993 | Mikhail |
| 5,228,459 A | 7/1993 | Caspari et al. |
| 5,234,433 A | 8/1993 | Bert et al. |
| 5,242,448 A | 9/1993 | Pettine et al. |
| 5,251,635 A | 10/1993 | Dumoulin et al. |
| 5,255,680 A | 10/1993 | Darrow et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,265,610 A | 11/1993 | Darrow et al. |
| 5,269,785 A | 12/1993 | Bonutti |
| 5,273,524 A | 12/1993 | Fox et al. |
| 5,274,565 A | 12/1993 | Reuben |
| 5,275,603 A | 1/1994 | Ferrante et al. |
| 5,282,803 A | 2/1994 | Lackey |
| 5,285,773 A | 2/1994 | Bonutti et al. |
| 5,299,288 A | 3/1994 | Glassman et al. |
| 5,300,077 A | 4/1994 | Howell |
| 5,304,181 A | 4/1994 | Caspari et al. |
| 5,305,244 A | 4/1994 | Newman et al. |
| 5,308,349 A | 5/1994 | Mikhail |
| 5,314,482 A | 5/1994 | Goodfellow et al. |
| 5,320,529 A | 6/1994 | Pompa |
| 5,320,625 A | 6/1994 | Bertin |
| 5,322,505 A | 6/1994 | Krause et al. |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,360,016 A | 11/1994 | Kovacevic |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,382,249 A | 1/1995 | Fletcher |
| 5,383,454 A | 1/1995 | Bucholz |
| 5,383,937 A | 1/1995 | Mikhail |
| 5,390,683 A | 2/1995 | Pisharodi |
| 5,395,376 A | 3/1995 | Caspari et al. |
| 5,405,395 A | 4/1995 | Coates |
| 5,408,409 A | 4/1995 | Glassman et al. |
| D358,647 S | 5/1995 | Cohen et al. |
| 5,415,662 A | 5/1995 | Ferrante et al. |
| 5,417,694 A | 5/1995 | Marik et al. |
| 5,423,827 A | 6/1995 | Mumme et al. |
| 5,440,496 A | 8/1995 | Andersson et al. |
| 5,443,475 A | 8/1995 | Auerbach et al. |
| 5,445,639 A | 8/1995 | Kuslich et al. |

| | | | | | | |
|---|---|---|---|---|---|---|
| 5,445,642 | A | 8/1995 | McNulty et al. | 5,749,875 A | 5/1998 | Puddu |
| 5,448,489 | A | 9/1995 | Reuben | 5,749,876 A | 5/1998 | Duvillier et al. |
| 5,452,407 | A | 9/1995 | Crook | 5,755,803 A | 5/1998 | Haines et al. |
| 5,454,816 | A | 10/1995 | Ashby | 5,757,339 A | 5/1998 | Williams et al. |
| 5,456,268 | A | 10/1995 | Bonutti | 5,762,125 A | 6/1998 | Mastrorio |
| 5,458,645 | A | 10/1995 | Bertin | 5,768,134 A | 6/1998 | Swaelens et al. |
| 5,462,549 | A | 10/1995 | Glock | 5,769,855 A | 6/1998 | Bertin et al. |
| 5,470,354 | A | 11/1995 | Hershberger et al. | 5,776,201 A | 7/1998 | Colleran et al. |
| 5,472,415 | A | 12/1995 | King et al. | 5,788,700 A | 8/1998 | Morawa et al. |
| 5,474,559 | A | 12/1995 | Bertin et al. | 5,791,212 A | 8/1998 | Han |
| 5,486,178 | A | 1/1996 | Hodge | 5,792,143 A | 8/1998 | Samuelson et al. |
| 5,490,854 | A | 2/1996 | Fisher et al. | 5,798,924 A | 8/1998 | Eufinger et al. |
| 5,496,324 | A | 3/1996 | Barnes | 5,799,055 A | 8/1998 | Peshkin et al. |
| 5,497,933 | A | 3/1996 | DeFonzo et al. | 5,799,099 A | 8/1998 | Wang et al. |
| 5,507,833 | A | 4/1996 | Bohn | 5,810,827 A | 9/1998 | Haines et al. |
| 5,510,066 | A | 4/1996 | Fink et al. | 5,810,831 A | 9/1998 | D'Antonio |
| 5,514,139 | A | 5/1996 | Goldstein et al. | 5,817,097 A | 10/1998 | Howard et al. |
| 5,514,143 | A | 5/1996 | Bonutti et al. | 5,824,085 A | 10/1998 | Sahay et al. |
| 5,514,519 | A | 5/1996 | Neckers | 5,844,656 A | 12/1998 | Ronzani et al. |
| 5,518,680 | A | 5/1996 | Cima et al. | 5,844,824 A | 12/1998 | Newman et al. |
| 5,520,692 | A | 5/1996 | Ferrante | 5,860,980 A | 1/1999 | Axelson, Jr. et al. |
| 5,520,694 | A | 5/1996 | Dance et al. | 5,860,981 A | 1/1999 | Bertin et al. |
| 5,520,695 | A | 5/1996 | Luckman | 5,869,170 A | 2/1999 | Cima et al. |
| 5,522,897 | A | 6/1996 | King et al. | 5,871,018 A | 2/1999 | Delp et al. |
| 5,527,317 | A | 6/1996 | Ashby et al. | 5,871,493 A | 2/1999 | Sjostrom et al. |
| 5,539,649 | A | 7/1996 | Walsh et al. | 5,876,456 A | 3/1999 | Sederholm et al. |
| 5,540,695 | A | 7/1996 | Levy | 5,879,354 A | 3/1999 | Haines et al. |
| 5,549,683 | A | 8/1996 | Bonutti | 5,879,393 A | 3/1999 | Whiteside et al. |
| 5,554,190 | A | 9/1996 | Draenert | 5,879,402 A | 3/1999 | Lawes et al. |
| 5,560,096 | A | 10/1996 | Stephens | 5,885,296 A | 3/1999 | Masini |
| 5,562,674 | A | 10/1996 | Stalcup et al. | 5,885,297 A | 3/1999 | Matsen, III |
| 5,562,675 | A | 10/1996 | McNulty et al. | 5,885,298 A | 3/1999 | Herrington et al. |
| 5,569,163 | A | 10/1996 | Francis et al. | 5,895,389 A | 4/1999 | Schenk et al. |
| 5,569,261 | A | 10/1996 | Marik et al. | 5,897,559 A | 4/1999 | Masini |
| 5,571,110 | A | 11/1996 | Matsen, III et al. | 5,899,907 A | 5/1999 | Johnson |
| 5,578,037 | A | 11/1996 | Sanders et al. | 5,899,914 A | 5/1999 | Zirps et al. |
| 5,578,039 | A | 11/1996 | Vendrely et al. | 5,901,060 A | 5/1999 | Schall et al. |
| 5,586,558 | A | 12/1996 | Riley | 5,908,424 A | 6/1999 | Bertin et al. |
| 5,593,448 | A | 1/1997 | Dong | 5,911,723 A | 6/1999 | Ashby et al. |
| 5,595,703 | A | 1/1997 | Swaelens et al. | 5,911,724 A | 6/1999 | Wehrli |
| 5,597,379 | A | 1/1997 | Haines et al. | 5,913,874 A | 6/1999 | Berns et al. |
| 5,601,563 | A | 2/1997 | Burke et al. | 5,916,219 A | 6/1999 | Matsuno et al. |
| 5,607,431 | A | 3/1997 | Dudasik et al. | 5,925,049 A | 7/1999 | Gustilo et al. |
| 5,609,603 | A | 3/1997 | Linden | 5,942,370 A | 8/1999 | Neckers |
| 5,620,448 | A | 4/1997 | Puddu | 5,967,777 A | 10/1999 | Klein et al. |
| 5,624,444 | A | 4/1997 | Wixon et al. | 5,967,980 A | 10/1999 | Ferre et al. |
| 5,634,927 | A | 6/1997 | Houston et al. | 5,976,149 A | 11/1999 | Masini |
| 5,643,272 | A | 7/1997 | Haines et al. | 5,980,526 A | 11/1999 | Johnson et al. |
| 5,649,947 | A | 7/1997 | Auerbach et al. | 5,989,261 A | 11/1999 | Walker et al. |
| 5,653,714 | A | 8/1997 | Dietz et al. | 6,007,537 A | 12/1999 | Burkinshaw et al. |
| 5,658,294 | A | 8/1997 | Sederholm | 6,012,456 A | 1/2000 | Schuerch |
| 5,662,656 | A | 9/1997 | White | 6,019,767 A | 2/2000 | Howell |
| 5,667,511 | A | 9/1997 | Vendrely et al. | 6,022,350 A | 2/2000 | Ganem |
| 5,667,512 | A | 9/1997 | Johnson | 6,024,746 A | 2/2000 | Katz |
| 5,677,107 | A | 10/1997 | Neckers | 6,033,415 A | 3/2000 | Mittelstadt et al. |
| 5,681,316 | A | 10/1997 | DeOrio et al. | 6,034,296 A | 3/2000 | Elvin et al. |
| 5,681,354 | A | 10/1997 | Eckhoff | 6,056,754 A | 5/2000 | Haines et al. |
| 5,682,886 | A | 11/1997 | Delp et al. | 6,056,756 A | 5/2000 | Eng et al. |
| 5,683,397 | A | 11/1997 | Vendrely et al. | 6,059,831 A | 5/2000 | Braslow et al. |
| 5,683,398 | A | 11/1997 | Carls et al. | 6,063,095 A | 5/2000 | Wang et al. |
| 5,688,279 | A | 11/1997 | McNulty et al. | 6,077,270 A | 6/2000 | Katz |
| 5,688,280 | A | 11/1997 | Booth, Jr. et al. | 6,077,287 A | 6/2000 | Taylor et al. |
| 5,690,635 | A | 11/1997 | Matsen, III et al. | 6,080,196 A | 6/2000 | Bertin |
| 5,702,447 | A | 12/1997 | Walch et al. | 6,086,593 A | 7/2000 | Bonutti |
| 5,702,460 | A | 12/1997 | Carls et al. | 6,090,122 A | 7/2000 | Sjostrom et al. |
| 5,702,475 | A | 12/1997 | Zahedi | 6,096,043 A | 8/2000 | Techiera et al. |
| 5,704,941 | A | 1/1998 | Jacober et al. | 6,099,313 A | 8/2000 | Dorken et al. |
| 5,707,350 | A | 1/1998 | Krause et al. | 6,102,850 A | 8/2000 | Wang et al. |
| 5,711,299 | A | 1/1998 | Manwaring | 6,106,529 A | 8/2000 | Techiera |
| 5,716,360 | A | 2/1998 | Baldwin et al. | 6,118,845 A | 9/2000 | Simon et al. |
| 5,719,743 | A | 2/1998 | Jenkins et al. | 6,120,509 A | 9/2000 | Wheeler |
| 5,719,744 | A | 2/1998 | Jenkins et al. | 6,120,510 A | 9/2000 | Albrektsson et al. |
| 5,720,752 | A | 2/1998 | Elliott et al. | 6,120,544 A | 9/2000 | Grundei et al. |
| 5,722,978 | A | 3/1998 | Jenkins, Jr. | 6,126,690 A | 10/2000 | Ateshian et al. |
| 5,725,376 | A | 3/1998 | Poirier | 6,139,574 A | 10/2000 | Vacanti et al. |
| 5,725,593 | A | 3/1998 | Caracciolo | 6,146,390 A | 11/2000 | Heilbrun et al. |
| 5,733,292 | A | 3/1998 | Gustilo et al. | 6,156,069 A | 12/2000 | Amstutz |
| 5,735,277 | A | 4/1998 | Schuster | 6,156,070 A | 12/2000 | Incavo et al. |
| 5,748,767 | A | 5/1998 | Raab | 6,159,246 A | 12/2000 | Mendes et al. |

| | | | | | | |
|---|---|---|---|---|---|---|
| 6,161,080 | A | 12/2000 | Aouni-Ateshian et al. | 6,552,899 B2 | 4/2003 | Ronzani et al. |
| 6,165,181 | A | 12/2000 | Heilbrun et al. | 6,554,837 B1 | 4/2003 | Hauri et al. |
| 6,167,145 | A | 12/2000 | Foley et al. | 6,554,838 B2 | 4/2003 | McGovern et al. |
| 6,176,874 | B1 | 1/2001 | Vacanti et al. | 6,556,008 B2 | 4/2003 | Thesen |
| 6,177,034 | B1 | 1/2001 | Ferrone | 6,558,391 B2 | 5/2003 | Axelson et al. |
| 6,185,315 | B1 | 2/2001 | Schmucker et al. | 6,567,681 B1 | 5/2003 | Lindequist |
| 6,187,010 | B1 | 2/2001 | Masini | 6,575,980 B1 | 6/2003 | Robie et al. |
| 6,195,615 | B1 | 2/2001 | Lysen | 6,575,982 B1 | 6/2003 | Bonutti |
| 6,197,064 | B1 | 3/2001 | Haines et al. | 6,584,174 B2 | 6/2003 | Schubert et al. |
| 6,198,794 | B1 | 3/2001 | Peshkin et al. | 6,591,581 B2 | 7/2003 | Schmieding |
| 6,205,411 | B1 | 3/2001 | DiGioia, III et al. | 6,602,259 B1 | 8/2003 | Masini |
| 6,206,927 | B1 | 3/2001 | Fell et al. | 6,625,563 B2 | 9/2003 | Kirsch et al. |
| 6,214,051 | B1 | 4/2001 | Badorf et al. | 6,629,999 B1 | 10/2003 | Serafin, Jr. |
| 6,220,122 | B1 | 4/2001 | Forsell et al. | 6,632,225 B2 | 10/2003 | Sanford et al. |
| 6,228,121 | B1 | 5/2001 | Khalili | 6,633,773 B1 | 10/2003 | Reisfeld |
| 6,241,671 | B1 | 6/2001 | Ritter et al. | 6,635,073 B2 | 10/2003 | Bonutti |
| 6,241,735 | B1 | 6/2001 | Marmulla | 6,640,127 B1 | 10/2003 | Kosaka et al. |
| 6,244,141 | B1 | 6/2001 | Han | 6,642,836 B1 | 11/2003 | Wang et al. |
| 6,246,900 | B1 | 6/2001 | Cosman et al. | 6,646,541 B1 | 11/2003 | Wang et al. |
| 6,254,604 | B1 | 7/2001 | Howell | 6,662,036 B2 | 12/2003 | Cosman |
| 6,258,127 | B1 | 7/2001 | Schmotzer | 6,668,941 B2 | 12/2003 | Phillips et al. |
| 6,264,698 | B1 | 7/2001 | Lawes et al. | 6,673,077 B1 | 1/2004 | Katz |
| 6,273,891 | B1 | 8/2001 | Masini | 6,676,662 B1 | 1/2004 | Bagga et al. |
| 6,277,136 | B1 | 8/2001 | Bonutti | 6,687,531 B1 | 2/2004 | Ferre et al. |
| 6,285,902 | B1 | 9/2001 | Kienzle, III et al. | 6,695,848 B2 | 2/2004 | Haines |
| 6,290,703 | B1 | 9/2001 | Ganem | 6,697,664 B2 | 2/2004 | Kienzle, III et al. |
| 6,290,704 | B1 | 9/2001 | Burkinshaw et al. | 6,701,174 B1 | 3/2004 | Krause et al. |
| 6,301,593 | B1 | 10/2001 | Toyosato | 6,702,821 B2 | 3/2004 | Bonutti |
| 6,314,310 | B1 | 11/2001 | Ben-Haim et al. | 6,709,462 B2 | 3/2004 | Hanssen |
| 6,319,006 | B1 | 11/2001 | Scherer et al. | 6,711,431 B2 | 3/2004 | Sarin et al. |
| 6,322,728 | B1 | 11/2001 | Brodkin et al. | 6,711,432 B1 | 3/2004 | Krause et al. |
| 6,325,806 | B1 | 12/2001 | Fox | 6,712,824 B2 | 3/2004 | Millard et al. |
| 6,327,491 | B1 | 12/2001 | Franklin et al. | 6,712,856 B1 | 3/2004 | Carignan et al. |
| 6,341,231 | B1 | 1/2002 | Ferre et al. | 6,716,249 B2 | 4/2004 | Hyde |
| 6,343,987 | B2 | 2/2002 | Hayama et al. | 6,724,922 B1 | 4/2004 | Vilsmeier |
| 6,351,659 | B1 | 2/2002 | Vilsmeier | 6,725,077 B1 | 4/2004 | Balloni et al. |
| 6,354,011 | B1 | 3/2002 | Albrecht | 6,725,080 B2 | 4/2004 | Melkent et al. |
| 6,361,506 | B1 | 3/2002 | Saenger et al. | 6,738,656 B1 | 5/2004 | Ferre et al. |
| 6,370,224 | B1 | 4/2002 | Simon et al. | 6,738,657 B1 | 5/2004 | Franklin et al. |
| 6,382,975 | B1 | 5/2002 | Poirier | 6,740,092 B2 | 5/2004 | Lombardo et al. |
| 6,383,228 | B1 | 5/2002 | Schmotzer | 6,749,638 B1 | 6/2004 | Saladino |
| 6,391,251 | B1 | 5/2002 | Keicher et al. | 6,750,653 B1 | 6/2004 | Zou et al. |
| 6,395,005 | B1 | 5/2002 | Lovell | 6,766,878 B2 | 7/2004 | Widmer et al. |
| 6,405,072 | B1 | 6/2002 | Cosman | 6,770,078 B2 | 8/2004 | Bonutti |
| 6,406,495 | B1 | 6/2002 | Schoch | 6,772,026 B2 | 8/2004 | Bradbury et al. |
| 6,409,722 | B1 | 6/2002 | Hoey et al. | 6,780,190 B2 | 8/2004 | Maroney |
| 6,421,232 | B2 | 7/2002 | Sallam | 6,786,930 B2 | 9/2004 | Biscup |
| 6,424,856 | B1 | 7/2002 | Vilsmeier | 6,798,391 B2 | 9/2004 | Peterson, III |
| 6,427,698 | B1 | 8/2002 | Yoon | 6,799,066 B2 | 9/2004 | Steines et al. |
| 6,430,434 | B1 | 8/2002 | Mittelstadt | 6,814,735 B1 | 11/2004 | Zirngibl et al. |
| 6,434,415 | B1 | 8/2002 | Foley et al. | 6,827,723 B2 | 12/2004 | Carson |
| 6,442,416 | B1 | 8/2002 | Schultz | 6,847,336 B1 | 1/2005 | Lemelson |
| D462,767 | S | 9/2002 | Meyer et al. | 6,859,660 B2 | 2/2005 | Vilsmeier |
| 6,445,943 | B1 | 9/2002 | Ferre et al. | 6,873,867 B2 | 3/2005 | Vilsmeier |
| 6,454,811 | B1 | 9/2002 | Sherwood et al. | 6,892,090 B2 | 5/2005 | Verard et al. |
| 6,458,135 | B1 | 10/2002 | Harwin et al. | 6,905,514 B2 | 6/2005 | Carignan et al. |
| 6,459,948 | B1 | 10/2002 | Ateshian et al. | 6,916,324 B2 | 7/2005 | Sanford et al. |
| 6,463,351 | B1 | 10/2002 | Clynch | 6,920,347 B2 | 7/2005 | Simon et al. |
| 6,463,361 | B1 | 10/2002 | Wang et al. | 6,923,817 B2 | 8/2005 | Carson et al. |
| 6,468,280 | B1 | 10/2002 | Saenger et al. | 6,923,831 B2 | 8/2005 | Fell et al. |
| 6,468,289 | B1 | 10/2002 | Bonutti | 6,932,842 B1 | 8/2005 | Litschko et al. |
| 6,474,341 | B1 | 11/2002 | Hunter et al. | 6,934,575 B2 | 8/2005 | Ferre et al. |
| 6,478,799 | B1 | 11/2002 | Williamson | 6,942,475 B2 | 9/2005 | Ensign et al. |
| 6,482,209 | B1 | 11/2002 | Engh et al. | 6,944,518 B2 | 9/2005 | Roose |
| 6,490,467 | B1 | 12/2002 | Bucholz et al. | 6,945,976 B2 | 9/2005 | Ball et al. |
| 6,491,702 | B2 | 12/2002 | Heilbrun et al. | 6,947,786 B2 | 9/2005 | Simon et al. |
| 6,493,573 | B1 | 12/2002 | Martinelli et al. | 6,953,480 B2 | 10/2005 | Mears et al. |
| 6,496,099 | B2 | 12/2002 | Wang et al. | 6,968,846 B2 | 11/2005 | Viswanathan |
| 6,499,488 | B1 | 12/2002 | Hunter et al. | 6,978,166 B2 | 12/2005 | Foley et al. |
| 6,503,255 | B1 | 1/2003 | Albrektsson et al. | 6,979,299 B2 | 12/2005 | Peabody et al. |
| 6,510,334 | B1 | 1/2003 | Schuster et al. | 6,990,220 B2 | 1/2006 | Ellis et al. |
| 6,514,259 | B2 | 2/2003 | Picard et al. | 6,994,549 B2 | 2/2006 | Brodkin et al. |
| 6,516,212 | B1 | 2/2003 | Bladen et al. | 7,029,477 B2 | 4/2006 | Grimm |
| 6,520,964 | B2 | 2/2003 | Tallarida et al. | 7,029,479 B2 | 4/2006 | Tallarida et al. |
| 6,530,958 | B1 | 3/2003 | Cima et al. | 7,048,741 B2 | 5/2006 | Swanson |
| 6,532,482 | B1 | 3/2003 | Toyosato | 7,050,877 B2 | 5/2006 | Iseki et al. |
| 6,533,737 | B1 | 3/2003 | Brosseau et al. | 7,060,074 B2 | 6/2006 | Rosa et al. |
| 6,535,756 | B1 | 3/2003 | Simon et al. | RE39,301 E | 9/2006 | Bertin |
| 6,545,279 | B1 | 4/2003 | Yoshida et al. | 7,104,997 B2 | 9/2006 | Lionberger et al. |

| | | | | | |
|---|---|---|---|---|---|
| 7,105,026 B2 | 9/2006 | Johnson et al. | 2003/0100906 A1 | 5/2003 | Rosa et al. |
| 7,115,131 B2 | 10/2006 | Engh et al. | 2003/0100907 A1 | 5/2003 | Rosa et al. |
| 7,141,053 B2 | 11/2006 | Rosa et al. | 2003/0109784 A1 | 6/2003 | Loh et al. |
| 7,172,597 B2 | 2/2007 | Sanford | 2003/0130665 A1 | 7/2003 | Pinczewski et al. |
| 7,172,599 B2 | 2/2007 | Steffensmeier et al. | 2003/0158606 A1 | 8/2003 | Coon et al. |
| 7,175,435 B2 | 2/2007 | Andersson et al. | 2003/0171757 A1 | 9/2003 | Coon et al. |
| 7,176,466 B2 | 2/2007 | Rousso et al. | 2003/0212403 A1 | 11/2003 | Swanson |
| 7,184,814 B2 | 2/2007 | Lang et al. | 2003/0216669 A1 | 11/2003 | Lang et al. |
| 7,194,295 B2 | 3/2007 | Vilsmeier | 2003/0216741 A1 | 11/2003 | Sanford et al. |
| 7,198,628 B2 | 4/2007 | Ondrla et al. | 2003/0220641 A1 | 11/2003 | Thelen et al. |
| 7,239,908 B1 | 7/2007 | Alexander et al. | 2003/0225413 A1 | 12/2003 | Sanford et al. |
| 7,255,702 B2 | 8/2007 | Serra et al. | 2004/0039259 A1 | 2/2004 | Krause et al. |
| 7,258,701 B2 | 8/2007 | Aram et al. | 2004/0039395 A1 | 2/2004 | Coon et al. |
| 7,261,719 B1 | 8/2007 | Twomey et al. | 2004/0068187 A1 | 4/2004 | Krause et al. |
| 7,275,218 B2 | 9/2007 | Petrella et al. | 2004/0073279 A1 | 4/2004 | Malackowski et al. |
| 7,282,054 B2 | 10/2007 | Steffensmeier et al. | 2004/0092932 A1 | 5/2004 | Aubin et al. |
| 7,294,133 B2 | 11/2007 | Zink et al. | 2004/0098133 A1 | 5/2004 | Carignan et al. |
| 7,297,164 B2 | 11/2007 | Johnson et al. | 2004/0102785 A1 | 5/2004 | Hodorek et al. |
| 7,309,339 B2 | 12/2007 | Cusick et al. | 2004/0102852 A1 | 5/2004 | Johnson et al. |
| 7,371,260 B2 | 5/2008 | Malinin | 2004/0102866 A1 | 5/2004 | Harris et al. |
| 7,383,164 B2 | 6/2008 | Aram et al. | 2004/0106926 A1 | 6/2004 | Leitner et al. |
| 7,388,972 B2 | 6/2008 | Kitson | 2004/0115586 A1 | 6/2004 | Andreiko et al. |
| 7,392,076 B2 | 6/2008 | Moctezuma de La Barrera | 2004/0122439 A1 | 6/2004 | Dwyer et al. |
| 7,427,272 B2 | 9/2008 | Richard et al. | 2004/0122787 A1 | 6/2004 | Avinash et al. |
| 7,474,223 B2 | 1/2009 | Nycz et al. | 2004/0122790 A1 | 6/2004 | Walker et al. |
| 7,488,324 B1 | 2/2009 | Metzger et al. | 2004/0124964 A1 | 7/2004 | Wang et al. |
| 7,527,631 B2 | 5/2009 | Maroney et al. | 2004/0128026 A1 | 7/2004 | Harris et al. |
| 7,534,263 B2 | 5/2009 | Burdulis, Jr. et al. | 2004/0133276 A1 | 7/2004 | Lang et al. |
| 7,542,791 B2 | 6/2009 | Mire et al. | 2004/0138670 A1 | 7/2004 | Metzger |
| 7,543,239 B2 | 6/2009 | Viswanathan et al. | 2004/0138754 A1 | 7/2004 | Lang et al. |
| 7,575,602 B2 | 8/2009 | Amirouche et al. | 2004/0143336 A1 | 7/2004 | Burkinshaw |
| 7,582,091 B2 | 9/2009 | Duncan et al. | 2004/0147927 A1 | 7/2004 | Tsougarakis et al. |
| 7,591,821 B2 | 9/2009 | Kelman | 2004/0153079 A1 | 8/2004 | Tsougarakis et al. |
| 7,601,155 B2 | 10/2009 | Petersen | 2004/0153087 A1 | 8/2004 | Sanford et al. |
| 7,604,639 B2 | 10/2009 | Swanson | 2004/0158254 A1 | 8/2004 | Eisermann |
| 7,611,516 B2 | 11/2009 | Maroney | 2004/0162619 A1 | 8/2004 | Blaylock et al. |
| 7,618,451 B2 | 11/2009 | Berez et al. | 2004/0167390 A1 | 8/2004 | Alexander et al. |
| 7,621,915 B2 | 11/2009 | Frederick et al. | 2004/0171924 A1 | 9/2004 | Mire et al. |
| 7,625,409 B2 | 12/2009 | Saltzman et al. | 2004/0172137 A1 | 9/2004 | Blaylock et al. |
| 7,651,501 B2 | 1/2010 | Penenberg et al. | 2004/0181144 A1 | 9/2004 | Cinquin et al. |
| 7,695,477 B2 | 4/2010 | Creger et al. | 2004/0185422 A1 | 9/2004 | Orth et al. |
| 7,704,253 B2 | 4/2010 | Bastian et al. | 2004/0204760 A1 | 10/2004 | Fitz et al. |
| 7,717,956 B2 | 5/2010 | Lang | 2004/0220583 A1 | 11/2004 | Pieczynski et al. |
| 7,780,672 B2 | 8/2010 | Metzger | 2004/0236424 A1 | 11/2004 | Berez et al. |
| 7,796,791 B2 | 9/2010 | Tsougarakis et al. | 2004/0243481 A1 | 12/2004 | Bradbury et al. |
| 7,799,077 B2 | 9/2010 | Lang et al. | 2004/0249385 A1 | 12/2004 | Faoro |
| 7,806,896 B1 | 10/2010 | Bonutti | 2004/0254584 A1 | 12/2004 | Sarin et al. |
| 7,824,181 B2 | 11/2010 | Sers | 2004/0260301 A1 | 12/2004 | Lionberger et al. |
| 7,935,119 B2 | 5/2011 | Ammann et al. | 2005/0015003 A1 | 1/2005 | Lachner et al. |
| 7,963,968 B2 | 6/2011 | Dees, Jr. | 2005/0015022 A1 | 1/2005 | Richard et al. |
| 7,967,868 B2 | 6/2011 | White et al. | 2005/0027303 A1 | 2/2005 | Lionberger et al. |
| 7,981,158 B2 | 7/2011 | Fitz et al. | 2005/0027361 A1 | 2/2005 | Reiley |
| 2001/0005797 A1 | 6/2001 | Barlow et al. | 2005/0037320 A1 | 2/2005 | Poirier |
| 2001/0018589 A1 | 8/2001 | Muller | 2005/0043835 A1 | 2/2005 | Christensen |
| 2001/0034554 A1 | 10/2001 | Pappas | 2005/0043837 A1 | 2/2005 | Rubbert et al. |
| 2001/0037155 A1 | 11/2001 | Merchant | 2005/0049524 A1 | 3/2005 | Lefevre et al. |
| 2001/0039421 A1 | 11/2001 | Heilbrun et al. | 2005/0049603 A1 | 3/2005 | Calton et al. |
| 2002/0007294 A1 | 1/2002 | Bradbury et al. | 2005/0059873 A1 | 3/2005 | Glozman et al. |
| 2002/0029038 A1 | 3/2002 | Haines | 2005/0065628 A1 | 3/2005 | Roose |
| 2002/0029045 A1 | 3/2002 | Bonutti | 2005/0070897 A1 | 3/2005 | Petersen |
| 2002/0052606 A1 | 5/2002 | Bonutti | 2005/0075641 A1 | 4/2005 | Singhatat et al. |
| 2002/0059049 A1 | 5/2002 | Bradbury et al. | 2005/0096535 A1 | 5/2005 | de la Barrera |
| 2002/0082741 A1 | 6/2002 | Mazumder et al. | 2005/0113840 A1 | 5/2005 | Metzger et al. |
| 2002/0087062 A1 | 7/2002 | Schmidt et al. | 2005/0113841 A1 | 5/2005 | Sheldon et al. |
| 2002/0087274 A1 | 7/2002 | Alexander et al. | 2005/0113846 A1 | 5/2005 | Carson |
| 2002/0147415 A1 | 10/2002 | Martelli | 2005/0119664 A1 | 6/2005 | Carignan et al. |
| 2002/0173797 A1 | 11/2002 | Van Zile et al. | 2005/0131662 A1 | 6/2005 | Ascenzi et al. |
| 2002/0183610 A1 | 12/2002 | Foley et al. | 2005/0133955 A1 | 6/2005 | Christensen |
| 2002/0183760 A1 | 12/2002 | McGovern et al. | 2005/0137708 A1 | 6/2005 | Clark |
| 2002/0188194 A1 | 12/2002 | Cosman | 2005/0148843 A1 | 7/2005 | Roose |
| 2002/0198529 A1 | 12/2002 | Masini | 2005/0149042 A1 | 7/2005 | Metzger |
| 2002/0198531 A1 | 12/2002 | Millard et al. | 2005/0170311 A1 | 8/2005 | Tardieu et al. |
| 2003/0009234 A1 | 1/2003 | Treacy et al. | 2005/0171545 A1 | 8/2005 | Walsh et al. |
| 2003/0011624 A1 | 1/2003 | Ellis | 2005/0177170 A1 | 8/2005 | Fisher et al. |
| 2003/0018338 A1 | 1/2003 | Axelson et al. | 2005/0182315 A1 | 8/2005 | Ritter et al. |
| 2003/0028196 A1 | 2/2003 | Bonutti | 2005/0203536 A1 | 9/2005 | Laffargue et al. |
| 2003/0055502 A1 | 3/2003 | Lang et al. | 2005/0203540 A1 | 9/2005 | Broyles |
| 2003/0069897 A1 | 4/2003 | Roy et al. | 2005/0222573 A1 | 10/2005 | Branch et al. |
| 2003/0088179 A1 | 5/2003 | Seeley et al. | 2005/0234461 A1 | 10/2005 | Burdulis, Jr. et al. |

| | | | | | | |
|---|---|---|---|---|---|---|
| 2005/0234468 A1 | 10/2005 | Carson | | 2007/0255412 A1 | 11/2007 | Hajaj et al. |
| 2005/0244239 A1 | 11/2005 | Shimp | | 2007/0276224 A1 | 11/2007 | Lang et al. |
| 2005/0245934 A1 | 11/2005 | Tuke et al. | | 2007/0276400 A1 | 11/2007 | Moore et al. |
| 2005/0245936 A1 | 11/2005 | Tuke et al. | | 2007/0276501 A1 | 11/2007 | Betz et al. |
| 2005/0261697 A1 | 11/2005 | Canonaco et al. | | 2007/0282451 A1 | 12/2007 | Metzger et al. |
| 2005/0267584 A1 | 12/2005 | Burdulis et al. | | 2007/0288030 A1* | 12/2007 | Metzger et al. .................. 606/87 |
| 2005/0273113 A1 | 12/2005 | Kuczynski | | 2008/0009952 A1 | 1/2008 | Hodge |
| 2005/0273114 A1 | 12/2005 | Novak | | 2008/0015602 A1 | 1/2008 | Axelson |
| 2005/0283252 A1 | 12/2005 | Coon et al. | | 2008/0015605 A1 | 1/2008 | Collazo |
| 2005/0283253 A1 | 12/2005 | Coon et al. | | 2008/0015607 A1 | 1/2008 | D'Alessio et al. |
| 2006/0004284 A1 | 1/2006 | Grunschlager et al. | | 2008/0021299 A1 | 1/2008 | Meulink |
| 2006/0015120 A1 | 1/2006 | Richard et al. | | 2008/0021567 A1 | 1/2008 | Meulink et al. |
| 2006/0030853 A1 | 2/2006 | Haines | | 2008/0027563 A1 | 1/2008 | Johnson et al. |
| 2006/0052725 A1 | 3/2006 | Santilli | | 2008/0051910 A1 | 2/2008 | Kammerzell et al. |
| 2006/0058803 A1 | 3/2006 | Cuckler et al. | | 2008/0058945 A1 | 3/2008 | Hajaj et al. |
| 2006/0058884 A1 | 3/2006 | Aram et al. | | 2008/0058947 A1 | 3/2008 | Earl et al. |
| 2006/0058886 A1 | 3/2006 | Wozencroft | | 2008/0114370 A1 | 5/2008 | Schoenefeld |
| 2006/0089621 A1 | 4/2006 | Fard | | 2008/0140081 A1 | 6/2008 | Heavener |
| 2006/0093988 A1 | 5/2006 | Swaelens et al. | | 2008/0140209 A1 | 6/2008 | Iannotti et al. |
| 2006/0094951 A1 | 5/2006 | Dean et al. | | 2008/0146969 A1 | 6/2008 | Kurtz |
| 2006/0095049 A1 | 5/2006 | Zannis et al. | | 2008/0147072 A1 | 6/2008 | Park et al. |
| 2006/0100832 A1 | 5/2006 | Bowman | | 2008/0161815 A1 | 7/2008 | Schoenefeld et al. |
| 2006/0111722 A1 | 5/2006 | Bouadi | | 2008/0172125 A1 | 7/2008 | Ek |
| 2006/0122616 A1 | 6/2006 | Bennett et al. | | 2008/0183177 A1 | 7/2008 | Fox et al. |
| 2006/0136058 A1 | 6/2006 | Pietrzak | | 2008/0195099 A1 | 8/2008 | Minas |
| 2006/0142657 A1 | 6/2006 | Quaid et al. | | 2008/0195107 A1 | 8/2008 | Cuckler et al. |
| 2006/0142671 A1 | 6/2006 | Solak | | 2008/0195216 A1 | 8/2008 | Philipp |
| 2006/0142774 A1 | 6/2006 | Metzger | | 2008/0208200 A1 | 8/2008 | Crofford |
| 2006/0142778 A1 | 6/2006 | Dees | | 2008/0215059 A1 | 9/2008 | Carignan et al. |
| 2006/0155380 A1 | 7/2006 | Clemow et al. | | 2008/0228189 A1 | 9/2008 | Fox et al. |
| 2006/0161167 A1 | 7/2006 | Myers et al. | | 2008/0234664 A1 | 9/2008 | May et al. |
| 2006/0184177 A1 | 8/2006 | Echeverri | | 2008/0234683 A1 | 9/2008 | May |
| 2006/0190086 A1 | 8/2006 | Clemow et al. | | 2008/0234685 A1 | 9/2008 | Gjerde |
| 2006/0195198 A1 | 8/2006 | James | | 2008/0234833 A1 | 9/2008 | Bandoh et al. |
| 2006/0204932 A1 | 9/2006 | Haymann et al. | | 2008/0243127 A1 | 10/2008 | Lang et al. |
| 2006/0210644 A1 | 9/2006 | Levin | | 2008/0257363 A1 | 10/2008 | Schoenefeld et al. |
| 2006/0229723 A1 | 10/2006 | Van Hoeck | | 2008/0262624 A1 | 10/2008 | White et al. |
| 2006/0235421 A1 | 10/2006 | Rosa et al. | | 2008/0269906 A1 | 10/2008 | Iannotti et al. |
| 2006/0271058 A1 | 11/2006 | Ashton et al. | | 2008/0275452 A1 | 11/2008 | Lang et al. |
| 2006/0276796 A1 | 12/2006 | Creger et al. | | 2008/0281328 A1 | 11/2008 | Lang et al. |
| 2006/0276797 A1 | 12/2006 | Botimer | | 2008/0281329 A1 | 11/2008 | Fitz et al. |
| 2006/0287733 A1 | 12/2006 | Bonutti | | 2008/0281426 A1 | 11/2008 | Fitz et al. |
| 2007/0006887 A1 | 1/2007 | Frank | | 2008/0287954 A1 | 11/2008 | Kunz et al. |
| 2007/0015995 A1 | 1/2007 | Lang et al. | | 2008/0294266 A1 | 11/2008 | Steinberg |
| 2007/0016209 A1 | 1/2007 | Ammann et al. | | 2008/0300600 A1 | 12/2008 | Guelat et al. |
| 2007/0027680 A1 | 2/2007 | Ashley et al. | | 2008/0306558 A1 | 12/2008 | Hakki |
| 2007/0059665 A1 | 3/2007 | Orentlicher et al. | | 2008/0312659 A1 | 12/2008 | Metzger et al. |
| 2007/0066917 A1 | 3/2007 | Hodorek et al. | | 2008/0319448 A1 | 12/2008 | Lavallee et al. |
| 2007/0083209 A1 | 4/2007 | Schenberger et al. | | 2009/0012526 A1 | 1/2009 | Fletcher |
| 2007/0083214 A1 | 4/2007 | Duncan et al. | | 2009/0018546 A1 | 1/2009 | Daley |
| 2007/0083266 A1 | 4/2007 | Lang | | 2009/0024131 A1 | 1/2009 | Metzger et al. |
| 2007/0100258 A1 | 5/2007 | Shoham et al. | | 2009/0043556 A1 | 2/2009 | Axelson et al. |
| 2007/0100462 A1 | 5/2007 | Lang et al. | | 2009/0076371 A1 | 3/2009 | Lang et al. |
| 2007/0118055 A1 | 5/2007 | McCombs | | 2009/0076512 A1 | 3/2009 | Ammann et al. |
| 2007/0118243 A1 | 5/2007 | Schroeder et al. | | 2009/0082770 A1 | 3/2009 | Worner et al. |
| 2007/0156066 A1 | 7/2007 | McGinley et al. | | 2009/0087276 A1 | 4/2009 | Rose |
| 2007/0162039 A1 | 7/2007 | Wozencroft | | 2009/0088674 A1 | 4/2009 | Caillouette et al. |
| 2007/0167741 A1 | 7/2007 | Sherman et al. | | 2009/0088753 A1 | 4/2009 | Aram et al. |
| 2007/0173946 A1 | 7/2007 | Bonutti | | 2009/0088754 A1 | 4/2009 | Aker et al. |
| 2007/0185498 A2 | 8/2007 | Lavallee | | 2009/0088755 A1 | 4/2009 | Aker et al. |
| 2007/0198022 A1 | 8/2007 | Lang et al. | | 2009/0088758 A1 | 4/2009 | Bennett |
| 2007/0203430 A1 | 8/2007 | Lang et al. | | 2009/0088759 A1 | 4/2009 | Aram et al. |
| 2007/0203605 A1 | 8/2007 | Melton et al. | | 2009/0088760 A1 | 4/2009 | Aram et al. |
| 2007/0213738 A1 | 9/2007 | Martin et al. | | 2009/0088761 A1 | 4/2009 | Roose et al. |
| 2007/0219639 A1 | 9/2007 | Otto et al. | | 2009/0088763 A1 | 4/2009 | Aram et al. |
| 2007/0225719 A1 | 9/2007 | Stone et al. | | 2009/0089034 A1 | 4/2009 | Penney et al. |
| 2007/0226986 A1 | 10/2007 | Park et al. | | 2009/0089081 A1 | 4/2009 | Haddad |
| 2007/0233121 A1 | 10/2007 | Carson et al. | | 2009/0093816 A1 | 4/2009 | Roose et al. |
| 2007/0233136 A1 | 10/2007 | Wozencroft | | 2009/0099567 A1 | 4/2009 | Zajac |
| 2007/0233140 A1 | 10/2007 | Metzger et al. | | 2009/0105837 A1 | 4/2009 | Lafosse et al. |
| 2007/0233141 A1 | 10/2007 | Park et al. | | 2009/0118736 A1 | 5/2009 | Kreuzer |
| 2007/0233269 A1 | 10/2007 | Steines et al. | | 2009/0131941 A1 | 5/2009 | Park et al. |
| 2007/0233272 A1 | 10/2007 | Boyce et al. | | 2009/0131942 A1 | 5/2009 | Aker et al. |
| 2007/0238069 A1 | 10/2007 | Lovald et al. | | 2009/0138020 A1 | 5/2009 | Park et al. |
| 2007/0239282 A1 | 10/2007 | Caylor et al. | | 2009/0149965 A1 | 6/2009 | Quaid |
| 2007/0239481 A1 | 10/2007 | DiSilvestro et al. | | 2009/0149977 A1 | 6/2009 | Schendel |
| 2007/0250169 A1 | 10/2007 | Lang | | 2009/0151736 A1 | 6/2009 | Belcher et al. |
| 2007/0253617 A1 | 11/2007 | Arata et al. | | 2009/0157083 A1 | 6/2009 | Park et al. |
| 2007/0255288 A1 | 11/2007 | Mahfouz et al. | | 2009/0163922 A1 | 6/2009 | Meridew et al. |

| | | | | | | |
|---|---|---|---|---|---|---|
| 2009/0163923 A1 | 6/2009 | Flett et al. | CA | 2505419 A1 | 6/2004 | |
| 2009/0164024 A1 | 6/2009 | Rudan et al. | CA | 2506849 A1 | 6/2004 | |
| 2009/0187193 A1 | 7/2009 | Maroney et al. | CA | 2546958 A1 | 6/2005 | |
| 2009/0209884 A1 | 8/2009 | Van Vorhis et al. | CA | 2546965 A1 | 6/2005 | |
| 2009/0209961 A1 | 8/2009 | Ferrante et al. | CA | 2588907 A1 | 6/2006 | |
| 2009/0222014 A1 | 9/2009 | Bojarski et al. | CA | 2590534 A1 | 6/2006 | |
| 2009/0222015 A1 | 9/2009 | Park et al. | CH | 117960 | 5/1927 | |
| 2009/0222016 A1 | 9/2009 | Park et al. | CN | 1630495 A | 6/2005 | |
| 2009/0228016 A1 | 9/2009 | Alvarez et al. | CN | 1728976 A | 2/2006 | |
| 2009/0234360 A1 | 9/2009 | Alexander | CN | 1729483 A | 2/2006 | |
| 2009/0248044 A1 | 10/2009 | Amiot et al. | CN | 1729484 A | 2/2006 | |
| 2009/0254093 A1 | 10/2009 | White et al. | CN | 1913844 A | 2/2007 | |
| 2009/0254367 A1 | 10/2009 | Belcher et al. | CN | 101111197 A | 1/2008 | |
| 2009/0270868 A1 | 10/2009 | Park et al. | DE | 337437 | 5/1921 | |
| 2009/0274350 A1 | 11/2009 | Pavlovskaia et al. | DE | 2830566 A1 | 1/1980 | |
| 2009/0306676 A1 | 12/2009 | Lang et al. | DE | 3339259 C1 | 3/1985 | |
| 2009/0307893 A1 | 12/2009 | Burdulis, Jr. et al. | DE | 3447365 A1 | 7/1986 | |
| 2009/0318836 A1 | 12/2009 | Stone et al. | DE | 3925488 A1 | 2/1990 | |
| 2010/0016947 A1 | 1/2010 | Dobak et al. | DE | 3902249 A1 | 8/1990 | |
| 2010/0016984 A1 | 1/2010 | Trabish | DE | 4016704 C1 | 9/1991 | |
| 2010/0016986 A1 | 1/2010 | Trabish | DE | 04219939 A1 | 12/1993 | |
| 2010/0023015 A1 | 1/2010 | Park | DE | 3717871 C3 | 5/1995 | |
| 2010/0030231 A1 | 2/2010 | Revie et al. | DE | 4421153 A1 | 12/1995 | |
| 2010/0042105 A1 | 2/2010 | Park et al. | EP | 97001 A1 | 12/1983 | |
| 2010/0049195 A1 | 2/2010 | Park et al. | EP | 0114505 A1 | 8/1984 | |
| 2010/0076439 A1 | 3/2010 | Hatch | EP | 0326768 A2 | 8/1989 | |
| 2010/0076505 A1 | 3/2010 | Borja | EP | 337901 A1 | 10/1989 | |
| 2010/0076563 A1 | 3/2010 | Otto et al. | EP | 0579868 A2 | 1/1994 | |
| 2010/0076571 A1 | 3/2010 | Hatch | EP | 0645984 | 4/1995 | |
| 2010/0082034 A1 | 4/2010 | Remia | EP | 0650706 A1 | 5/1995 | |
| 2010/0082035 A1 | 4/2010 | Keefer | EP | 756735 | 2/1997 | |
| 2010/0087829 A1 | 4/2010 | Metzger et al. | EP | 0908836 A2 | 4/1999 | |
| 2010/0094295 A1 | 4/2010 | Schnieders et al. | EP | 0916324 A2 | 5/1999 | |
| 2010/0105011 A1 | 4/2010 | Karkar et al. | EP | 1013231 A2 | 6/2000 | |
| 2010/0121335 A1 | 5/2010 | Penenberg et al. | EP | 1020734 A2 | 7/2000 | |
| 2010/0137869 A1 | 6/2010 | Borja et al. | EP | 1136041 A2 | 9/2001 | |
| 2010/0137924 A1 | 6/2010 | Tuke et al. | EP | 904158 B1 | 7/2002 | |
| 2010/0145343 A1 | 6/2010 | Johnson et al. | EP | 1321097 A2 | 6/2003 | |
| 2010/0145344 A1 | 6/2010 | Jordan et al. | EP | 1321107 A1 | 6/2003 | |
| 2010/0152782 A1 | 6/2010 | Stone et al. | EP | 709061 B1 | 7/2003 | |
| 2010/0160917 A1 | 6/2010 | Fitz et al. | EP | 1348393 A1 | 10/2003 | |
| 2010/0168754 A1 | 7/2010 | Fitz et al. | EP | 1437102 A1 | 7/2004 | |
| 2010/0168857 A1 | 7/2010 | Hatch | EP | 1486900 A1 | 12/2004 | |
| 2010/0185202 A1 | 7/2010 | Lester et al. | EP | 1498851 A1 | 1/2005 | |
| 2010/0191244 A1 | 7/2010 | White et al. | EP | 1 669 033 A1 | 6/2006 | |
| 2010/0212138 A1 | 8/2010 | Carroll et al. | EP | 1444957 B1 | 3/2007 | |
| 2010/0217109 A1 | 8/2010 | Belcher | EP | 1669033 B1 | 2/2009 | |
| 2010/0217270 A1 | 8/2010 | Polinski et al. | FR | 1111677 | 3/1956 | |
| 2010/0217338 A1 | 8/2010 | Carroll et al. | FR | 2429582 A1 | 1/1980 | |
| 2010/0228257 A1 | 9/2010 | Bonutti | FR | 2659226 A1 | 9/1991 | |
| 2010/0249657 A1 | 9/2010 | Nycz et al. | FR | 2721195 A1 | 12/1995 | |
| 2010/0249796 A1 | 9/2010 | Nycz | FR | 2768916 A1 | 4/1999 | |
| 2010/0262150 A1 | 10/2010 | Lian | FR | 2819168 A1 | 7/2002 | |
| 2010/0274253 A1 | 10/2010 | Ure | GB | 2094590 A | 9/1982 | |
| 2010/0281678 A1 | 11/2010 | Burdulis, Jr. et al. | GB | 2197790 A | 6/1988 | |
| 2010/0286700 A1 | 11/2010 | Snider et al. | GB | 2426200 A | 11/2006 | |
| 2010/0292743 A1 | 11/2010 | Singhal et al. | GB | 2437003 A | 10/2007 | |
| 2010/0305573 A1 | 12/2010 | Fitz et al. | GB | 2442441 A | 4/2008 | |
| 2010/0305574 A1 | 12/2010 | Fitz et al. | JP | 59157715 A | 9/1984 | |
| 2010/0324692 A1 | 12/2010 | Uthgenannt et al. | JP | 60231208 A | 11/1985 | |
| 2011/0004317 A1 | 1/2011 | Hacking et al. | JP | 2002291706 A | 10/2002 | |
| 2011/0015636 A1 | 1/2011 | Katrana et al. | KR | 20050072500 A | 7/2005 | |
| 2011/0015639 A1 | 1/2011 | Metzger et al. | KR | 20050084024 A | 8/2005 | |
| 2011/0029091 A1 | 2/2011 | Bojarski et al. | RU | 2083179 C1 | 7/1997 | |
| 2011/0029116 A1 | 2/2011 | Jordan et al. | RU | 2113182 C1 | 6/1998 | |
| 2011/0046735 A1 | 2/2011 | Metzger et al. | RU | 2125835 C1 | 2/1999 | |
| 2011/0054478 A1 | 3/2011 | Vanasse et al. | RU | 2138223 C1 | 9/1999 | |
| 2011/0066193 A1 | 3/2011 | Lang et al. | RU | 2175534 C2 | 11/2001 | |
| 2011/0071528 A1 | 3/2011 | Carson | RU | 2187975 C1 | 8/2002 | |
| 2011/0071529 A1 | 3/2011 | Carson | TW | 1231755 | 5/2005 | |
| 2011/0071530 A1 | 3/2011 | Carson | WO | 8807840 A1 | 10/1988 | |
| 2011/0071532 A1 | 3/2011 | Carson | WO | 8909028 A1 | 10/1989 | |
| 2011/0071533 A1 | 3/2011 | Metzger et al. | WO | 8911257 | 11/1989 | |
| 2011/0092804 A1 | 4/2011 | Schoenefeld et al. | WO | 8911257 A1 | 11/1989 | |
| 2011/0093086 A1 | 4/2011 | Witt et al. | WO | 9107139 A1 | 5/1991 | |
| FOREIGN PATENT DOCUMENTS | | | WO | 93/25157 A1 | 12/1993 | |
| | | | WO | 9325157 A1 | 12/1993 | |
| CA | 2501041 A1 | 4/2004 | WO | 9413218 A1 | 6/1994 | |
| CA | 2505371 A1 | 5/2004 | WO | 95/28688 A1 | 10/1995 | |

| | | |
|---|---|---|
| WO | 9528688 | 10/1995 |
| WO | 9528688 A1 | 10/1995 |
| WO | 9607361 | 3/1996 |
| WO | 9729703 | 8/1997 |
| WO | 9732671 A1 | 9/1997 |
| WO | 9800072 A1 | 1/1998 |
| WO | 9832384 A1 | 7/1998 |
| WO | 9901073 A1 | 1/1999 |
| WO | 9932045 A1 | 7/1999 |
| WO | 9952473 A1 | 10/1999 |
| WO | 9959106 A1 | 11/1999 |
| WO | 0170142 A1 | 9/2001 |
| WO | 0184479 A1 | 11/2001 |
| WO | 0218019 | 3/2002 |
| WO | 0226145 A2 | 4/2002 |
| WO | 0236024 A1 | 5/2002 |
| WO | 0237935 | 5/2002 |
| WO | 02067783 | 9/2002 |
| WO | 02096268 A2 | 12/2002 |
| WO | 03042968 | 5/2003 |
| WO | 03051210 A2 | 6/2003 |
| WO | 03051211 A1 | 6/2003 |
| WO | 03077101 | 9/2003 |
| WO | 2004000139 A1 | 12/2003 |
| WO | 2004032806 A1 | 4/2004 |
| WO | 2004017842 A2 | 6/2004 |
| WO | 2004049981 A2 | 6/2004 |
| WO | 2004051301 A2 | 6/2004 |
| WO | 2004061744 A2 | 7/2004 |
| WO | 2004069041 A2 | 8/2004 |
| WO | 2004070580 A2 | 8/2004 |
| WO | 2004075771 A1 | 9/2004 |
| WO | 2004078069 A2 | 9/2004 |
| WO | 2004084725 A1 | 10/2004 |
| WO | 2005027755 A1 | 3/2005 |
| WO | 2005051239 A1 | 6/2005 |
| WO | 2005051240 A1 | 6/2005 |
| WO | 2005053564 A2 | 6/2005 |
| WO | 2005077039 A2 | 8/2005 |
| WO | 2005/084558 | 9/2005 |
| WO | 2005/084558 A1 | 9/2005 |
| WO | 2005099636 A1 | 10/2005 |
| WO | 2005119505 A2 | 12/2005 |
| WO | 2006058057 A2 | 6/2006 |
| WO | 2006060795 A1 | 6/2006 |
| WO | 2006092600 A1 | 9/2006 |
| WO | 2006127486 A2 | 11/2006 |
| WO | 2006134345 A1 | 12/2006 |
| WO | 2007041375 A2 | 4/2007 |
| WO | 2007053572 A2 | 5/2007 |
| WO | 2007062079 A2 | 5/2007 |
| WO | 2007/097854 | 8/2007 |
| WO | 2007/097854 A2 | 8/2007 |
| WO | 2007092841 A2 | 8/2007 |
| WO | 2007097853 A2 | 8/2007 |
| WO | 2007137327 A1 | 12/2007 |
| WO | 2007145937 A2 | 12/2007 |
| WO | 2008014618 A1 | 2/2008 |
| WO | 2008021494 A2 | 2/2008 |
| WO | 2008040961 A1 | 4/2008 |
| WO | 2008044055 A1 | 4/2008 |
| WO | 2008101090 A2 | 8/2008 |
| WO | 2008112996 A1 | 9/2008 |
| WO | 2008117028 A1 | 10/2008 |
| WO | 2008140748 A1 | 11/2008 |
| WO | 2009001083 A1 | 12/2008 |
| WO | 2009025783 A1 | 2/2009 |
| WO | 2009045960 A1 | 4/2009 |
| WO | 2009111512 A2 | 9/2009 |
| WO | 2009129063 A1 | 10/2009 |
| WO | 2009129067 A1 | 10/2009 |
| WO | 2010033431 A1 | 3/2010 |

OTHER PUBLICATIONS

Berry, Seedhom, et al., "Personalised image-based templates for intra-operative guidance," Proceedings of the Institution of Mechanical Engineers, Part H: Journal of Engineering in Medicine, 111-118, 2005.

Radermacher et al., "Computer-Integrated Orthopaedic Surgery: Connection of Planning and Execution in Surgical Intervention," Computer Integrated Surgery, 451-463, 1995.

Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P. Nolte and R. Ganz, eds, 42-52, Hogrefe & Huber Publishing 1999.

Radermacher er at., "Computer Assisted Orthopaedic Surgery with Image Based Individual Templates", Clin Orthopaedics and Related Research 354, 28-38, 1998 (11 pages).

Hafez et al., "Computer-assisted Total Kneed Arthroplasty Using Patient-specific Templating", Clin Orthopaedics and Related Research, 444, 184-192, 2006 (9 pages).

PCT Search Report for Application PCT/US2008/078143 (17 pages), dated Apr. 9, 2009.

Accuracy of CT-Based Patient Specific Total Knee Arthroplasty Instruments; AAHKS 20th Annual Meeting, Submission Record, Submission ID # 4177, Apr. 14, 2010.

"Personalised image-based templates for intra-operative guidance," Proceddings of the Institution of Mechanical Engineers, Part H: Journal of Engineering in Medicine, 111-118, 2005.

"Computer-assisted Total Kneed Arthroplasty Using Patient-specific Templating," Clinical Orthopaedics and Related Research, 444, 184-192, (12 pages), 2006.

"A home-based pedometer-driven walking program to increase physical actifvity in order adults with osteoarthritis of the knee: a preliminary study," Journal of the American Geriatrics Society, vol. 51, No. 3, 6 pages, 2003.

"Measuring functional abilities of patients with knee problems; rationale and construction of the DynaPort knee test," Knee Surgery, Sports Traumatology, Arthroscopy, vol. 10, pp. 204-212, 2002.

"Automated physical activity monitoring: validation and comparison with physiological and self-report measures," Psychophysiology, vol. 30, pp. 296-305, 1993.

"Moven—inertial motion capturing." [Online] <http://www.xsens.com/index.php?mainmenu=products&submenu=human_motion&subsubmenu=Moven>, 4 pages, 2007.

European Search Report for European Patent Application No. 10150487.6-2310, May 12, 2010, 6 pages.

European Search Report for European Patent Application No. 0917188.7-2310, Sep. 24, 2010, 7 pages.

Chinese First Office Action, Chinese Patent Application No. 200880118434.4, Sep. 7, 2011, 12 pages.

* cited by examiner

CUSTOMIZED PATIENT-SPECIFIC INSTRUMENTATION AND METHOD FOR PERFORMING A BONE RE-CUT

This application claims priority under 35 U.S.C. §119(e) to U.S. Provisional Patent Application Ser. No. 60/976,447 entitled "Method and Apparatus for Fabricating Customized Patent Instrumentation," which was filed on Sep. 30, 2007 by Dan Auger et al.; U.S. Provisional Patent Application Ser. No. 60/976,448 entitled "Adjustable Customized Patient-Specific Orthopaedic Surgical Instrumentation," which was filed on Sep. 30, 2007 by Luke Aram et al.; U.S. Provisional Patent Application Ser. No. 60/976,451 entitled "Customized Patient-Specific Instrumentation For Use In Orthopaedic Surgical Procedures," which was filed on Sep. 30, 2007 by Jeff Roose et al.; U.S. Provisional Patent Application Ser. No. 60/976,444 entitled "Method and Apparatus for Patient-Specific Positioning of Orthopaedic Surgical Instrumentation," which was filed on Sep. 30, 2007 by Luke Aram et al.; and U.S. Provisional Patent Application Ser. No. 60/976,446 entitled "Method and Apparatus for Aligning Customized Patient-Specific Orthopaedic Surgical Instruments," which was filed on Sep. 30, 2007 by Luke Aram et al., each of which is assigned to the same assignee as the present application, and each of which is hereby incorporated by reference.

CROSS-REFERENCE TO RELATED U.S. PATENT APPLICATIONS

Cross-reference is made to co-pending U.S. patent application Ser. No. 12/240,990 entitled "Customized Patient-Specific Instrumentation for Use In Orthopaedic Surgical Procedures," which was filed by Luke Aram et al.; co-pending U.S. patent application Ser. No. 12/240,988 entitled "Orthopaedic Bone Saw And Method of Use Thereof," which was filed by Travis Bennett; co-pending U.S. patent application Ser. No. 12/240,992 entitled "Customized Patient-Specific Bone Cutting Blocks," which was filed by Eric Zajac; co-pending U.S. patent application Ser. No. 12/240,994 entitled "Customized Patient-Specific Multi-Cutting Blocks," which was filed by Christopher Aker et al.; co-pending U.S. patent application Ser. No. 12/240,996 entitled "Customized Patient-Specific Bone Cutting Instrumentation," which was filed by Luke Aram et al.; co-pending U.S. patent application Ser. No. 12/240,997 entitled "Femoral/Tibial Customized Patient Specific Orthopaedic Surgical Instrumentation," which was filed by Christopher Aker et al.; co-pending U.S. patent application Ser. No. 12/240,998 entitled "Adjustable Customized Patient-Specific Orthopaedic Surgical Instrumentation," which was filed by Christopher Aker et al.; co-pending U.S. patent application Ser. No. 12/241,006 entitled "System and Method For Fabricating A Customized Patient-Specific Surgical Instrument," which was filed by Jeff Roose et al.; co-pending U.S. patent application Ser. No. 12/241,002 entitled "Customized Patient-Specific Bone Cutting Block With External Reference," which was filed by Luke Aram et al.; co-pending U.S. patent application Ser. No. 12/241,001 entitled "Apparatus and Method for Fabricating A Customized Patient-Specific Orthopaedic Instrument," which was filed by Bryan Rose; and co-pending U.S. patent application Ser. No. 12/240,999 entitled "Patient-Customizable Device And System For Performing An Orthopaedic Surgical Procedures," which was filed by Jeff Roose, each of which is assigned to the same assignee as the present application, each of which is filed concurrently herewith, and each of which is hereby incorporated by reference.

TECHNICAL FIELD

The present disclosure relates generally to customized patient-specific orthopaedic surgical instruments and to methods, devices, and systems for fabricating and positioning such instruments.

BACKGROUND

Joint arthroplasty is a well-known surgical procedure by which a diseased and/or damaged natural joint is replaced by a prosthetic joint. A typical knee prosthesis includes a tibial tray, a femoral component, a polymer insert or bearing positioned between the tibial tray and the femoral component, and, in some cases, a polymer patella button. To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

SUMMARY

According to one aspect, a method of performing an orthopaedic surgical procedure on a bone of a patient is disclosed. The method may include positioning a customized patient-specific cutting block in contact with the bone of a patient. In some embodiments, the method may include positioning the customized patient-specific cutting block in contact with a femur of the patient. In some embodiments, the method may include positioning the customized patient-specific cutting block in contact with a tibia of the patient. The method may include inserting a pair of guide pins into a pair of guide pin holes defined in the customized patient-specific cutting block. The method may also include making a first cut in the bone of the patient with the customized patient-specific cutting block. In some embodiments, the method may include making the first cut in the femur of the patient with the customized patient-specific cutting block. In other embodiments, the method may include making the first cut in the tibia of the patient with the customized patient-specific cutting block. The method may also include removing the customized patient-specific cutting block from the bone of the patient without removing the guide pins from the bone of the patient.

The method may include inserting the pair of guide pins into a pair of guide pin holes defined in a patient-universal re-cut block and making a second cut in the bone of the patient with the patient-universal re-cut block. In some embodiments, the method may include making the second cut in the femur of the patient with the patient-universal re-cut block. The method may also include making the second cut in the femur of the patient substantially parallel to the first cut. Additionally, in some embodiments, the method may include making the second cut in the femur oriented in an angled position relative to the first cut.

In some embodiments, the method may include making the second cut in the tibia of the patient with the patient-universal re-cut block. The method may include making the second cut in the tibia of the patient substantially parallel to the first cut. Additionally, in some embodiments, the method may include making the second cut in the tibia oriented in an angled position relative to the first cut.

In some embodiments, the method may include inserting the pair of guide pins into the pair of guide pin holes defined in the patient-universal re-cut block such that a cutting guide of the patient-universal re-cut block is substantially parallel to the first cut. The method may include making the second cut in the bone of the patient with the patient-universal re-cut block such that the second cut is substantially parallel to the first cut. Additionally, in some embodiments, the cutting guide of the patient-universal re-cut block may be oriented in an angled position relative to the first cut. The method may include making the second cut in the bone of the patient with the patient-universal re-cut block such that the second cut is oriented in an angled position relative to the first cut.

In some embodiments, the method may include determining an amount of additional bone to be removed from the bone of the patient subsequent to making the first cut in the bone of the patient with the customized patient-specific cutting block. The method may include selecting a pair of guide pin holes from a plurality of pairs of guide pin holes defined in the patient-universal re-cut block that corresponds to the amount of additional bone to be removed from the bone of a patient. The method may include inserting the pair of guide pins into the selected pair of guide pin holes defined in the patient-universal re-cut block that corresponds to the amount of additional bone to be removed from the bone of a patient.

According to another aspect, an orthopaedic instrument assembly may include a customized patient-specific cutting block and a patient-universal re-cut block. In some embodiments, the customized patient-specific cutting block may be a patient-specific femoral cutting block and the patient-universal re-cut block may be a patient-universal femoral re-cut block. In other embodiments, the customized patient-specific cutting block may be a patient-specific tibial cutting block and the patient-universal re-cut block may be a patient-universal femoral re-cut block.

The customized patient-specific cutting block may include a cutting guide and a pair of guide pin holes. The patient-universal re-cut block may include a cutting guide and a plurality of pairs of guide pin holes. Each pair of guide pin holes of patient-universal re-cut block may correspond in diameter and spacing with the pair of guide pin holes of the customized patient-specific cutting block.

In some embodiments, the cutting guide of the patient-universal re-cut block may be substantially parallel to the cutting guide of the customized patient-specific cutting block when a one pair of guide pin holes of the patient universal re-cut block is aligned with the pair of guide pin holes of the customized patient-specific cutting block. In some embodiments, the cutting guide of the patient-universal re-cut block may be oriented in an angled position relative to the cutting guide of the customized patient-specific cutting block when a one pair of guide pin holes of the patient universal re-cut block is aligned with the pair of guide pin holes of the customized patient-specific cutting block.

In another aspect, a method of performing an orthopaedic surgical procedure on a femur of a patient is disclosed. The method may include positioning or placing a customized patient-specific cutting block in contact with the femur of the patient and inserting a pair of guide pins into a pair of guide pin holes defined in the customized patient-specific cutting block. The method may also include making a first cut in the femur of the patient with the customized patient-specific cutting block. The method may include removing the customized patient-specific cutting block without removing the guide pins from the femur of the patient. The method may also include determining an amount of additional bone to be removed from the femur of the patient subsequent to making the first cut in the femur and selecting a pair of guide pin holes from a plurality of pairs of guide pin holes defined in a patient-universal re-cut block which corresponds to the amount of additional bone to be removed from the femur of the patient.

The method may further include inserting the pair of guide pins into the selected pair of guide pin holes defined in the patient-universal re-cut block which corresponds to the amount of additional bone to be removed from the femur of the patient. The method may include making a second cut in the femur of the patient with the patient-universal re-cut block. In some embodiments, the method may include inserting the pair of guide pins into the selected pair of guide pin holes such that a cutting guide of the patient-universal re-cut block is substantially parallel to the first cut. The method may include making the second cut in the femur of the patient with the patient-universal re-cut block such that the second cut is substantially parallel to the first cut. Additionally, in some embodiments, the method may include inserting the pair of guide pins into the selected pair of guide pin holes such that a cutting guide of the patient-universal re-cut block is oriented in an angled position relative to the first cut. The method may include making the second cut in the femur of the patient with the patient-universal re-cut block such that the second cut is oriented in an angled position relative to the first cut.

According to one aspect, an orthopaedic bone saw for cutting the bone of a patient is disclosed. The orthopaedic bone saw may include a chuck configured to receive a bone saw blade and a guide configured to receive one or more surgical guide pins to align the bone saw in a predetermined position relative to the bone of the patient. In some embodiments, the guide may include a body having one or more openings to receive the one or more surgical guide pins. Additionally, in some embodiments, the guide may have an elongated body with a slot, and the slot may be configured to receive the one or more surgical guide pins.

In some embodiments, the orthopaedic bone saw may have a swivel secured to the guide that permits the chuck and the guide to swivel relative to one another. In some embodiments, the orthopaedic bone saw may have a handle and a housing secured to the handle. The chuck may be secured to the housing, and the swivel may be positioned between the housing and the guide. The guide may swivel relative to the housing. In some embodiments, both the chuck and the guide may be secured to the housing.

According to another aspect, an orthopaedic bone saw tool for cutting the bone of a patient is disclosed. The orthopaedic bone saw tool may include a bone saw and a bone saw blade. The bone saw may have a housing, a handle secured to the housing, and a chuck secured to the housing. The bone saw blade may be secured to the chuck.

The bone saw may include a guide secured to the housing that is configured to receive one or more surgical guide pins. In some embodiments, the guide may have a body that has one or more openings to receive the one or more surgical guide pins. In some embodiments, the guide may have an elongated body that has a slot. The slot may be configured to receive the one or more surgical guide pins. In some embodiments, the bone saw may include a swivel positioned between the housing and the guide. The swivel may permit the guide and the bone saw blade to swivel relative to one another.

According to another aspect, a method of performing an orthopaedic surgical procedure on a bone of a patient is disclosed. The method may include inserting a first end of one or more surgical guide pins into the bone of the patient. The method may also include advancing a second end of the one or more surgical guide pins into a guide secured to a bone saw so as to position the bone saw in a predetermined position relative to the bone of the patient. The method may include making a cut in the bone of the patient with the bone saw while the one or more surgical guide pins are positioned in the guide.

In some embodiments, the guide may have a body having one or more openings defined therein. The method may include advancing the second end of the one or more surgical guide pins into the one or more openings of the body of the guide. Additionally, in some embodiments, the guide may include an elongated body having a slot. The method may include advancing the second end of the one or more surgical guide pins into the slot of the elongated body of the guide.

In some embodiments, the bone saw may include a bone saw blade secured to chuck and a swivel positioned between the chuck and the guide. The method may include swiveling the chuck relative the guide while making the cut in the bone of the patient.

In some embodiments, the method may include positioning a customized patient-specific cutting block in contact with the bone of the patient. The method may also include inserting the first end of the one or more surgical guide pins through one or more guide pin holes defined in the customized patient-specific cutting block and into the bone of the patient. The method may further include removing the customized patient-specific cutting block from the bone of the patient without removing the one or more surgical guide pins from the bone of the patient.

According to one aspect, a customized patient-specific orthopaedic instrument is disclosed. The customized patient-specific orthopaedic instrument may include a customized patient-specific femoral cutting block that may include a body having a bone-facing surface having a customized patient-specific negative contour configured to receive a portion of an anterior side of a patient's femur that has a corresponding positive contour. The customized patient-specific orthopaedic instrument may also include at least one tab extending posteriorly from the body, the at least one tab having a bone-facing surface having a customized patient-specific negative contour configured to receive a portion of the distal side of the patient's femur that has a corresponding positive contour. The customized patient-specific orthopaedic instrument may include a lip extending superiorly from an end of the at least one tab, the lip having a bone-facing surface having a customized patient-specific negative contour configured to receive a portion of the posterior side of the patient's femur that has a corresponding position contour.

In some embodiments, the customized patient-specific femoral cutting block may include a first tab extending posteriorly from the body and a second tab extending posteriorly from the body. Each of the first tab and the second tab may have a customized patient-specific negative contour configured to receive a respective portion of the distal end of the patient's femur that has a corresponding positive contour, and the first tab and the second tab defining an opening therebetween. In some embodiments, the customized patient-specific femoral cutting block may include a first lip extending superiorly from an end of the first tab and a second lip extending superiorly from an end of the second tab, each of the first tab and the second tab having a customized patient-specific negative contour configured to receive a respective portion of the posterior side of the patient's femur that has a corresponding positive contour.

In some embodiments, the first tab may extend posteriorly from the body a first distance and the second tab may extend posteriorly form the body a second distance, the first and second distances being substantially different. In some embodiments, the body of the customized patient-specific femoral cutting block may define a vertical plane and the first tab and second tab may extend obliquely from the body with respect to the vertical plane. Additionally, in some embodiments, the body of the customized patient-specific femoral cutting block may include a cutting slot defined therein, the cutting slot being positioned to allow a surgeon to perform a distal cut on the patient's femur using the cutting slot.

In some embodiments, the customized patient-specific femoral cutting block may include a cutting guide coupled to the body, the cutting guide having a cutting slot defined therein, the cutting guide being formed from a material different from the body and being positioned to allow a surgeon to perform a distal cut on the patient's femur using the cutting slot. In some embodiments, the cutting guide may be formed from a metallic material and overmolded to the body of the customized patient-specific femoral cutting block.

In some embodiments, the customized patient-specific femoral cutting block may include a plurality of anterior guide pin bushings coupled to the body, each of the anterior guide pin bushings being formed from a material different from the body and having a passageway defined therethrough sized to receive a corresponding guide pin. In some embodiments, the body of the customized patient-specific femoral cutting block may include a plurality of passageways extending therethrough, each of the plurality of anterior guide pin bushings being received in a corresponding passageway of the plurality of passageways and positioned such that a bone-facing end of each anterior guide pin bushing is recessed with respect to the bone-facing surface of the body.

In some embodiments, one of the plurality of passageways may be oblique with respect to the other plurality of passageways. In some of the embodiments, each of the passageways of the body of the customized patient-specific femoral cutting block may be counterbored on the bone-facing surface. In some embodiments, the customized patient-specific femoral cutting block may include a distal guide pin bushing coupled to the at least one tab, the distal guide pin bushing being formed from a material different from the at least one tab and having a passageway defined therethrough sized to receive a corresponding guide pin. In some embodiments, the body of the customized patient-specific femoral cutting block may include an opening defined therein, the opening extending superiorly from the cutting guide to a point on the body that is more superior than the superior-most point of each of the plurality of anterior guide pin bushings.

In some embodiments, the at least one tab may include a groove extending laterally across the bone-facing side of the at least one tab, the groove and the cutting guide defining a transverse plane. In some embodiments, the customized patient-specific femoral cutting block may include a post extending anteriorly from the body, the post including a passageway defined therein, the passageway extending through the post to the bone-facing surface of the body and being sized to receive a corresponding guide pin. In some embodiments, the body of the customized patient-specific femoral cutting block may include an outer surface opposite the bone-facing surface, the outer surface including a recessed area. In some embodiments, the customized patient-specific femoral cutting block may include an arcuate bracket extending from the body, the arcuate bracket including a posterior bone-facing surface having a negative contour configured to receive a portion of the posterior side of the patient's femur that has a corresponding positive contour. Additionally, in some embodiments, the body of the customized patient-specific femoral cutting block may include an outer surface opposite the bone-facing surface. The outer surface may include a recessed area sized to receive an end of a surgeon's finger. The recessed area may correspond to a location on the body at which pressure is to be applied to couple the customized patient-specific femoral cutting block to the patient's femur.

According to another aspect, the customized patient-specific orthopaedic instrument may include a customized patient-specific tibial cutting block that may include a body having a bone-facing surface having a customized patient-specific negative contour configured to receive a portion of an anterior side of a patient's tibia that has a corresponding contour and a portion of a medial side of the patient's tibia that has a corresponding contour such that an angle greater than zero is defined between a vertically-extending, bisecting plane of the body and a bisecting saggital plane of the patient's tibia when the portions of the patient's tibia are received in the customized patient-specific negative contour of the body. The body may also include at least one tab extending posteriorly from the body, the at least one tab having a bone-facing surface having a customized patient-specific negative contour configured to receive a portion of the proximal side of the patient's tibia that has a corresponding contour.

In some embodiments, the customized patient-specific tibial cutting block may include a first tab extending posteriorly from the body and a second tab extending posteriorly from the body, each of the first tab and the second tab having a bone-facing surface having a customized patient-specific negative contour configured to receive a respective portion of the proximal end of the patient's tibia that has a corresponding contour, the first tab and the second tab defining an opening therebetween. In some embodiments, each of the first tab and second tab may include an enclosed elongated opening defined therein.

In some embodiments, the body of the customized patient-specific tibial cutting bock may include a superior end and an outer surface opposite the bone-facing surface of the body. The superior end may include a notch defined therein and the notch extending from the outer surface to the bone-facing surface of the body. In some embodiments, the first tab may extend posteriorly from the body a first distance and the second tab may extend posteriorly form the body a second distance, the first and second distances being substantially different.

In some embodiments, the body of the customized patient-specific tibial cutting block may define a vertical plane and the first tab and second tab extend obliquely from the body with respect to the vertical plane. In some embodiments, the first tab may have a maximum thickness and the second tab may have a maximum thickness, the maximum thickness of the first tab being greater than the maximum thickness of the second tab. In some embodiments, the body of the customized patient-specific tibial cutting block may include a cutting slot defined therein, the cutting slot being positioned to allow a surgeon to perform a proximal cut on the patient's femur using the cutting slot.

In some embodiments, the customized patient-specific tibial cutting block may include a cutting guide coupled to the body, the cutting guide having a cutting slot defined therein, the cutting guide being formed from a material different from the body and being positioned to allow a surgeon to perform a distal cut on the patient's femur using the cutting slot. In some embodiments, the cutting guide may be formed from a metallic material and overmolded to the body of the customized patient-specific tibial cutting block. In some embodiments, the customized patient-specific tibial cutting block may include an outer surface opposite the bone-facing surface and a ledge extending outwardly from the outer surface, the ledge having a top surface coplanar with a bottom surface of the cutting slot of the cutting guide.

In some embodiments, the customized patient-specific tibial cutting block may include a plurality of anterior guide pin bushings coupled to the body, each of the anterior guide pin bushings being formed from a material different from the body and having a passageway defined therethrough sized to receive a corresponding guide pin. In some embodiments, the body of the customized patient-specific tibial cutting block includes a plurality of passageways extending therethrough, each of the plurality of anterior guide pin bushings being received in a corresponding passageway of the plurality of passageways and positioned such that a bone-facing end of each anterior guide pin bushing is recessed with respect to the bone-facing surface of the body. In some embodiments, one of the plurality of passageways may be oblique with respect to the other plurality of passageways.

In some embodiments, each of the passageways of the body of the customized patient-specific tibial cutting block may be counterbored on the bone facing surface. Additionally, in some embodiments, the customized patient-specific tibial cutting block may include a proximal guide pin bushing coupled to the at least one tab, the proximal guide pin bushing being formed from a material different from the at least one tab and having a passageway defined therethrough sized to receive a corresponding guide pin. In some embodiments, the body of the customized patient-specific tibial cutting block may include an outer surface opposite the bone-facing surface, the outer surface including a recessed area.

In some embodiments, the angle defined between the vertically-extending, bisecting plane of the body and the bisecting sagittal plane of the patient's tibia may be between ten degrees and thirty degrees. Additionally, in some embodiments, the angle defined between the vertically-extending, bisecting plane of the body and the bisecting sagittal plane of the patient's tibia may be about twenty degrees. In some embodiments, the tab may have a decreasing thickness in the anterior-to-posterior direction. In some embodiment, the at least one tab has a top surface that may have a concave cross-section in the sagittal plane. In some embodiments, a portion of the customized patient-specific negative contour of the bone-facing surface of the body substantially may define a compound angle. In some embodiments, the bone-facing surface of the at least one tab may include a central recess to define a rim therearound, the customized patient-specific negative contour of the bone facing surface of the at least one tab being defined on the rim.

According to another aspect, a customized patient-specific orthopaedic instrument is disclosed. A customized patient-specific orthopaedic instrument is a customized patient-specific cutting block. The customized patient-specific cutting block may have a bone-facing surface including a negative contour configured to receive a portion of a patient's bone having a corresponding contour, the negative contour being scaled with respect to the contour of the patient's bone by a predetermined amount based on the thickness of the cartilage present on the patient's bone.

According to one aspect, a customized patient-specific orthopaedic instrument is disclosed. The customized patient-specific orthopaedic instrument includes a customized patient-specific cutting block. The customized patient-specific cutting block may include an anterior body piece, an end body piece that is separate from the anterior body piece, and a number of fasteners securing the anterior body piece and the end body piece to one another. In some embodiments, the customized patient-specific cutting block may be a customized patient-specific femoral cutting block. Additionally, in some embodiments, the customized patient-specific cutting block may be a customized patient-specific tibial cutting block.

The anterior body piece may include a bone-facing surface, an outer surface opposite the bone-facing surface, and a cutting guide. The bone-facing surface may have a customized patient-specific negative contour configured to receive a portion of an anterior side of a bone of a patient that has a corresponding contour. In some embodiments, the anterior body piece of the customized patient-specific cutting block further may include a pair of guide pin holes that extend from the outer surface to the bone-facing surface. In some embodiments, the cutting guide of the anterior body piece may be a captured cutting guide.

The end body piece may include a bone-facing surface and an outer surface opposite the bone-facing surface. The bone-facing surface may have a customized patient-specific negative contour configured to receive a portion of the bone of the patient that has a corresponding contour. In some embodiments, the end body piece may include a pair of guide pin holes defined therein that extend from the outer surface to the bone-facing surface.

In some embodiments, the number of fasteners includes a number of pins. The anterior body piece and the end body piece may each have a number of holes. The number of pins may be positioned in the number of holes defined in the anterior body piece and the number of holes defined in the end body piece so as to secure the anterior body piece and the end body piece to one another.

According to another aspect, a method of performing an orthopaedic surgical procedure on a bone of a patient is disclosed. The method may include inserting an anterior body piece of a customized patient-specific cutting block through an incision. The method may also include inserting an end body piece of the customized patient-specific cutting block through the incision, the end body piece being separate from the anterior body piece. The method may include securing the anterior body piece and the end body piece to one another subsequent to the insertion of both pieces to create an assembled customized patient-specific cutting block. In some embodiments, the anterior body piece and the end body piece may be secured to one another with a number of pins.

The method may include positioning the assembled customized patient-specific cutting block in contact with the bone of the patient and making a cut in the bone of the patient with the assembled customized patient-specific cutting block. In some embodiments, the method may include positioning the assembled customized patient-specific cutting block in contact with the femur of the patient. The method may also include making a cut in the femur of the patient with the assembled customized patient-specific cutting block. Additionally, in some embodiments, the method may include positioning the assembled customized patient-specific cutting block in contact with the tibia of the patient. The method may also include making a cut in the tibia of the patient with the assembled customized patient-specific cutting block. In some embodiments, the method may also include inserting a pair of guide pins into a pair of guide pin holes defined in the assembled customized patient-specific cutting block prior to making the cut in the bone of the patient.

According to another aspect, a customized patient-specific orthopaedic instrument is disclosed. The customized patient-specific orthopaedic instrument may have a customized patient-specific cutting block that includes a body. In some embodiments, the customized patient-specific cutting block may be a customized patient-specific femoral cutting block. Additionally, in some embodiments, the customized patient-specific cutting block may be a customized patient-specific tibial cutting block.

The body may have a bone-facing surface, an outer surface opposite the bone-facing surface, and a non-captured cutting guide. The bone-facing surface may have a customized patient-specific negative contour configured to receive a portion of an anterior side of a bone of a patient that has a corresponding contour. In some embodiments, the body of the customized patient-specific cutting block may have a pair of guide pin holes defined therein that extend from the outer surface to the bone-facing surface. The non-captured cutting guide may be defined by a sidewall extending from the outer surface to the bone-facing surface.

According to one aspect, a customized patient-specific orthopaedic instrument is disclosed. The customized patient-specific orthopaedic instrument may include a cutting block that has an anterior bone-facing surface and a distal bone-facing surface.

The anterior bone-facing surface may be configured to receive a portion of an anterior side of a bone of a patient. The anterior bone-facing surface may include a first flat surface that extends distally in a direction away from the proximal-most edge of the bone cutting block and toward the distal bone-facing surface of the cutting block. The anterior bone-facing surface may include an anterior customized patient-specific negative contour surface that extends distally away from the first flat surface, the anterior customized patient-specific negative contour surface being configured to receive the portion of the anterior side of the bone of the patient that has a corresponding contour. The anterior bone-facing surface may also include a second flat surface that extends distally from the anterior customized patient-specific negative contour surface toward the distal bone-facing surface The distal bone-facing surface may be configured to receive a portion of a distal side of the bone of the patient. The distal bone-facing surface may include a first flat surface that extends posteriorly in a direction away from the anterior bone-facing surface of the bone cutting block and toward the posterior-most edge of the cutting block. The distal bone-facing surface may include a distal customized patient-specific negative contour surface that extends posteriorly away from the first flat surface, the distal customized patient-specific negative contour surface being configured to receive the portion of the distal side of the bone of the patient that has a corresponding contour. The distal bone-facing surface may also include a second flat surface that extends posteriorly from the distal customized patient-specific negative contour surface toward the posterior-most edge of the cutting block.

In some embodiments, the cutting block may be generally L-shaped and may have an anterior plate and a distal plate secured to, and extending away from, the anterior plate. The anterior bone-facing surface may be defined in the anterior plate and the distal bone-facing surface may be defined in the distal place.

In some embodiments, the anterior plate may have a distal cutting guide extending through the anterior plate. Additionally, in some embodiments, the distal plate may have both an anterior cutting guide and a posterior cutting guide extending through the distal plate. In some embodiments, the distal plate may have a pair of angled cutting guides extending through the distal plate. In some embodiments, the distal plate may have an anterior cutting guide extending through the distal plate. In some embodiments, the distal plate may have a posterior cutting guide extending through the distal plate.

In some embodiments, the first flat surface of the anterior bone-facing surface may transition to the anterior customized patient-specific negative contour surface. The anterior customized patient-specific negative contour surface may transition to the second flat surface of the anterior bone-facing surface. Additionally, in some embodiments, the first flat surface of the distal bone-facing surface may transition to the distal customized patient-specific negative contour surface. The distal customized patient-specific negative contour surface may transition to the second flat surface of the distal bone-facing surface.

According to another aspect, a method of performing an orthopaedic surgical procedure on a bone of a patient is disclosed. The method may include securing a customized patient-specific cutting block to the bone of the patient such that an anterior side of the bone of the patient is received into an anterior customized patient-specific negative contour surface of the cutting block and a distal side of the bone of the patient is received into a distal customized patient-specific negative contour surface of the cutting block. The method may include making an anterior cut in the bone of the patient with the cutting block such that a flat surface is formed on the anterior side of the bone of the patient and making a distal cut in the bone of the patient with the cutting block such that a flat surface is formed on the distal side of the bone of the patient. The method may also include determining an amount of additional bone to be removed from the bone of the patient subsequent to making the anterior cut and the distal cut in the bone of the patient.

The method may include securing the customized patient-specific cutting block to the bone of the patient such that the flat surface formed in the anterior side of the bone of the patient is positioned against at least one flat surface formed in an anterior bone-facing surface the cutting block and the flat surface formed in the distal side of the bone of the patient is positioned against at least one flat surface formed in a distal bone-facing surface the cutting block. The method may further include making at least one of an additional anterior cut in the bone of the patient with the cutting block such that additional bone is removed from the flat surface formed on the anterior side of the bone of the patient and an additional distal cut in the bone of the patient with the cutting block such that additional bone is removed from the flat surface formed on the distal side of the bone of the patient.

In some embodiments, the method may include securing the customized patient-specific cutting block to a femur of the patient such that an anterior side of the femur of the patient is received into the anterior customized patient-specific negative contour surface of the cutting block and a distal side of the femur of the patient is received into the distal customized patient-specific negative contour surface of the cutting block. In some embodiments, the method may include making both an additional anterior cut in the bone of the patient with the cutting block such that additional bone is removed from the flat surface formed on the anterior side of the bone of the patient and an additional distal cut in the bone of the patient with the cutting block such that additional bone is removed from the flat surface formed on the distal side of the bone of the patient.

According to another aspect, a customized patient-specific orthopaedic instrument is disclosed. The customized patient-specific orthopaedic instrument may include a cutting block having an anterior customized patient-specific negative contour surface that is configured to receive a portion of the anterior side of the bone of the patient that has a corresponding contour. The cutting block may have a distal customized patient-specific negative contour surface that is configured to receive a portion of the distal side of the bone of the patient that has a corresponding contour. The cutting block may also have a posterior customized patient-specific negative contour surface that is configured to receive a portion of the posterior side of the bone of the patient that has a corresponding contour.

In some embodiments, the cutting block may be generally U-shaped and have an anterior plate, a distal plate, and a posterior plate. The anterior bone-facing surface may be defined in the anterior plate, the distal bone-facing surface may be defined in the distal plate, and the posterior bone-facing surface is defined in the posterior plate.

In some embodiments, the anterior plate may have a distal cutting guide extending through the anterior plate. Additionally, in some embodiments, the distal plate may have both an anterior cutting guide and a posterior cutting guide extending through the distal plate. In some embodiments, the distal plate may have a pair of angled cutting guides extending through the distal plate. In some embodiments, the distal plate may have an anterior cutting guide extending through the distal plate. In some embodiments, the distal plate may have a posterior cutting guide extending through the distal plate.

According to one aspect, an orthopaedic instrument assembly is disclosed. The orthopaedic instrument assembly may include a customized patient-specific femoral cutting block, a customized patient-specific tibial cutting block, and a mechanical linkage positioned between the customized patient-specific femoral cutting block and the customized patient-specific tibial cutting block. The customized patient-specific femoral cutting block may include a customized patient-specific negative contour surface that is configured to receive a portion of a distal femur of a patient that has a corresponding contour and a cutting guide. The customized patient-specific tibial cutting block may include a customized patient-specific negative contour surface that is configured to receive a portion of a proximal tibia of a patient that has a corresponding contour and a cutting guide. The mechanical linkage may be operable to move the customized patient-specific femoral cutting block and the customized patient-specific tibial cutting block away from and toward one another.

In some embodiments, the mechanical linkage may include a number of threaded shafts. The rotation of the threaded shafts in a first direction may cause the customized patient-specific femoral cutting block and the customized patient-specific tibial cutting block to be moved away from one another. The rotation of the threaded shafts in a second, opposite direction may cause the customized patient-specific femoral cutting block and the customized patient-specific tibial cutting block to be moved toward one another.

In some embodiments, the mechanical linkage may include a number of thumbscrews coupled to the number of threaded shafts. The rotation of the thumbscrews in the first direction may cause rotation of the threaded shafts in the first direction. The rotation of the thumbscrews in the second direction may cause rotation of the threaded shafts in the second direction.

In some embodiments, the mechanical linkage may include a number of thumbscrews. The rotation of the thumbscrews in a first direction may cause the customized patient-specific femoral cutting block and the customized patient-specific tibial cutting block to be moved away from one another. The rotation of the thumbscrews in a second, opposite direction may cause the customized patient-specific femoral cutting block and the customized patient-specific tibial cutting block to be moved toward one another.

In some embodiments, both the customized patient-specific femoral cutting block and the customized patient-specific tibial cutting block have a number of guide pin holes. In some embodiments, the cutting guide of the customized patient-specific femoral cutting block is substantially parallel to the cutting guide of the customized patient-specific tibial cutting block.

According to another aspect, the orthopaedic instrument assembly may include a customized patient-specific femoral cutting block and a ligament balancer secured to the femoral cutting block. The customized patient-specific femoral cutting block may have a customized patient-specific negative contour surface that is configured to receive a portion of a distal femur of a patient that has a corresponding contour and a cutting guide. The ligament balancer may have a tibial base plate and a pair of femoral paddles each of which is movable relative to the tibial base plate.

In some embodiments, the orthopaedic instrument assembly may include a bracket having a first end secured to the femoral cutting block and a second end secured to the ligament balancer. Additionally, in some embodiments, the second end of the bracket may be secured to the tibial base plate of the ligament balancer. In some embodiments, the first end of the bracket may have a pair of guide pin holes defined therein. In some embodiments, the bracket may have a first end secured to the femoral cutting block and a second end secured to the ligament balancer. The bracket may also have a receiver configured to receive an intramedullary rod.

In some embodiments, the customized patient-specific femoral cutting block may include a customized patient-specific anterior bone-facing surface configured to receive a portion of an anterior side of a femur of a patient and a customized patient-specific distal bone-facing surface configured to receive a portion of a distal side of the femur of the patient. In some embodiments, the ligament balancer has a pair of cylinders secured to the tibial base plate and each of the pair of femoral paddles is received into a respective one of the pair of cylinders.

According to another aspect, a method of an orthopaedic surgical procedure on a patient is disclosed. The method may include securing a customized patient-specific femoral cutting block to the femur of the patient and securing a ligament balancer to the tibia of the patient. The method may include securing the ligament balancer to the customized patient-specific femoral cutting block. The method may also include operating the ligament balancer to position the femur of the patient in a desired position relative to the tibia. The method may further include making a cut in the femur of the patient with the customized patient-specific cutting block.

In some embodiments, the securing of the customized patient-specific femoral cutting block may include positioning the customized patient-specific femoral cutting block in contact with the femur of the patient. The method may also include inserting at least one guide pin into at least one guide pin hole defined in the customized patient-specific femoral cutting block so as to secure the customized patient-specific femoral cutting block to the femur of the patient.

In some embodiments, the method may include the ligament balancer having a first end of a bracket secured thereto. The second end of the bracket may have at least one guide pin hole defined therein. The method may also include advancing the at least one guide pin into the at least one guide pin hole of the bracket so as to secure the second end of the bracket to the customized patient-specific femoral cutting block. In some embodiments, the method the ligament balancer having a first end of a bracket secured thereto and securing a second end of the bracket to the customized patient-specific femoral cutting block. Additionally, in some embodiments, the method may include independently moving each of a pair of femoral paddles of the ligament balancer.

According to one aspect, an orthopaedic instrument assembly is disclosed. The orthopaedic instrument assembly includes a femoral cutting block and a tibial cutting block. The femoral cutting block may include a negative contour surface that is configured to receive a portion of a distal femur of a patient, a cutting guide, and a pair of trial condylar surfaces formed in the distal end of the femoral cutting block. In some embodiments, the negative contour surface of the femoral cutting block may include a customized patient-specific negative contour surface that is configured to receive a portion of a distal femur of a patient that has a corresponding contour. In some embodiments, the pair of trial condylar surfaces formed in the distal end of the femoral cutting block may include a medial condylar surface having a concave outer profile which resembles a natural medial condyle of a femur and a lateral condylar surface having a concave outer profile which resembles a natural lateral condyle of the femur.

The tibial cutting block may have a negative contour surface that is configured to receive a portion of a proximal tibia of the patient, a cutting guide, and a pair of trial articular surfaces formed in the proximal end of the tibial cutting block, the pair of trial articular surfaces being configured to receive the pair of trial condylar surfaces formed in the distal end of the femoral cutting block. In some embodiments, the negative contour surface of the tibial cutting block may include a customized patient-specific negative contour surface that is configured to receive a portion of a proximal tibia of a patient that has a corresponding contour. In some embodiments, the pair of trial articular surfaces formed in the proximal end of the tibial cutting block may include a medial articular surface having a convex outer profile which resembles a natural articular surface of a medial condyle of a tibia and a lateral articular surface having a convex outer profile which resembles a natural articular surface of a lateral condyle of a tibia.

In some embodiments, both the femoral cutting block and the tibial cutting block may have a number of guide pin holes defined therein. In some embodiments, the cutting guide of the femoral cutting block may be substantially parallel to the cutting guide of the tibial cutting block.

According to another aspect, a customized patient-specific orthopaedic instrument is disclosed. The customized patient-specific orthopaedic instrument may include a customized patient-specific cutting block having a body having a femoral-facing surface having a customized patient-specific negative contour configured to receive a portion of a femur of a patient that has a corresponding contour. The customized patient-specific cutting block may also have a tibial-facing surface having a customized patient-specific negative contour configured to receive a portion of a tibia of the patient that has a corresponding contour. The customized patient-specific cutting block may further have an outer surface opposite the femoral-facing surface and the tibial-facing surface and at least one cutting guide.

In some embodiments, the body of the customized patient-specific cutting block may have a tibial guide pin hole extending through the body from the outer surface to the tibial-facing surface. Additionally, in some embodiments, the at least one cutting guide may include a tibial cutting guide extending through the body from the outer surface to the tibial facing surface.

In some embodiments, the body of the customized patient-specific cutting block further may have a femoral guide pin hole extending through the body from the outer surface to the femoral-facing surface. Additionally, in some embodiments, the at least one cutting guide may include a femoral cutting guide extending through the body from the outer surface to the femoral-facing surface.

In some embodiments, the body of the customized patient-specific cutting block may include an elongated tongue positioned between the femoral-facing surface and the tibial-facing surface and extending in a general direction away from the outer surface. In some embodiments, the body of the customized patient-specific cutting block may define a monolithic body.

According to another aspect, a method of performing an orthopaedic surgical procedure on a knee of a patient may include securing a customized patient-specific cutting block to the knee of the patient such that a portion of a femur of the patient is received into a femoral-facing surface having a customized patient-specific negative contour and a portion of a tibia of the patient is received into a tibial-facing surface having a customized patient-specific negative contour. The method may also include making a cut in at least one of the tibia of the patient and the femur of the patient with the customized patient-specific cutting block. In some embodiments, the method may include making a cut in the femur of the patient with the customized patient-specific cutting block. In some embodiments, the method may include making a cut in the tibia of the patient with the customized patient-specific cutting block.

In some embodiments, the method may include inserting a guide pin through a tibial guide pin hole and into the tibia of the patient. In some embodiments, the method may include inserting a guide pin through a femoral guide pin hole and into the femur of the patient.

According to one aspect, a customized patient-specific orthopaedic instrument is disclosed. The customized patient-specific orthopaedic instrument may include a customized patient-specific cutting block having a body. In some embodiments, the customized patient-specific cutting block may be a customized patient-specific femoral cutting block. Additionally, in some embodiments, the customized patient-specific cutting block may be a customized patient-specific tibial cutting block.

The body may include a bone-facing surface having a customized patient-specific negative contour configured to receive a portion of a bone of a patient that has a corresponding contour and an outer surface opposite the bone-facing surface. The body may also include a first cutting guide corresponding to a predetermined customized patient-specific cutting plane and a second cutting guide that is parallel to the first cutting guide and spaced apart from the first cutting guide by a predetermined distance. In some embodiments, the body of the customized patient-specific cutting block may have at least one guide pin hole defined therein that extends from the outer surface to the bone-facing surface.

In some embodiments, the second cutting guide may be usable to remove a greater amount of the bone of the patient relative to the first cutting guide when the customized patient-specific cutting block is secured to the bone of the patient. In some embodiments, the customized patient-specific orthopaedic instrument may include a breakaway tab covering the second cutting guide. In some embodiments, the breakaway tab may be transparent.

In some embodiments, the body of the customized patient-specific cutting block may include a third cutting guide. The third cutting may be parallel to the first cutting guide and spaced apart from the first cutting guide by the predetermined distance, and the first cutting guide may be positioned between the second cutting guide and the third cutting guide.

In some embodiments, the third cutting guide may be usable to remove a lesser amount of the bone of the patient relative to the first cutting guide when the customized patient-specific cutting block is secured to the bone of the patient. In some embodiments, a first transparent breakaway tab may cover the second cutting guide. In some embodiments, a second transparent breakaway tab may cover the third cutting guide.

According to another aspect, the customized patient-specific orthopaedic instrument may include a customized patient-specific cutting block and a plurality of insert blocks each of which is configured to be received into the aperture of the customized patient-specific cutting block. The customized patient-specific cutting block may have a body that includes a bone-facing surface having a customized patient-specific negative contour configured to receive a portion of a bone of a patient that has a corresponding contour and an outer surface opposite the bone-facing surface. An aperture may extend through the body.

Each of the plurality of insert blocks may have a cutting guide defined therein. In some embodiments, a first insert block of the plurality of insert blocks may include a first cutting guide corresponding to a predetermined customized patient-specific cutting plane when the first insert block is positioned in the aperture of the customized patient-specific cutting block. A second insert block of the plurality of insert blocks may include a second cutting guide. When the second insert block is positioned in the aperture of the customized patient-specific cutting block, the second cutting guide may be arranged in a parallel relationship relative to the orientation in which the first cutting guide is arranged when the first insert block is positioned in the aperture of the customized patient-specific cutting block and positioned in a position that is spaced apart by a first predetermined distance from the position in which the first cutting guide is positioned when the first insert block is positioned in the aperture of the customized patient-specific cutting block. In some embodiments, the second cutting guide may be usable to remove a greater amount of the bone of the patient relative to the first cutting guide.

In some embodiments, a third insert block of the plurality of insert blocks includes a third cutting guide. When the third insert block is positioned in the aperture of the customized patient-specific cutting block, the third cutting guide is arranged in a parallel relationship relative to the orientation in which the first cutting guide is arranged when the first insert block is positioned in the aperture of the customized patient-specific cutting block and positioned in a position that is spaced apart by a second predetermined distance from the position in which the first cutting guide is positioned when the first insert block is positioned in the aperture of the customized patient-specific cutting block, the second predetermined distance being greater than the first predetermined distance.

In some embodiments, a first insert block of the plurality of insert blocks may be rectangular in shape and may include a first cutting guide which extends through the center of the first insert block in the direction of the long axis of the first insert block. A second insert block of the plurality of insert blocks may be rectangular in shape and may include a second cutting guide which extends in the direction of the long axis of the second insert block at a positioned that is spaced apart from the center of the second insert block.

In some embodiments, the body of the customized patient-specific cutting block may have at least one guide pin hole defined therein that extends from the outer surface to the bone-facing surface. In some embodiments, the customized patient-specific cutting block may be a customized patient-specific femoral cutting block. Additionally, in some embodiments, the customized patient-specific cutting block may be a customized patient-specific tibial cutting block.

Further, in some embodiments, a first block of the plurality of insert blocks may include a first cutting guide. The first block may be positionable in the aperture in a first orientation and a second orientation. The first cutting guide may be offset from a longitudinal axis of the first block such the first cutting guide defines a first cutting plane when in the first orientation and a second cutting plane within the second orientation. The first cutting guide may be usable by a surgeon when in the first orientation to remove a greater amount of the bone of the patient relative to the first cutting guide when in the second orientation.

According to another aspect, a customized patient-specific orthopaedic instrument may comprise a customized patient-specific cutting block having a body. The body may include a bone-facing surface having a customized patient-specific negative contour configured to receive a portion of a bone of a patient that has a corresponding positive contour, an outer surface opposite the bone-facing surface, an aperture extending through the body, and an adjustable cutting guide positioned in the aperture. The adjustable cutting guide may correspond to a cutting plane of the bone of the patient and may be movable within the aperture to modify the position of the cutting plane. IN some embodiments, the body may include a thumbwheel coupled to the adjustable cutting guide. In such embodiments, the thumbwheel may be operable to move the adjustable cutting guide.

According to one aspect, a customized patient-specific cutting block is disclosed. The customized patient-specific cutting block may include a cutting block body, a plurality of guide pins, and a securing device. In some embodiments, customized patient-specific cutting block may be a customized patient-specific femoral cutting block. In some embodiments, the customized patient-specific cutting block may be a customized patient-specific tibial cutting block. The cutting block body may include a bone facing surface, an outer surface opposite the bone-facing surface, a plurality of guide pin holes formed in the body of the cutting block, and a cutting guide extending through the cutting block body.

The plurality of guide pins that may be respectively positioned in one of the plurality of guide pin holes. Each of the plurality of guide pins may include a bone-contacting end that extends out of the bone-facing surface of the cutting block body and may be movable relative to the cutting block body such that the bone-contacting ends of the plurality of guide pins collectively create a customized patient-specific negative contour configured to receive a portion of a bone of a patient that has a corresponding contour. The securing device may be operable to lock each of the plurality of guide pins in a desired position so as to create the customized patient-specific negative contour. In some embodiments, each of the plurality of guide pins may also include an outer end that extends out of the outer surface of the cutting block body. In some embodiments, each of the plurality of guide pins may be independently movable relative to each other.

According to another aspect, a customized patient-specific orthopaedic instrument is disclosed. The customized patient-specific orthopaedic instrument includes a customized patient-specific cutting block and an electronic programming device. The customized patient-specific cutting block may have a body with a cutting guide extending therethrough and a plurality of guide pins, each of which includes a bone-contacting end that extends out of the body of the cutting block.

Each of the plurality of guide pins may also be movable relative to the body of the cutting block such that the bone-contacting ends of the plurality of guide pins collectively create a customized patient-specific negative contour configured to receive a portion of a bone of a patient that has a corresponding contour. In some embodiments, the customized patient-specific cutting block may include a securing device operable to lock each of the plurality of guide pins in the desired position. In some embodiments, each of the plurality of guide pins may be independently movable relative to each other.

The electronic programming device may include a housing having an aperture formed therein and one or more electrically-operated actuators operable to position each of the plurality of guide pins in a desired position so as to create the customized patient-specific negative contour. The aperture may be configured to receive the customized patient-specific cutting block therein. In some embodiments, the electronic programming device further may include a coupler configured to operate the securing device of the customized patient-specific cutting block.

In some embodiments, the electronic programming device may include a plurality of holes each of which is configured to receive one of the plurality of guide pins of the customized patient-specific cutting block. One of a plurality of push rods may be located in each of the holes. One or more electrically-operated actuators may be operable to position the plurality of push rods in a respective position so as to position each of the plurality of guide pins in the desired position.

In some embodiments, the electronic programming device may also include a processor and a memory device electrically coupled to the processor. The memory device may have stored therein a plurality of instructions which, when executed by the processor, cause the processor to operate the one or more electrically-operated actuators to position each of the plurality of guide pins in the desired position. In some embodiments, the electronic programming device may include an input port electrically coupled to the memory device.

In some embodiments, each of the plurality of guide pins may be independently movable relative to each other. In some embodiments, customized patient-specific cutting block may be a customized patient-specific femoral cutting block. In some embodiments, the customized patient-specific cutting block may be a customized patient-specific tibial cutting block.

According to one aspect, a method for a vendor to create a customized patient-specific orthopaedic instrument for a patient of a healthcare facility that is external to the vendor is disclosed. The method may include receiving an instrument request that includes data relevant to the patient from the healthcare facility external to the vendor. In some embodiments, the data of the instrument request may include one or more medical images that depict at least one bone of the patient. Receiving may include receiving the instrument request that includes the one or more medical images.

The method may also include creating a design plan that has been customized for the patient per data of the instrument request in response to receiving the instrument request. In some embodiments, the design plan may be created based upon one or more medical images that depict at least one bone of the patient. The method may include sending the design plan to the healthcare facility. Sending may include transmitting the design plan to the healthcare facility via a network. Second may also include mailing the design plan to the healthcare facility.

The method may further include operating a milling machine located at the healthcare facility to fabricate the customized patient-specific orthopaedic instrument per data of the design plan. In some embodiments, the method may include generating a plurality of instructions for the design plan that are executed by a processor of the milling machine to fabricate the customized patient-specific orthopaedic instrument. In some embodiments, the method may include generating the plurality of instructions based upon one or more medical images that depict at least one bone of the patient.

In some embodiments, operating may include operating the milling machine located at the healthcare facility to fabricate a customized patient-specific cutting block per data of the design plan. In some embodiments, operating may include operating the milling machine located at the healthcare facility to fabricate a customized patient-specific femoral cutting block per data of the design plan. Additionally, in some embodiments, operating may include operating the milling machine located at the healthcare facility to fabricate a customized patient-specific tibial cutting block per data of the design plan.

According to another aspect, a system for creating a customized patient-specific orthopaedic instrument for a patient of a healthcare facility is disclosed. The system may include a client to generate an instrument request that includes data relevant to the patient, a design plan system to receive the instrument request and to generate a design plan that has been customized based upon the data of the instrument request, the design plan system being located at a vendor, and a milling machine located at the healthcare facility which is external to the vendor, the milling machine being operable to fabricate the customized patient-specific orthopaedic instrument per data of the design plan generated by the design plan system.

In some embodiments, the design plan system may generate the design plan based upon at least one image of the instrument request. In some embodiments, the client may be communicatively coupled to the design plan system via a network. In some embodiments, the design plan system may be communicatively coupled to the milling machine via a network. In some embodiments, the client may be communicatively coupled to the design plan system via a network.

In some embodiments, the milling machine may be operable to fabricate a customized patient-specific cutting block per data of the design plan generated by the design plan system. In some embodiments, the milling machine may be operable to fabricate a customized patient-specific femoral cutting block per data of the design plan generated by the design plan system. In some embodiments, the milling machine may be operable to fabricate a customized patient-specific tibial cutting block per data of the design plan generated by the design plan system.

According to one aspect, a customized patient-specific orthopaedic instrument assembly is disclosed. The customized patient-specific orthopaedic instrument assembly may include a customized patient-specific cutting block, an ankle brace, and an external alignment rod. In some embodiments, the customized patient-specific cutting block may be a customized patient-specific femoral cutting block. In some embodiments, customized patient-specific cutting block may be a customized patient-specific tibial cutting block. The customized patient-specific cutting block may include a bone-facing surface having a customized patient-specific negative contour configured to receive a portion of an anterior side of a bone of a knee of a patient that has a corresponding contour, an outer surface opposite the bone-facing surface, at least one guide pin hole, and a cutting guide.

The ankle brace may be configured to be secured externally to an ankle of the patient. In some embodiments, the ankle brace may include a rear strap configured to wrap around the posterior side of the ankle of the patient. The external alignment rod may have a first end secured to the customized patient-specific cutting block and a second end secured to the ankle brace. In some embodiments, the alignment rod may be telescoping and may have a first rod which is received into a second rod. In some embodiments, the alignment rod may also include a securing device that is operable to lock the first rod and the second rod in a fixed position relative to one another.

According to another aspect, the customized patient-specific orthopaedic instrument assembly may include a customized patient-specific cutting block, an alignment cord having a first end secured to the customized patient-specific cutting block, and a weight secured to a second end of the alignment cord. The customized patient-specific cutting block may include a bone-facing surface having a customized patient-specific negative contour configured to receive a portion of an anterior side of a bone of a knee of a patient that has a corresponding contour. The customized patient-specific cutting block may also include an outer surface opposite the bone-facing surface, at least one guide pin hole, and a cutting guide. In some embodiments, the customized patient-specific cutting block may be a customized patient-specific femoral cutting block. In some embodiments, customized patient-specific cutting block may be a customized patient-specific tibial cutting block.

In some embodiments, the customized patient-specific cutting block may include an extension rod extending anteriorly from the outer surface thereof, and the first end of the alignment cord may be secured to the extension rod. Additionally, in some embodiments, the alignment cord may extend inferiorly from the extension rod. In some embodiments, the alignment cord may extend inferiorly from the customized patient-specific cutting block.

According to another aspect, the customized patient-specific orthopaedic instrument assembly may include a customized patient-specific cutting block and an external alignment device. The customized patient-specific cutting block may include a bone-facing surface having a customized patient-specific negative contour configured to receive a portion of an anterior side of a bone of a knee of a patient that has a corresponding contour. The customized patient-specific cutting block may also include an outer surface opposite the bone-facing surface, at least one guide pin hole, and a cutting guide. In some embodiments, the customized patient-specific cutting block may be a customized patient-specific femoral cutting block. In some embodiments, customized patient-specific cutting block may be a customized patient-specific tibial cutting block.

The external alignment device may have a first end secured to the customized patient-specific cutting block and second end that extends inferiorly from the customized patient-specific cutting block. In some embodiments, the external alignment device may include an elongated rod. In some embodiments, the external alignment device may include an ankle brace configured to be secured externally to an ankle of the patient. The external alignment device may also include a first end of the elongated rod is secured to the customized patient-specific cutting block and a second end of the elongated rod is secured to the ankle brace. In some embodiments, the elongated rod may be a telescoping rod.

In some embodiments, the external alignment device may include an alignment cord having a first end secured to the customized patient-specific cutting block and a weight secured to a second end of the alignment cord. Additionally, in some embodiments, the customized patient-specific cutting block may have an extension rod extending anteriorly from the outer surface thereof and the first end of the alignment cord may be secured to the extension rod.

According to one aspect, a method for designing a customized patient-specific bone cutting block for use in an orthopaedic surgical procedure to perform a bone cut on a patient's bone is disclosed. The method may include determining a cartilage thickness value indicative of the average thickness of the cartilage present on a relevant end of the patient's bone and determining a reference contour based on a surface contour of the relevant end of the patient's bone. The method may also include generating a scaled reference contour by scaling the reference contour based on the cartilage thickness value. The method may include defining a customized patient-specific negative contour of the customized patient-specific bone cutting block using the scaled reference contour.

In some embodiments, the method may include determining the cartilage thickness value based on the gender of the patient. In some embodiments, the method may include determining a reference contour based on a surface contour of a three-dimensional model of the patient's bone. In some embodiments, the method may include determining a reference point in the three-dimensional model of the patient's bone and increasing the distance between the reference point and a point on the reference contour.

In some embodiments, the method may include generating a first line segment extending from a first point defined on the surface contour of a medial side of the three-dimensional model to a second point defined on the surface contour of a lateral side of the three-dimensional model. The method may include generating a second line segment extending from a third point defined on the surface contour of an anterior side of the three-dimensional model to a fourth point defined on the surface contour of a posterior side of the three-dimensional model, wherein the first, second, third, and forth points are coplanar. The method may include determining a point of intersection between the first line segment and the second line segment, the point of intersection corresponding to the reference point. Determining the reference point may include moving the reference point away from the point of intersection a distance approximately equal to half the length of the second line segment.

In some embodiments, the method may include determining a length value equal to a percentage of the distance between the reference point and the point on the reference contour and increasing the distance between the reference point and the point on the reference contour by the length value. In some embodiments, the method may include determining areas of the relevant end of the patient's bone having a reduced thickness of cartilage and adjusting the scaled reference contour to compensate for the areas of reduced thickness of cartilage of the relevant end of the patient's bone. In some embodiments, determining areas of the relevant end of the patient's bone having the reduced thickness of cartilage may include identifying points of bone-on-bone contact between the patient's femur and the patient's tibia based on a medical image of the femur and tibia.

In some embodiments, adjusting the scaled reference contour may include decreasing the distance between the reference point and a point on the reference contour corresponding to the areas of reduced thickness of cartilage. In some embodiments, reference contour may include an anterior side, a medial side, and a lateral side. Generating the scaled reference contour may include increasing the distance between the reference point and the anterior side and subsequently reducing the distance between the reference point and the medial side and between the reference point and the lateral side.

In some embodiments, the method may include determining a reference contour based on a surface contour of an osteophite of the patient's bone. In some embodiments, the method may include generating a scaled reference contour having a superior end defining a negative contour corresponding to a surface contour of the patient's femur located superiorly to a cartilage demarcation line of the patient's femur. In some embodiments, the method may include generating a scaled reference contour having an inferior end defining a negative contour corresponding to a surface contour of the patient's tibia located inferiorly to a cartilage demarcation line of the patient's tibia.

In some embodiments, the method may include determining a position of a cutting guide of the customized patient-specific cutting block. In some embodiments, the position of the cutting guide may be determined based on an angle defined between a mechanical axis of the patient's femur and a mechanical axis of the patient's tibia.

According to another aspect, a method for generating a customized patient-specific negative contour of a customized patient-specific bone cutting block is disclosed. The method may include determining a cartilage thickness value indicative of the average thickness of the cartilage present on a relevant end of a patient's bone. The method may also include determining a reference contour corresponding to a surface contour of a three-dimensional model of the relevant end of the patient's bone. The method may include determining a reference point in the three-dimensional model of the patient's bone and increasing the distance between the reference point and a point on the reference contour. The method may include defining a customized patient-specific negative contour of the customized patient-specific bone cutting block using the scaled reference contour.

In some embodiments, determining the reference point may include generating a first line segment extending from a first point defined on the surface contour of a medial side of the three-dimensional model to a second point defined on the surface contour of a lateral side of the three-dimensional model. The method may also include generating a second line segment extending from a third point defined on the surface contour of an anterior side of the three-dimensional model to a fourth point defined on the surface contour of a posterior side of the three-dimensional model, wherein the first, second, third, and forth points are coplanar. The method may include determining a point of intersection between the first line segment and the second line segment, the point of intersection corresponding to the reference point.

In some embodiments, determining the reference point may include moving the reference point away from the point of intersection a distance approximately equal to half the length of the second line segment. In some embodiments, increasing the distance between the reference point and the point on the reference contour may include determining a length value equal to a percentage of the distance between the reference point and the point on the reference contour. In some embodiments, the percentage may be about ten percent. Increasing the distance between the reference point and the point on the reference contour may also include increasing the distance between the reference point and the point on the reference contour by the length value.

In some embodiments, the method may include determining areas of the relevant end of the patient's bone having a reduced thickness of cartilage and adjusting the scaled reference contour to compensate for the areas of reduced thickness of cartilage of the relevant end of the patient's bone. In some embodiments, adjusting the scaled reference contour may include decreasing the distance between the reference point and a point on the reference contour corresponding to the areas of reduced thickness of cartilage.

In some embodiments, the reference contour may include an anterior side, a medial side, and a lateral side. Scaling the reference contour may include increasing the distance between the reference point and the anterior side and subsequently reducing the distance between the reference point and the medial side and between the reference point and the lateral side. In some embodiments, the method may include determining a reference contour based on a surface contour of an osteophite of the patient's bone.

According to another aspect, a method for fabricating a customized patient-specific bone cutting block is disclosed. The method may include determining a cartilage thickness value indicative of the average thickness of the cartilage present on a relevant end of a patient's bone. The method may include determining a reference contour corresponding to a surface contour of the relevant end of a three-dimensional image of the patient's bone. The method may also include generating a scaled reference contour by scaling the reference contour based on the cartilage thickness value. The method may include establishing a customized patient-specific negative contour on a bone cutting block blank based on the scaled reference contour. In some embodiments, the method may include determining areas of the relevant end of the patient's bone having a reduced thickness of cartilage and adjusting the scaled reference contour to compensate for the areas of reduced thickness of cartilage of the relevant end of the patient's bone.

BRIEF DESCRIPTION OF THE DRAWINGS

The detailed description particularly refers to the following figures, in which.

DETAILED DESCRIPTION OF THE DRAWINGS

Figure 1:
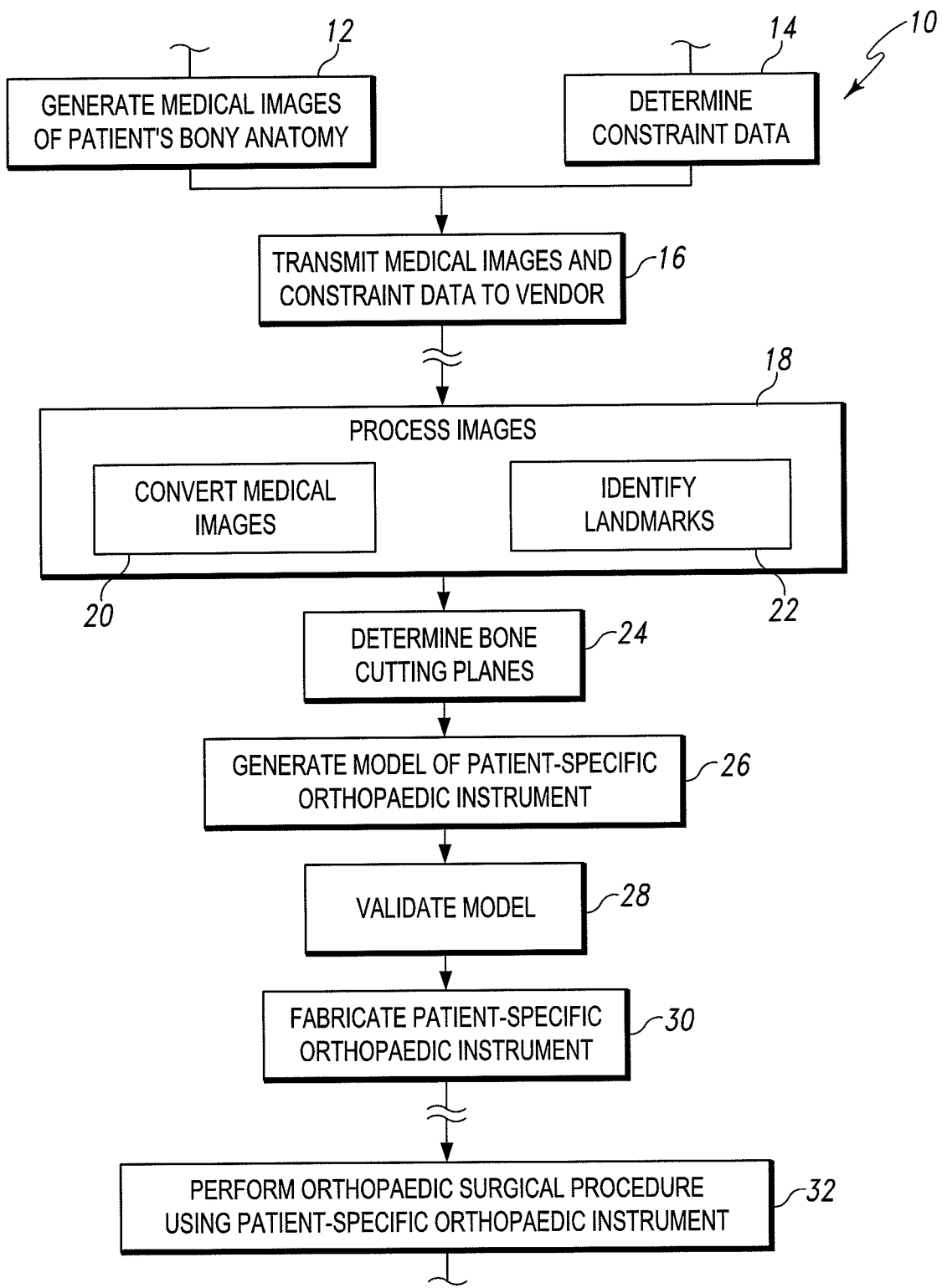
FIG. 1 is a simplified flow diagram of an algorithm for designing and fabricating a customized patient-specific orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments that are intended for use on a variety of different patients. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

In some embodiments, the customized patient-specific orthopaedic surgical instrument may be customized to the particular patient based on the location at which the instrument is to be coupled to one or more bones of the patient, such as the femur and/or tibia. For example, in some embodiments, the customized patient-specific orthopaedic surgical instrument may include a bone-contacting or facing surface having a negative contour that matches or substantially matches the contour of a portion of the relevant bone of the patient. As such, the customized patient-specific orthopaedic surgical instrument is configured to be coupled to the bone of a patient in a unique location and position with respect to the patient's bone. That is, the negative contour of the bone-contacting surface is configured to receive the matching contour surface of the portion of the patient's bone. As such, the orthopaedic surgeon's guesswork and/or intra-operative decision-making with respect to the placement of the orthopaedic surgical instrument are reduced. For example, the orthopaedic surgeon may not be required to locate landmarks of the patient's bone to facilitate the placement of the orthopaedic surgical instrument, which typically requires some amount of estimation on part of the surgeon. Rather, the orthopaedic surgeon may simply couple the customized patient-specific orthopaedic surgical instrument on the bone or bones of the patient in the unique location. When so coupled, the cutting plane, drilling holes, milling holes, and/or other guides are defined in the proper location relative to the bone and intended orthopaedic prosthesis. The customized patient-specific orthopaedic surgical instrument may be embodied as any type of orthopaedic surgical instrument such as, for example, a bone-cutting block, a drilling guide, a milling guide, or other type of orthopaedic surgical instrument configured to be coupled to a bone of a patient.

As shown in FIG. 1, the algorithm 10 includes process steps 12 and 14, in which an orthopaedic surgeon performs pre-operative planning of the orthopaedic surgical procedure to be performed on a patient. The process steps 12 and 14 may be performed in any order or contemporaneously with each other. In process step 12, a number of medical images of the relevant bony anatomy or joint of the patient are generated. To do so, the orthopaedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as any number of computed tomography (CT) images, magnetic resonance imaging (MRI) images, or other three-dimensional medical images. Additionally or alternatively, as discussed in more detail below in regard to process step 18, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's knee joint.

In process step 14, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, the constraint data may include the orthopaedic surgeon's preference for a metal-on-metal interface, amount of inclination for implantation, the thickness of the bone to resect, size range of the orthopaedic implant, and/or the like. In some embodiments, the orthopaedic surgeon's preferences are saved as a surgeon's profile, which may used as a default constraint values for further surgical plans.

In process step 16, the medical images and the constraint data, if any, are transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor processes the images in step 18. The orthopaedic surgical instrument vendor or manufacturer processes the medical images to facilitate the determination of the bone cutting planes, implant sizing, and fabrication of the customized patient-specific orthopaedic surgical instrument as discussed in more detail below. For example, in process step 20 the vendor may convert or otherwise generate three-dimensional images from the medical images. For example, in embodiments wherein the medical images are embodied as a number of two-dimensional images, the vendor may use a suitable computer algorithm to generate one or more three-dimensional images from the number of two-dimensional images. Additionally, in some embodiments, the medical images may be generated based on an established standard such as the Digital Imaging and Communications in Medicine (DICOM) standard. In such embodiments, an edge-detection, thresholding, watershead, or shape-matching algorithm may be used to convert or reconstruct images to a format acceptable in a computer aided design application or other image processing application. Further, in some embodiments, an algorithm may be used to account for tissue such as cartilage not discernable in the generated medical images. In such embodiments, any three-dimensional model of the patient-specific instrument (see, e.g., process step 26 below) may be modified according to such algorithm to increase the fit and function of the instrument.

In process step 22, the vendor may process the medical images, and/or the converted/reconstructed images from process step 20, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In process step 24, the cutting planes of the patient's bone are determined. The planned cutting planes are determined based on the type, size, and position of the orthopaedic prosthesis to be used during the orthopaedic surgical procedure, on the process images such as specific landmarks identified in the images, and on the constraint data supplied by the orthopaedic surgeon in process steps 14 and 16. The type and/or size of the orthopaedic prosthesis may be determined based on the patient's anatomy and the constraint data. For example, the constraint data may dictate the type, make, model, size, or other characteristic of the orthopaedic prosthesis. The selection of the orthopaedic prosthesis may also be modified based on the medical images such that an orthopaedic prosthesis that is usable with the bony anatomy of the patient and that matches the constraint data or preferences of the orthopaedic surgeon is selected.

In addition to the type and size of the orthopaedic prosthesis, the planned location and position of the orthopaedic prosthesis relative to the patient's bony anatomy is determined. To do so, a digital template of the selected orthopaedic prosthesis may be overlaid onto one or more of the processed medical images. The vendor may use any suitable algorithm to determine a recommended location and orientation of the orthopaedic prosthesis (i.e., the digital template) with respect to the patient's bone based on the processed medical images (e.g., landmarks of the patient's bone defined in the images) and/or the constraint data. Additionally, any one or more other aspects of the patient's bony anatomy may be used to determine the proper positioning of the digital template.

In some embodiments, the digital template along with surgical alignment parameters may be presented to the orthopaedic surgeon for approval. The approval document may include the implant's rotation with respect to bony landmarks such as the femoral epicondyle, posterior condyles, sulcus groove (Whiteside's line), and the mechanical axis as defined by the hip, knee, and/or ankle centers.

The planned cutting planes for the patient's bone(s) may then be determined based on the determined size, location, and orientation of the orthopaedic prosthesis. In addition, other aspects of the patient's bony anatomy, as determined in process step 22, may be used to determine or adjust the planned cutting planes. For example, the determined mechanical axis, landmarks, and/or other determined aspects of the relevant bones of the patient may be used to determine the planned cutting planes.

In process step 26, a model of the customized patient-specific orthopaedic surgical instrument is generated. In some embodiments, the model is embodied as a three-dimensional rendering of the customized patient-specific orthopaedic surgical instrument. In other embodiments, the model may be embodied as a mock-up or fast prototype of the customized patient-specific orthopaedic surgical instrument. The particular type of orthopaedic surgical instrument to be modeled and fabricated may be determined based on the orthopaedic surgical procedure to be performed, the constraint data, and/or the type of orthopaedic prosthesis to be implanted in the patient. As such, the customized patient-specific orthopaedic surgical instrument may be embodied as any type of orthopaedic surgical instrument for use in the performance of an orthopaedic surgical procedure. For example, the orthopaedic surgical instrument may be embodied as a bone-cutting block, a drilling guide, a milling guide, and/or any other type of orthopaedic surgical tool or instrument.

The particular shape of the customized patient-specific orthopaedic surgical instrument is determined based on the planned location of the orthopaedic surgical instrument relative to the patient's bony anatomy. The location of the customized patient-specific orthopaedic surgical instrument with respect to the patient's bony anatomy is determined based on the type and determined location of the orthopaedic prosthesis to be used during the orthopaedic surgical procedure. That is, the planned location of the customized patient-specific orthopaedic surgical instrument relative to the patient's bony anatomy may be selected based on, in part, the planned cutting planes of the patient's bone(s) as determined in step 24. For example, in embodiments wherein the customized patient-specific orthopaedic surgical instrument is embodied as a bone-cutting block, the location of the orthopaedic surgical instrument is selected such that the cutting guide of the bone-cutting block matches one or more of the planned cutting planes determined in process step 24. Additionally, the planned location of the orthopaedic surgical instrument may be based on the identified landmarks of the patient's bone identified in process step 22.

In some embodiments, the particular shape or configuration of the customized patient-specific orthopaedic surgical instrument may be determined based on the planned location of the instrument relative to the patient's bony anatomy. That is, the customized patient-specific orthopaedic surgical instrument may include a bone-contacting surface having a negative contour that matches the contour of a portion of the bony anatomy of the patient such that the orthopaedic surgical instrument may be coupled to the bony anatomy of the patient in a unique location, which corresponds to the pre-planned location for the instrument. When the orthopaedic surgical instrument is coupled to the patient's bony anatomy in the unique location, one or more guides (e.g., cutting or drilling guide) of the orthopaedic surgical instrument may be aligned to one or more of the bone cutting plane(s) as discussed above.

One illustrative embodiment of a method 40 for generating a model, such as a computer model, of a patient-specific orthopaedic instrument is illustrated in FIGS. 2 through 9. The method 40 begins with a step 42 in which a cartilage thickness value is determined. The cartilage thickness value is indicative of the average thickness of the cartilage of the patient's bone. As such, in one embodiment, the cartilage thickness value is equal to the average thickness of cartilage for an individual having similar characteristics as the patient. For example, the cartilage thickness value may be equal to the average thickness value of individuals of the same gender as the patient, the same age as the patient, having the same activity level of the patient, and/or the like. In other embodiments, the cartilage thickness value is determined based on one or more medical images of the patient's bone, such as those images transmitted in process step 16.

In step 44, a reference contour of the patient's relevant bone is determined. The reference contour is based on the surface contour of a three-dimensional model of the patient's relevant bone, such as the three-dimensional model generated in step 20. Initially the reference contour is identical to a region (i.e. the region of interest such as the distal end of the patient's femur or the proximal end of the patient's tibia) of the patient's bone. That is, in some embodiments, the reference contour is juxtaposed on the surface contour of the region of the patient's bone.

Subsequently, in step 46, the reference contour is scaled to compensate for the cartilage thickness value determined in step 42. To do so, in one embodiment, the scale of the reference contour is increased based on the cartilage thickness value. For example, the scale of the reference contour may be increased by an amount equal to or determined from the cartilage thickness value. However, in other embodiments, the reference contour may be scaled using other techniques designed to scale the reference contour to a size at which the reference contour is compensated for the thickness of the cartilage on the patient's bone.

Figure 3:
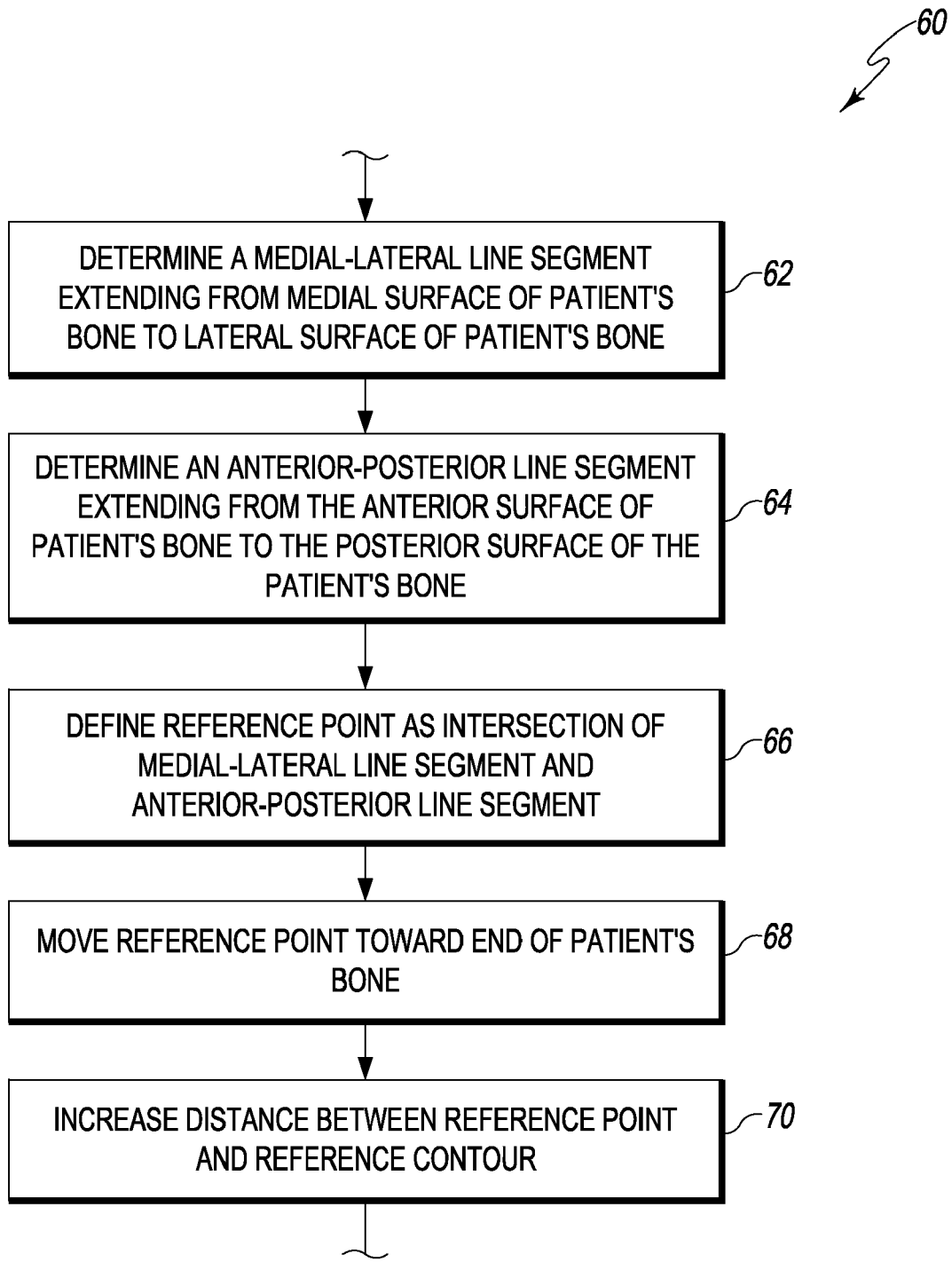
FIG. 3 is a simplified flow diagram of a method for scaling a reference contour.

For example, in one particular embodiment, the reference contour is scaled by increasing the distance between a fixed reference point and a point lying on, and defining in part, the reference contour. To do so, in one embodiment, a method 60 for scaling a reference contour as illustrated in FIG. 3 may be used. The method 60 begins with step 62 in which a medial/lateral line segment is established on the three-dimensional model of the patient's relevant bone. The medial/lateral line segment is defined or otherwise selected so as to extend from a point lying on the medial surface of the patient's bone to a point lying on lateral surface of the patient's bone. The medial surface point and the lateral surface point may be selected so as to define the substantially maximum local medial/lateral width of the patient's bone in some embodiments.

In step 64, an anterior/posterior line segment is established on the three-dimensional model of the patient's relevant bone. The anterior/posterior line segment is defined or otherwise selected so as to extend from a point lying on the anterior surface of the patient's bone to a point lying on posterior surface of the patient's bone. The anterior surface point and the posterior surface point may be selected so as to define the substantially maximum local anterior/posterior width of the patient's bone in some embodiments.

The reference point from which the reference contour will be scaled is defined in step 66 as the intersection point of the medial/lateral line segment and anterior/posterior line segment. As such, it should be appreciated that the medial surface point, the lateral surface point, the anterior surface point, and the posterior surface point lie on the same plane. After the reference point is initially established in step 66, the reference point is moved or otherwise translated toward an end of the patient's bone in step 68. For example, in embodiments wherein the patient's bone is embodied as a femur, the reference point is moved inferiorly toward the distal end of the patient's femur. Conversely, in embodiments when the patient's bone is embodied as a tibia, the reference point is moved superiorly toward the proximal end of the patient's tibia. In one embodiment, the reference point is moved a distance equal to about half the length of the anterior/posterior line segment as determined in step 64. However, in other embodiments, the reference point may be moved other distances sufficient to compensate the reference contour for thickness of the cartilage present on the patient's bone.

Once the location of the reference point has been determined in step 68, the distance between the reference point and each point lying on, and defining in part, the reference contour is increased in step 70. To do so, in one particular embodiment, each point of the reference contour is moved a distance away from the reference point based on a percentage value of the original distance defined between the reference point and the particular point on the reference contour. For example, in one embodiment, each point lying on, and defining in part, the reference contour is moved away from the reference point by a distance equal to a percentage value of the original distance between the reference point and the particular point. In one embodiment, the percentage value is in the range of about 5 percent to about thirty percent. In one particular embodiment, the percentage value is about ten percent.

Figure 4:
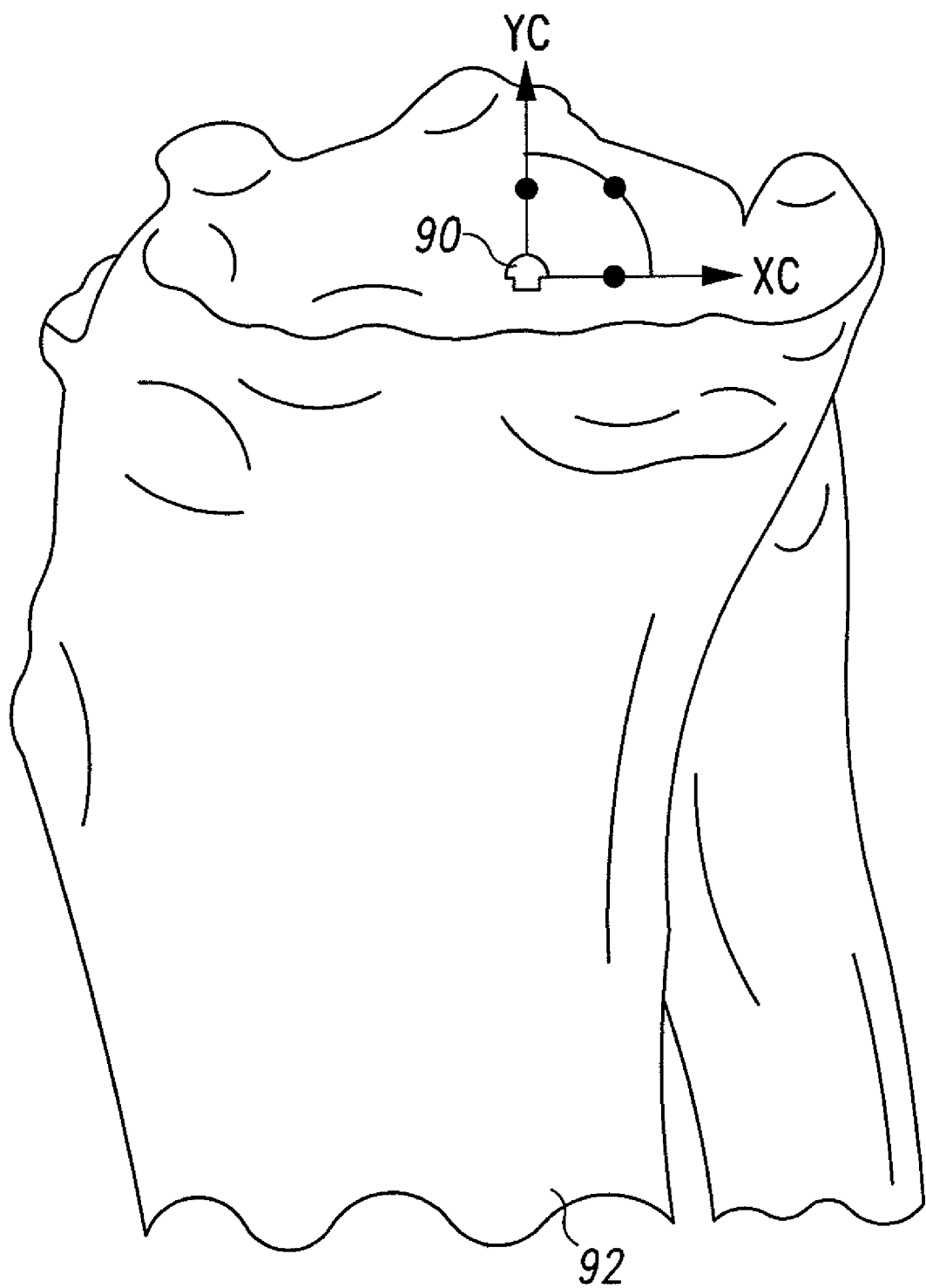
FIGS. 4-6 are three-dimensional model's of a patient's tibia.
Figure 5:
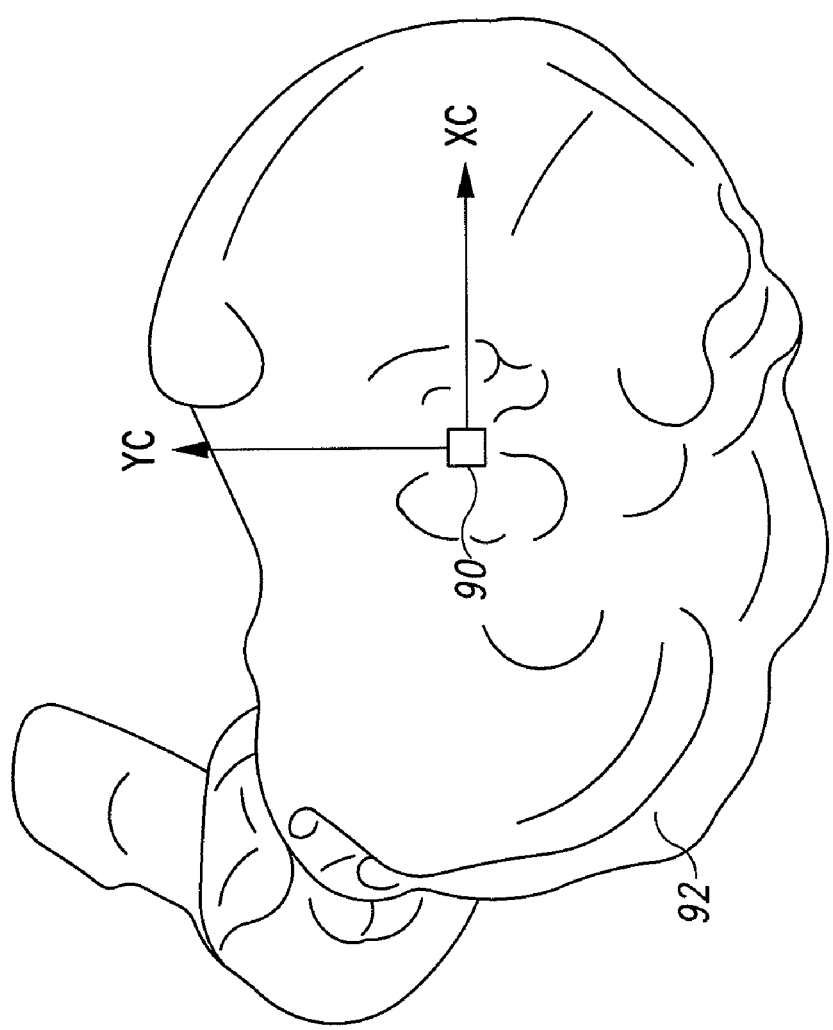
Figure 6:
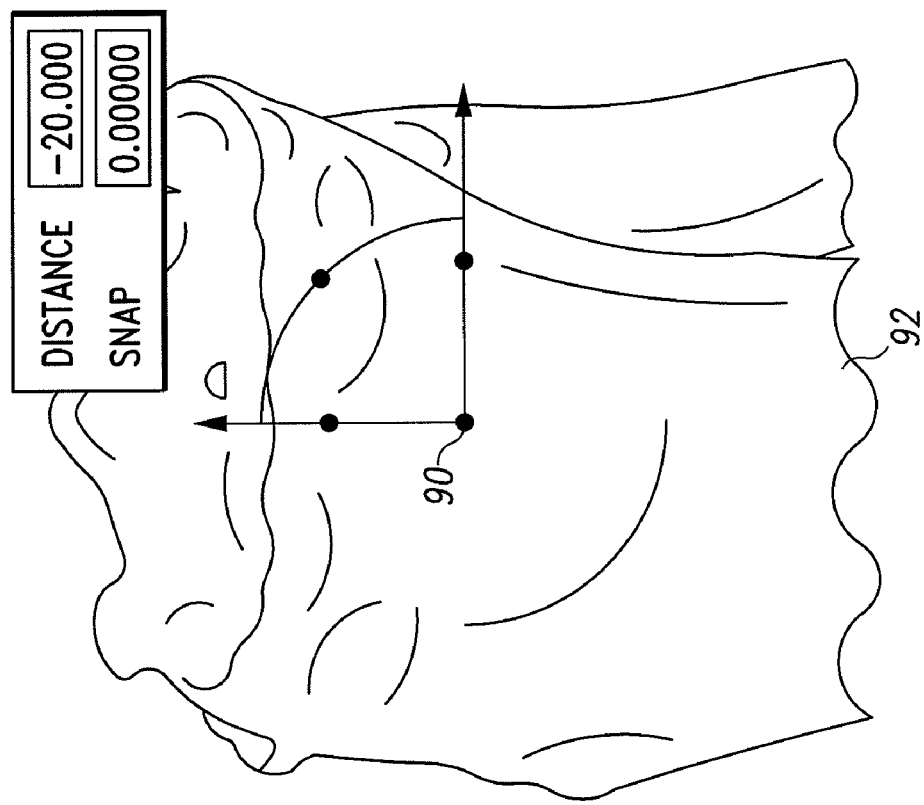

Referring now to FIGS. 4-9, in another embodiment, the reference contour is scaled by manually selecting a local "high" point on the surface contour of the three-dimensional image of the patient's bone. For example, in embodiments wherein the relevant patient's bone is embodied as a tibia as illustrated in FIGS. 4-6, the reference point 90 is initially located on the tibial plateau high point of the tibial model 92. Either side of the tibial plateau may be used. Once the reference point 90 is initially established on the tibial plateau high point, the reference point 90 is translated to the approximate center of the plateau as illustrated in FIG. 5 such that the Z-axis defining the reference point is parallel to the mechanical axis of the tibial model 92. Subsequently, as illustrated in FIG. 6, the reference point is moved in the distal direction by a predetermined amount. In one particular embodiment, the reference point is moved is the distal direction by about 20 millimeters, but other distances may be used in other embodiments. For example, the distance over which the reference point is moved may be based on the cartilage thickness value in some embodiments.

Figure 7:
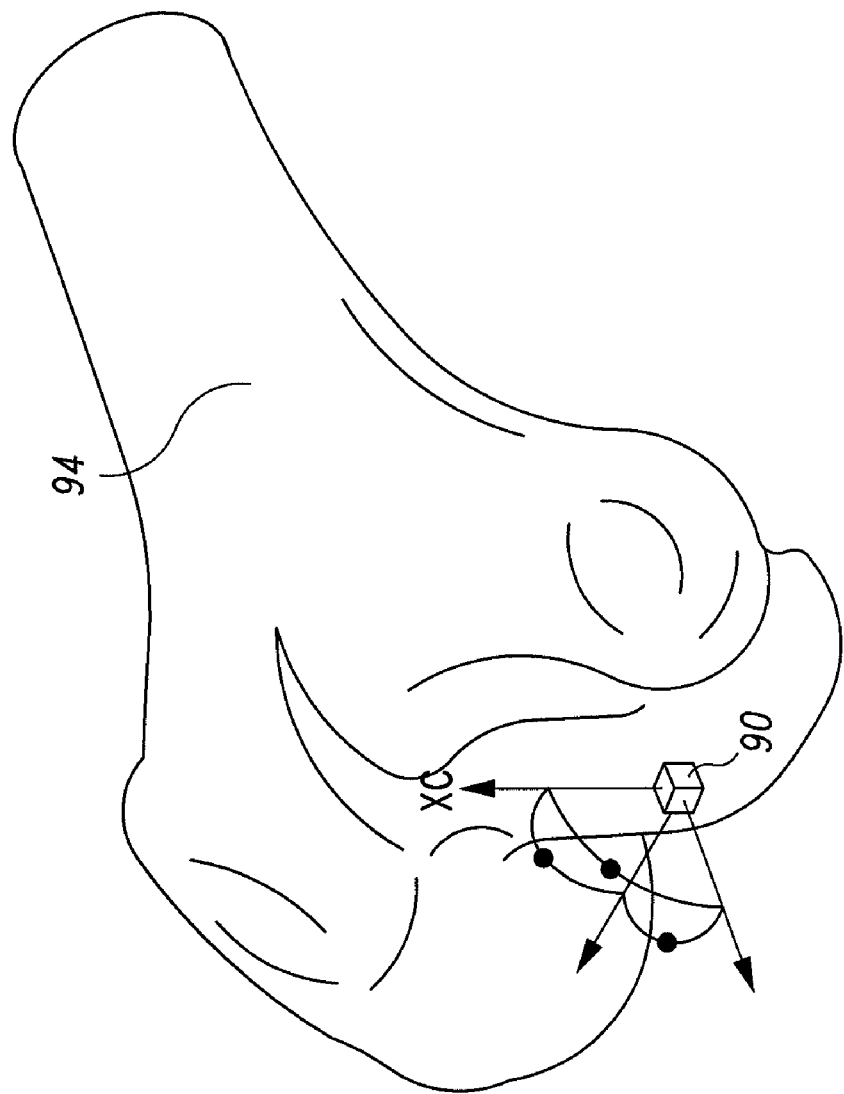
FIGS. 7-9 are three-dimensional models of a patient's femur.
Figure 8:
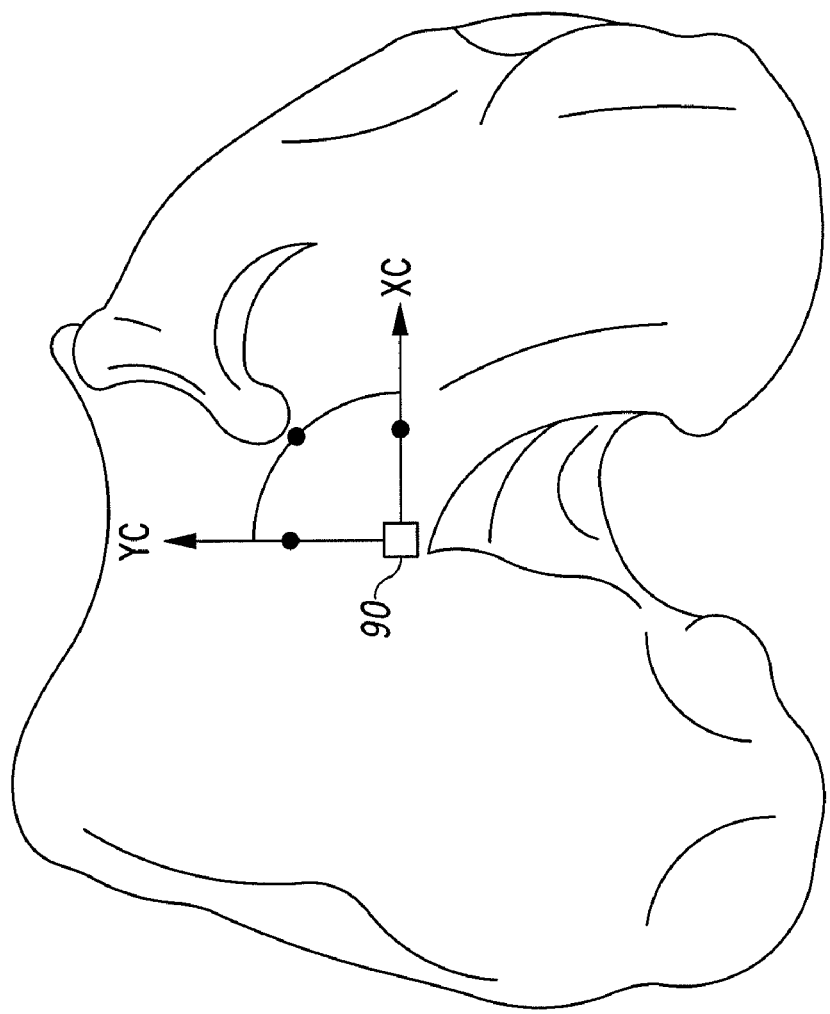
Figure 9:
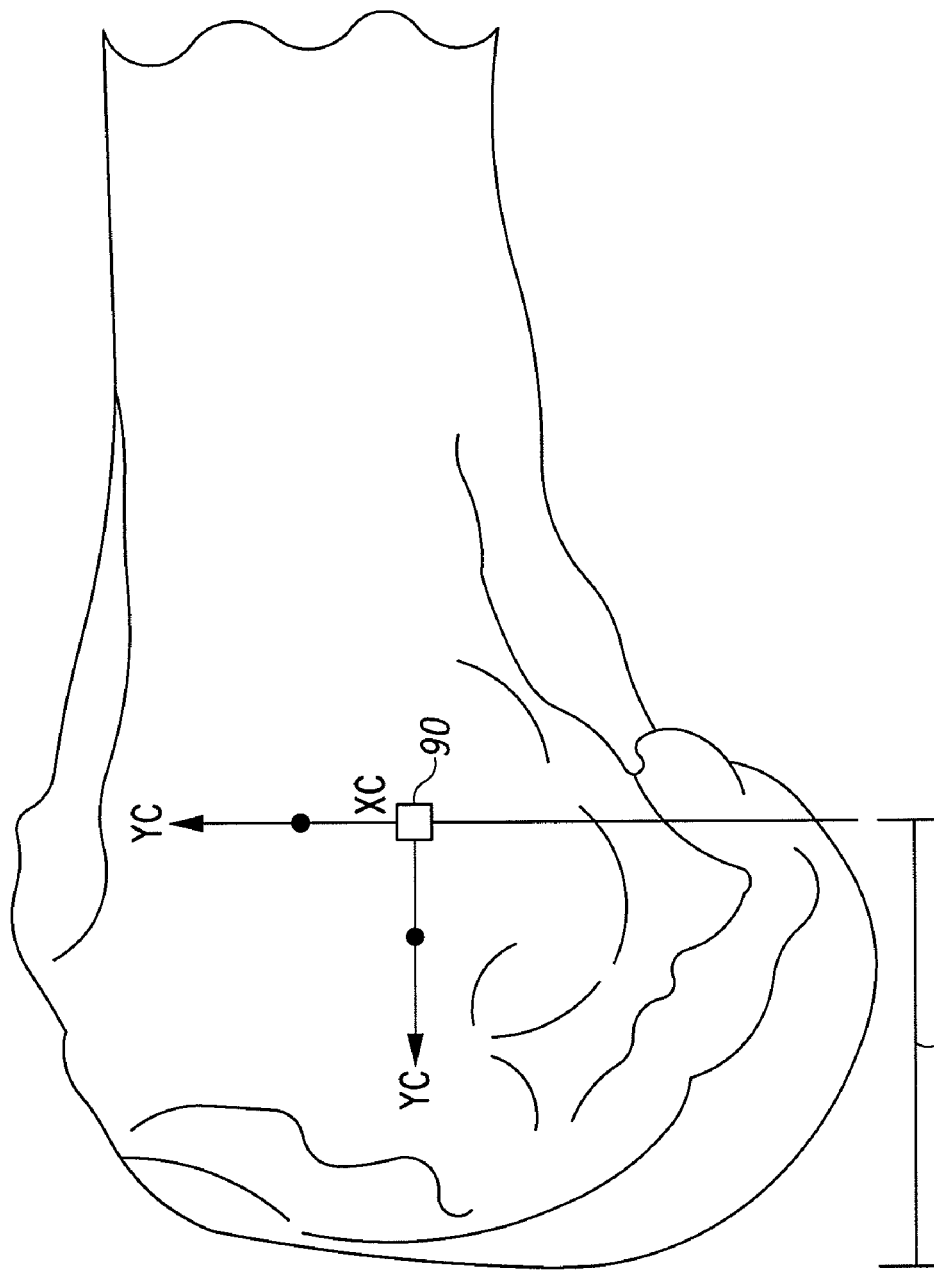

Conversely, in embodiments wherein the relevant patient's bone is embodied as a femur as illustrated in FIGS. 7-9, the reference point 90 is initially located on the most distal point of the distal end of the femoral model 94. Either condyle of the femoral model 94 may be used in various embodiments. Once the reference point 90 is initially established on the most distal point, the reference point 90 is translated to the approximate center of the distal end of the femoral model 94 as illustrated in FIG. 8 such that the Z-axis defining the reference point 90 is parallel to the mechanical axis of the femoral model 92. The anterior-posterior width 96 of the distal end of the femoral model 94 is also determined. Subsequently, as illustrated in FIG. 9, the reference point is moved or otherwise translated in the proximal or superior direction by a distance 98. In one particular embodiment, the reference point is moved in the distal or superior direction by a distance 98 equal to about half the distance 96. As such, it should be appreciated that one of a number of different techniques may be used to define the location of the reference point based on, for example, the type of bone.

Figure 2:
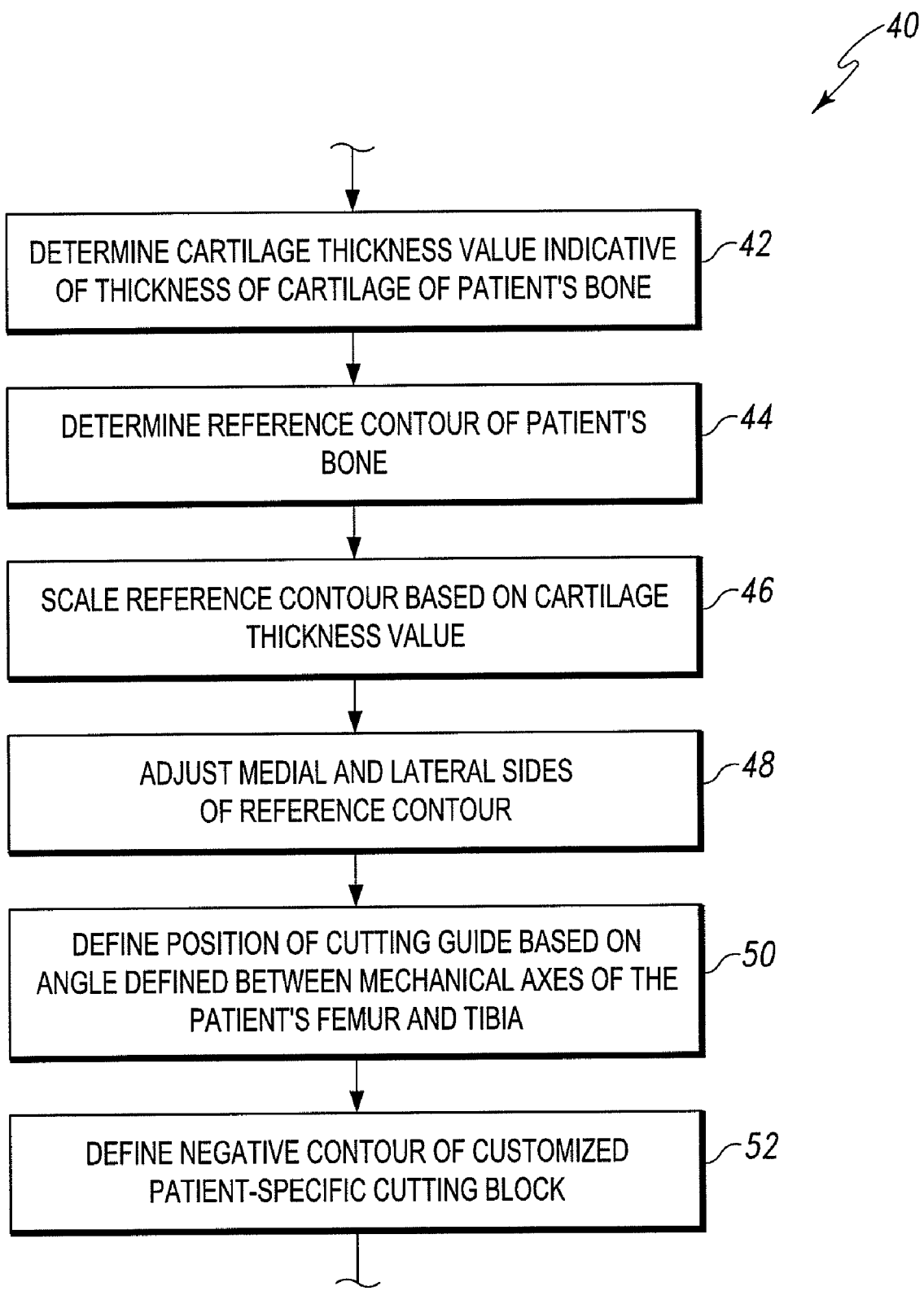
FIG. 2 is a simplified flow diagram of a method for generating a model of a patient-specific orthopaedic instrument.

Referring now back to FIG. 2, once the reference contour has been scaled in step 46, the medial/lateral sides of the reference contour are adjusted in step 48. To do so, in one embodiment, the distance between the reference point and each point lying on, and defining in part, the medial side and lateral side of the reference contour is decreased. For example, in some embodiments, the distance between the reference point and the points on the medial and lateral sides of the scaled reference contour are decreased to the original distance between such points. As such, it should be appreciated that the reference contour is offset or otherwise enlarged with respect to the anterior side of the patient's bone and substantially matches or is otherwise not scaled with respect to the medial and lateral sides of the patient's bone.

The reference contour may also be adjusted in step 48 for areas of the patient's bone having a reduced thickness of cartilage. Such areas of reduced cartilage thickness may be determined based on the existence of bone-on-bone contact as identified in a medical image, simulation, or the like. Additionally, information indicative of such areas may be provided by the orthopaedic surgeon based on his/her expertise. If one or more areas of reduced cartilage thickness are identified, the reference contour corresponding to such areas of the patient's bone is reduced (i.e., scaled back or down).

Additionally, in some embodiments, one or more osteophytes on the patient's bone may be identified; and the reference contour may be compensated for such presence of the osteophytes. By compensating for such osteophytes, the reference contour more closely matches the surface contour of the patient's bone. Further, in some embodiments, a distal end (in embodiments wherein the patient's bone is embodied as a tibia) or a proximal end (in embodiments wherein the patient's bone is embodied as a femur) of the reference contour may be adjusted to increase the conformity of the reference contour to the surface contour of the bone. For example, in embodiments wherein the patient's bone is a femur, the superior end of the scaled reference contour may be reduced or otherwise moved closer to the surface contour of the patient's femur in the region located superiorly to a cartilage demarcation line defined on the patient's femur. Conversely, in embodiments wherein the patient's bone is embodied as a tibia, an inferior end of the scaled reference contour may be reduced or otherwise moved closer to the surface contour of the patient's tibia in the region located inferiorly to a cartilage demarcation line of the patient's tibia. As such, it should be appreciated that the scaled reference contour is initially enlarged to compensate for the thickness of the patient's cartilage on the patient's bone. Portions of the scaled reference contour are then reduced or otherwise moved back to original positions and/or toward the reference point in those areas where cartilage is lacking, reduced, or otherwise not present.

Once the reference contour has been scaled and adjusted in steps 46 and 48, the position of the cutting guide is defined in step 50. In particular, the position of the cutting guide is defined based on an angle defined between a mechanical axis of the patient's femur and a mechanical axis of the patient's tibia. The angle may be determined by establishing a line segment or ray originating from the proximal end of the patient's femur to the distal end of the patient's femur and defining a second line segment or ray extending from the patient's ankle through the proximal end of the patient's tibia. The angle defined by these two line segments/rays is equal to the angle defined between the mechanical axis of the patient's femur and tibia. The position of the bone cutting guide is then determined based on the angle between the mechanical axes of the patient's femur and tibia. It should be appreciated that the position of the cutting guide defines the position and orientation of the cutting plane of the customized patient-specific cutting block. Subsequently, in step 52, a negative contour of the customized patient-specific cutting block is defined based on the scaled and adjusted reference contour and the angle defined between the mechanical axis of the femur and tibia.

Referring back to FIG. 1, after the model of the customized patient-specific orthopaedic surgical instrument has been generated in process step 26, the model is validated in process step 28. The model may be validated by, for example, analyzing the rendered model while coupled to the three-dimensional model of the patient's anatomy to verify the correlation of cutting guides and planes, drilling guides and planned drill points, and/or the like. Additionally, the model may be validated by transmitting or otherwise providing the model generated in step 26 to the orthopaedic surgeon for review. For example, in embodiments wherein the model is a three-dimensional rendered model, the model along with the three-dimensional images of the patient's relevant bone(s) may be transmitted to the surgeon for review. In embodiments wherein the model is a physical prototype, the model may be shipped to the orthopaedic surgeon for validation.

After the model has been validated in process step 28, the customized patient-specific orthopaedic surgical instrument is fabricated in process step 30. The customized patient-specific orthopaedic surgical instrument may be fabricated using any suitable fabrication device and method. Additionally, the customized patient-specific orthopaedic instrument may be formed from any suitable material such as a metallic material, a plastic material, or combination thereof depending on, for example, the intended use of the instrument. The fabricated customized patient-specific orthopaedic instrument is subsequently shipped or otherwise provided to the orthopaedic surgeon. The surgeon performs the orthopaedic surgical procedure in process step 32 using the customized patient-specific orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

Figure 10:
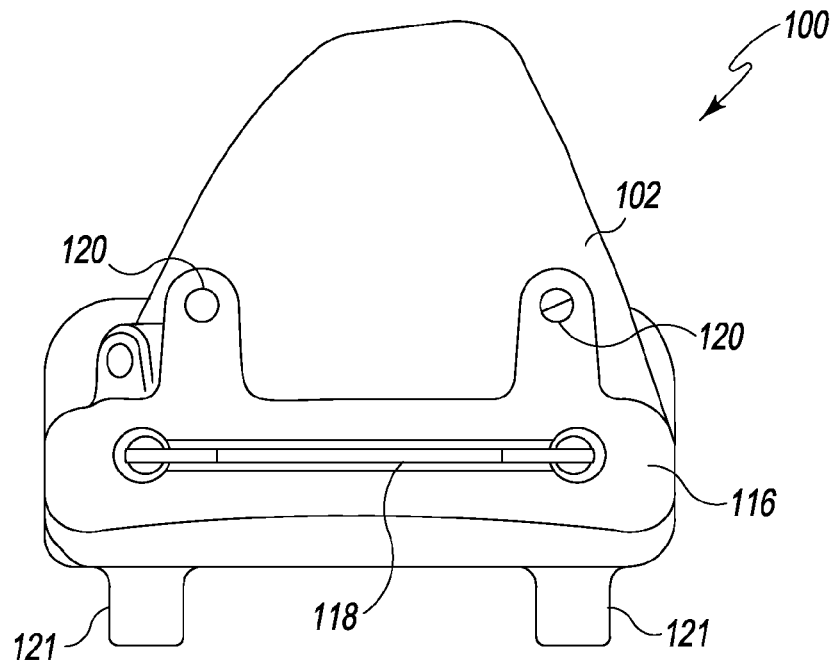
FIG. 10 is an elevation view of one embodiment of a customized patient-specific orthopaedic surgical instrument.
Figure 11:
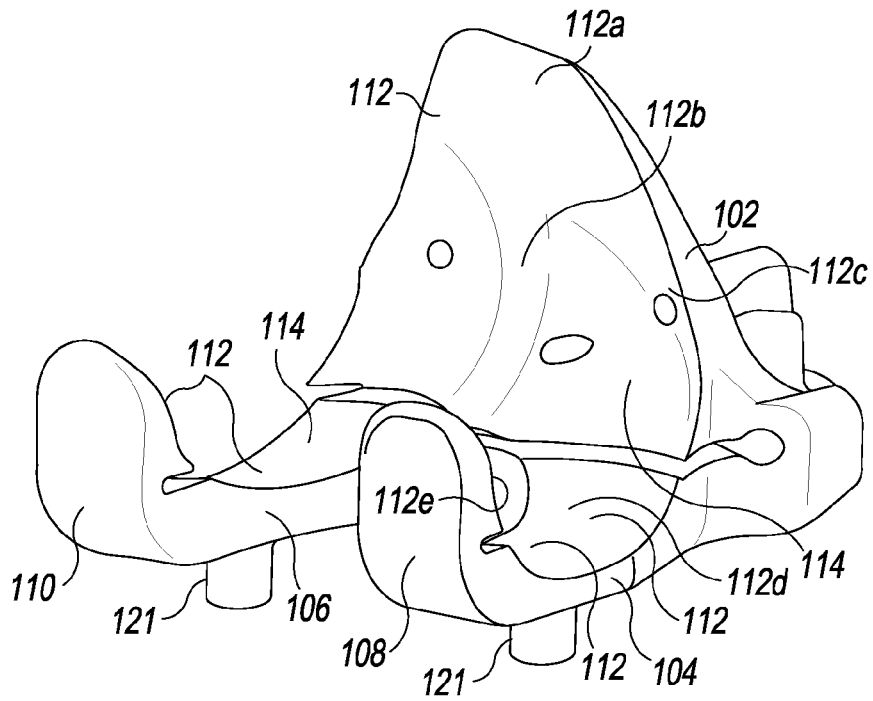
FIG. 11 is a perspective view of the customized patient-specific orthopaedic surgical instrument of FIG. 10.
Figure 12:
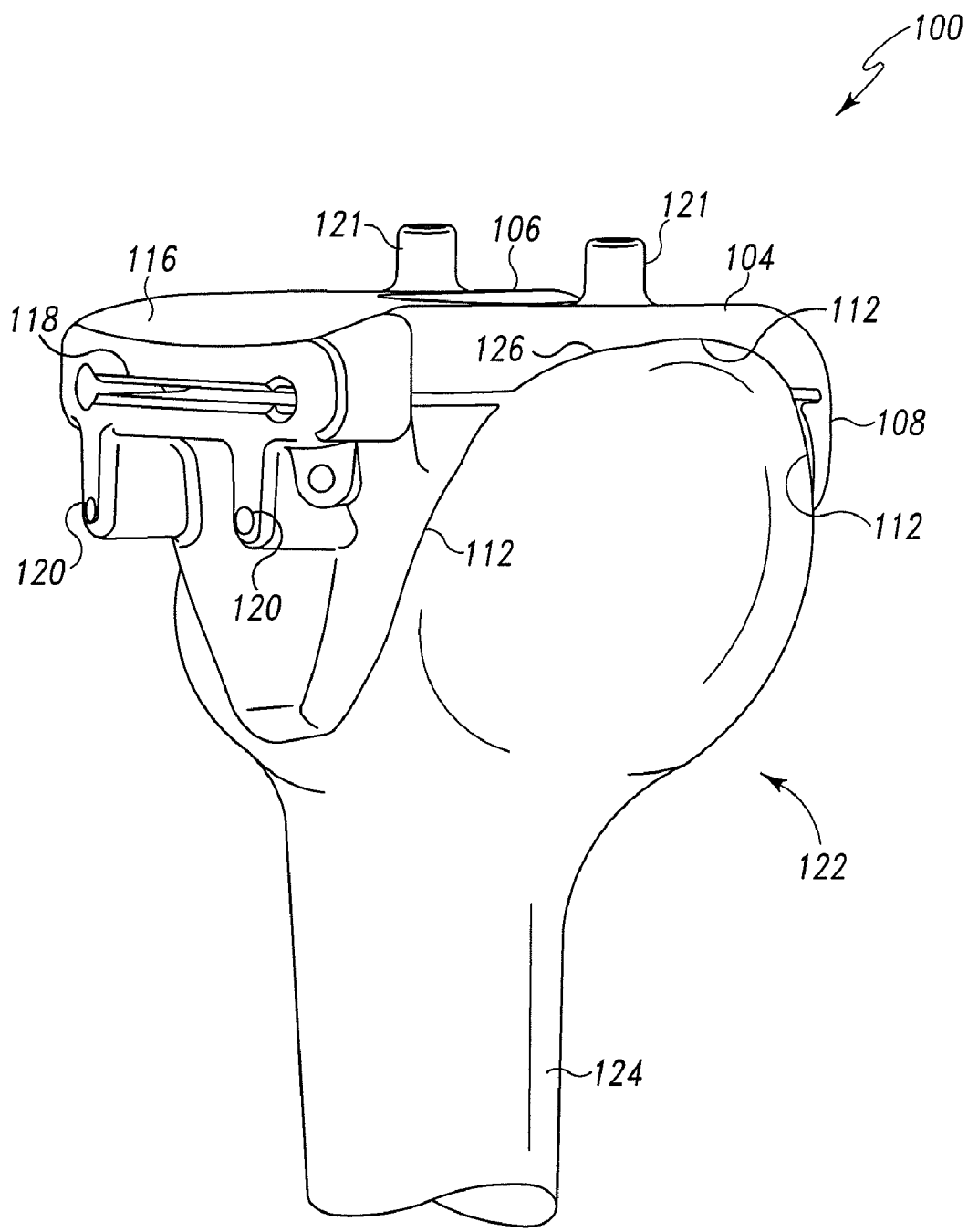
FIG. 12 is a perspective view of the customized patient-specific orthopaedic surgical instrument of FIG. 10 secured to a bone of a patient.

Referring now to FIGS. 10-12, in one embodiment, the customized patient-specific orthopaedic surgical instrument may be embodied as a femoral cutting block 100. The cutting block 100 is configured to be coupled to a femur 124 of a patient as illustrated in FIG. 12. The cutting block 100 includes a body 102 configured to be coupled to the anterior side of the femur 124. Two tabs 104, 106 extend orthogonally from the body 102 and are configured to wrap around the end of the femur 124 as discussed in more detail below. Each of the tabs 104, 106 includes an inwardly curving lip 108, 110, respectively, that reference the posterior condyles of the femur. The femoral cutting block 100 includes a bone-contacting or bone-facing surface 112 defined on the inside of the body 102, the tabs 104, 106, and the lips 108, 110. The bone-contacting surface 112 includes a negative contour 114 configured to receive a portion of the patient's bone having a corresponding contour. As discussed above, the negative contour 114 of the bone-contacting surface 112 allows the positioning of the cutting block 100 on the patient's bone in a unique pre-determined location and orientation.

In some embodiments, the bone-contacting surface 112 of the cutting block 100 (as well as each bone-contacting surface discussed in regard to other embodiments) may or may not be an exact negative of the three-dimensional bone model generated from the medical image (see step 26 of algorithm 10 illustrated and described above in regard to FIG. 1). Instead, the bone-contacting surface may be a fixed offset of the bone model to compensate for the patient's cartilage that may or may not appear in the medical image. This offset typically varies from about 0.5 millimeters to about 5 millimeters depending on location, patient gender, and disease state of the patient's joint. The cartilages is usually thickest in regions 112*b*, 112*d*, and 112*e*. It is often thin, or non-existent in regions 112*a* and 112*c*. Thus the femoral cutting block 100 incorporates varying offsets on its bone contacting surface 112.

The cutting block 100 includes a cutting guide platform 116 raised above the body 102. The cutting guide platform 116 includes a cutting guide 118 defined therein. The platform 116 also includes a pair of anterior pin guides 120. A pair of distal pin guides 121 is defined on the tabs 104, 106. In some embodiments, the pin guides 120, 121 may be used as drill guides to establish guide pinholes in the femur 124 of the patient. However, in other embodiments, guide pins may not be used. That is, the cutting block 100 may be coupled to the femur 124 of the patient via pressure applied by the body 102 and the tabs 104, 106 as discussed below.

In use, the femoral cutting block 100 is coupled to the end 122 of a patient's femur 124 as illustrated in FIG. 12. Again, because the bone-contacting surface 112 of the cutting block 100 includes negative contour 114, the block 100 may be coupled to the femur 124 in a pre-planned, unique position. When so coupled, the tabs 104, 106 wrap around the distal end 126 of the femur 124 and the lips 108, 110 of the tabs 104, 106 wrap around the posterior side of the femur 124. Additionally, when the block 100 is coupled to the patient's femur 124, a portion of the anterior side of the femur 124 is received in the negative contour 112 of the body 102, a portion of the distal end 126 is received in the negative contour 112 of the tabs 104, 106, and a portion of the posterior side of the femur 124 is received in the negative contour (if any) of the lips 108, 110. As such, the anterior, distal, and posterior surfaces of the femur 124 are referenced by the femur cutting block 100. The body 102, the tabs 104, 106, and the lips 108, 110 of the femoral cutting block 100 cooperate to secure the instrument 100 to the femur 124. That is, the body 102, the tabs 104, 106, and the lips 108, 110 apply an amount of pressure to the femur 124 to hold the block 100 in place. However, in other embodiments, a number of guide pins (not shown) may be inserted into the pin guides 120, 121 and into the femur 124 to secure the femoral cutting block 100 to the femur 124. Furthermore, pin guides 120, 121 may be used to create holes in the femur 124 that are useful references in future procedural steps, such as orienting a re-cut block (not shown) or a chamfer block (not shown).

After the block 100 has been secured to the patient's femur 124, the orthopaedic surgeon may use the femoral cutting block to resect a pre-planned amount of the femur 124. That is, the bone cut made using the cutting guide 118 corresponds to the cutting plane determined during the fabrication of the cutting block 100 (see process step 24 of algorithm 10 described above in regard to FIG. 1). It should be appreciated that because the cutting guide platform 116 is raised above the body 102, the depth of the cutting guide 118 is increased, which provides stability to the blade of the orthopaedic bone saw or other cutting device during use.

Figure 13:
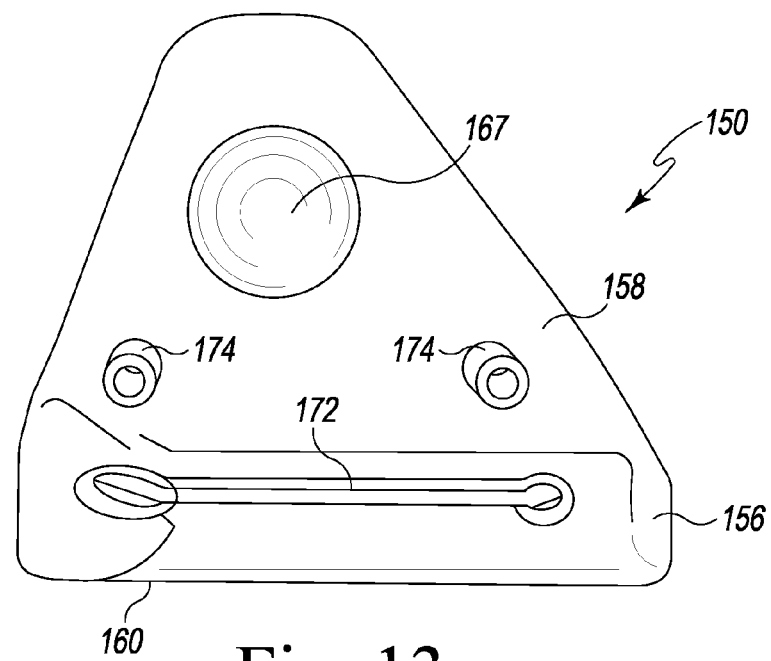
FIG. 13 is an elevation view of another embodiment of a customized patient-specific orthopaedic surgical instrument.
Figure 14:
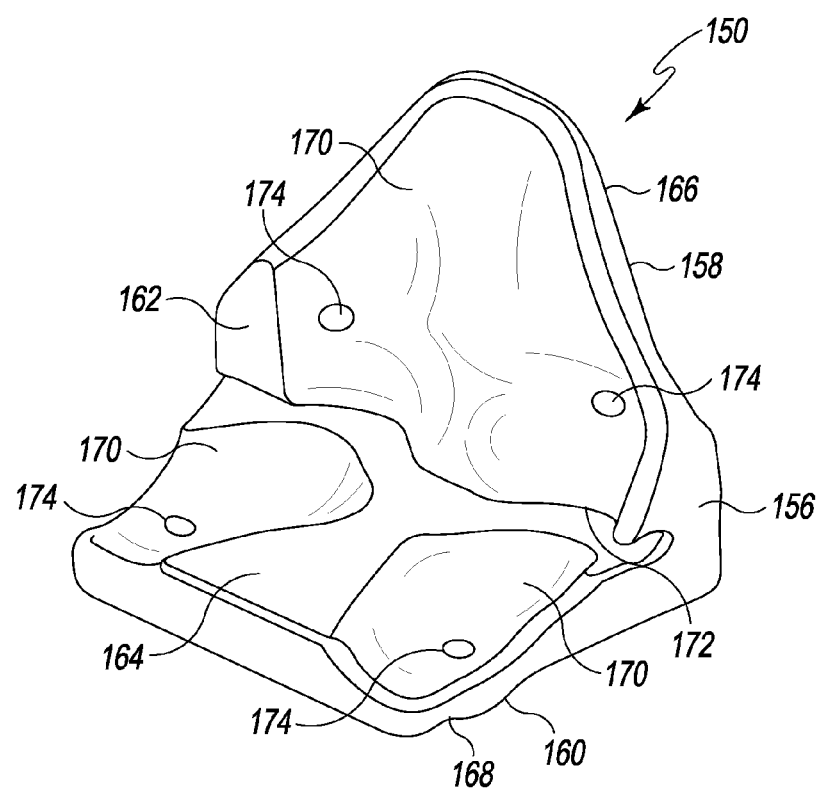
FIG. 14 is a perspective view of the customized patient-specific orthopaedic surgical instrument of FIG. 13.
Figure 15:
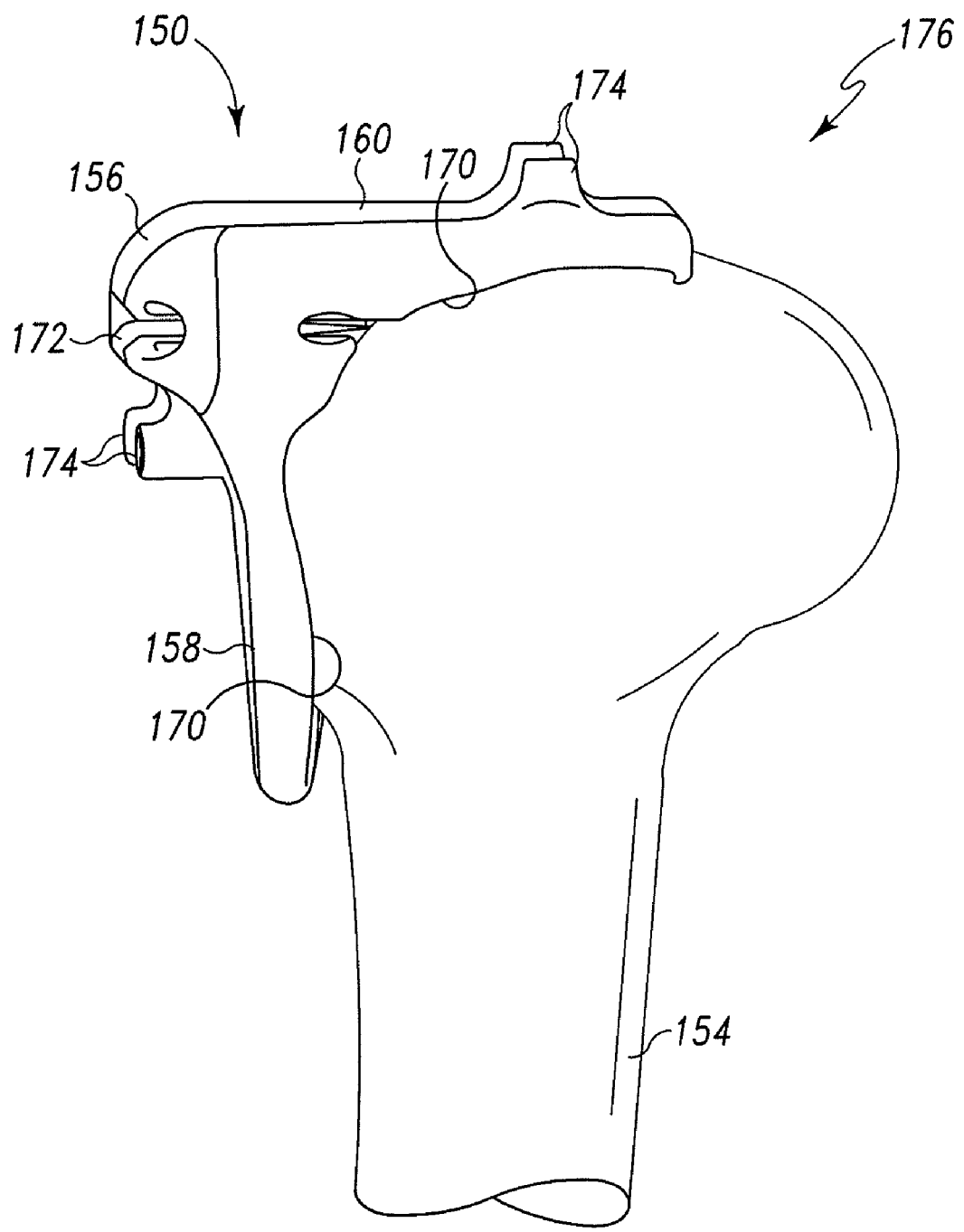
FIG. 15 is a perspective view of the customized patient-specific orthopaedic surgical instrument of FIG. 13 secured to a bone of a patient.

Referring now to FIGS. 13-15, in another embodiment, the customized patient-specific orthopaedic surgical instrument may be embodied as a femoral cutting block 150. The cutting block 150 is configured to be coupled to a femur 154 of a patient as illustrated in FIG. 15. The cutting block 150 includes a body 156 having an anterior wall 158 and a distal wall 160. During use, the anterior wall 158 is configured to contact an anterior side of the femur 154 and the distal wall 160 is configured to contact a distal end of the femur 154 as discussed in more detail below. Each of the walls 158, 160 of the cutting block 150 includes a bone-contacting or bone-facing surface 162, 164, and an outer surface 166, 168, respectively. A negative contour 170 is defined in the bone-contacting surfaces 162, 164. The negative contour 170 is configured to receive a portion of the patient's femur 154 having a corresponding contour. As discussed above, the negative contour 170 of the bone-contacting surface surfaces 162, 164 allows the positioning of the cutting block 150 on the patient's femur 154 in a unique pre-determined location and orientation.

The cutting block 150 includes a cutting guide 172 defined in the anterior wall 158. Illustratively, the cutting guide 172 is a captured cutting guide. The femoral cutting block 150 also includes an indent or recess 167 that indicates to the surgeon a recommended location on the block 150 to hold while positioning the block. The femoral cutting block 150 also includes a number of pin guides 174. The pin guides 174 are used as drill guides to establish guide pin holes in the femur 154 of the patient. A number of guide pins (not shown) may then be inserted into the pin guides 174 and the femur 154 to secure the cutting block 150 to the femur 154.

In use, the femoral cutting block 150 is coupled to the distal end 176 of the patient's femur 154 as illustrated in FIG. 15. Again, because the bone-contacting surfaces 162, 164 of the cutting block 150 includes the negative contour 170, the block 150 may be coupled to the femur 154 in a pre-planned, unique position. When so coupled, a portion of the anterior side of the femur 154 is received in the negative contour 170 of the anterior wall 158 of the block 150 and a portion of the distal end of the femur 154 is received in the negative contour 170 of the distal wall 160 of the block 150. After the femoral cutting block 150 has been coupled to the patient's femur 154, the orthopaedic surgeon may resect the femur 154 using the cutting block 150. It should be appreciated that the shape of the distal wall 160 allows the surgeon to evaluate the rotation and position of the final orthopaedic implant. That is, because the distal wall 160 does not completely cover the condyles of the patient's femur, the orthopaedic surgeon can visibly observe the position of the femur 154 and the cutting block 150. Additionally, the bone-contacting or bone-facing surface 162 of the distal wall 160 forms an extended guide for the saw blade of the orthopaedic bone saw or other cutting device, which may reduce the likelihood of scything.

Figure 16:
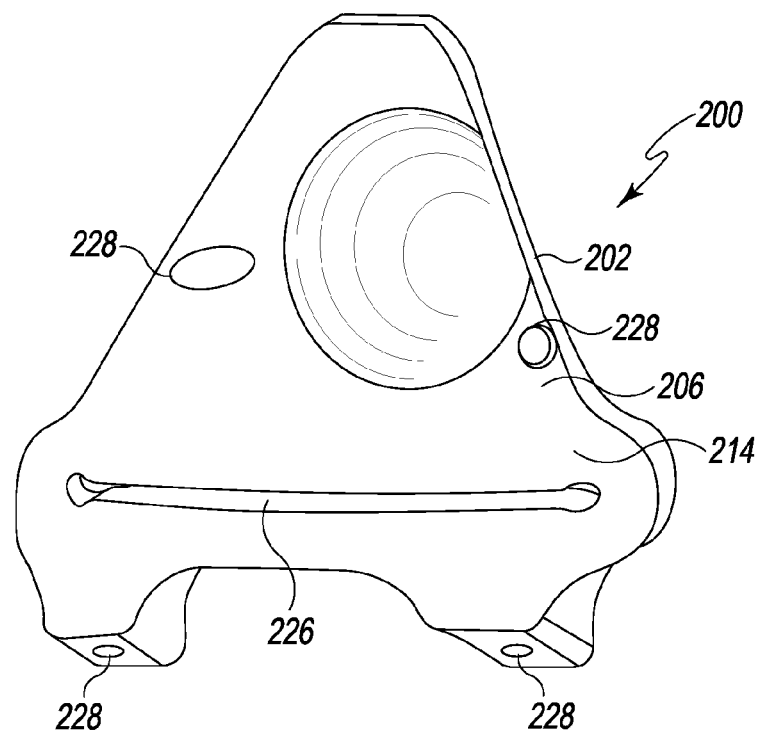
FIG. 16 is an elevation view of another embodiment of a customized patient-specific orthopaedic surgical instrument.
Figure 17:
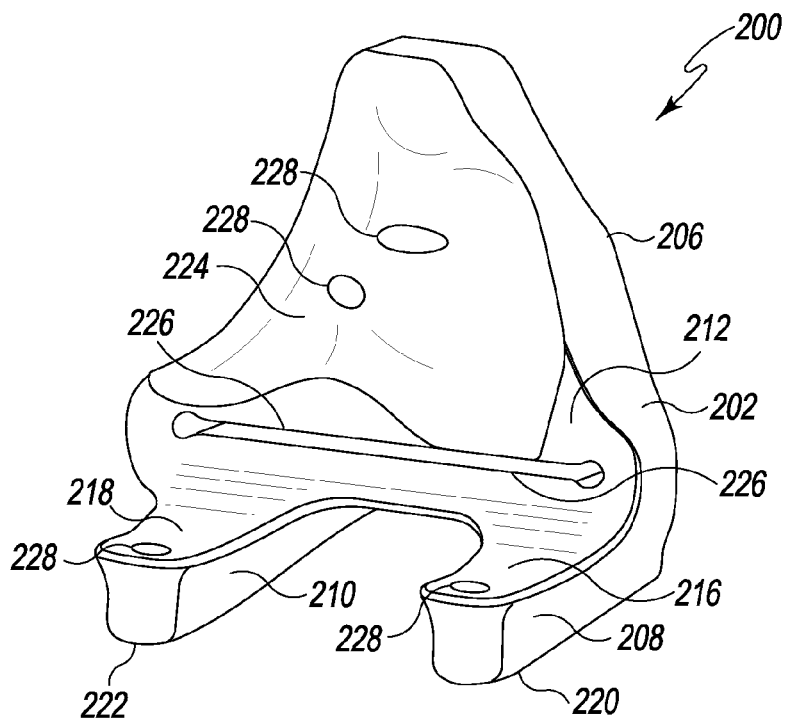
FIG. 17 is a perspective view of the customized patient-specific orthopaedic surgical instrument of FIG. 16.
Figure 18:
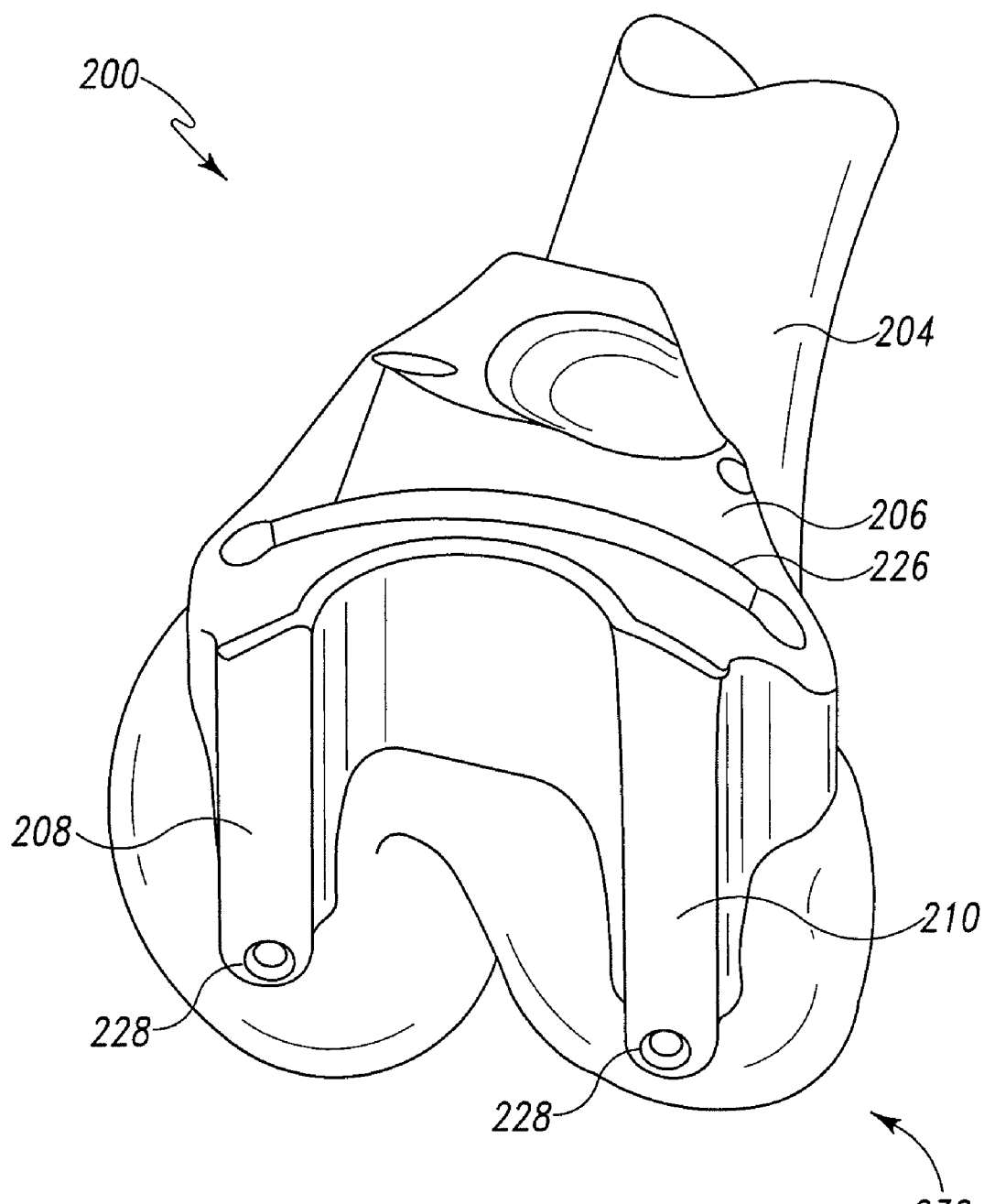
FIG. 18 is a perspective view of the customized patient-specific orthopaedic surgical instrument of FIG. 16 secured to a bone of a patient.

Referring now to FIGS. 16-18, in another embodiment, the customized patient-specific orthopaedic surgical instrument may be embodied as a femoral cutting block 200. The cutting block 200 is configured to be coupled to a femur 204 of a patient as illustrated in FIG. 18. The cutting block 200 includes a body 202 having an anterior wall 206 and a pair of distal tabs 208, 210 extending out from the anterior wall 206. During use, the anterior wall 206 is configured to contact an anterior side of the femur 204 and the distal tabs 208, 210 are configured to extend over the distal end of the femur 204 as discussed in more detail below. The anterior wall 206 includes a bone-contacting or bone-facing surface 212 and an outer surface 214. Each of the distal tabs 208, 210 include a substantially planar bone-facing surface 216, 218 and an outer surface 220, 222, respectively. A negative contour 224 is defined in the bone-contacting surfaces 212 of the anterior wall of the body 202. The negative contour 224 is configured to receive a portion of the patient's femur 204 having a corresponding contour. As discussed above, the negative contour 224 of the bone-contacting surface 212 allows the positioning of the cutting block 200 on the patient's femur 204 in a unique pre-determined location and orientation.

The cutting block 200 includes a cutting guide 226 defined in the anterior wall 206. The thickness of the anterior wall 206 around the cutting guide 226 is increased relative to other portions of the wall 206 to increase the depth of the cutting guide 226. Illustratively, the cutting guide 226 is a captured cutting guide. The femoral cutting block 200 also includes a number of pin guides 228 defined in the anterior wall 206 and each distal tab 208, 210. The pin guides 228 are used as drill guides to establish guide pin holes in the femur 204 of the patient. Illustratively, the pin guides 228 are divergent to prevent the cutting block 200 from loosening under the vibrations of an orthopaedic bone saw. A number of guide pins (not shown) may then be inserted into the pin guides 228 and the femur 204 to secure the cutting block 200 to the femur 204. In one particular embodiment, the pin guides 228 located on the distal tabs 208, 210 are used only as drill guides to establish pin holes in the femur 204 for subsequent orthopaedic instruments.

In use, the femoral cutting block 200 is coupled to the distal end 230 of the patient's femur 204 as illustrated in FIG. 18. Again, because the bone-contacting surface 212 of the cutting block 200 includes the negative contour 224, the block 200 may be coupled to the femur 204 in a pre-planned, unique position. When so coupled, a portion of the anterior side of the femur 204 is received in the negative contour 224 of the anterior wall 206 of the block 200 and the distal tabs 208, 210 extend over the end of the femur 204. In one particular embodiment, the distal tabs 208, 210 extend over the end of the femur 204, but do not contact the surface of the femur. As such, only the anterior side of the femur 204 is referenced. Additionally, in the illustrative embodiment, the tabs 208, 210 extend form the anterior wall 206 at an angle such that the femoral cutting block 200 is offset to one side (e.g., the medial side) of the patient's femur 204 when coupled thereto. After the femoral cutting block 200 has been coupled to the patient's femur 204, the orthopaedic surgeon may resect the femur 204 using the cutting block 200. It should be appreciated that the increased thickness of the anterior wall 206 and resulting increased depth of the cutting guide 226 may improve the stability of the saw blade of the orthopaedic bone saw or other cutting device.

Figure 19:
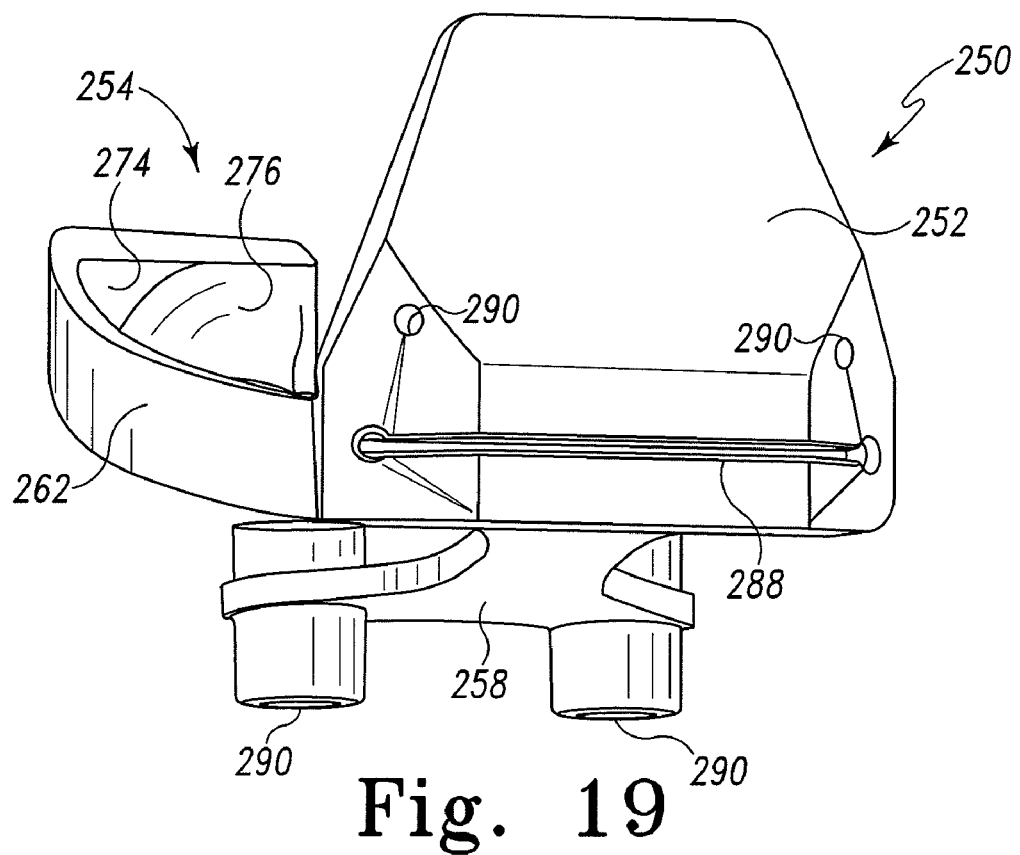
FIG. 19 is an elevation view of another embodiment of a customized patient-specific orthopaedic surgical instrument.
Figure 20:
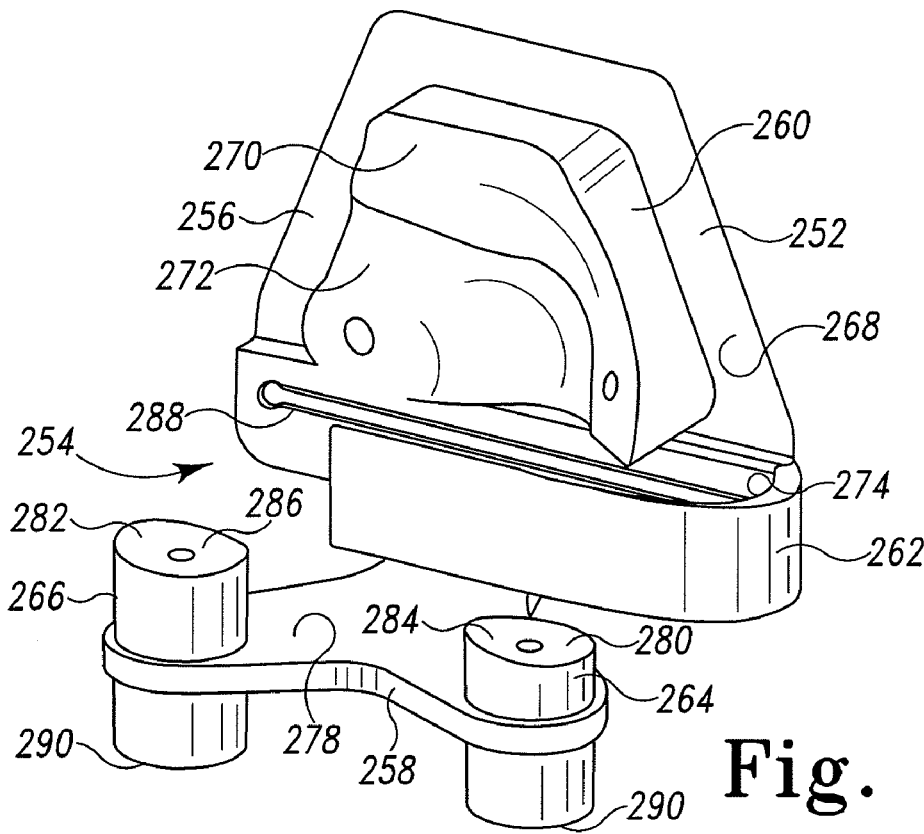
FIG. 20 is a perspective view of the customized patient-specific orthopaedic surgical instrument of FIG. 19.
Figure 21:
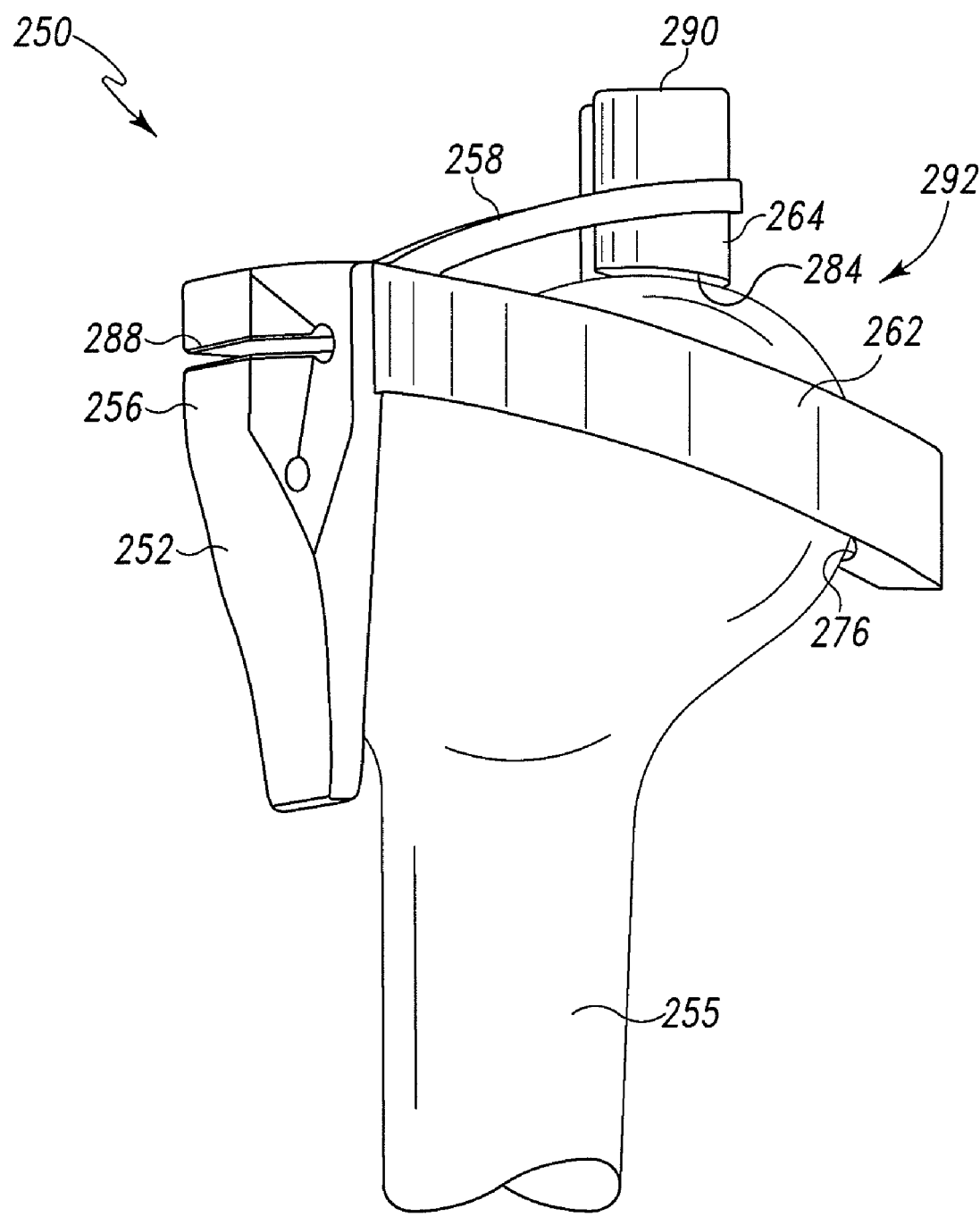
FIG. 21 is a perspective view of the customized patient-specific orthopaedic surgical instrument of FIG. 19 secured to a bone of a patient.

Referring now to FIGS. 19-21, in another embodiment, a customized patient-specific orthopaedic surgical instrument 250 includes a patient-universal femoral cutting block 252 and a patient-specific, disposable insert 254 removably coupled to the femoral cutting block 252. The femoral cutting block 252 includes an anterior wall 256 and a distal tab 258. The cutting block 250 is configured to be coupled to a femur 255 of a patient as illustrated in FIG. 21. During use, the anterior wall 256 is configured to confront the anterior side of the femur 255 and the distal tab 258 is configured to confront the distal end of the femur 255 as discussed in more detail below.

The patient-specific insert 254 includes an anterior platform 260, a posterior clip or arcuate bracket 262, and a pair of distal feet 264, 266. The platform 260, clip 262, and feet 264, 266 are configured to be removably coupled to the femoral cutting block 252. In particular, the platform 260 is removably coupled to a bone-facing surface 268 of the anterior wall 256. The platform 260 includes a bone-contacting surface 270 having a negative contour 272 defined therein. The negative contour 272 of the platform 260 is configured to receive a portion of an anterior side of the patient's femur 255. The clip 262 is coupled to the platform 260 and extends therefrom in an inwardly curving arc. The clip 262 also includes a bone-contacting surface 274 having a negative contour 276 defined therein. The negative contour 276 of the clip 262 is configured to receive a portion of a posterior condyle of the patient's femur 255. The feet 264, 266 are removably coupled to a bone-facing surface 278 of the distal tab 262 of the block 252. Each of the feet 264, 266 includes a bone-contacting surface 280, 282, respectively. Each of the bone-contacting surface 280, 282 includes a negative contour 284, 286, respectively, defined therein. The feet 264, 266 are positioned on the distal tab 258 such that the feet 264, 266 contact the distal end of the femur 255. That is, the negative contours 284, 286 are configured to receive portions of the distal end of the femur. As discussed above, the negative contours 272, 276, 284, 286 of the bone-contacting surface surfaces 270, 274, 280, 282 allows the positioning of the instrument 250 on the patient's femur 255 in a unique pre-determined location and orientation.

The cutting block 252 includes a cutting guide 288 defined in the anterior wall 256. Illustratively, the cutting guide 288 is a captured cutting guide. The femoral cutting block 252 also includes a number of pin guides 290. The pin guides 290 are used as drill guides to establish guide pin holes in the femur 255 of the patient. A number of guide pins (not shown) may then be inserted into the pin guides 290 and the femur 255 to secure the customized patient-specific surgical instrument 250 to the patient's femur 255. The cutting guide 288 and the pin guides 290 also extend through the patient-specific insert 254.

In use, the patient-specific insert 254 is initially coupled to the femoral cutting block 252. The customized patient-specific surgical instrument 250 may then be coupled to the distal end 292 of the patient's femur 255 as illustrated in FIG. 21. Again, because the bone-contacting surface surfaces 270, 274, 280, 282 of the patient-specific insert 254 includes the respective negative contours 272, 276, 284, 286, the instrument 250 may be coupled to the femur 255 in a pre-planned, unique position. When so coupled, a portion of the anterior side of the femur 255 is received in the negative contour 272 of the platform 260 of the insert 254. The clip 262 wraps around the medial side of the distal end 292 of the patient's femur 255. A portion of the posterior medial condyle of the patient's femur is received in the negative contour 276 of the clip 262. Additionally, each of the feet 264, 266 contact the distal end of the condyles of the patient's femur. A portion of the distal condyles is received in the negative contours 284, 286 of the feet 264, 266, respectively. After the instrument 250 has been coupled to the patient's femur 255, the orthopaedic surgeon may resect the femur 255 using the instrument 250. After the orthopaedic surgical procedure is completed, the patient-specific insert 254 may be discarded. The femoral cutting block 252 may be sterilized and reused in subsequent surgical procedures with a new patient-specific insert.

Figure 22:
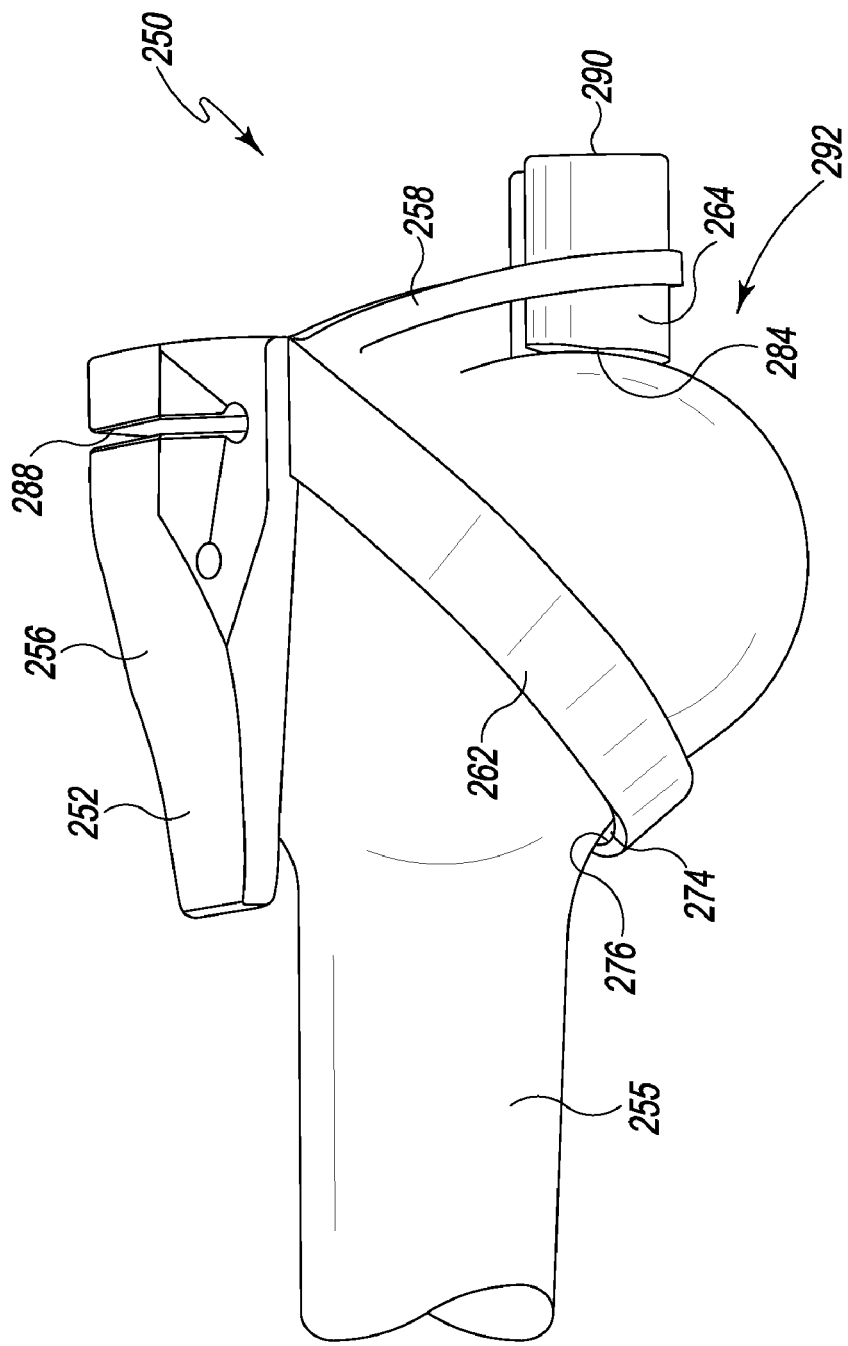
FIG. 22 is a perspective view of another embodiment of the customized patient-specific orthopaedic surgical instrument of FIG. 19 secured to a bone of a patient.

In other embodiments, the clip 262 may be oriented to reference the proximal surface of the posterior condyle of the femur 255 as illustrated in FIG. 22. That is, the clip 262 may be angled proximally relative to the femoral cutting block 252. As discussed above, the clip 262 also includes the bone-contacting surface 274, which includes the negative contour 276 configured to receive a corresponding contour of the proximal posterior condyle of the femur 255. It should be appreciated that the position of the clip 262 provides space for or otherwise avoids interfering with particular soft tissue such particular ligaments of the patient's joint.

Figure 23:
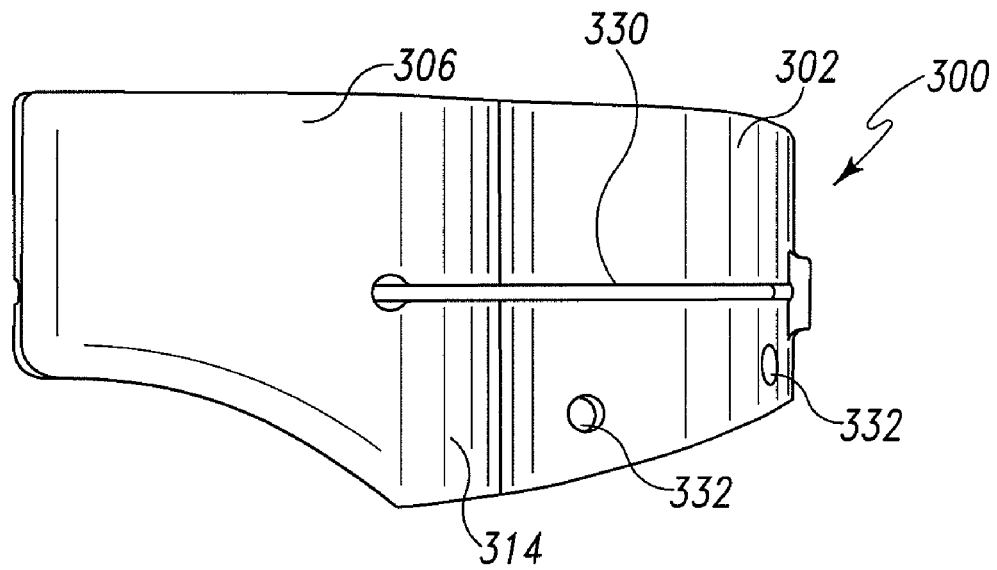
FIG. 23 is an elevation view of another embodiment of a customized patient-specific orthopaedic surgical instrument.
Figure 24:
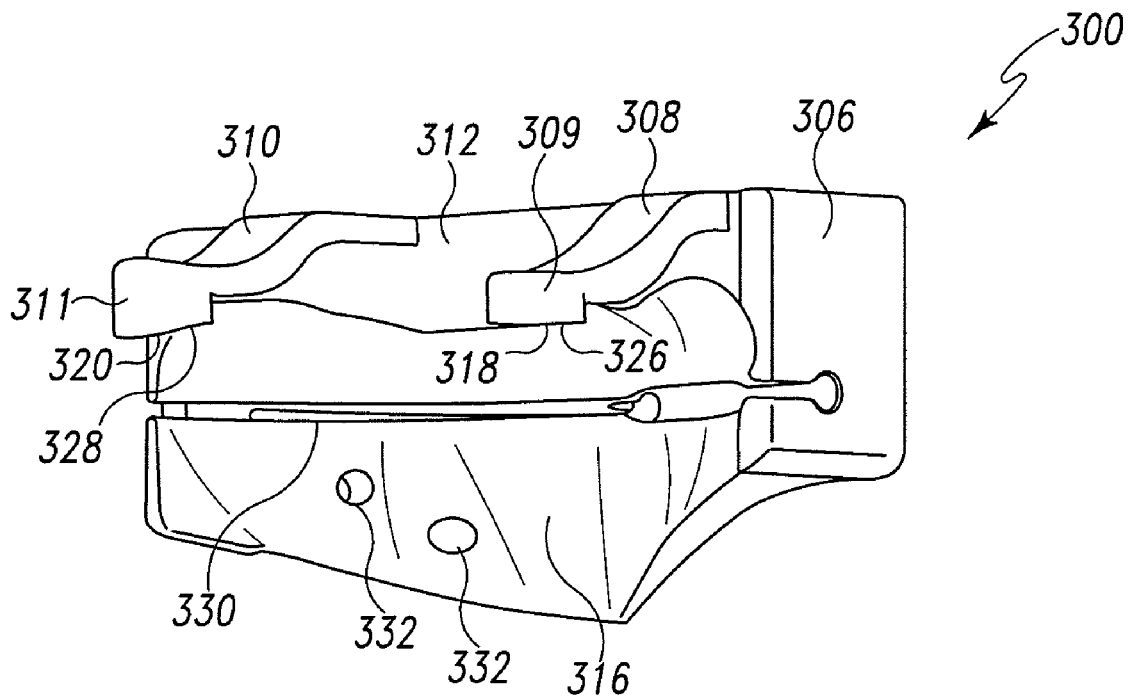
FIG. 24 is a perspective view of the customized patient-specific orthopaedic surgical instrument of FIG. 23.
Figure 25:
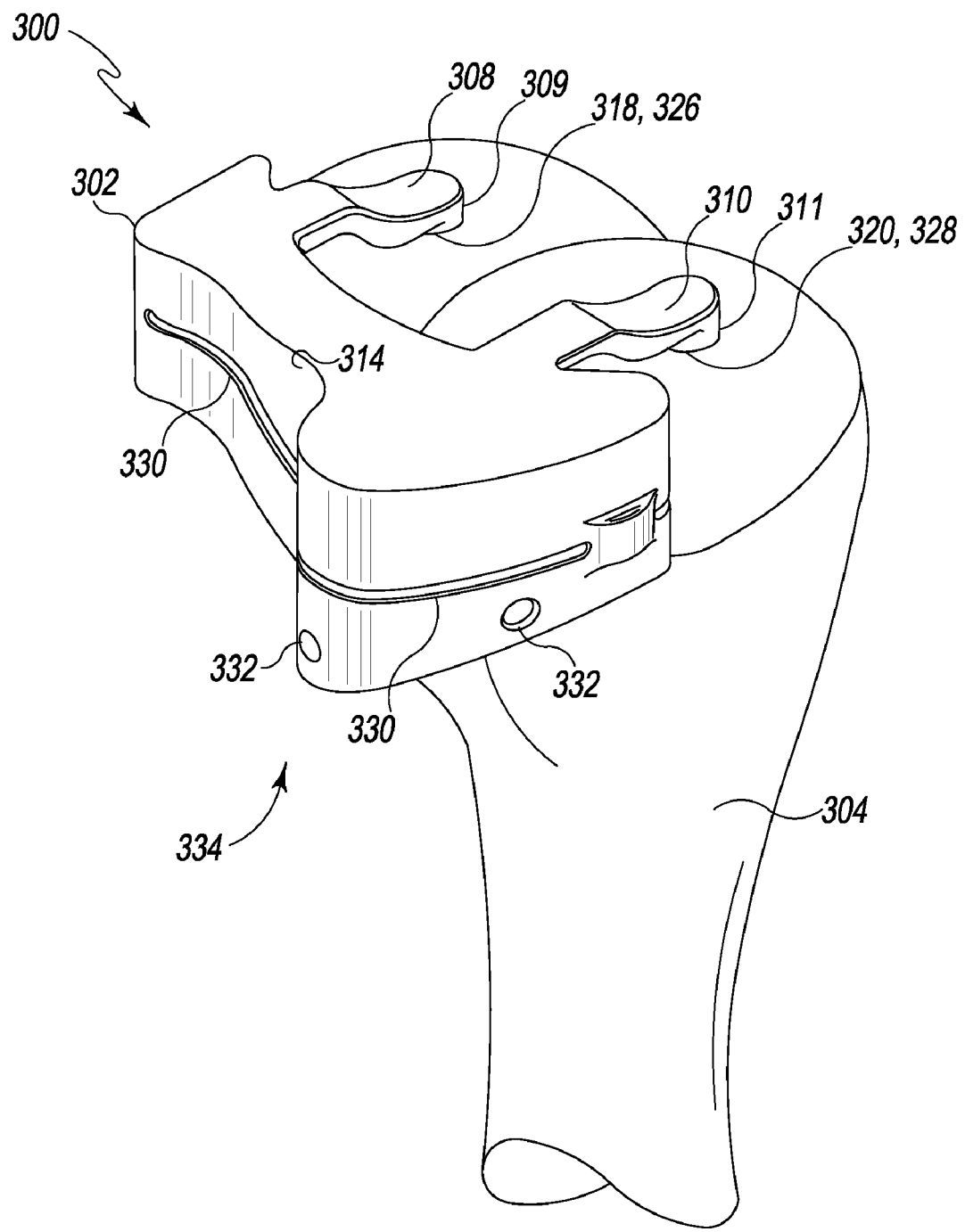
FIG. 25 is a perspective view of the customized patient-specific orthopaedic surgical instrument of FIG. 23 secured to a bone of a patient.

Referring now to FIGS. 23-25, in another embodiment, the customized patient-specific orthopaedic surgical instrument may be embodied as a tibial cutting block 300. The cutting block 300 is configured to be coupled to a tibia 304 of a patient as illustrated in FIG. 25. The cutting block 300 includes a body 302 having an anterior wall 306 and a pair of tabs 308, 310 extending out from the anterior wall 306. During use, the anterior wall 306 is configured to contact an anterior side of the tibia 304 and the tabs 308, 310 are configured to extend over the medial and lateral condyles of the tibia 304 as discussed in more detail below. The anterior wall 306 includes a bone-contacting or bone-facing surface 312 and an outer surface 314. A negative contour 316 is defined in the bone-contacting surface 312 of the anterior wall 306. Each of the tabs 308, 310 includes a footpad 309, 311 extending downwardly from an end of the tabs 308, 310. Each of the footpads 309, 311 includes a bone-contacting or bone-facing surface 318, 320, respectively. A negative contour 326, 328 is defined in the bone-contacting surfaces 318, 320 of the tabs 308, 310, respectively. Each of the negative contours 316, 326, 328 is configured to receive a portion of the patient's tibia 304. For example, the negative contour 316 of the anterior wall 306 is configured to receive a portion of the anterior side of the patient's tibia 304. Similarly, the negative contours 326, 328 of the tabs 308, 310 are configured to receive a portion of the proximal end of the patient's tibia 304. As discussed above, the negative contours 316, 326, 328 allow the positioning of the tibial cutting block 300 on the patient's tibia 304 in a unique pre-determined location and orientation.

The cutting block 300 includes a cutting guide 330 defined in the anterior wall 306. Because the anterior wall 306 is designed to wrap around the anterior side of the patient's tibia 304, the length of the cutting guide 300 is increased. The tibial cutting block 300 also includes a number of pin guides 332 defined in the anterior wall 306. The pin guides 332 are used as drill guides to establish guide pin holes in the tibia 304 of the patient. A number of guide pins (not shown) may then be inserted into the pin guides 332 and the tibia 304 to secure the cutting block 300 and/or other non-patient specific instruments (not shown) to the tibia 304.

In use, the tibial cutting block 300 is coupled to the proximal end 334 of the patient's tibia 304 as illustrated in FIG. 25. Again, because the bone-contacting surfaces 312, 318, 320 of the cutting block 300 includes the negative contours 316, 326, 328, the cutting block 300 may be coupled to the tibia 304 in a pre-planned, unique position. When so coupled, a portion of the anterior side of the tibia 304 is received in the negative contour 316 of the anterior wall 306 and a portion of the proximal end of the tibia 304 is received in the negative contours 318, 320 of the footpads 309, 311 of the tabs 308, 310. As such, the anterior side and the proximal side of the patient's tibia 304 are referenced by the cutting block 300. After the tibial cutting block 300 has been coupled to the patient's femur 304, the orthopaedic surgeon may resect the tibia 304 using the cutting block 300.

Figure 26:
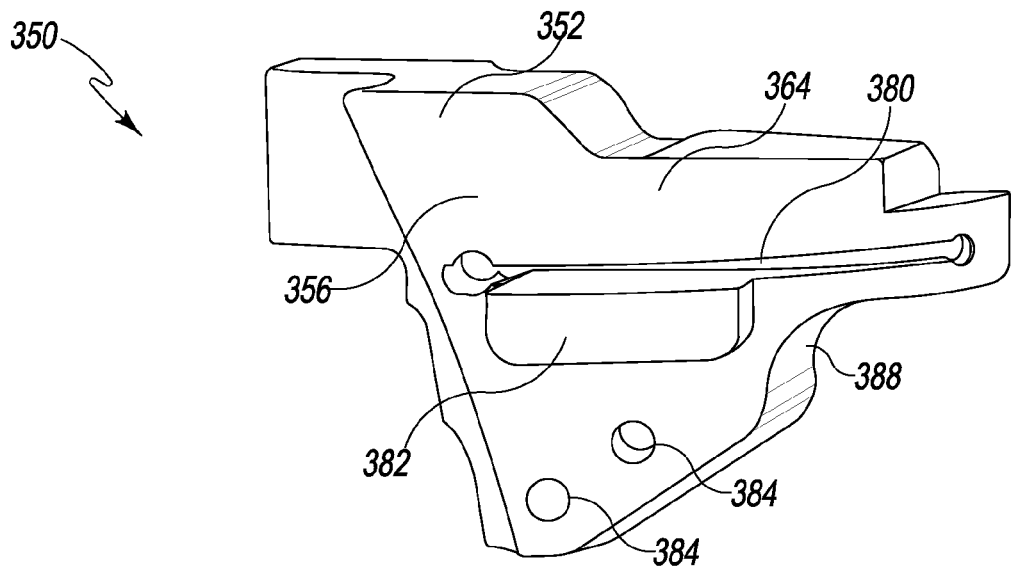
FIG. 26 is an elevation view of another embodiment of a customized patient-specific orthopaedic surgical instrument.
Figure 27:
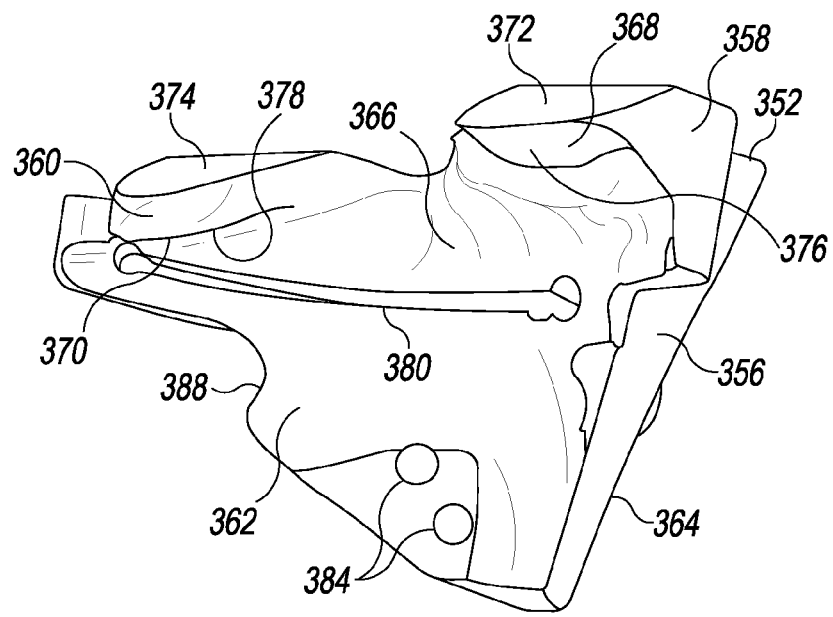
FIG. 27 is a perspective view of the customized patient-specific orthopaedic surgical instrument of FIG. 26.
Figure 28:
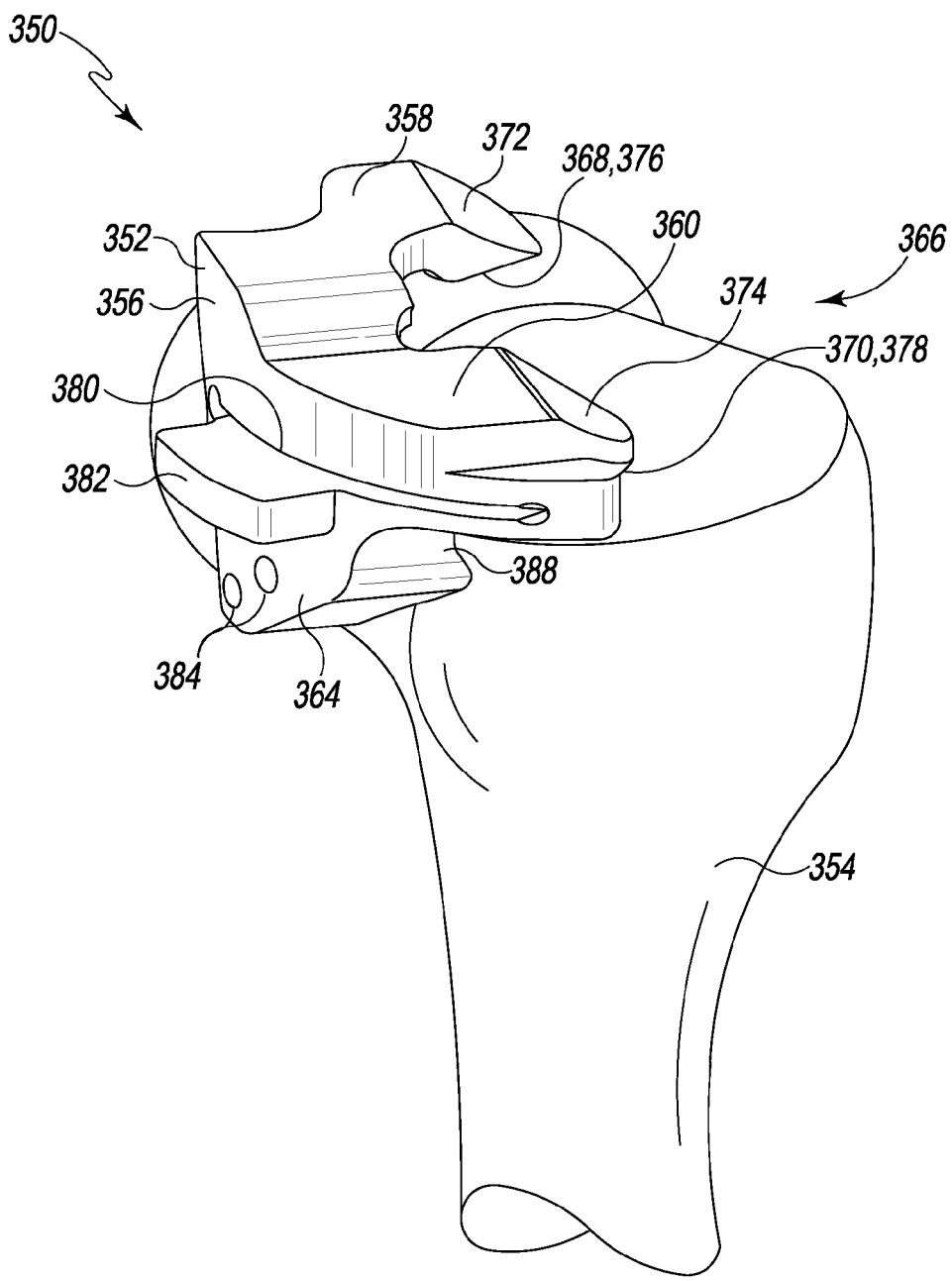
FIG. 28 is a perspective view of the customized patient-specific orthopaedic surgical instrument of FIG. 26 secured to a bone of a patient.

Referring now to FIGS. 26-28, in another embodiment, the customized patient-specific orthopaedic surgical instrument may be embodied as a tibial cutting block 350. The cutting block 350 is configured to be coupled to a tibia 354 of a patient as illustrated in FIG. 28. The cutting block 350 includes a body 352 having an anterior wall 356 and a pair of tabs 358, 360 extending out from the anterior wall 306. During use, the anterior wall 356 is configured to contact an anterior side of the tibia 354 and the tabs 358, 360 are configured to extend over the proximal end of the tibia 354 as discussed in more detail below. The anterior wall 356 includes a bone-contacting or bone-facing surface 362 and an outer surface 364. A negative contour 366 is defined in the bone-contacting surface 362 of the anterior wall 356. Similarly, each of the tabs 358, 360 includes a bone-contacting or bone-facing surface 368, 370 and an outer surface 372, 374, respectively. A negative contour 376, 378 is defined in the bone-contacting surfaces 368, 370 of the tabs 358, 360, respectively. Each of the outer surfaces 372, 374 of the tabs 358, 360 have a downward slope to reduce the likelihood of contact between the tabs 358, 360 and the femur of the patient when the tibia cutting block 350 is secured to the patient's tibia 354. Each of the negative contours 366, 376, 378 is configured to receive a portion of the patient's tibia 354. For example, the negative contour 366 of the anterior wall 356 is configured to receive a portion of the anterior side of the patient's tibia 354. Similarly, the negative contours 376, 378 of the tabs 358, 360 are configured to receive a portion of the proximal end of the patient's tibia 354. As discussed above, the negative contours 366, 376, 378 allow the positioning of the tibial cutting block 350 on the patient's tibia 354 in a unique pre-determined location and orientation.

The cutting block 350 includes a cutting guide 380 defined in the anterior wall 356. Because the anterior wall 356 is designed to wrap around the anterior side of the patient's tibia 354, the length of the cutting guide 380 is increased. Additionally, the block 350 includes a cutting guide support 382 extending outwardly from the anterior wall 356 below the cutting guide 380. The cutting guide support 382 extends or increases the effective depth of the cutting guide 380, which may increase the stability of a bone saw blade of an orthopaedic bone saw or other cutting device during use of the block 350.

The tibial cutting block 350 also includes a number of pin guides 384 defined in the anterior wall 356. The pin guides 384 are used as drill guides to establish guide pin holes in the tibia 354 of the patient. A number of guide pins (not shown) may then be inserted into the pin guides 384 and the tibia 354 to secure the cutting block 350 to the tibia 354.

In use, the tibial cutting block 350 is coupled to the distal end 366 of the patient's tibia 354 as illustrated in FIG. 28. Again, because the bone-contacting surfaces 362, 368, 370 of the cutting block 350 includes the negative contours 366, 376, 378, the cutting block 350 may be coupled to the tibia 354 in a pre-planned, unique position. When so coupled, a portion of the anterior side of the tibia 354 is received in the negative contour 366 of the anterior wall 356 and a portion of the proximal end of the tibia 364 is received in the negative contours 376, 378 of the tabs 358, 360. As such, the anterior side and the proximal side of the patient's tibia 354 are referenced by the cutting block 350. Additionally, in some embodiments, the anterior wall 356 is relieved laterally to provide room for the patellar tendon during use of the block 350. That is, in some embodiments, the anterior wall 356 includes a notched out region 388 configured to reduce the likelihood of contact of the block 350 and the patellar tendon. After the tibial cutting block 350 has been coupled to the patient's femur 354, the orthopaedic surgeon may resect the tibia 354 using the cutting block 350.

Figure 29:
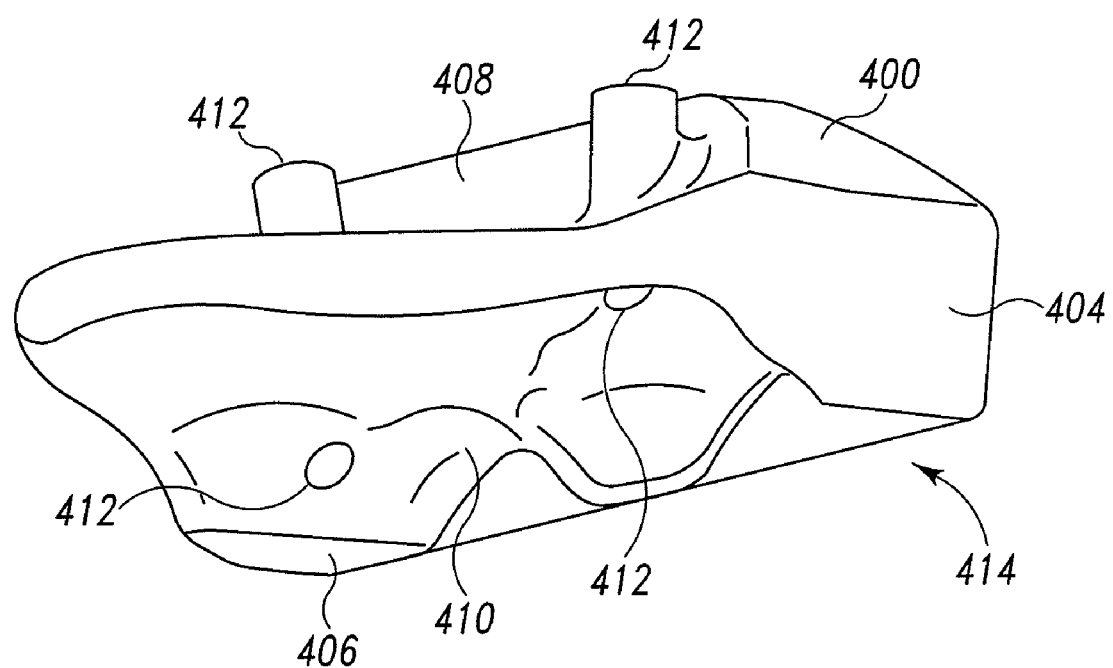
FIG. 29 is a perspective view of another embodiment of a customized patient-specific orthopaedic surgical instrument.
Figure 30:
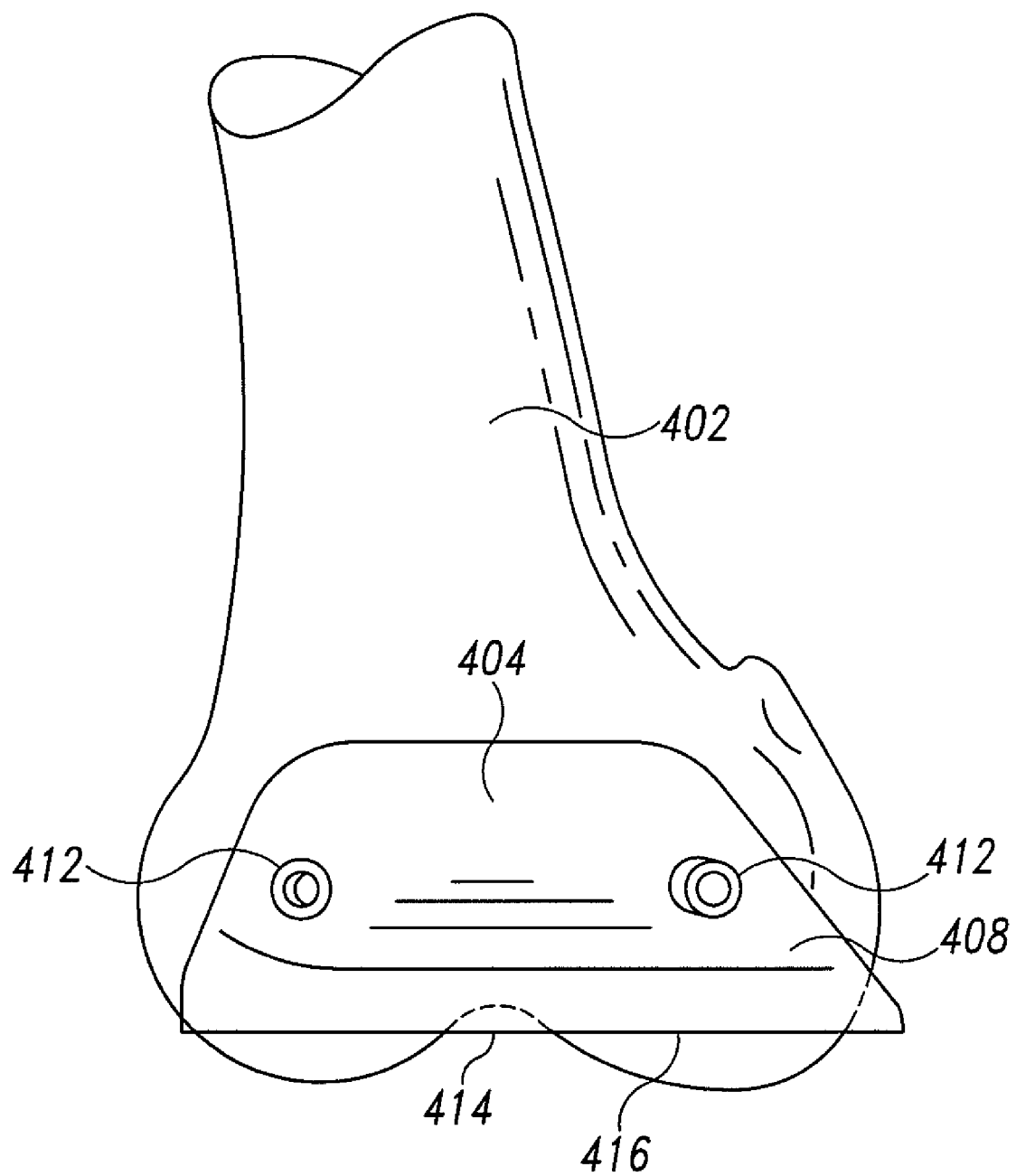
FIG. 30 is an elevation view of the customized patient-specific orthopaedic surgical instrument of FIG. 29 coupled to a bone of a patient.

Referring now to FIGS. 29-30, in another embodiment, the customized patient-specific orthopaedic surgical instrument may be embodied as a cutting block 400. The cutting block 400 is configured to be coupled to a bone 402, such as the patient's femur or tibia, as illustrated in FIG. 30. The cutting block includes a body 404 having a bone-contacting or bone-facing surface 406 and an outside surface 408. The bone-contacting surface 406 includes a negative contour 410 configured to receive a portion of the patient's bone having a corresponding contour. As discussed above, the negative contour 410 of the bone-contacting surface 406 allows the positioning of the cutting block 400 on the patient's bone in a unique pre-determined location and orientation.

The cutting block 400 also includes a number of pin guides 412. In use, the pin guides 412 are used as drill guides to establish guide pin holes in the bone of the patient for securing a number of guide pins (not shown) to the bone. The cutting block 400 may then be coupled and secured to the patient's bone 402 via the guide pins. The cutting block 400 also includes a cutting guide 414 defined in the body 404 of the block 400. Illustratively, the cutting guide 414 is a non-captured or open cutting guide. That is, the cutting guide 414 is defined by a sidewall 416 of the body 404 of the cutting block 400. However, in other embodiments, the cutting guide 414 may be embodied as a captured cutting guide.

In use, the cutting block 400 is coupled to the end 418 of a patient's bone 402 as illustrated in FIG. 30. Again, because the bone-contacting surface 406 of the cutting block 400 includes negative contour 410, the block 400 may be coupled to the patient's bone 402 in a pre-planned, unique position. When so coupled, a portion of the anterior side of the bone 402 is received in the negative contour 410. Again, because the bone-contacting surface 406 of the cutting block 400 includes the negative contour 410, the block 400 may be coupled to the bone 402 in a pre-planned, unique position. The cutting block 400 may be secured to the bone 402 via use of a number of guide pins (not shown) received in the pin guides 412 and the bone 402. After the cutting block 400 has been secured to the patient's bone 402, the orthopaedic surgeon may use the cutting block 400 to resect a pre-planned amount of the bone 402. That is, the bone cut made using the cutting guide 414 corresponds to the cutting plane determined during the fabrication of the cutting block 400 (see process step 24 of algorithm 10 described above in regard to FIG. 1).

Figure 31:
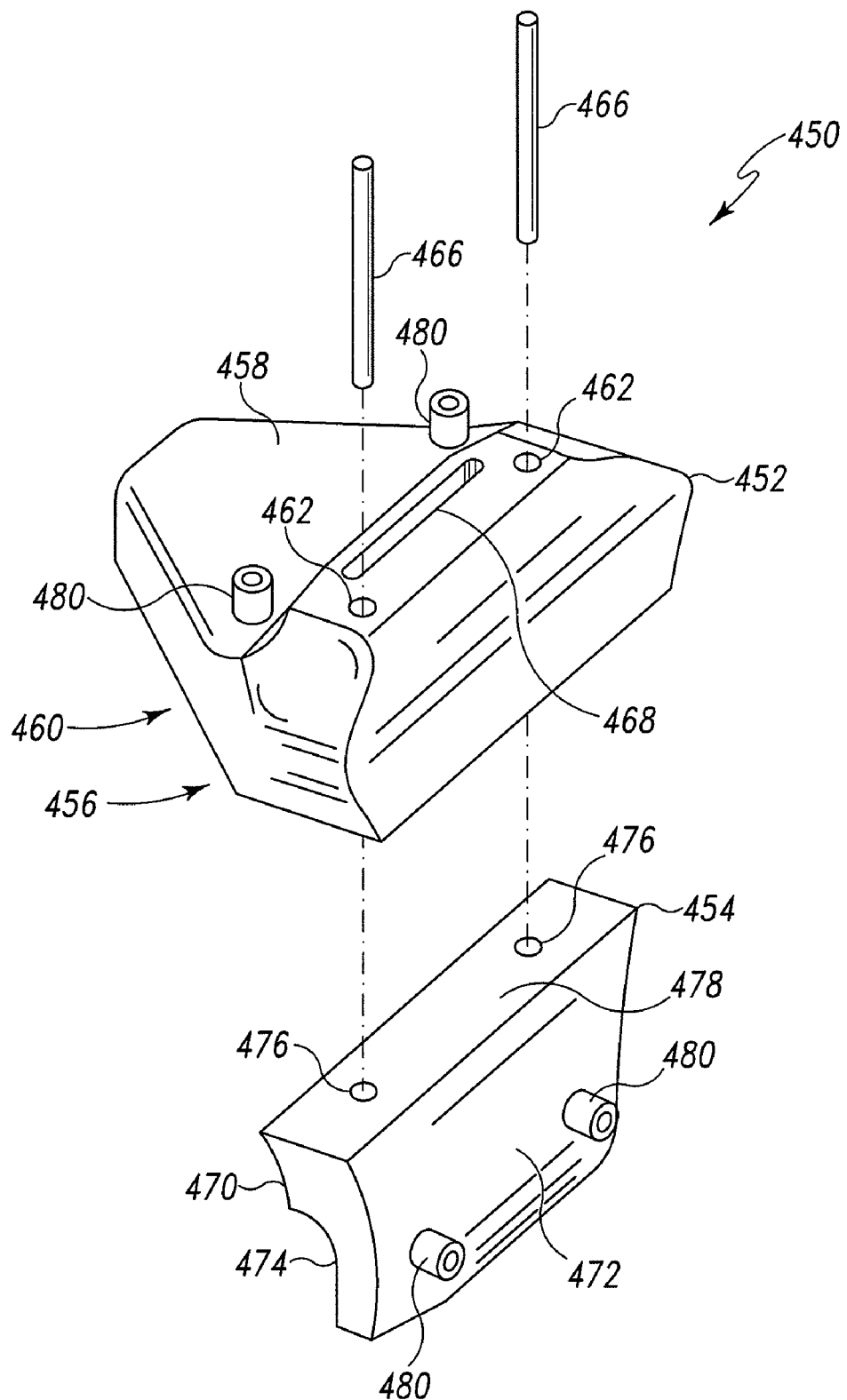
FIG. 31 is an exploded perspective view of another embodiment of a customized patient-specific orthopaedic surgical instrument.
Figure 32:
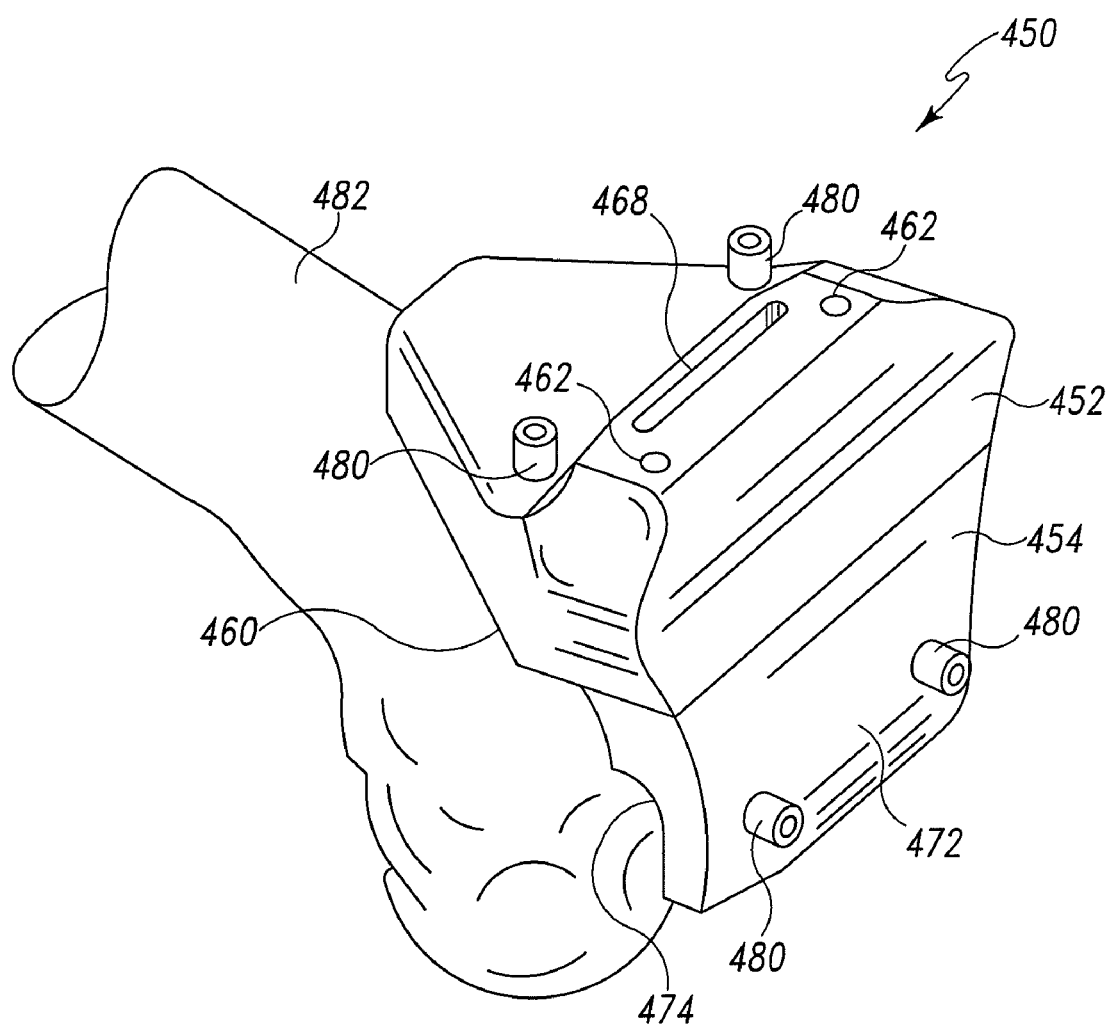
FIG. 32 is a perspective view of the customized patient-specific orthopaedic surgical instrument of FIG. 31 in an assembled configuration and coupled to a bone of a patient

In some embodiments, the customized patient-specific orthopaedic surgical instrument may be formed from a number of separate pieces. For example, as illustrated in FIGS. 31-32, the customized patient-specific orthopaedic surgical instrument may be embodied as a cutting block 450 including an anterior wall piece 452 and an end wall piece 454 separate from the anterior wall piece 454.

The anterior wall piece 452 includes a bone-contacting or bone-facing surface 456 and an outside surface 458. The bone-contacting surface 456 includes a negative contour 460 configured to receive a portion of the patient's bone having a corresponding contour. The anterior wall piece 452 also includes a number of apertures 462 defined therethough and configured to receive a number of fasteners or securing devices 466, such as pins, bolts, or the like, to facilitate the coupling of the anterior wall piece 452 to the end wall piece 454. The anterior wall piece 452 also includes a cutting guide 468. Illustratively, the cutting guide 468 is a captured cutting guide, but may be embodied as a non-captured or open cutting guide in other embodiments.

The end wall piece 454 includes a bone-contacting or bone-facing surface 470 and an outside surface 472. The bone-contacting surface 470 includes a negative contour 474 configured to receive a portion of the patient's bone having a corresponding contour. The end wall piece 454 also includes a number of apertures 476 defined in a sidewall 478. The apertures 476 are located in the sidewall 478 corresponding to the position of the apertures 462 of the anterior wall piece 452 such that the wall pieces 452, 454 may be coupled together via the securing devices 466 as discussed below.

Each of the wall pieces 454, 456 also includes a number of pin guides 480. In use, the pin guides 480 are used as drill guides to establish guide pin holes in the bone of the patient for securing a number of guide pins (not shown) to the bone. The cutting block 450 may then be coupled and secured to the patient's bone 482 via the guide pins.

In use, the cutting block 450 is configured to be constructed inside the incision site of the patient. That is, the orthopaedic surgeon may insert the anterior wall piece 452 and the end wall piece 454 into the incision site of the patient. Once so inserted, the surgeon may couple the wall pieces 452, 454 together using the securing device 466 to thereby form the cutting block 450. The cutting block 450 may then be coupled to the bone 482 of the patient. When so coupled, a portion of the anterior side of the bone 482 is received in the negative contour 460 and a portion of the end of the bone is received in the negative contour 474. Again, because the bone-contacting surfaces 456, 470 of the cutting block 450 include the negative contours 460, 474, the block 450 may be coupled to the bone 482 in a pre-planned, unique position. The cutting block 450 may be secured to the bone 482 via use of a number of guide pins (not shown) received in the pin guides 480 and the bone 482. After the cutting block 450 has been secured to the patient's bone 482, the orthopaedic surgeon may use the cutting block 450 to resect a pre-planned amount of the bone 402. That is, the bone cut made using the cutting guide 468 corresponds to the cutting plane determined during the fabrication of the cutting block 450 (see process step 24 of algorithm 10 described above in regard to FIG. 1).

Figure 33:
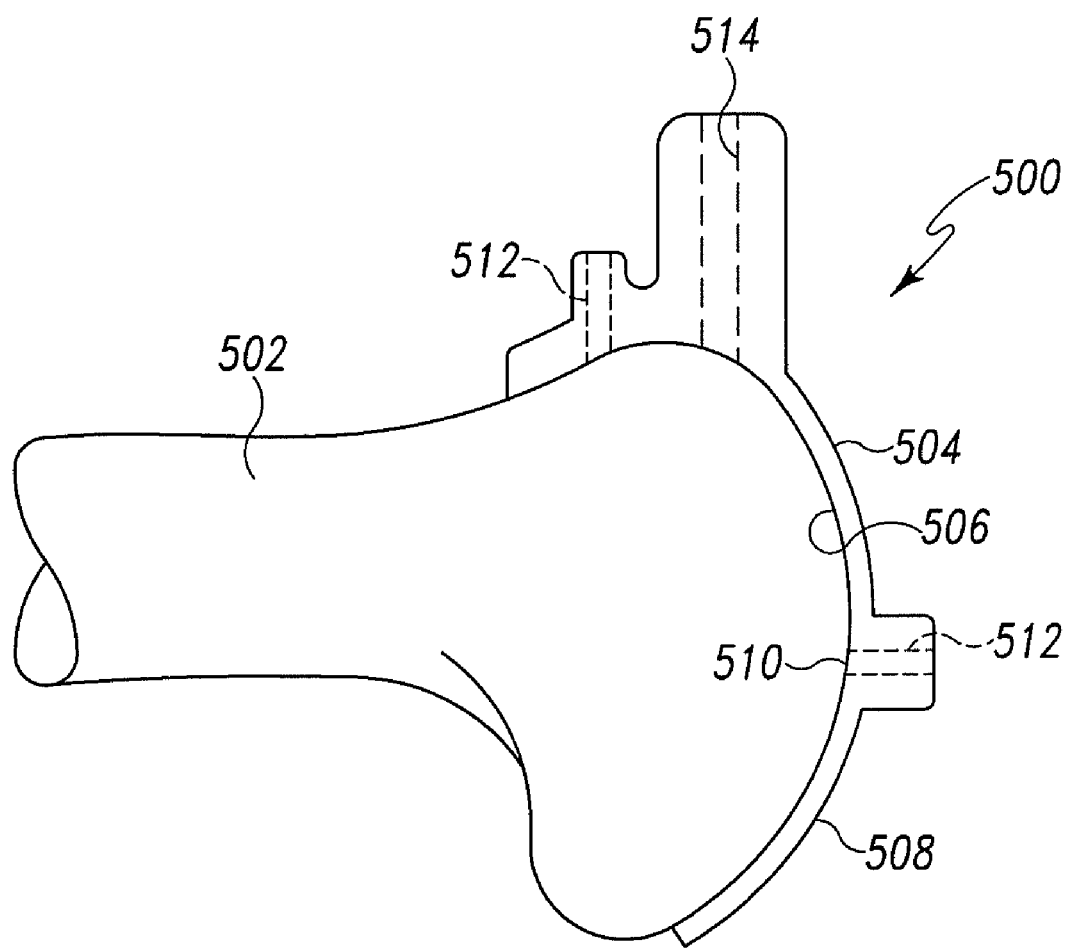
FIG. 33 is a side elevation view of another embodiment of a customized patient-specific orthopaedic surgical instrument.

Referring now to FIG. 33, in another embodiment, the customized patient-specific orthopaedic surgical instrument may be embodied as a cutting block 500. The cutting block 500 is configured to be coupled to a bone 502, such as femur or tibia, of a patient. The cutting block 500 includes a body 504. As shown in FIG. 33, the body 504 is configured to have a relatively small thickness. The body 504 includes a bone-contacting or bone-facing surface 506 and an outer surface 508. The bone-contacting surface 506 includes a negative contour 510 configured to receive a portion of the patient's bone 502 having a corresponding contour. As discussed above, the negative contour 510 of the bone-contacting surface 506 allows the positioning of the cutting block 500 on the patient's bone in a unique pre-determined location and orientation.

The cutting block 500 also includes a number of pin guides 512. In use, the pin guides 512 are used as drill guides to establish guide pin holes in the bone of the patient for securing a number of guide pins (not shown) to the bone. The cutting block 500 may then be coupled and secured to the patient's bone via the guide pins. The cutting block 500 also includes a captured cutting guide 514. The captured cutting guide 514 is extended outwardly from the body 504 such that the depth of the cutting guide 514 is increased.

In use, the cutting block 500 is configured to be coupled to a patient's bone 502, such as the femur or tibia. Again, because the bone-contacting surface 506 of the cutting block 500 includes the negative contour 510, the block 500 may be coupled to the bone 502 in a pre-planned, unique position. The cutting block 500 may be secured to the bone 502 via use of a number of guide pins (not shown) received in the pin guides 512 and the bone 502. It should be appreciated that the reduced thickness of the body 504 may increase the ability of the surgeon to position the cutting block 500 in the knee joint of the patient. After the cutting block 500 has been secured to the patient's bone 502, the orthopaedic surgeon may use the cutting block 500 to resect a pre-planned amount of the bone 502. It should also be appreciated that because the cutting guide 514 has an increased depth, the stability of the bone saw blade of the orthopaedic bone saw or other cutting device may be increased.

Figure 34:
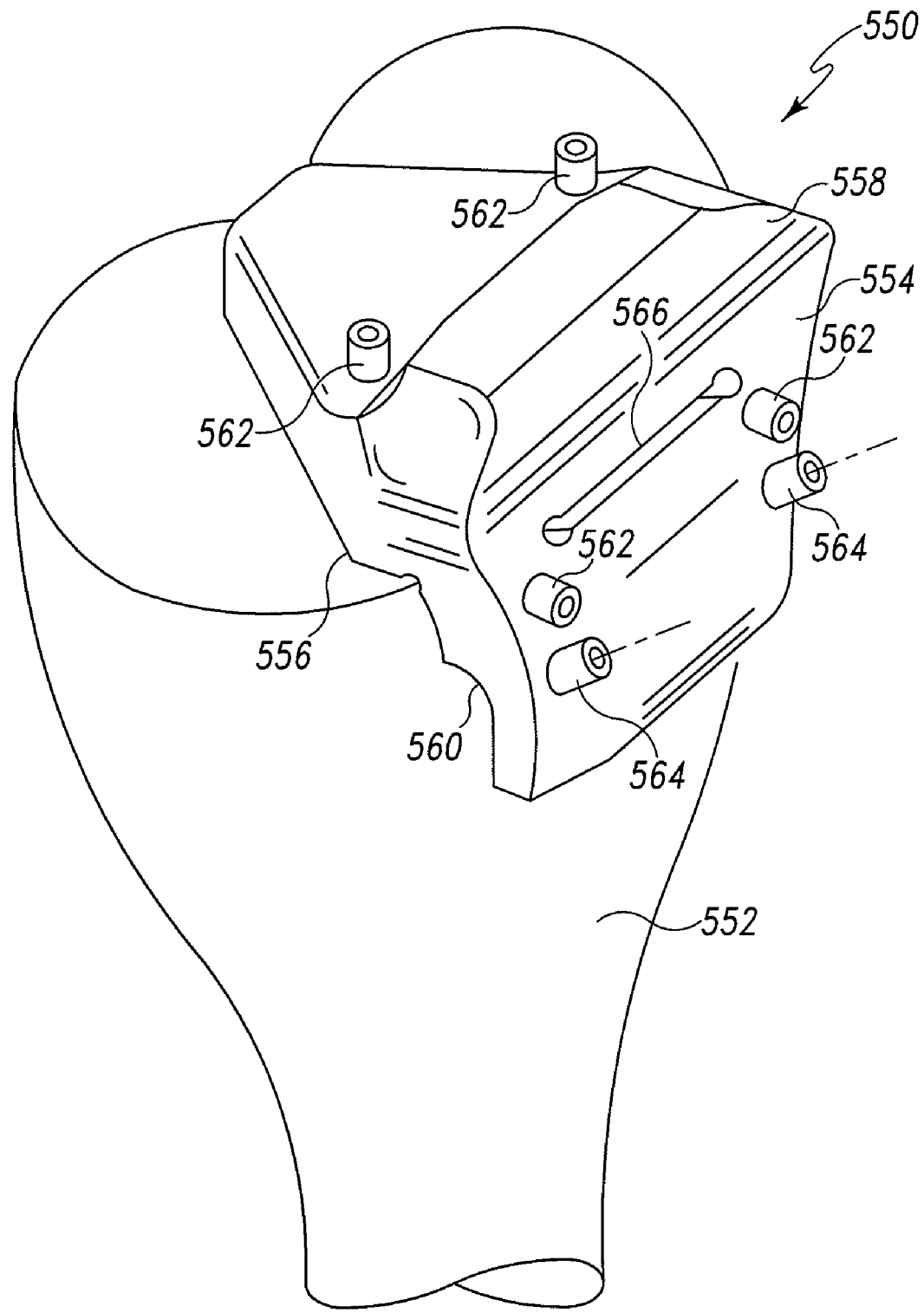
FIG. 34 is a perspective view of another embodiment of a customized patient-specific orthopaedic surgical instrument coupled to a bone of a patient.

Referring now to FIG. 34, in another embodiment, the customized patient-specific orthopaedic surgical instrument may be embodied as a cutting block 550. The cutting block 550 is configured to be coupled to a bone 552, such as femur or tibia, of a patient. The cutting block 550 includes a body 554 having a bone-contacting or bone-facing surface 556 and an outer surface 558. The bone-contacting surface 556 includes a negative contour 560 configured to receive a portion of the patient's bone 552 having a corresponding contour. As discussed above, the negative contour 560 of the bone-contacting surface 556 allows the positioning of the cutting block 550 on the patient's bone in a unique pre-determined location and orientation.

The cutting block 550 also includes a number of pin guides 562, 564. In use, the pin guides 562, 564 are used as drill guides to establish guide pin holes in the bone of the patient for securing a number of guide pins (not shown) to the bone. The cutting block 550 may then be coupled and secured to the patient's bone via the guide pins. The pin guides 562 are positioned substantially orthogonal to outside surface 558 of the body 554 of the cutting block 500. Conversely, the pin guides 564 are positioned at an angle with respect to the outside surface 558 of the body 554. The cutting block 550 also includes a captured cutting guide 566.

In use, the cutting block 550 is configured to be coupled to a patient's bone 552, such as the femur or tibia. Again, because the bone-contacting surface 556 of the cutting block 550 includes the negative contour 560, the block 550 may be coupled to the bone 552 in a pre-planned, unique position. The cutting block 500 may be secured in one of two configurations relative to the patient's bone. That is, the pin guides 562 may be used to position the block 500 with respect to the patient's bone 502 such that a planar cut may be made with the cutting guide 566. Alternatively, the pin guides 564 may be used to position the block 550 at an angle with respect to the patient's bone 552 such that an angular or inclined cut may be performed on the patient's bone.

Figure 35:
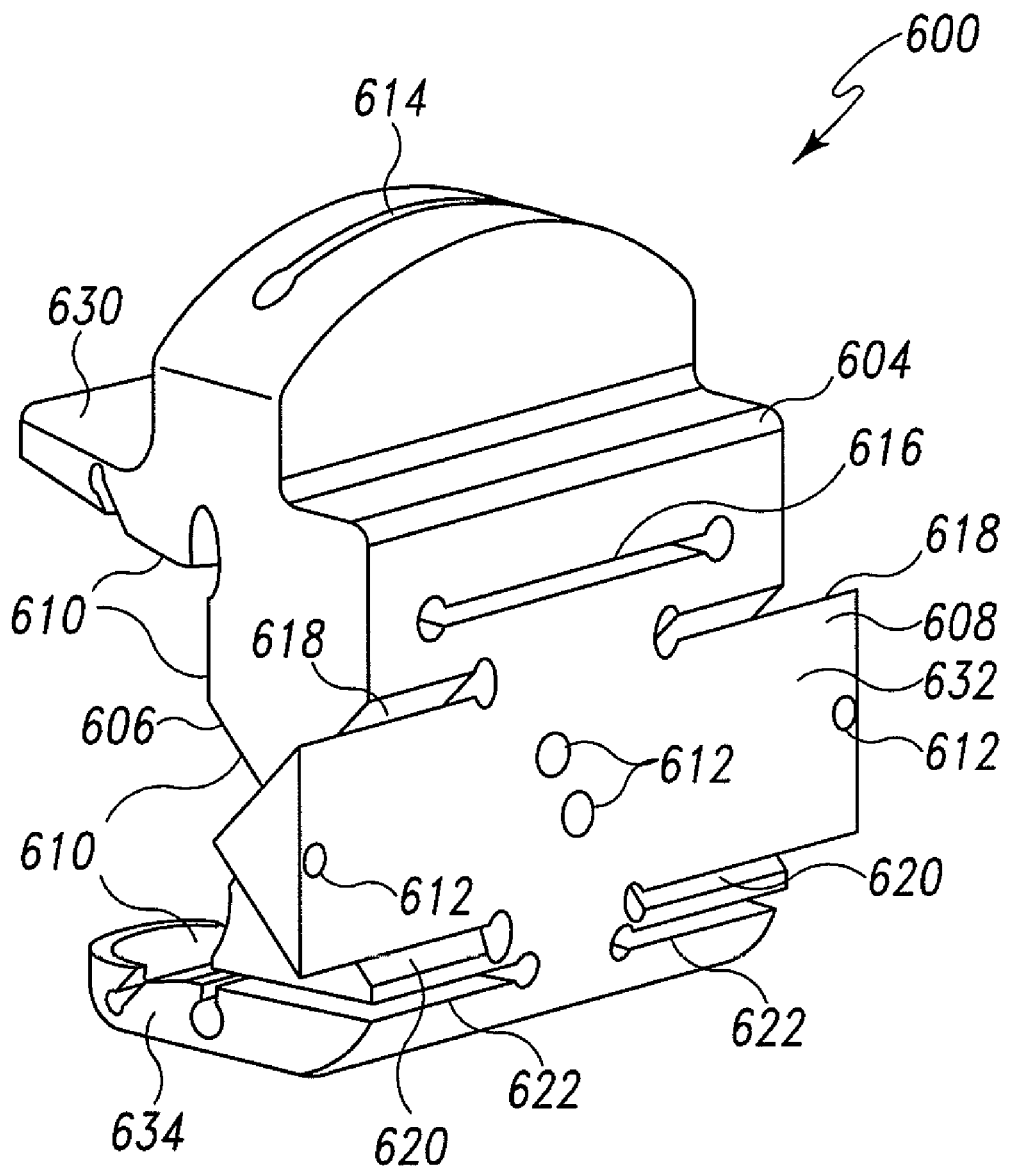
FIG. 35 is a perspective view of another embodiment of a customized patient-specific orthopaedic surgical instrument.
Figure 36:
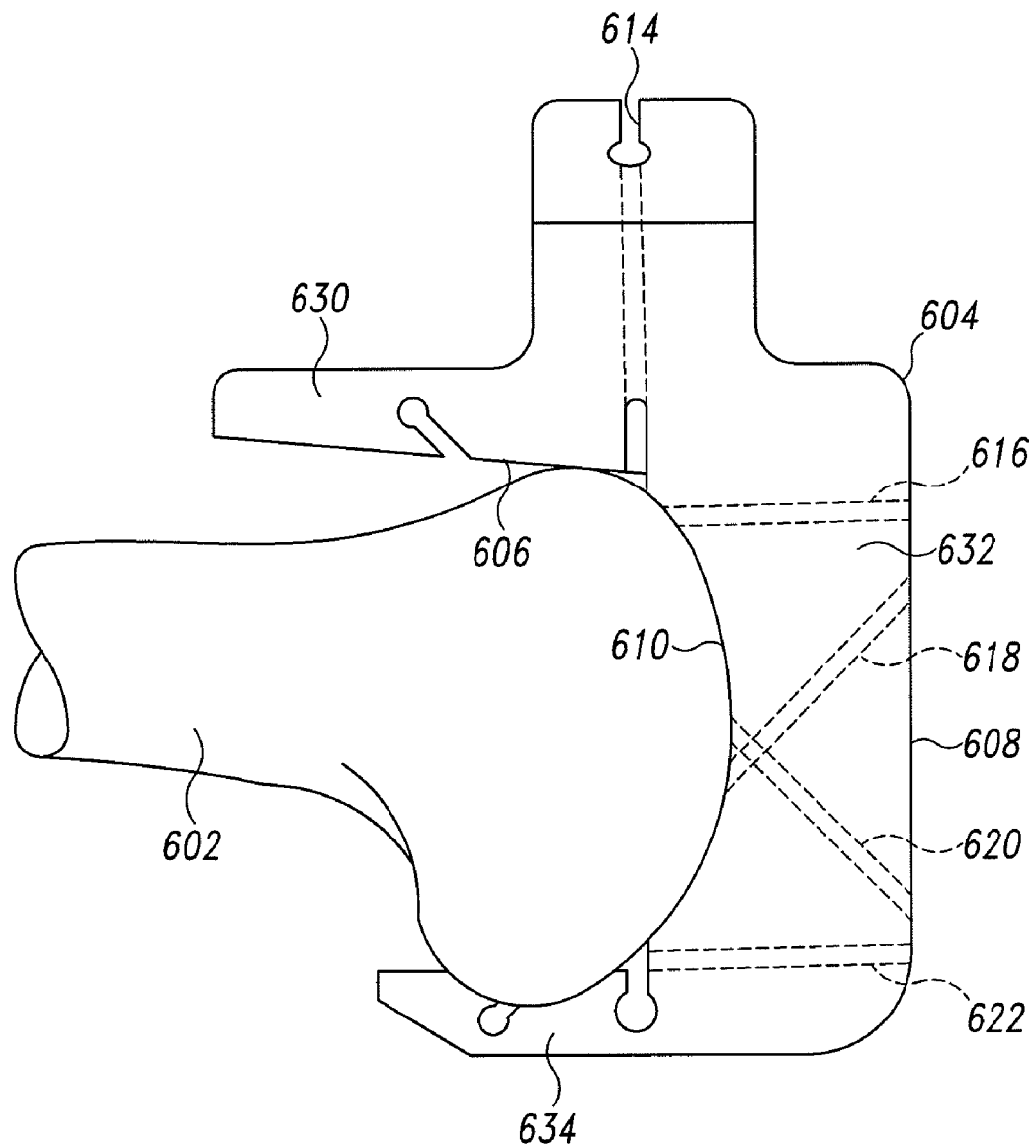
FIG. 36 is a side elevation view of the customized patient-specific orthopaedic surgical instrument of FIG. 35 coupled to a bone of a patient.

Referring now to FIGS. 35-36, in another embodiment, the customized patient-specific orthopaedic surgical instrument may be embodied as a 5-in-1 cutting block 600. The cutting block 600 is configured to be coupled to a bone 602, such as femur or tibia, of a patient as illustrated in FIG. 36. The cutting block 600 includes a body 604 having a bone-contacting or bone-facing surface 606 and an outer surface 608. The bone-contacting surface 606 includes a negative contour 610 configured to receive a portion of the patient's bone 602 having a corresponding contour. As discussed above, the negative contour 610 of the bone-contacting surface 606 allows the positioning of the cutting block 600 on the patient's bone 602 in a unique pre-determined location and orientation. As shown in FIGS. 35 and 36, the cutting block 600 is generally U-shaped and is configured to reference features on the anterior, distal, and posterior sides of the patient's bone. Specifically, the cutting block 600 has a customized patient-specific negative contour 610 defined in each of an anterior plate 630 which is configured to receive a portion of the anterior side of the patient's bone, a distal plate 632 which is configured to receive a portion of the distal side of the patient's bone, and a posterior plate 634 which is configured to receive a portion of the posterior side of the patient's bone.

The cutting block 600 also includes a number of pin guides 612. In use, the pin guides 612 are used as drill guides to establish guide pinholes in the bone 602 of the patient for securing a number of guide pins (not shown) to the bone. The cutting block 600 may then be coupled and secured to the patient's bone 602 via the guide pins.

The cutting block 600 also includes five captured cutting guides 614, 616, 618, 620, 622. The illustrative cutting guide 614 is a distal cutting guide, the cutting guide 616 is an anterior cutting guide, and the cutting guide 622 is a posterior cutting guide. The cutting guides 618, 620 are angled cutting guides used to prepare the femoral chamfer. It should be appreciated that the cutting guides 614, 616, 618, 620, 622 allow the orthopaedic surgeon to perform up to five different bone cuts using the same cutting block 600.

In use, the cutting block 600 is configured to be coupled to a patient's bone 602, such as the femur or tibia. Again, because the bone-contacting surface 606 of the cutting block 600 includes negative contour 610, the block 600 may be coupled to the bone 602 in a pre-planned, unique position. The cutting block 600 may be secured to the bone 602 via use of a number of guide pins (not shown) received in the pin guides 612 and the bone 602. After the cutting block 600 has been secured to the patient's bone 602 as illustrated in FIG. 36, the orthopaedic surgeon may use the block 600 to perform any one of a number of resections of the bone 602 using one or more of the cutting guides 614, 616, 618, 620, 622. It should be appreciated that, in some embodiments, a single cutting block 600 may be used to orient and complete all femoral bone cuts required for a total knee arthroplasty (TKA).

Figure 37:
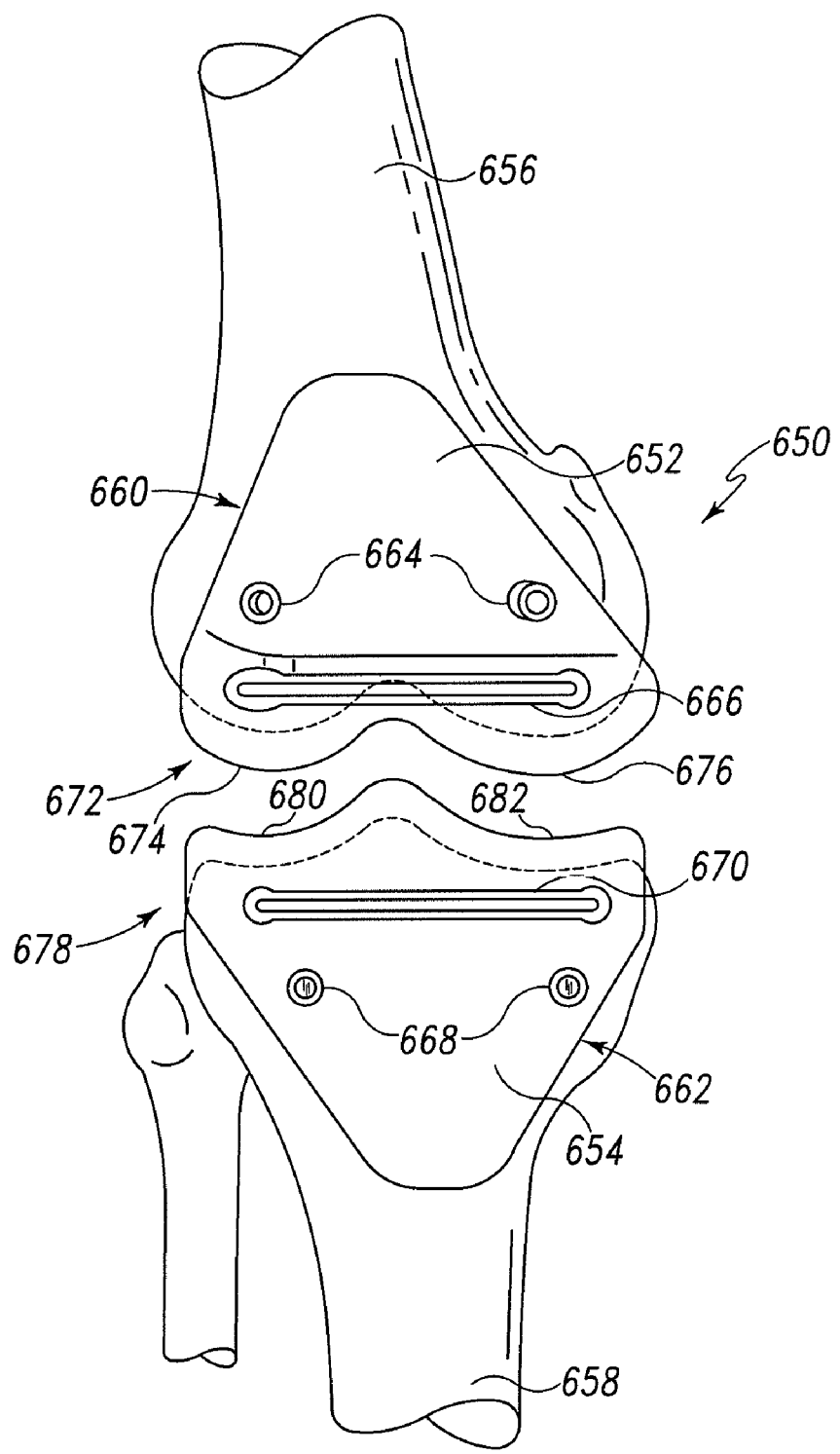
FIG. 37 is a anterior elevation view of another embodiment of a customized patient-specific orthopaedic surgical instrument coupled to the bony anatomy of a patient.

Referring now to FIG. 37, in another embodiment, the customized patient-specific orthopaedic surgical instrument 650 may be embodied as a pair of bone-cutting blocks 652, 654. The bone-cutting block 652 is a femoral cutting block and is configured to be coupled to a femur 656 of the patient. The bone-cutting block 654 is a tibial cutting block and is configured to be coupled to a tibia 658 of the patient. The bone-cutting block 652 includes a bone-contacting or bone-facing surface 660 having a negative contour (not shown) matching a portion of the contour of the femur 656. Similarly, the bone-cutting block 654 includes a bone-contacting or bone-facing surface 662 having a negative contour (not shown) matching a portion of the contour of the tibia 658. As discussed above, the negative contours of the blocks 652, 654 allow the positioning of the patient-specific cutting blocks 652, 654 on the patient's respective bone in a unique pre-determined location and orientation.

The femoral cutting block 652 includes a pair of pin guides 664. In use, the pin guides 664 are used as drill guides to establish guide pin holes in the femur 656. The cutting block 652 also includes a cutting guide 666. Illustratively, the cutting guide 666 is a captured cutting guide, but may be embodied as a non-captured or open cutting guide in other embodiments. Similarly, the tibial cutting block 654 includes a pair of pin guides 668 and a cutting guide 670. As discussed above, the cutting guides 666, 670 are used to guide a bone saw blade or other cutting device.

The cutting blocks 652, 654 also form a pair of trial blocks, such that the orthopaedic surgeon may analyze the motion of the patient's knee while performing the resectioning. That is, the distal end 672 of the femoral cutting block 652 includes a pair of trial condylar surfaces 674, 676 which have concave outer profiles that resemble the natural condyles of a femur. The proximal end 678 of the tibial cutting block 654 includes a pair of trial articular surfaces 680, 682 which have convex outer profiles which resemble the natural articular surfaces of the condyles of a tibia. The trial articular surfaces 680, 682 are configured to receive the trial condylar surfaces 674, 676 of the tibial cutting block 652.

In use, the cutting blocks 652, 654 are configured to be coupled to patient's femur 656 and tibia 658, respectively. Again, because each of the blocks 652, 654 include the respective negative contours, the blocks 652, 654 may be coupled to the respective bone 656, 658 in a pre-planned, unique position such that the cutting guides 666, 670 are positioned in a desired location relative to the respective bone 656, 658. After the cutting blocks 652, 654 have been secured to the femur 656 and tibia 658 of the patient, the orthopaedic surgeon may resect the femur 656 and the tibia 658 using the cutting guides 666, 670 with a bone saw or other cutting device. To do so, the surgeon may insert a bone saw blade of the bone saw into the cutting guide 666, 670. It should be appreciated that because the position of the cutting guides 666, 670 are pre-determined due to the configuration of the respective bone cutting blocks 652, 654, any bone cuts made using the patient-specific cutting blocks 652, 654 correspond to the predetermined bone cutting planes (see process step 24 of algorithm 10 described above in regard to FIG. 1). Additionally, the surgeon may manipulate the joint to analysis the movement of the joint using the trial-shaped ends of the blocks 652, 654.

Figure 38:
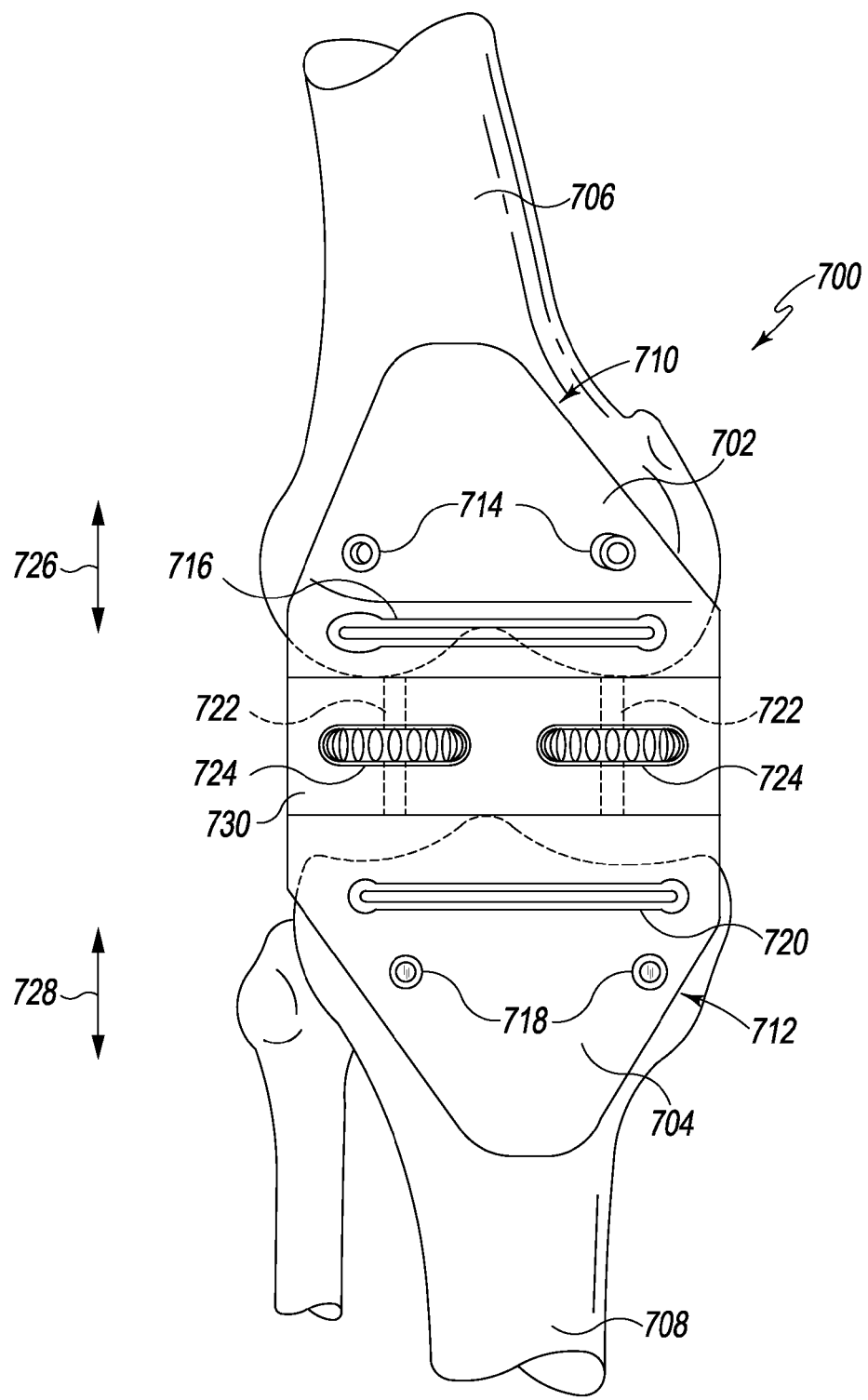
FIG. 38 is a anterior elevation view of another embodiment of a customized patient-specific orthopaedic surgical instrument coupled to the bony anatomy of a patient.

Referring now to FIG. 38, in another embodiment, the customized patient-specific orthopaedic surgical instrument 700 may be embodied as a pair of bone-cutting blocks 702, 704. The bone-cutting block 702 is a femoral cutting block and is configured to be coupled to a femur 706 of the patient. The bone-cutting block 704 is a tibial cutting block and is configured to be coupled to a tibia 708 of the patient. The bone-cutting block 702 includes a bone-contacting or bone-facing surface 710 having a negative contour (not shown) matching a portion of the contour of the femur 706. Similarly, the bone-cutting block 704 includes a bone-contacting or bone-facing surface 712 having a negative contour (not shown) matching a portion of the contour of the tibia 708. As discussed above, the negative contours of the blocks 702, 704 allow the positioning of the patient-specific cutting blocks 702, 704 on the patient's respective bone in a unique pre-determined location and orientation.

The femoral cutting block 702 includes a pair of pin guides 714. In use, the pin guides 714 are used as drill guides to establish guide pin holes in the femur 706. The cutting block 702 also includes a cutting guide 716. Illustratively, the cutting guide 716 is a captured cutting guide, but may be embodied as a non-captured or open cutting guide in other embodiments. Similarly, the tibial cutting block 704 includes a pair of pin guides 718 and a cutting guide 720. As discussed above, the cutting guides 716, 720 are used to guide a bone saw blade or other cutting device.

The cutting blocks 702, 704 are coupled to each other via a mechanical linkage 722. The mechanical linkage 722 may be embodied as any number of threaded bolts, gears, and the like for performing the functions described herein. Namely, rotation of the threaded shafts of the mechanical linkage 722 in one direction or the other moves the cutting blocks 702, 704 away from or toward each other. A pair of thumbwheels 724 are operably coupled to the mechanical linkage 722. The thumbwheels 724 are usable by the surgeon to operate the linkage 722 to move the cutting blocks 702, 704 away from or toward each other by, for example, rotating the threaded shafts of the mechanical linkage 722. That is, the thumbwheels 724 may be operated to move the femoral cutting block 702 in the direction of arrow 726 and the tibial cutting block 704 in the direction of arrow 728. In some embodiments, the mechanical linkage 722 may be positioned in a housing 730 positioned between the cutting blocks 702, 704.

In use, the cutting blocks 702, 704 are configured to be coupled to patient's femur 706 and tibia 708, respectively. Again, because each of the blocks 702, 708 include the respective negative contours, the blocks 702, 708 may be coupled to the respective bone 706, 708 in a pre-planned, unique position such that the cutting guides 716, 720 are positioned in a desired location relative to the respective bone 706, 708. After the cutting blocks 702, 704 have been secured to the femur 706 and tibia 708 of the patient, the orthopaedic surgeon may operate the thumbwheels 724 to adjust the relative position of the cutting blocks 702, 704 (e.g., move the blocks 702, 704 toward or away from each other).

After the position of the cutting blocks 702, 704 relative to each other has been adjusted, the surgeon may resect the femur 706 and the tibia 708 using the cutting guides 716, 720 with a bone saw or other cutting device. It should be appreciated that because the position of the cutting guides 716, 720 are pre-determined due to the configuration of the respective bone cutting blocks 702, 704 any bone cuts made using the patient-specific cutting blocks 702, 704 correspond to the predetermined bone cutting planes (see process step 24 of algorithm 10 described above in regard to FIG. 1).

Figure 39:
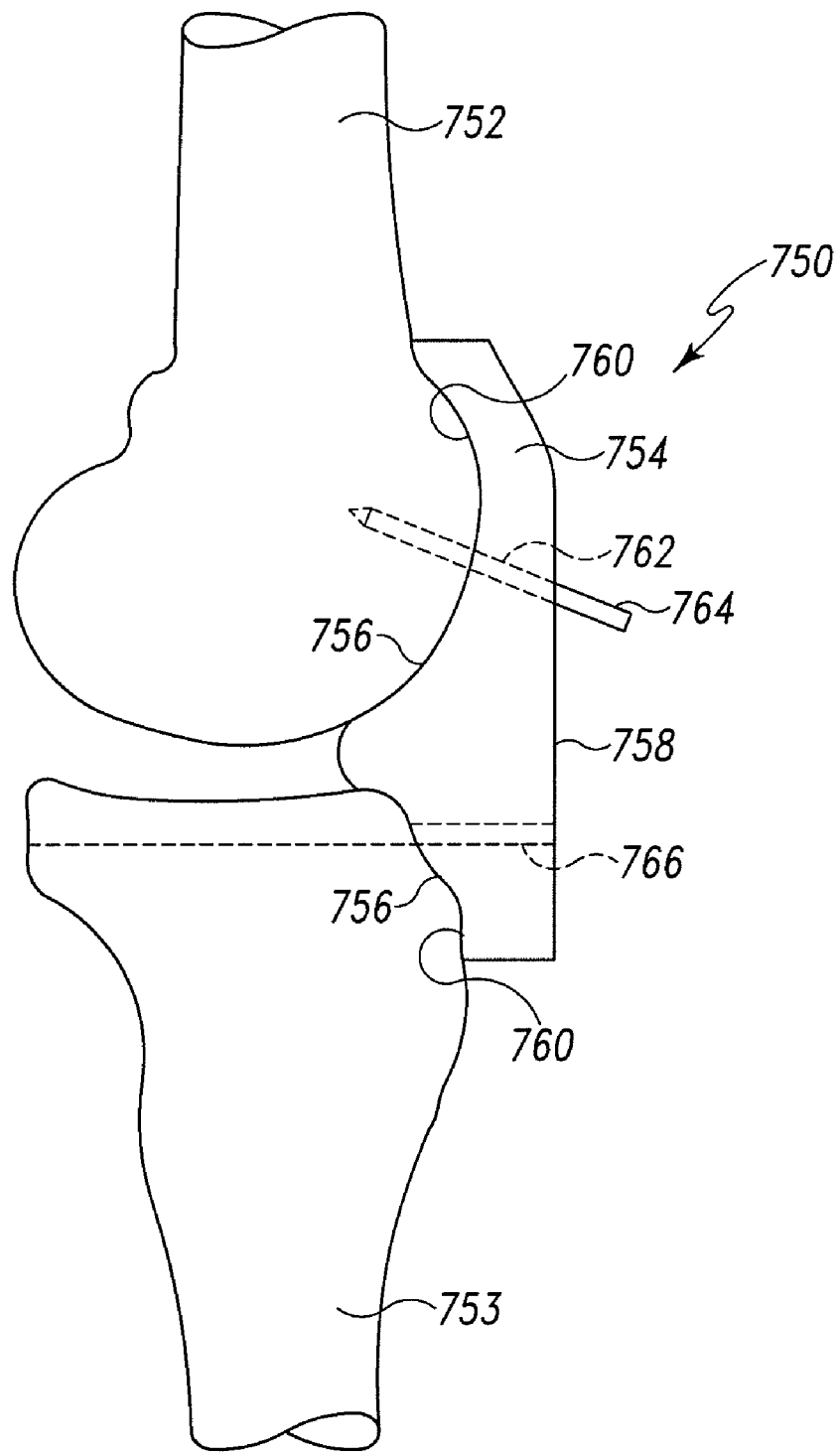
FIG. 39 is a side elevation view of another embodiment of a customized patient-specific orthopaedic surgical instrument coupled to a bone of a patient.

Referring now to FIG. 39, in another embodiment, the customized patient-specific orthopaedic surgical instrument may be embodied as a cutting block 750 configured to be coupled to or otherwise contact the femur 752 and/or tibia 753 of the patient. The cutting block 750 includes a body 754 having a bone-contacting or bone-facing surface 756 and an outer surface 758. In the illustrative embodiment shown in FIGS. 39-41, the body 754 is monolithic. The bone-contacting surface 756 includes a negative contour 760 configured to receive a portion of the patient's bone 752, 753 having a corresponding contour. As discussed above, the negative contour 760 of the bone-contacting surface 756 allows the positioning of the cutting block 750 on the patient's bone in a unique pre-determined location and orientation.

The cutting block 750 also includes a number of pin guides 762. In the illustrative embodiment of FIG. 39, the pin guides 762 are positioned on the body 754 of the cutting block 750 such that the cutting block 750 may be secured to the femur 752. That is, the guides 762 may be used as a drill guide to establish guide pin holes in the femur 752 of the patient for securing a number of guide pins 764 to the femur 752. The cutting block 750 may then be coupled and secured to the femur 752 via the guide pins 764. The cutting block 750 also includes a tibial cutting guide 766. Illustratively, the cutting guide 766 is a captured cutting guide, but may be embodied as a non-captured or open cutting guide in other embodiments.

In use, the cutting block 750 is configured to be coupled to the patient's femur 752 and tibia 753. That is, the guides 762 may be used to secure the cutting block 750 to the femur using a number of guide pins 764. The cutting block 750, however, is not secured to the patient's tibia 753. Again, because the bone-contacting surface 756 of the block 750 includes the negative contour 760, the block 750 may be coupled to the femur 752 and tibia 753 in a pre-planned, unique position. After the cutting block 750 has been secured to the patient's femur 752 via the guide pins 764, the surgeon may resect the patient's tibia 753 using the cutting guide 766. Because the cutting block 750 references the femur 752 and the tibia 753, the stability of the block 750 may be increased relative to cutting blocks that reference only the tibia 753. That is, because the femur 752 provides a larger surface area to reference with the block 750 relative to referencing only the tibia 753, the stability of the cutting block 750 may be improved. Additionally, in the illustrative embodiment of FIG. 39, the cutting block 750 is secured to the femur 752, rather than the tibia, to further stabilize the block.

Figure 40:
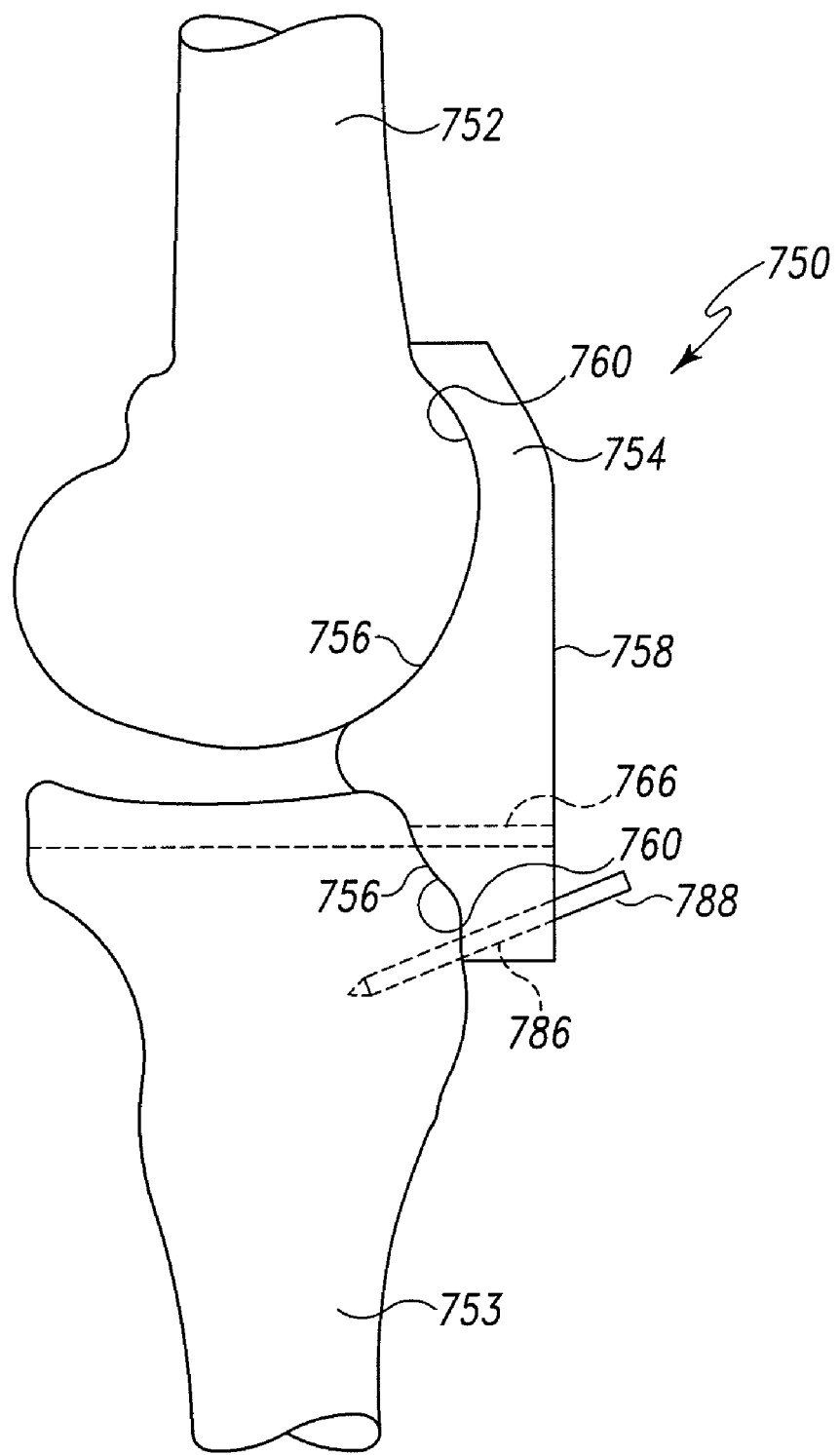
FIG. 40 is a side elevation view of another embodiment of a customized patient-specific orthopaedic surgical instrument coupled to a bone of a patient.

In other embodiments, the cutting block 750 may be secured to the tibia 753 rather than the femur 752 as illustrated in FIG. 40. In such embodiments, the cutting block 750 includes a tibial pin guide 786 for securing the block 750 to the tibia 753 via a number of guide pings 788. Although the cutting block 750 is secured to the tibia 753, the stability of the block 750 may be increased relative to cutting blocks that reference only the tibia 753 because the cutting block 750 references the femur 752 and the tibia 753 as discussed above.

Figure 41:
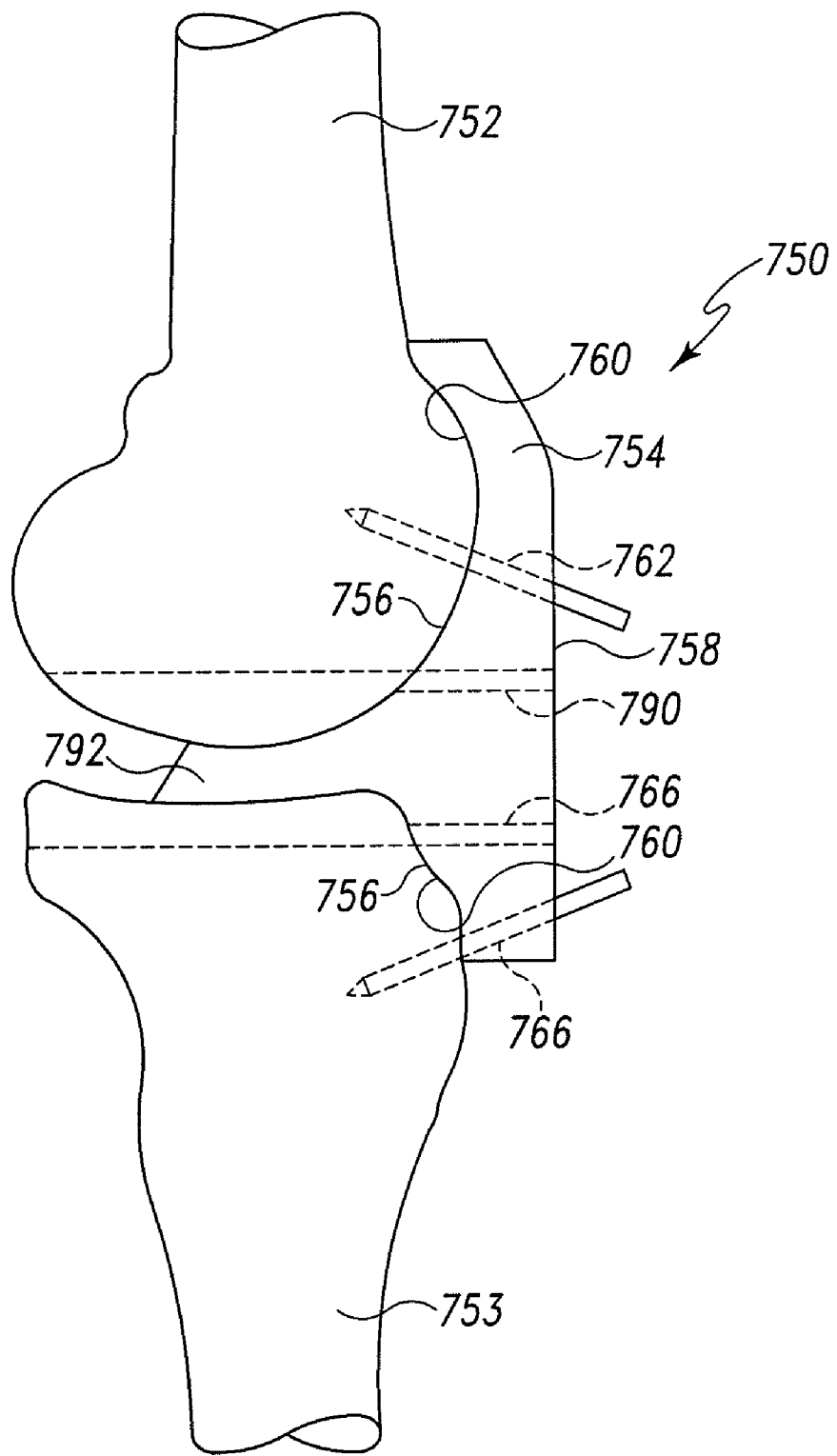
FIG. 41 is a side elevation view of another embodiment of a customized patient-specific orthopaedic surgical instrument coupled to a bone of a patient.

Additionally, in other embodiments, the cutting block 750 may be configured to be secured to the femur 752 and the tibia 753 as illustrated in FIG. 41. In such embodiments, the cutting block includes the femoral pin guides 762 and the tibial pin guides 766. Additionally, the cutting block 750 may include a femoral cutting guide 790 in addition to the tibia cutting guide 766. In such embodiments, the cutting block 750 may be used to resect the femur 752 and/or the tibia 753. Additionally, in such embodiment, the cutting block 750 may include a tongue 792 extending from the body 754. The tongue 792 is configured to be received between the femur 752 and the tibia 753 to further stabilize the cutting block 750. Again, because the cutting block 750 references the femur 752 and the tibia 753, the stability of the block 750 may be increased relative to cutting blocks that reference only the femur 752 or the tibia 753.

Figure 42:
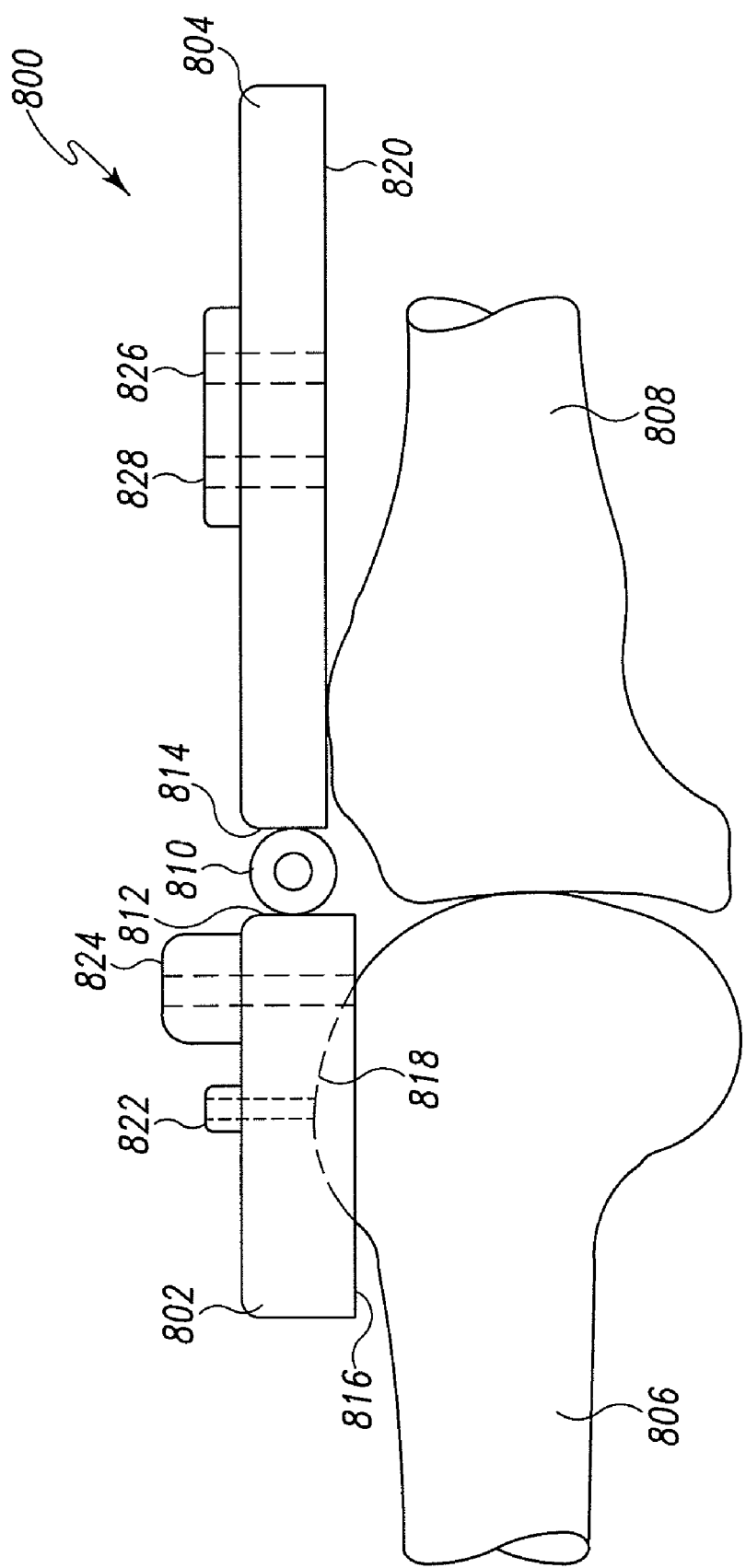
FIG. 42 is a side elevation view of another embodiment of a customized patient-specific orthopaedic surgical instrument coupled to the knee of a patient in extension.
Figure 43:
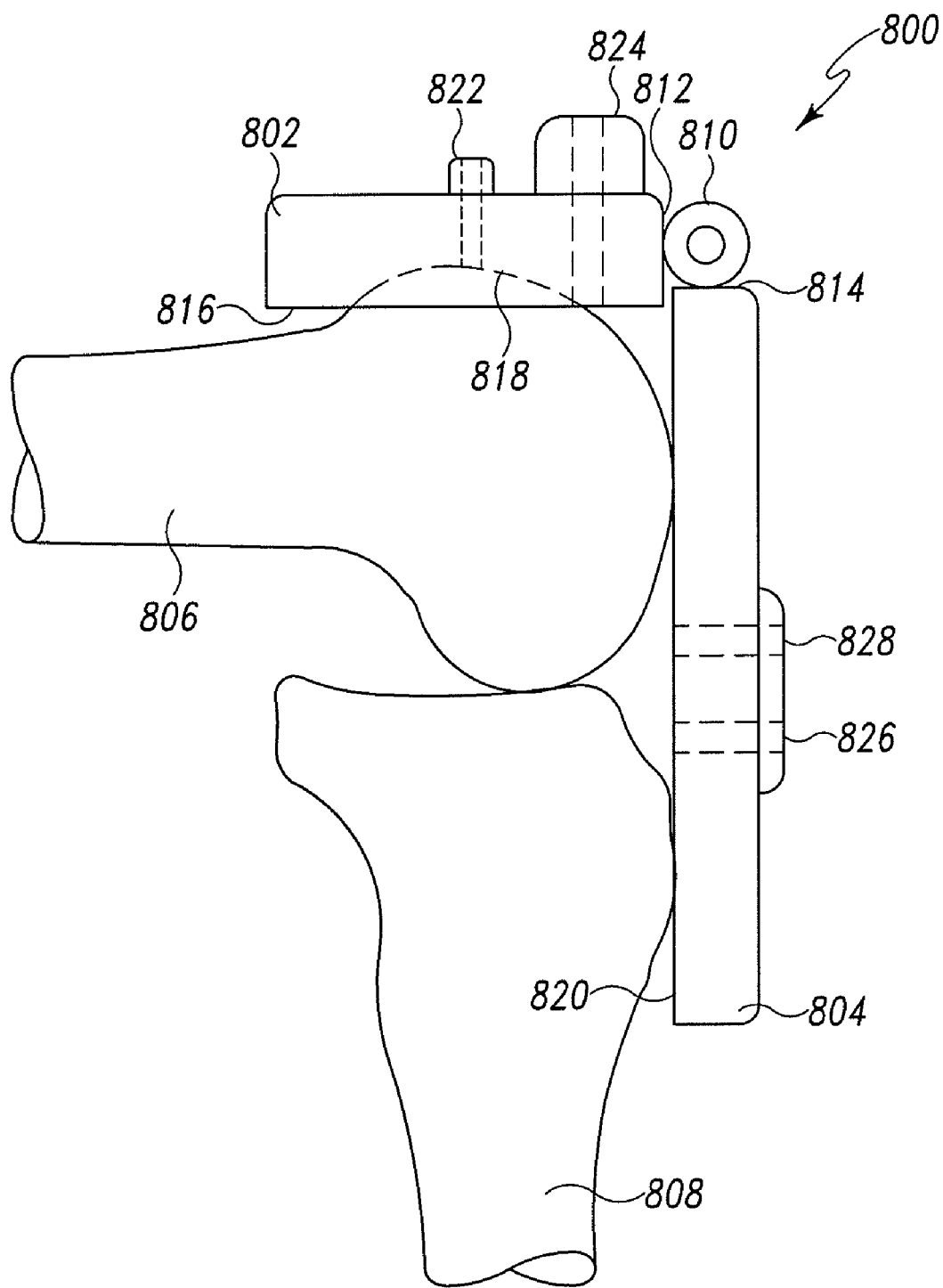
FIG. 43 is a side elevation view of the customized patient-specific orthopaedic surgical instrument of FIG. 42 with the patient's knee in flexion.
Figure 44:
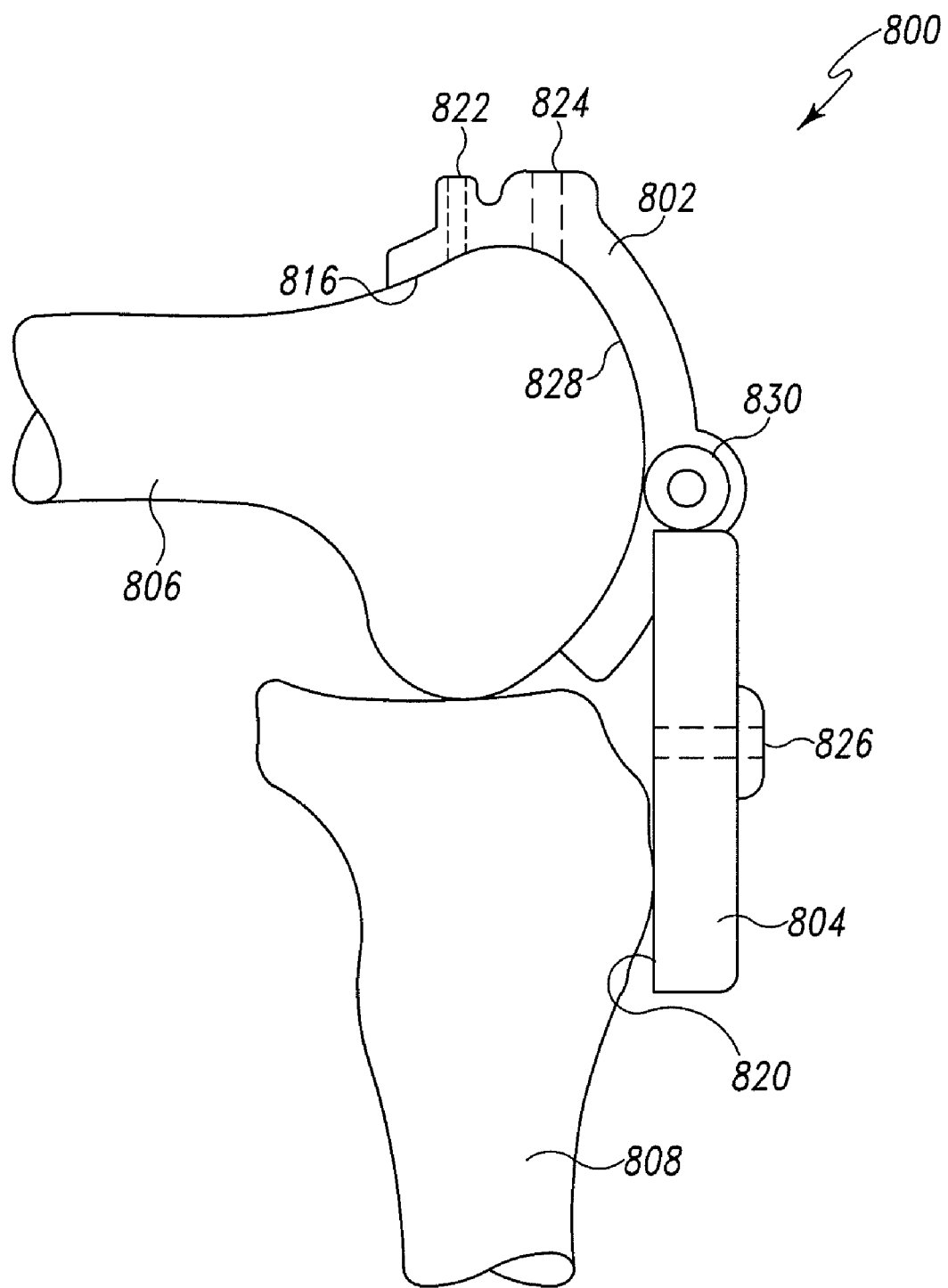
FIG. 44 is a side elevation view of another embodiment of a customized patient-specific orthopaedic surgical instrument coupled to a patient's knee in flexion.

Referring now to FIGS. 42-44, in another embodiment, the customized patient-specific orthopaedic surgical instrument 800 may be embodied as a pair of bone-cutting blocks 802, 804. The bone-cutting block 802 is a femoral cutting block and is configured to be secured to a femur 806 of the patient. The bone-cutting block 804 is a tibial cutting block and is configured to be coupled to or otherwise confront a tibia 808 of the patient. The cutting blocks 802, 804 are coupled to each via a hinge 810 secured to an end 812, 814 of each block 802, 804, respectively.

The femoral cutting block 802 includes a bone-contacting or bone-facing surface 816 having a negative contour 818 matching a portion of the contour of the femur 806. As discussed above, the negative contour 818 of the femoral cutting block 802 allows the positioning of the patient-specific femoral cutting block 802 on the patient's femur 806 in a unique pre-determined location and orientation. The tibia block 804 also includes a bone-contacting or bone-facing surface 820. In some embodiments, the bone-contacting surface 820 may be substantially planar. Alternatively, in other embodiments, the bone-contacting surface 820 may include a negative contour (not shown) matching a portion of the contour of the patient's tibia 808.

The femoral cutting block 802 includes a pair of pin guides 822. In use, the pin guides 822 are used as drill guides to establish guide pin holes in the femur 806. The femoral cutting block 802 also includes a distal femoral cutting guide 824. Illustratively, the cutting guide 824 is a captured cutting guide, but may be embodied as a non-captured or open cutting guide in other embodiments. Similarly, the tibial cutting block 804 includes a proximal tibial cutting guide 826. Additionally, in some embodiments, the tibial cutting block 804 may include a posterior femoral cutting guide 828.

In use, the femoral cutting block 802 is coupled to the patient's femur 806. Again, because the cutting block 802 includes the negative contour 818, the femoral cutting block 802 may be coupled to the femur 806 in a pre-planned, unique position. The femoral cutting block 802 is secured to the patient's femur 806 in extension using the pin guides 822. While the patient's leg is in extension, the orthopaedic surgeon may resect the distal end of the femur 806 using the femoral cutting guide 824. The orthopaedic surgeon may then position the patient's leg in flexion as illustrated in FIG. 43. When the patient's leg is moved to flexion, the tibial cutting block 804 follows the tibia 808 and is positioned relative to the tibia 808 such that the surgeon may perform a proximal cut on the tibia 808 using the tibial cutting guide 826. In embodiments wherein tibial cutting block 804 also includes the posterior femoral cutting guide 828, the orthopaedic surgeon may resect the posterior condyles of the femur 806 using the guide 828.

In some embodiments, the tibial cutting block 804 may be coupled to the femoral cutting block 802 via a hinge 830 positioned on the side of the femoral cutting block 802 as illustrated in FIG. 44. That is, the femoral cutting block 802 and the tibial cutting block 804 may be coupled by the hinge 830, which is positioned toward the medial or lateral side of the blocks 802, 804. In such a configuration, the femoral cutting block 802 may be configured to wrap around the distal end of the femur 806 as shown in FIG. 44 to provide additional stability to the cutting blocks 802, 804.

Figure 45:
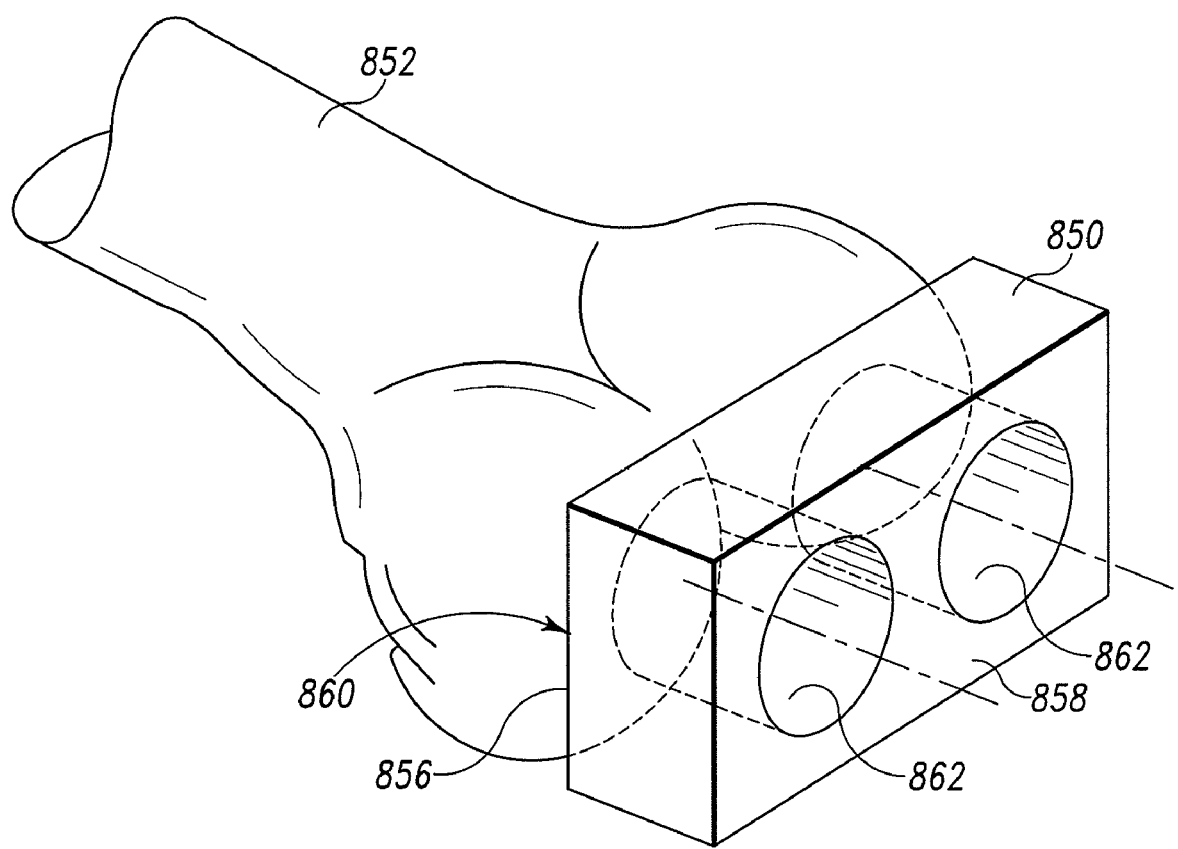
FIG. 45 is a perspective view of another embodiment of a customized patient-specific orthopaedic surgical instrument coupled to a bone of a patient.
Figure 46:
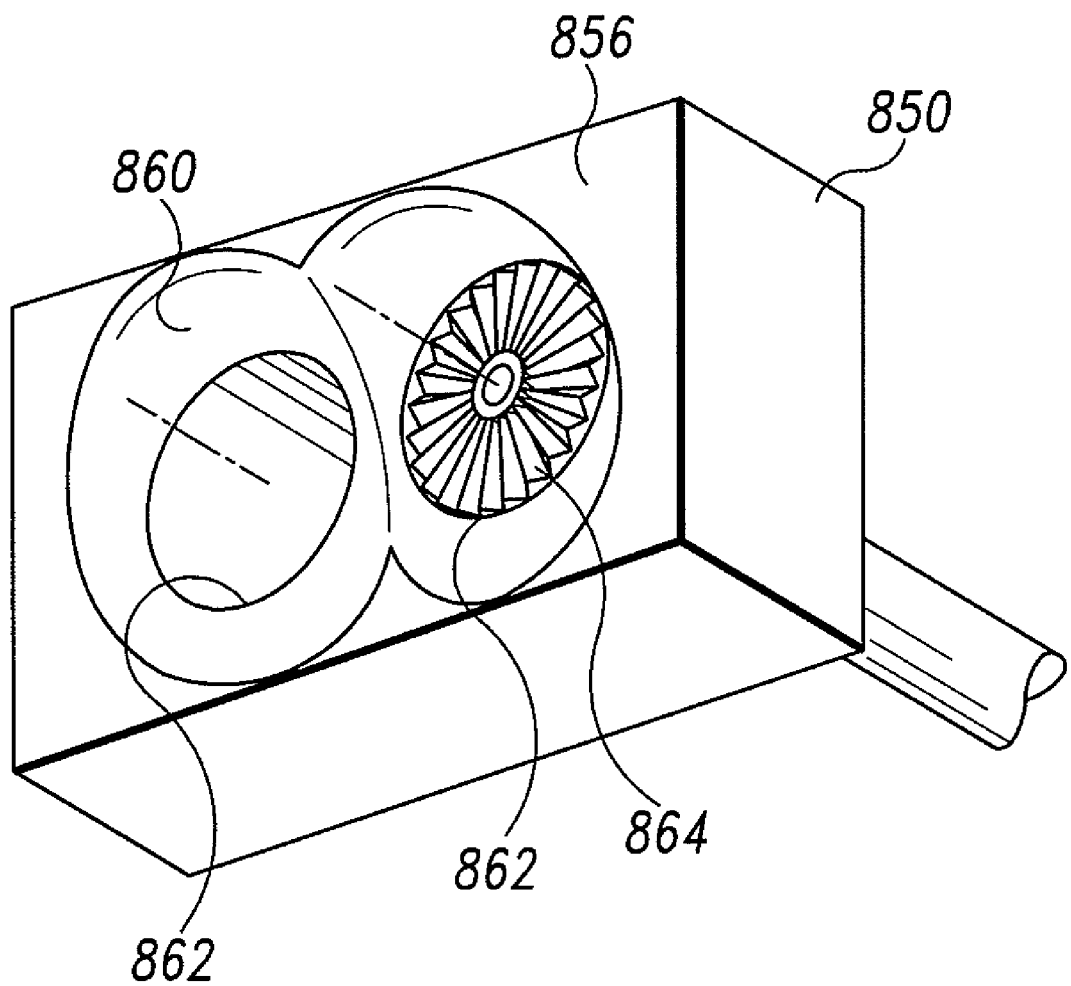
FIG. 46 is another perspective view of the customized patient-specific orthopaedic surgical instrument of FIG. 45.

Referring now to FIGS. 45-46, in another embodiment, the customized patient-specific orthopaedic surgical instrument may be embodied as a milling guide 850. The milling guide 850 is configured to be coupled to a bone 852, such as femur or tibia, of a patient. The milling guide 850 includes a bone-contacting or bone-facing surface 856 and an outer surface 858. The bone-contacting surface 856 includes a negative contour 860 (see FIG. 46) configured to receive a portion of the patient's bone 852 having a corresponding contour. As discussed above, the negative contour 860 of the bone-contacting surface 856 allows the positioning of the milling guide 850 on the patient's bone in a unique pre-determined location and orientation.

The milling guide 850 also includes a number of apertures 862. The apertures 862 are sized to guide the burr 864 of a milling machine. In use, the milling guide 850 may be coupled to the end of a patient's bone 852. Again, because the bone-contacting surface 856 of the milling guide 850 includes the negative contour 860, the guide 850 may be coupled to the bone 852 in a pre-planned, unique position. After the milling guide 850 has been coupled to the bone 852, the burr 864 may be inserted into one of the apertures 862 and operated to mill the bone as desired.

Figure 47:
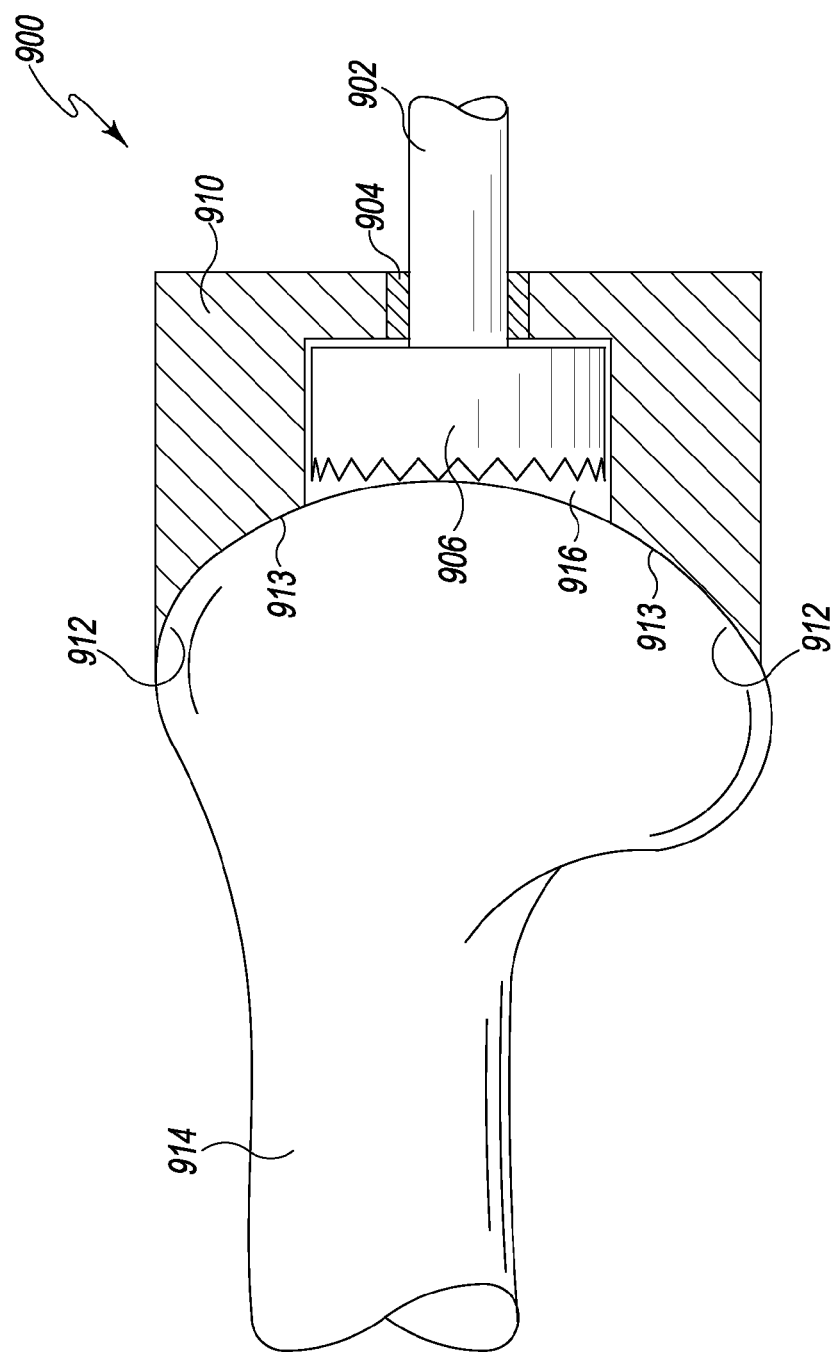
FIG. 47 is a cross-sectional elevation view of another embodiment of a customized patient-specific orthopaedic surgical instrument.

Referring now to FIG. 47, in another embodiment, the customized patient-specific orthopaedic surgical instrument may be embodied as a burring guide 900. The burring guide 900 is configured to be coupled to the end of a burring or milling machine. For example, the burring guide 900 may be coupled to the shaft 902 of the burring machine via a bushing 904. The busing 904 allows the shaft 902 and the burr end 906 of the burring machine to rotate while maintaining the burring guide 900 in a fixed position against the bone.

The burring guide 900 includes a body 910 having a bone-contacting or bone-facing surface 912. The bone-facing surface 912 includes a negative contour 913 defined therein. The negative contour 913 of the bone-contacting surface 912 is configured to receive a portion of the patient's bone 914 when the burring guide 900 is contacted thereto. Additionally, the bone-facing surface 912 includes an aperture 916 in which the burr end 906 is received.

Figure 48:
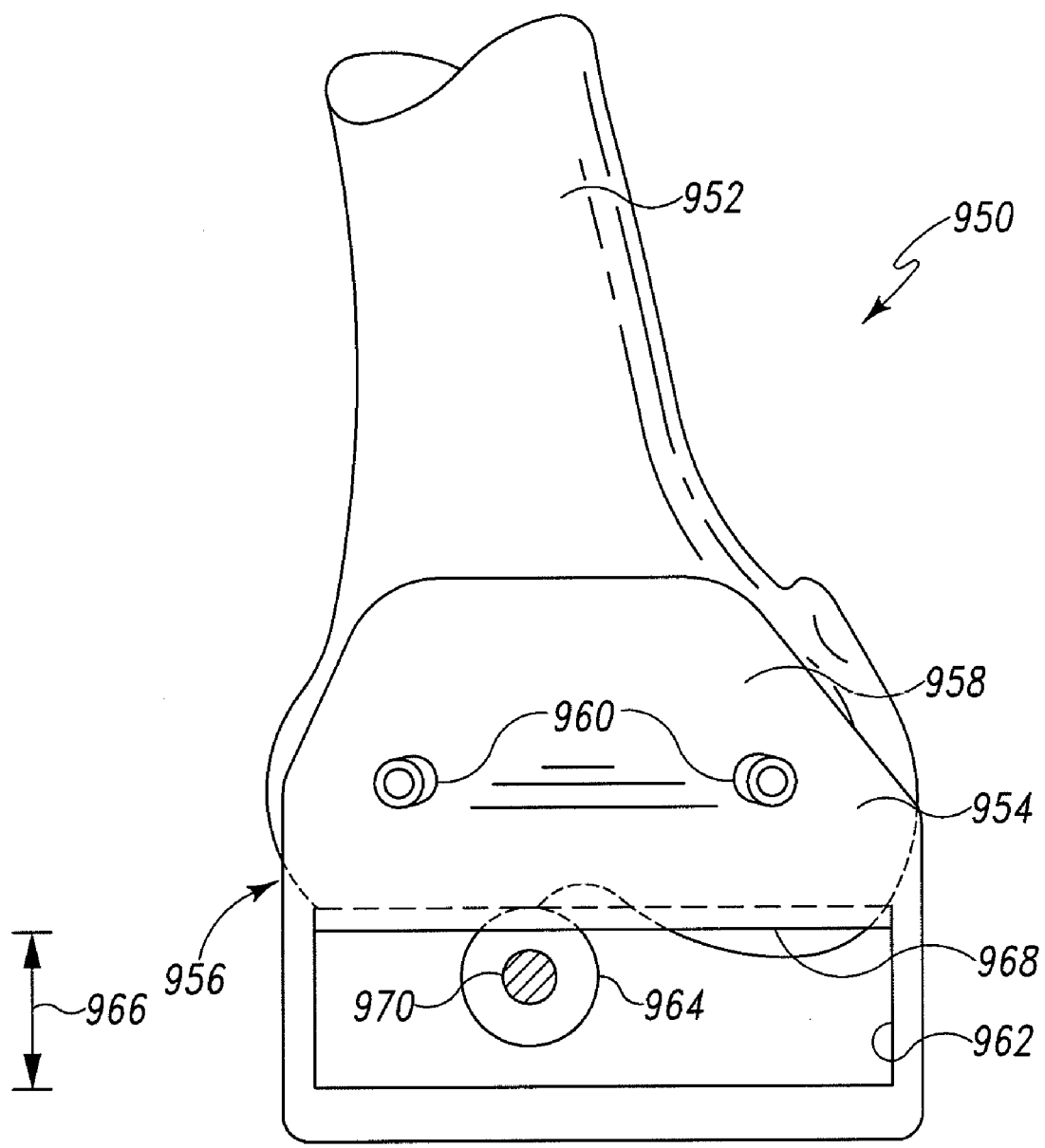
FIG. 48 is an anterior elevation view of another embodiment of a customized patient-specific orthopaedic surgical instrument coupled to a bone of a patient.
Figure 49:
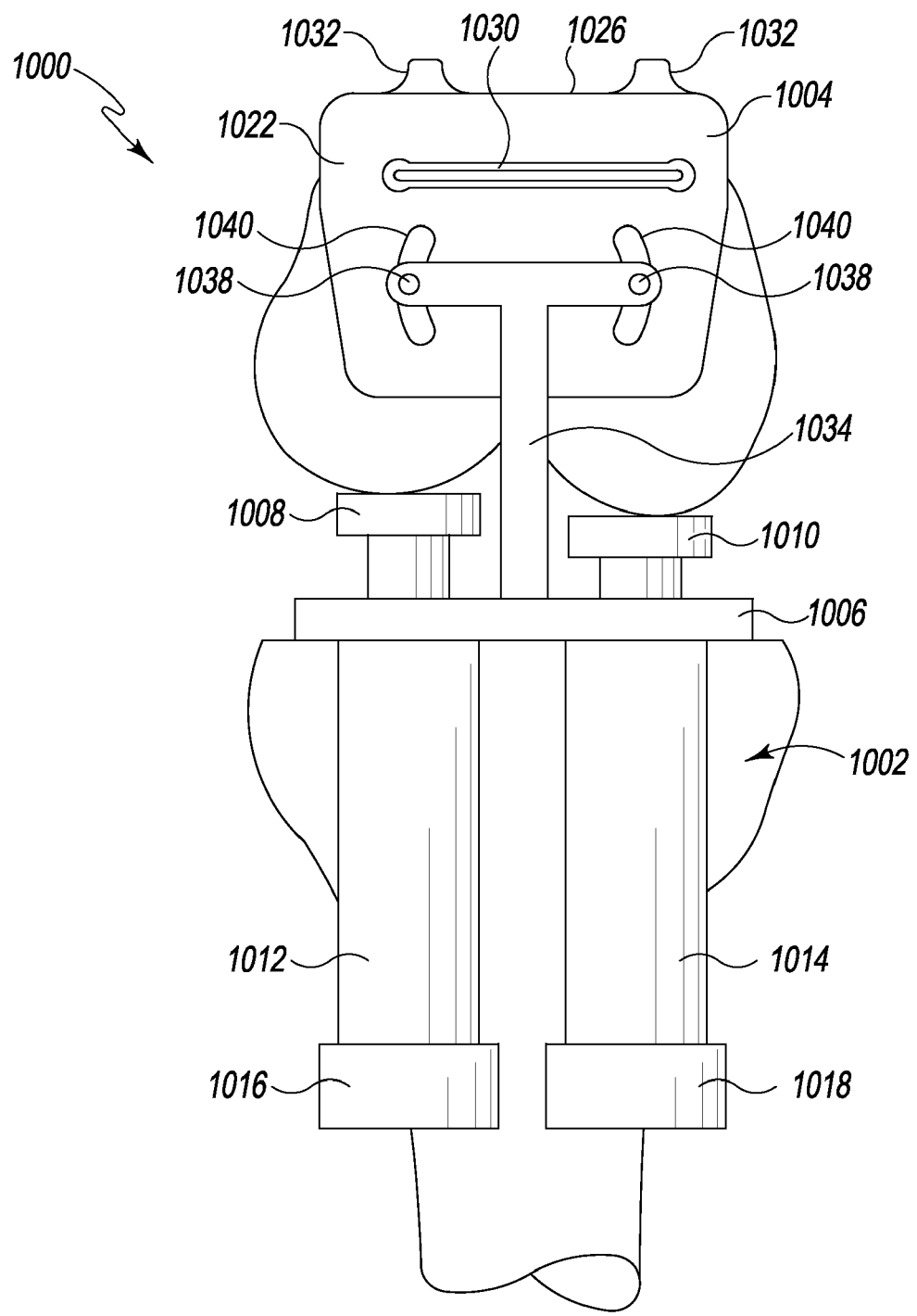
FIG. 49 is an anterior elevation view of another embodiment of a customized patient-specific orthopaedic surgical instrument coupled to a bone of a patient.

Referring now to FIG. 48, in another embodiment, the customized patient-specific orthopaedic surgical instrument may be embodied as a burring block 950. The burring block 950 is configured to be coupled to a bone 952, such as femur or tibia, of a patient. The burring block 950 includes a body 954 having a bone-contacting or bone-facing surface 956 and an outer surface 958. The bone-contacting surface 956 includes a negative contour (not shown) configured to receive a portion of the patient's bone 952 having a corresponding contour. As discussed above, the negative contour of the bone-contacting surface 956 allows the positioning of the burring block 950 on the patient's bone 952 in a unique pre-determined location and orientation.

The burring block 950 also includes a number of pin guides 960. In use, the pin guides 960 are used as drill guides to establish guide pin holes in the bone of the patient for securing a number of guide pins (not shown) to the bone. The burring block 950 may then be coupled and secured to the patient's bone 952 via the guide pins.

The burring block 950 also includes a burring aperture 962 defined in the body 954. The burring aperture 962 is sized to allow the burring end 964 of a burr machine to be inserted therein. That is, the burring aperture 962 has a width 966 sufficient to accept the diameter of the burring end 964 in addition to the portion of the bone 952 that extends therein. The inner wall 968, which defines the aperture 962, forms a burring guide. That is, during use, the shaft 970 of the burring machine may be run along the inner wall 968 as a guide to generate a planar resection on the bone 952.

Referring now to FIGS. 49-52, in another embodiment, the customized patient-specific orthopaedic surgical instrument 1000 includes a ligament balancer 1002 and a patient-specific femoral cutting block 1004 coupled to the ligament balancer 1002. The ligament balancer 1002 includes a tibial base plate 1006 and a pair of femoral paddles 1008, 1010, which are received in corresponding cylindrical housings 1012, 1014. A pair of knobs or other control devices 1016, 1018 are positioned at the base of the housings 1012, 1014 and are operatively coupled to the femoral paddles 1008, 1010. The knobs 1016, 1018 may be used to independently move each femoral paddles 1008, 1010 away from or toward the tibial base plate 1006 and tense the knee joint under proper tension to cause the femur to move to its optimal rotation with respect to the tibia.

Figure 50:
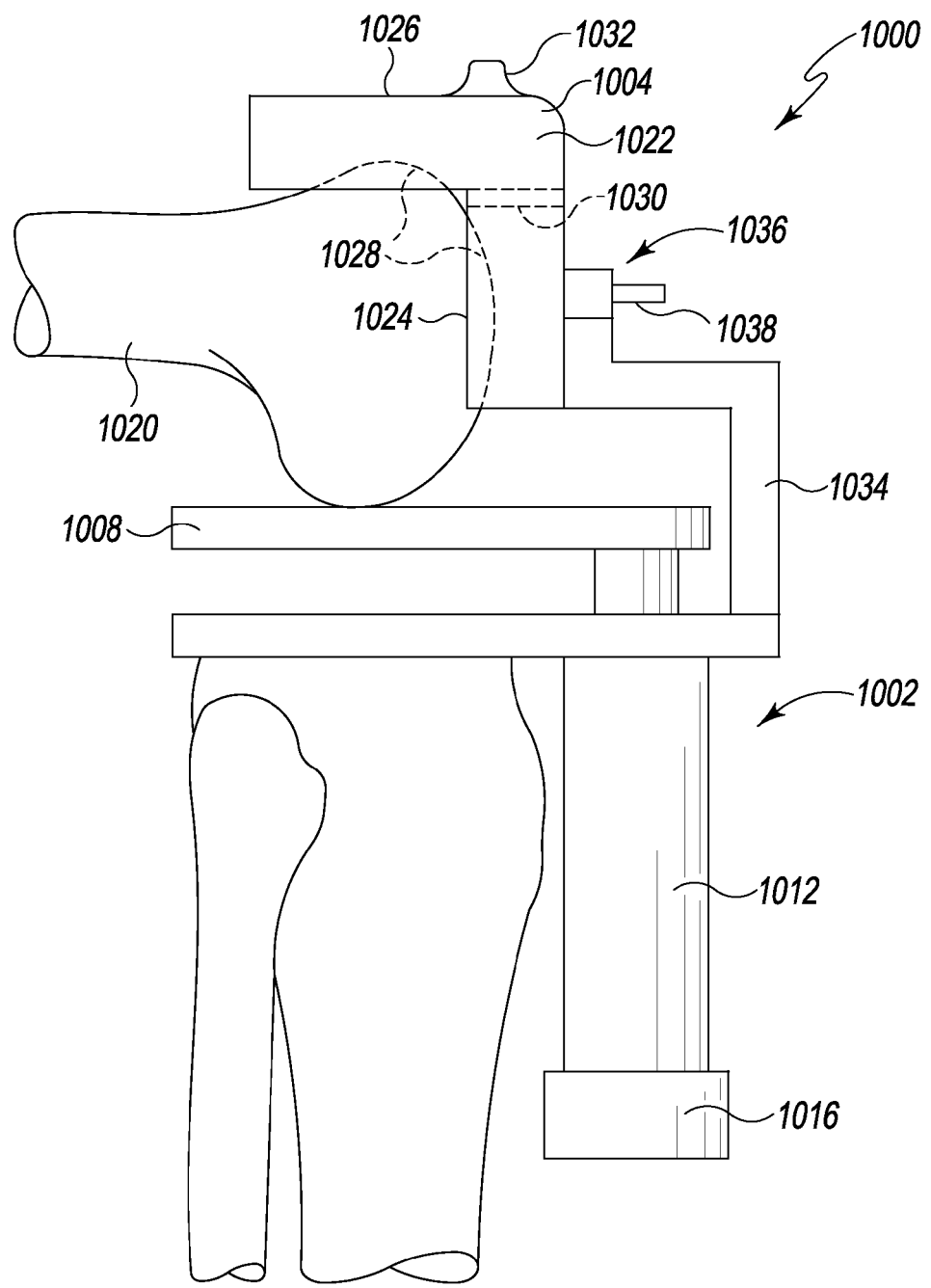
FIG. 50 is a side elevation view of the customized patient-specific orthopaedic surgical instrument of FIG. 49.

The cutting block 1004 is configured to be coupled to a bone 1020, such as femur or tibia, of a patient as illustrated in FIG. 50. The cutting block 1004 includes a body 1022 having a bone-contacting or bone-facing surface 1024 and an outer surface 1026. The bone-contacting surface 1024 includes a negative contour 1028 configured to receive a portion of the patient's bone 1020 having a corresponding contour. As discussed above, the negative contour 1028 of the bone-contacting surface 1024 allows the positioning of the cutting block 1004 on the patient's bone 1020 in a unique pre-determined location and orientation.

The cutting block 1004 also includes a femoral cutting guide 1030. The illustrative cutting guide 1030 is a captured cutting guide, but may be embodied as a non-captured or open cutting guide in other embodiments. The cutting block 1004 also includes a number of pin guides 1032 In use, the pin guides 1032 are used as drill guides to establish guide pin holes in the bone 1020 of the patient for securing a number of guide pins (not shown) to the bone.

The cutting block 1004 is coupled to the ligament balancer 1002 via a bracket 1034. The bracket 1034 includes a pair of apertures 1036 in which are received a pair of pins 1038. The body 1022 of the cutting block 1004 includes a pair of inwardly curving, elongated apertures 1040. The pins 1038 are received in the elongated apertures 1040 of the cutting block 1004 and secured into the bone 1020 of the patient. Additionally, the bracket 1034 orients the pair of pins 1038 in a line that is parallel to proximal surface of the tibia 1103. It should be appreciated that the elongated apertures 1040 allow the cutting block 1004 to be rotated relative to the ligament balancer 1002 as described below.

In use, the cutting block 1004 is coupled to the end of a patient's bone 1020, such as the femur. Again, because the bone-contacting surface 1024 includes the negative contour 1028, the block 1004 may be coupled to the bone 1020 in a pre-planned, unique position. The cutting block 1004 may be secured to the bone 1020 via use of the guide pins 1038. That is, the guide pins 1038 may be inserted into the elongated apertures 1040 and into the bone 1020 of the patient. The ligament balancer 1002 may then be coupled to the patient's bony anatomy. To do so, the base 1006 is placed on the proximal end of the patient's tibia and each paddle 1008, 1010 engages a condyle of the patient's femur 1020. The apertures 1036 of the bracket 1034 receive portions of the guide pins 1038, which extend from the elongated openings 1040 of the cutting block 1004. The orthopaedic surgeon may then adjust the ligament balancer as desired and resect the patient's bone 1020 using the femoral cutting guide 1030.

Figure 51:
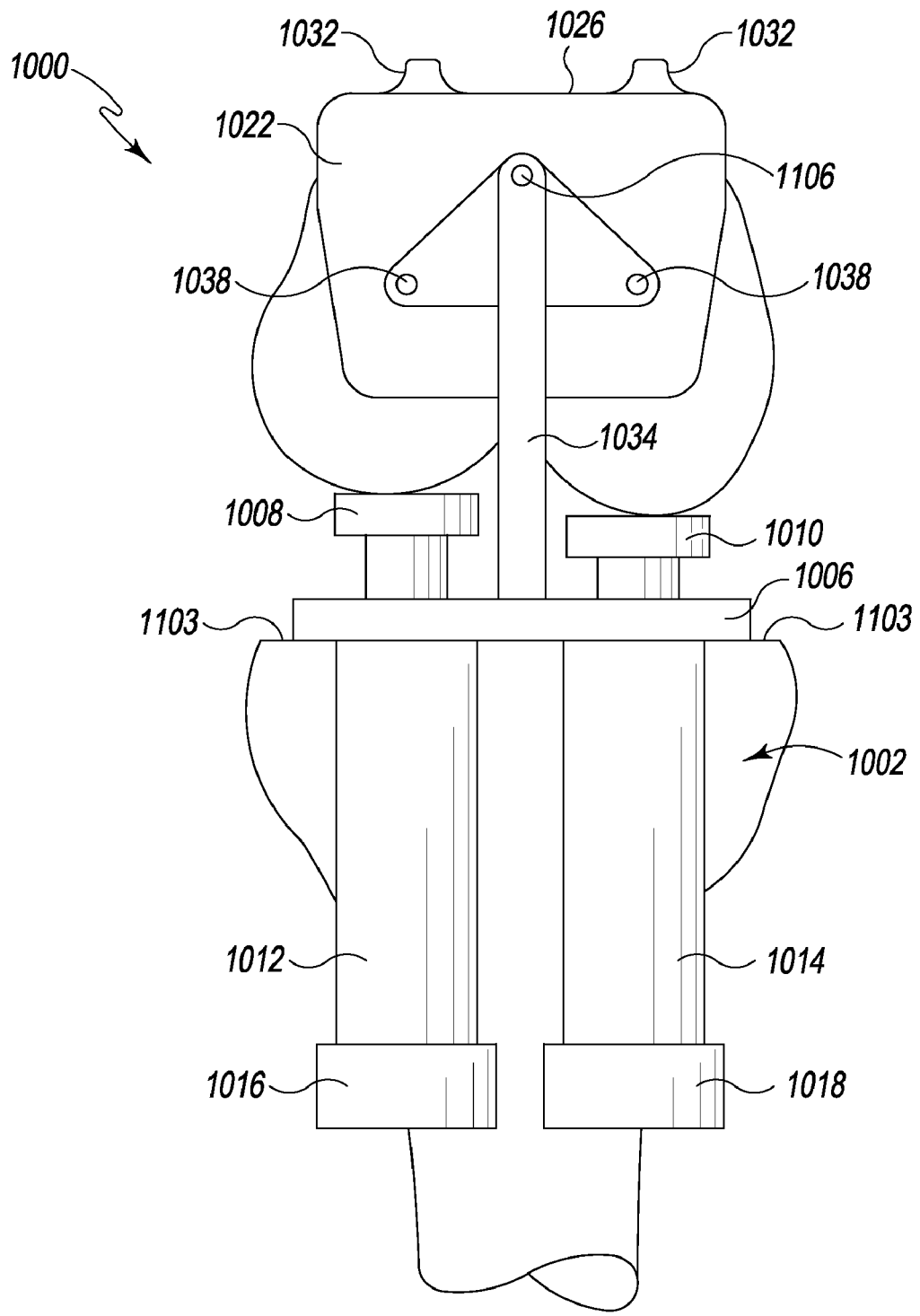
FIG. 51 is an anterior elevation view of another embodiment of a customized patient-specific orthopaedic surgical instrument.
Figure 52:
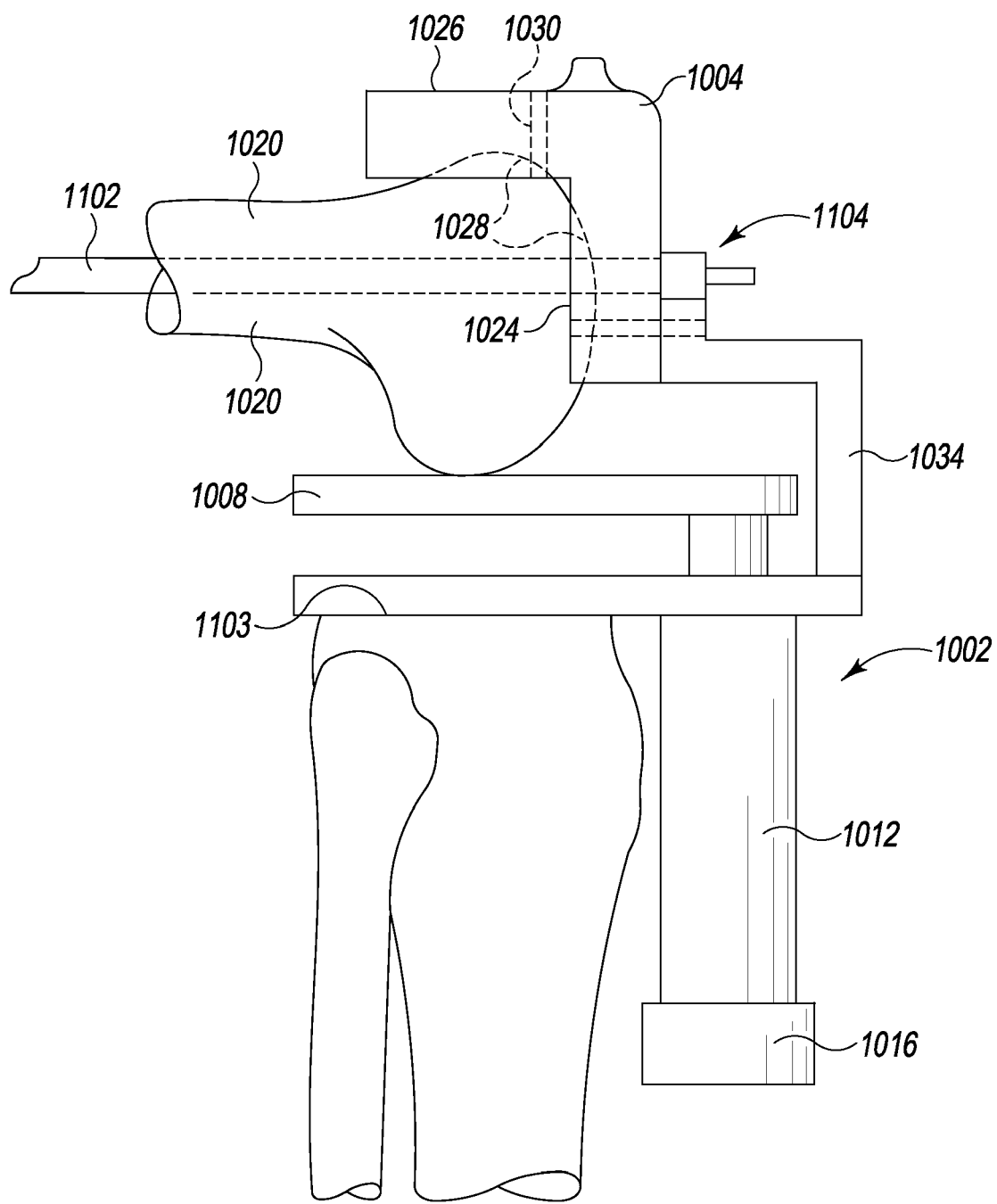
FIG. 52 is a side elevation view of another embodiment of a customized patient-specific orthopaedic surgical instrument coupled to a bone of a patient.
Figure 53:
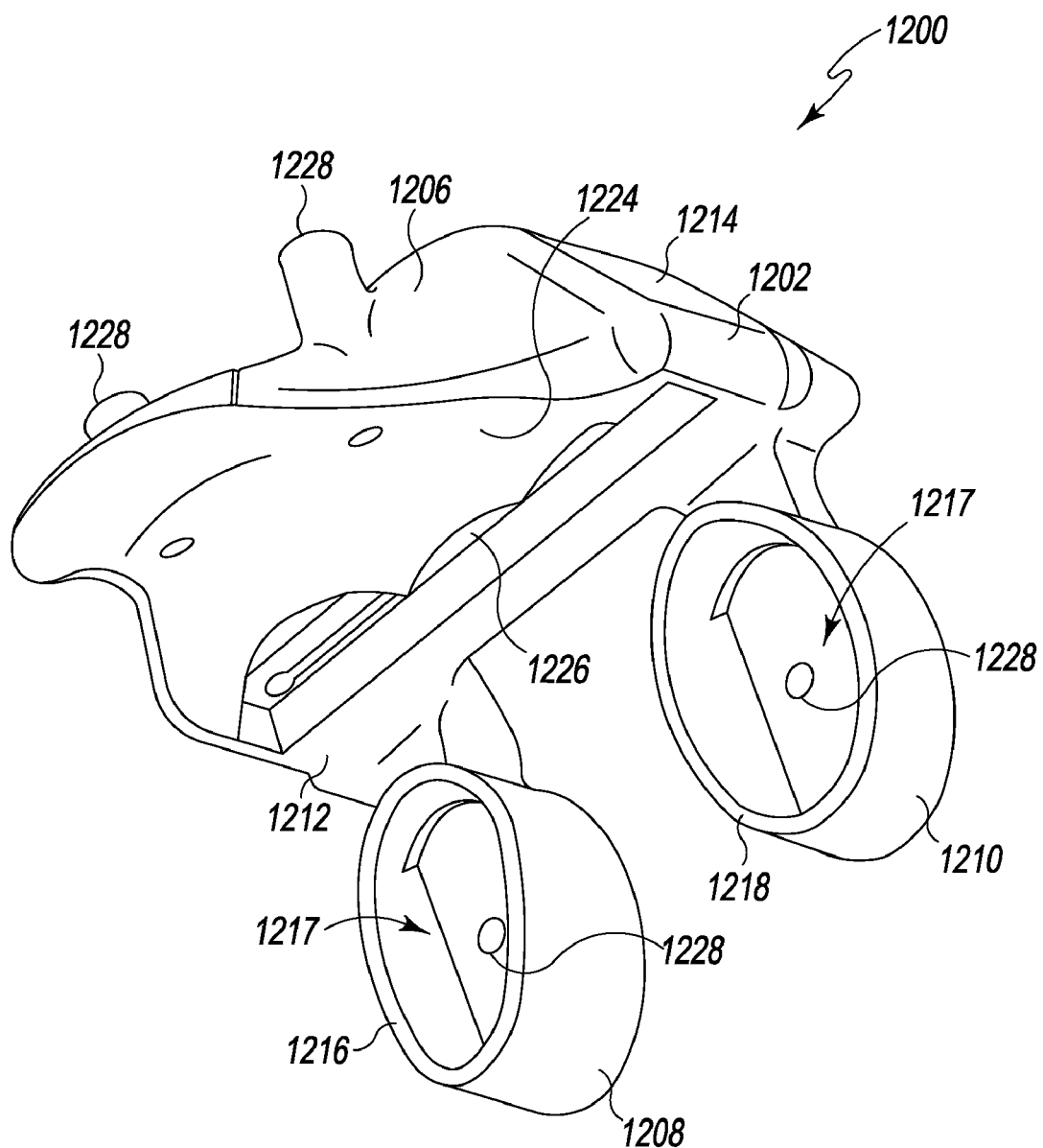
FIG. 53 is a perspective view of another embodiment of a customized patient-specific orthopaedic surgical instrument.
Figure 54:
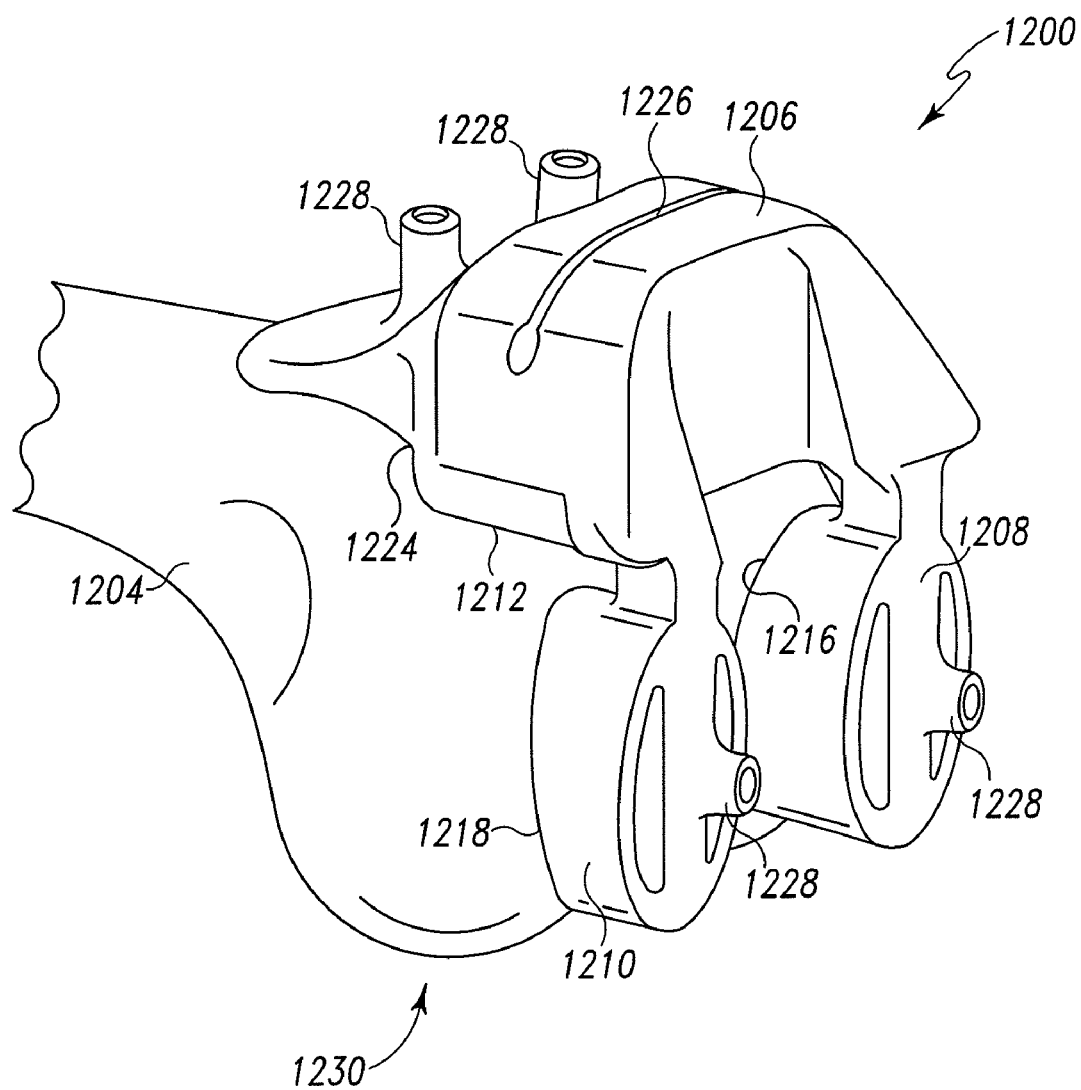
FIG. 54 is a perspective view of the customized patient-specific orthopaedic surgical instrument of FIG. 53 coupled to a bone of a patient.

In other embodiments, the ligament balancer 1002 may be configured to reference an intramedullar rod 1102 as illustrated in FIGS. 51-52. In such embodiments, the bracket 1034 includes a receiver 1104 configured to couple to the rod 1102. The intramedullar rod 1102 references the intramedullary canal of the femur 1020. The bracket 1034 of the ligament balancer 1002 provides a pivot point 1106 about which the femur 1020 may rotate while maintaining the pins 1038 in an approximate parallel orientation relative to the proximal surface 1103 of the patient's tibia Referring now to FIGS. 53-54, in another embodiment, the customized patient-specific orthopaedic surgical instrument may be embodied as a femoral cutting block 1200. The cutting block 1200 is configured to be coupled to a femur 1204 of a patient as illustrated in FIG. 54. The cutting block 1200 includes a body 1202 having an anterior wall 1206 and a pair of distal tabs 1208, 1210 extending out from the anterior wall 1206. During use, the anterior wall 1206 is configured to contact an anterior side of the femur 1204 and the distal tabs 1208, 1210 are configured to extend over the distal end of the femur 1204 as discussed in more detail below. The tabs 1208, 1210 each include a footpad 1216, 1218, respectively. The footpads 1216, 1218 are embodied as oval rings, each having a central recess 1217. As discussed in more detail below, the footpads 1216, 1218 are negatively contoured to contact a potion of the distal end of the femur 1204. In other embodiments, the footpads 1216, 1218 may have other configurations such as a circular shape.

The anterior wall 1206 includes a bone-contacting or bone-facing surface 1212 and an outer surface 1214. A negative contour 1224 is defined in the bone-contacting surfaces 1212 of the anterior wall of the body 1202. The negative contour 1224 is configured to receive a portion of the patient's femur 1204 having a corresponding contour. As discussed above, the negative contour 1224 of the bone-contacting surface 1212 allows the positioning of the cutting block 1200 on the patient's femur 1204 in a unique pre-determined location and orientation.

The cutting block 1200 includes a cutting guide 1226 defined in the anterior wall 1206. The thickness of the anterior wall 1206 around the cutting guide 1226 is increased relative to other portions of the wall 1206 to increase the depth of the cutting guide 1226. Illustratively, the cutting guide 1226 is a captured cutting guide. The femoral cutting block 1200 also includes a number of pin guides 1228 defined in the anterior wall 1206 and each distal tab 1208, 1210. The pin guides 1228 are used as drill guides to establish guide pin holes in the femur 1204 of the patient. Illustratively, the pin guides 1228 are divergent to prevent the cutting block 1200 from loosening under the vibrations of an orthopaedic bone saw. A number of guide pins (not shown) may then be inserted into the pin guides 1228 and the femur 1204 to secure the cutting block 1200 to the femur 1204. In one particular embodiment, the pin guides 1228 located on the distal tabs 1208, 1210 are used only as drill guides to establish pin holes in the femur 1204 for subsequent orthopaedic instruments.

In use, the femoral cutting block 1200 is coupled to the distal end 1230 of the patient's femur 1204 as illustrated in FIG. 54. Again, because the bone-contacting surface 1212 of the cutting block 1200 includes the negative contour 1224, the block 1200 may be coupled to the femur 1204 in a pre-planned, unique position. When so coupled, a portion of the anterior side of the femur 1204 is received in the negative contour 1224 of the anterior wall 1206 of the block 1200 and the distal tabs 1208, 1210 extend over the end of the femur 1204. The footpads 1216, 1218 of the tabs 1208, 1210 contact the distal end of the patient's femur 1204. However, the portions of the femur 1204 over which the recess 1217 is positioned are not referenced. That is, the recess 1217 may or may not receive portions of the patient's femur 1204. As such, the footpads 1216, 1218 may be positioned relative to the body 1202 of the cutting block 1200 such that the recess 1217 are positioned over portions of the femur 1204 that are not visible in the medical images (see process steps 12, 20, 24 of the algorithm 10 illustrated in and described above in regard to FIG. 1). As such, those portions of the femur 1204 that are not reproduced in the medical images because, for example, of limitations of the imaging modality or aspects of the patient's particular bony anatomy, are not referenced to improve the fitting of the block 1200. After the femoral cutting block 1200 has been coupled to the patient's femur 1204, the orthopaedic surgeon may resect the femur 1204 using the cutting block 1200.

Figure 55:
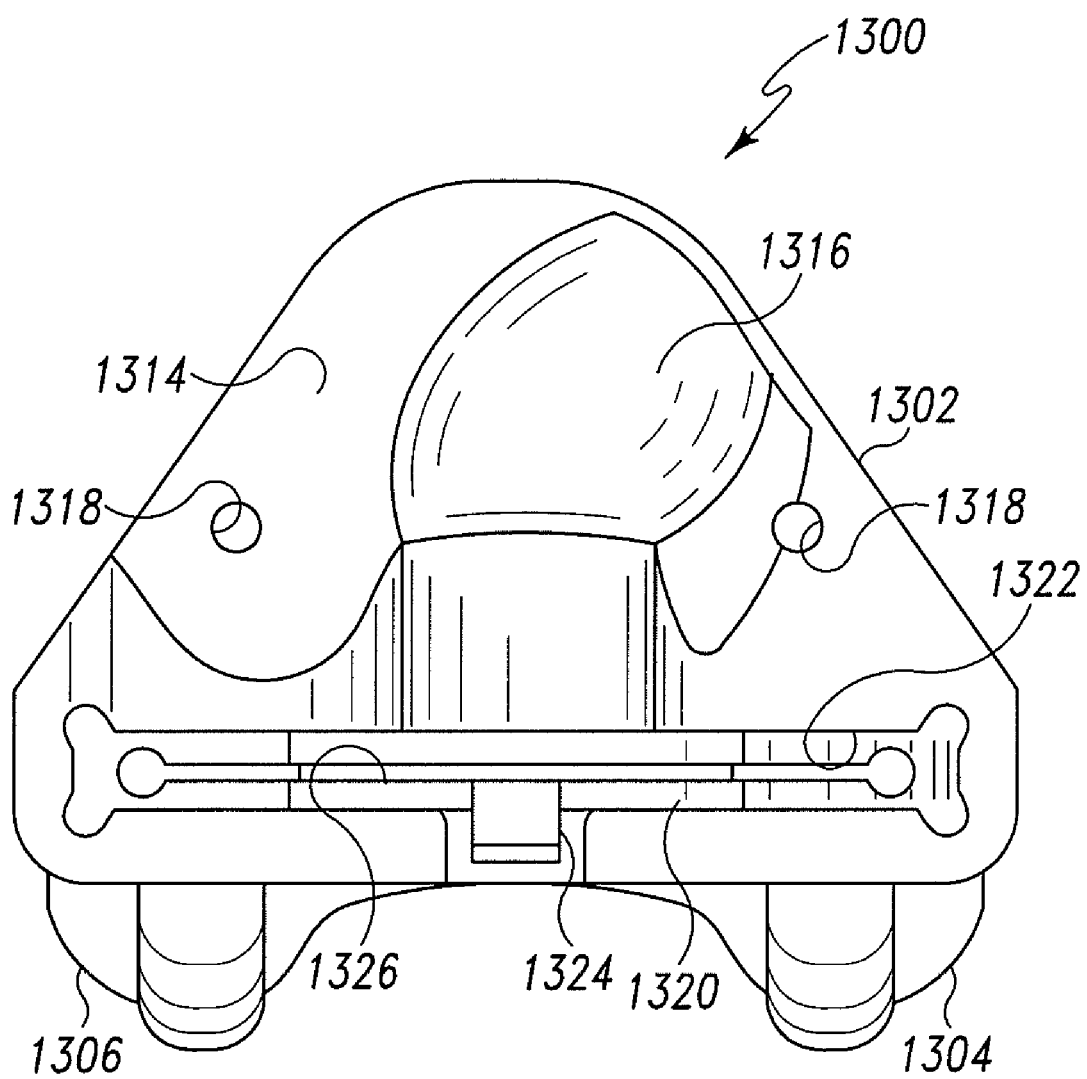
FIG. 55 is an anterior elevation view of another embodiment of a customized patient-specific orthopaedic surgical instrument.
Figure 56:
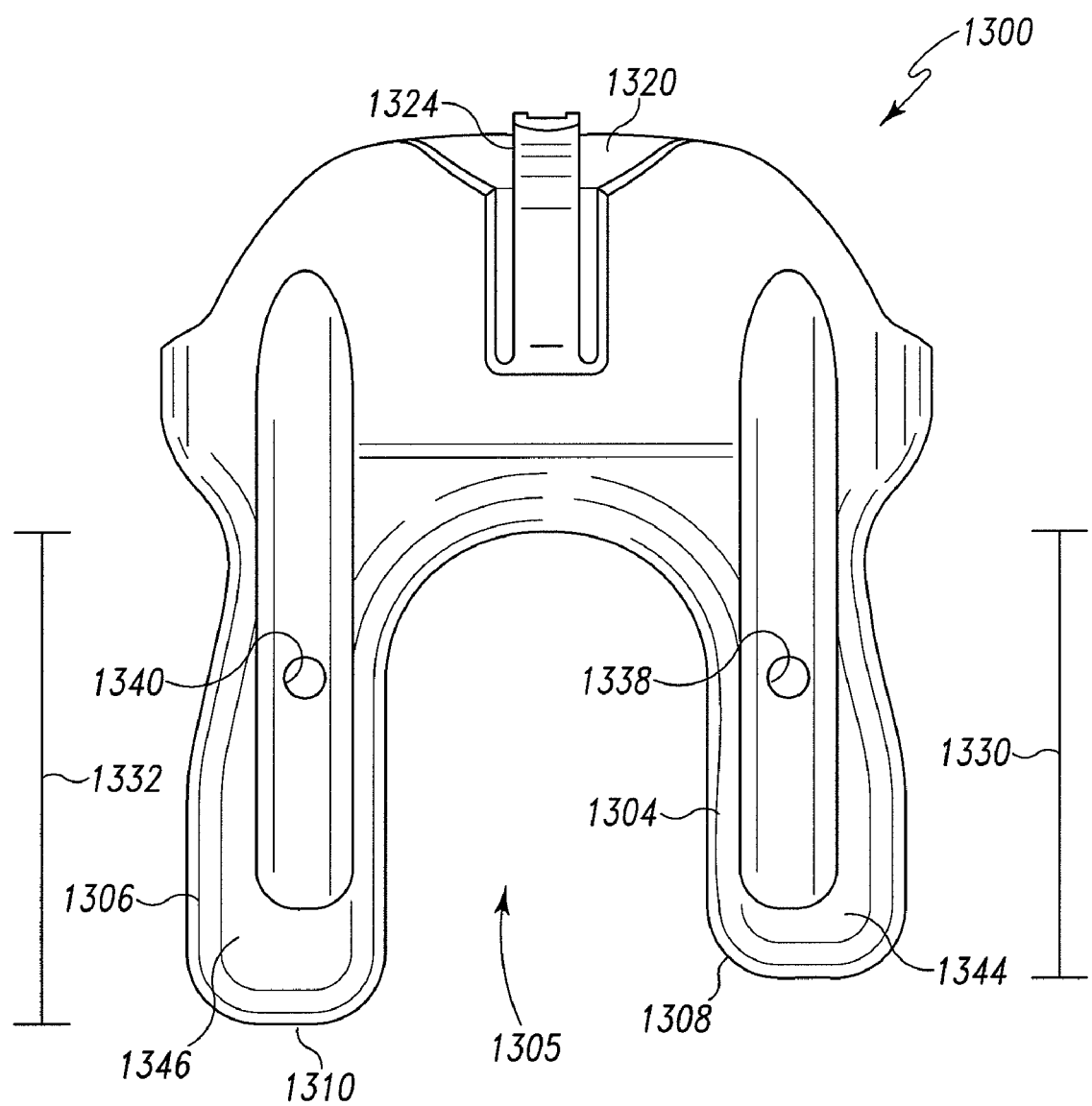
FIG. 56 is a top plan view of the customized patient-specific orthopaedic surgical instrument of FIG. 55.
Figure 57:
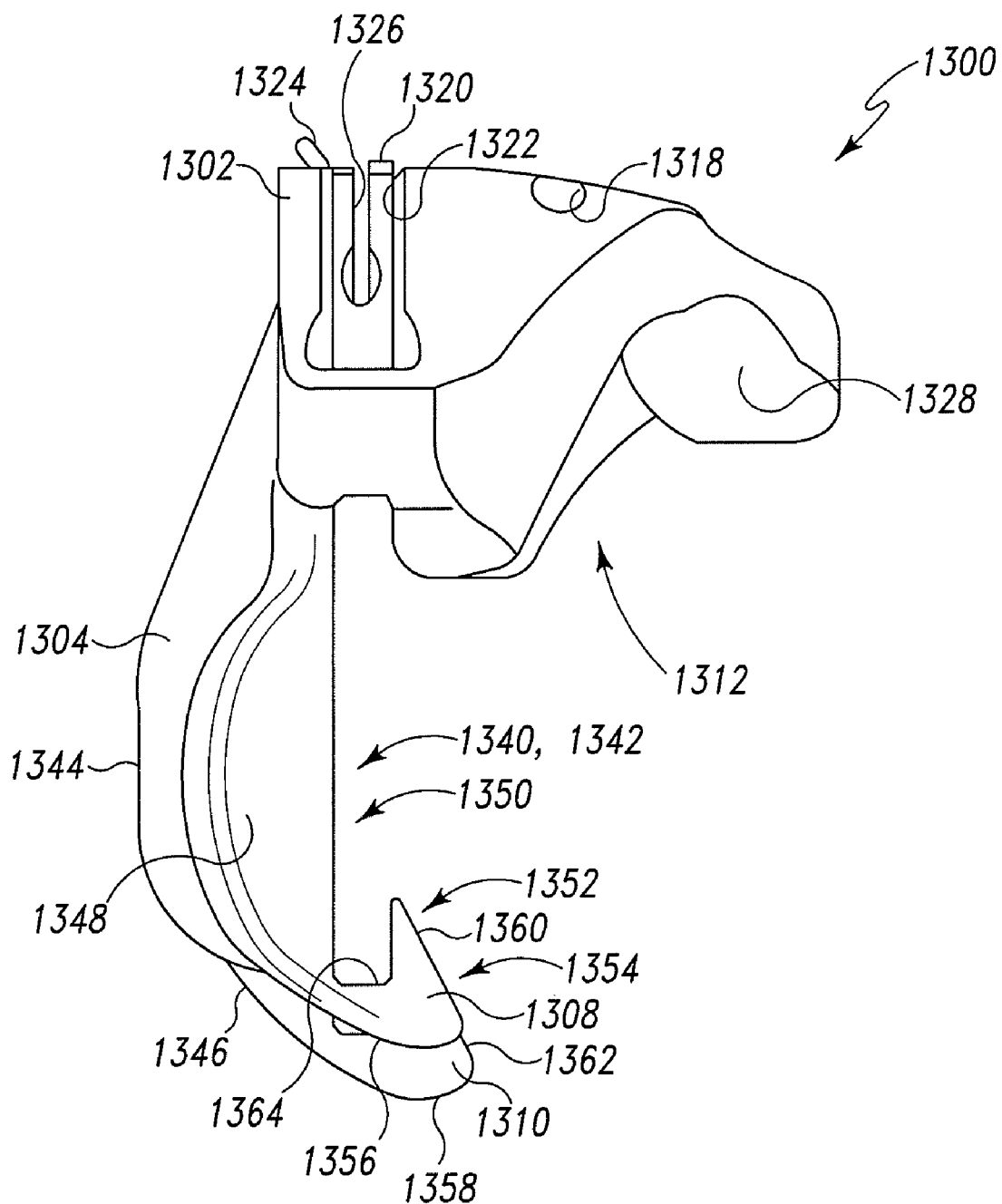
FIG. 57 is a side elevation view of the customized patient-specific orthopaedic surgical instrument of FIG. 55.

Referring now to FIGS. 55-57, in another embodiment, the customized patient-specific orthopaedic surgical instrument may be embodied as a femoral cutting block 1300. The cutting block 1300 is configured to be coupled to a femur of a patient similar to the cutting block 100 described above. The cutting block 1300 includes a body 1302 configured to be coupled to the anterior side of the patient's femur and two arms or tabs 1304, 1306, which extend away from the body 1302 in a posteriorly direction. The tabs 1304, 1306 are configured to wrap around a distal end of the femur as discussed in more detail below. Each of the tabs 1304, 1306 includes an inwardly-curving or otherwise superiorly extending lip 1308, 1310, respectively, which references the posterior condyles of the femur. The cutting block 1300 may be formed from any suitable material. For example, the cutting block 1300 may be formed from a material such as a plastic or resin material. In some embodiments, the cutting block 1300 may be formed from a photo-curable or laser-curable resin. In one particular embodiment, the cutting block 1300 is formed from a Vero resin, which is commercially available from Objet Geometries Ltd. of Rehovot, Israel using a rapid prototype fabrication process. However, the cutting block 1300 may be formed from other materials in other embodiments. For example, in another particular embodiment, the cutting block 1300 is formed from a polyimide thermoplastic resin, such as a Ultem resin, which is commercially available from Saudi Basic Industries Corporation Innovative Plastics of Riyhadh, Saudi Arabia.

The body 1302 includes a bone-contacting or bone-facing surface 1312 and an outer surface 1314 opposite the bone-facing surface 1312. The outer surface 1314 includes a depression or recessed area 1316, which provides an indication to a surgeon where to apply pressure to the body 1302 when coupling the cutting block 1300 to the patient's femur. Additionally, a number of guide pin holes or passageways 1318 are defined through the body 1302 and have a diameter sized to receive respective guide pins to secure the block 1300 to the patient's femur. In some embodiments, one or more of the guide pin holes 1318 may be oblique or otherwise angled with respect to the remaining guide pin holes 1318 to further secure the block 1300 to the patient's bone.

The body 1302 includes a modular cutting guide 1320. That is, the body 1302 includes a cutting guide receiver slot 1322 in which the cutting guide 1320 is received. A latch 1324 or other locking device secures the cutting guide 1320 in place in the cutting guide receiver slot 1322. As such, one of a number of different cutting guides 1320 having a cutting guide slot 1326 defined in various offset positions may be coupled to the body 1302 to allow a surgeon to selectively determine the amount of bone of the patient's bone is removed during the bone cutting procedure. For example, a cutting guide 1320 having a cutting guide slot 1326 offset by +2 millimeters, with respect to a neutral reference cutting guide 1320, may be used if the surgeon desires to remove a greater amount of the patient's bone. The cutting guide 1320 may be formed from the same material as the body 1302 or from a different material. In one particular embodiment, the cutting guide 1320 is formed form a metallic material such as stainless steel.

The bone-facing surface 1312 of the body 1302 includes a negative contour 1328 configured to receive a portion of the anterior side of the patient's femur having a corresponding contour. As discussed above, the customized patient-specific negative contour 1328 of the bone-contacting surface 1312 allows the positioning of the cutting block 1300 on the patient's femur in a unique pre-determined location and orientation.

As discussed above, the arms or tabs 1304, 1306 extend posteriorly from the body 1300 to define a U-shaped opening 1305 therebetween. The tabs 1304, 1306 may extend from the body the same distance or a different distance. For example, as shown in FIG. 56, the tab 1304 extends from the body 1300 a distance 1330 and the tab 1306 extends from the body 1330 a distance 1332, which is greater than the distance 1330. Each of the tabs 1304, 1306 includes a respective guide pin holes or passageways 1338, 1340 defined therethrough. The guide pin holes 1338, 1340 have a diameter sized to receive respective guide pin to further secure the block 1300 to the patient's femur.

The tabs 1304, 1306 include a bone-contacting or bone-facing surface 1340, 1342, respectively, and an outer surface 1344, 1346, respectively, opposite the bone-facing surface 1340, 1342. The bone-facing surface 1340 of the tab 1304 includes a negative contour 1348 configured to receive a portion of the distal side of the patient's femur having a respective corresponding contour. Similarly, the bone-facing surface 1342 of the tab 1306 includes a negative contour 1350 configured to receive a portion of the distal side of the patient's femur having a respective corresponding contour.

The lips 1308, 1310 of the tabs 1304, 1306 also include a bone-contacting or bone-facing surface 1352, 1354, respectively, and an outer surface 1356, 1358, respectively, opposite the bone-facing surface 1352, 1354. The bone-facing surface 1352 of the lip 1308 includes a negative contour 1360 configured to receive a portion of the posterior side of the patient's femur having a respective corresponding contour. Similarly, the bone-facing surface 1354 of the lip 1310 includes a negative contour 1362 configured to receive a portion of the distal side of the patient's femur having a respective corresponding contour. Each the lips 1308, 1310 include a lateral slot 1364 that forms a saw relieve slot and is configured to provide an amount of clearance for the bone saw blade used to remove a portion of the patient's bone. That is, during the performance of the orthopaedic surgical procedure, a distal end of the bone saw blade may be received in the slot 1364.

In some embodiments, the negative contours 1328, 1348, 1350, 1356, 1358 of the bone-contacting surfaces 1312, 1340, 1342, 1352, 1354 of the cutting block 1300 may or may not match the corresponding contour surface of the patient's bone. That is, as discussed above, the negative contours 1328, 1348, 1350, 1356, 1358 may be scaled or otherwise resized (e.g., enlarged) to compensate for the patient's cartilage or lack thereof.

In use, the femoral cutting block 1300 is coupled to the distal end of the patient's femur. Again, because the bone-contacting surfaces 1312, 1340, 1342, 1352, 1354 of the cutting block 1300 include the negative contours 1328, 1348, 1350, 1356, 1358 the block 1300 may be coupled to the patient's femur in a pre-planned, unique position. When so coupled, the tabs 1304, 1306 wrap around the distal end of the patient's femur and the lips 1308, 1310 of the tabs 1304, 1306 wrap around the posterior side of the patient's femur. Additionally, when the block 1300 is coupled to the patient's femur, a portion of the anterior side of the femur is received in the negative contour 1328 of the body 1302, a portion of the distal side of the patient's femur is received in the negative contours 1348, 1350 of the tabs 1304, 1306, and a portion of the posterior side of the femur is received in the negative contours 1356, 1358 of the lips 1308, 1310. As such, the anterior, distal, and posterior surfaces of the patient femur are referenced by the femoral cutting block 1300.

Figure 58:
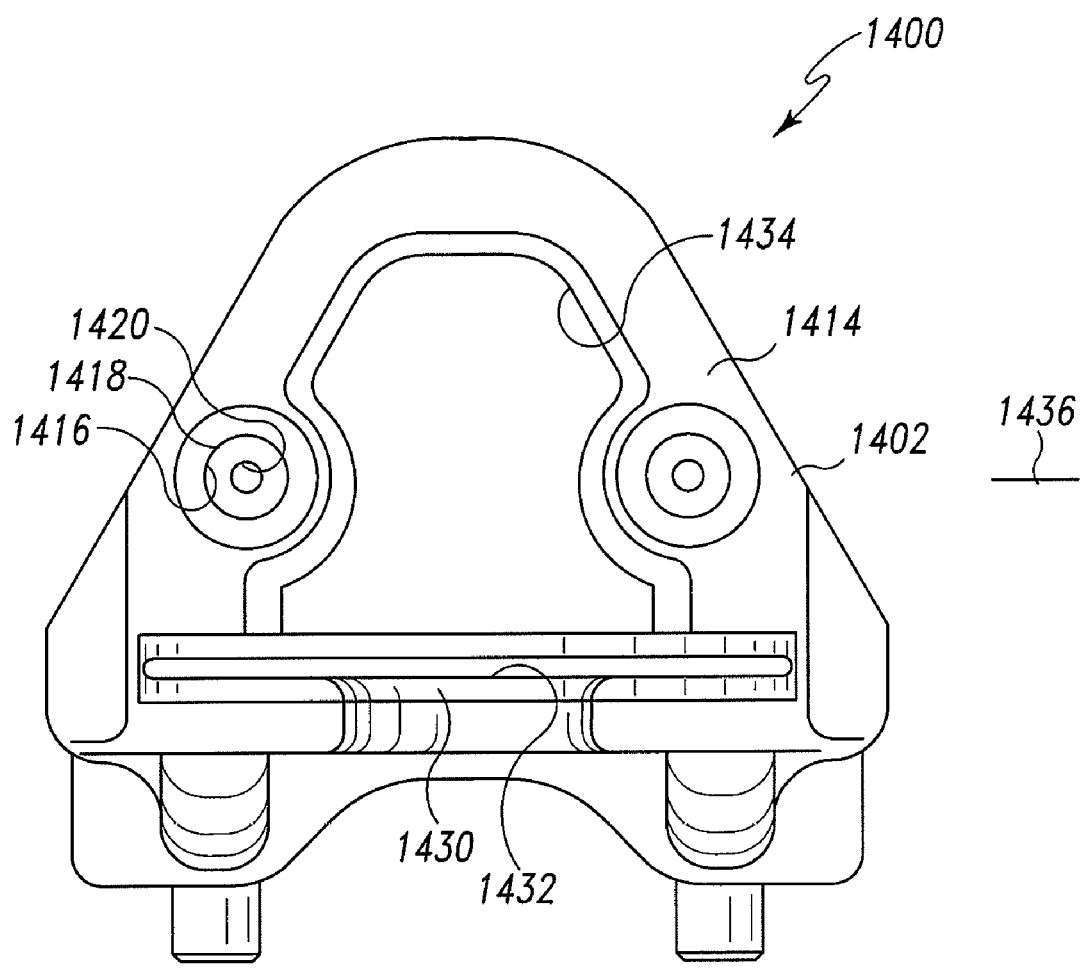
FIG. 58 is an anterior elevation view of another embodiment of a customized patient-specific orthopaedic surgical instrument.
Figure 59:
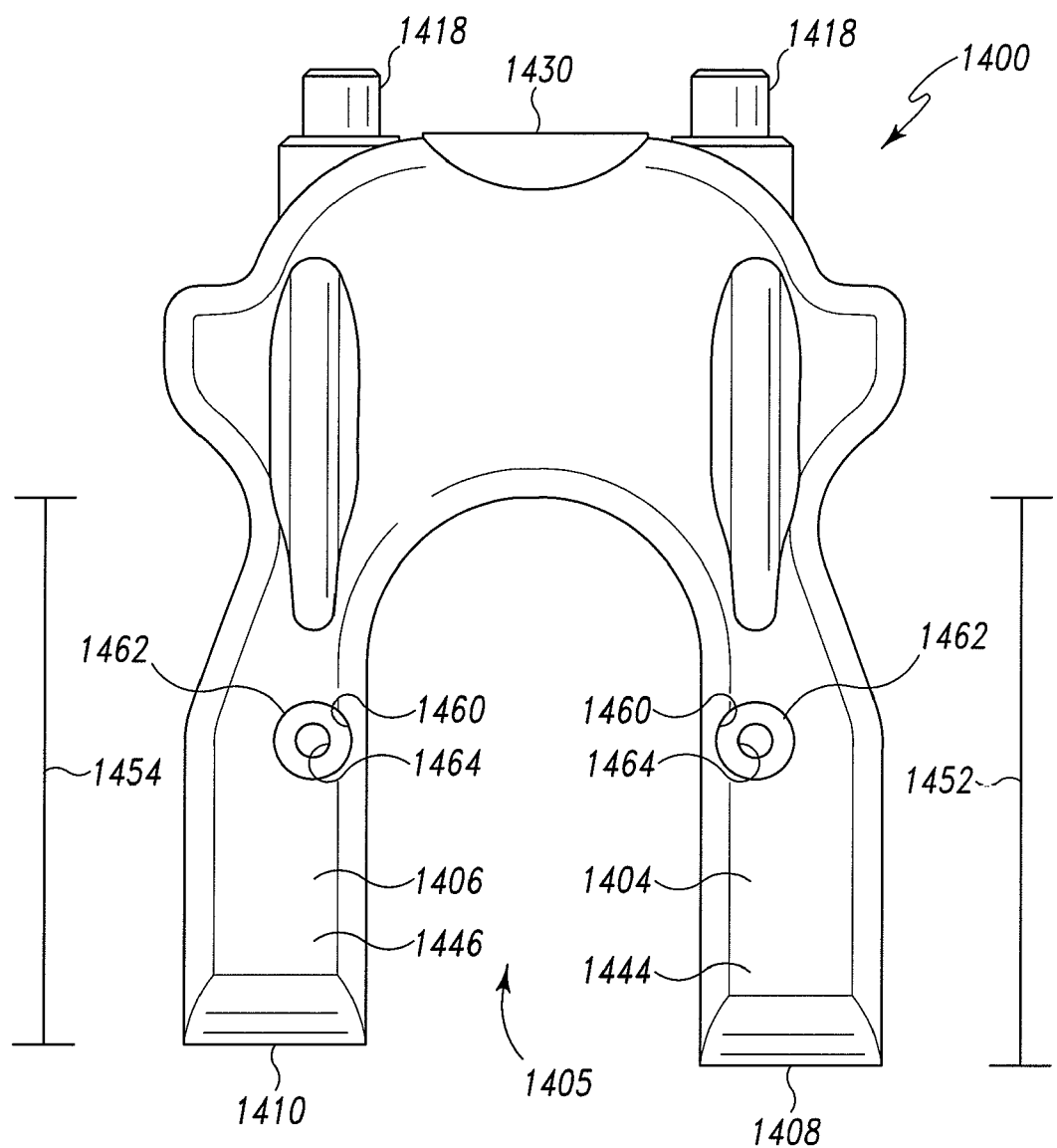
FIG. 59 is a top plan view of the customized patient-specific orthopaedic surgical instrument of FIG. 58.
Figure 60:
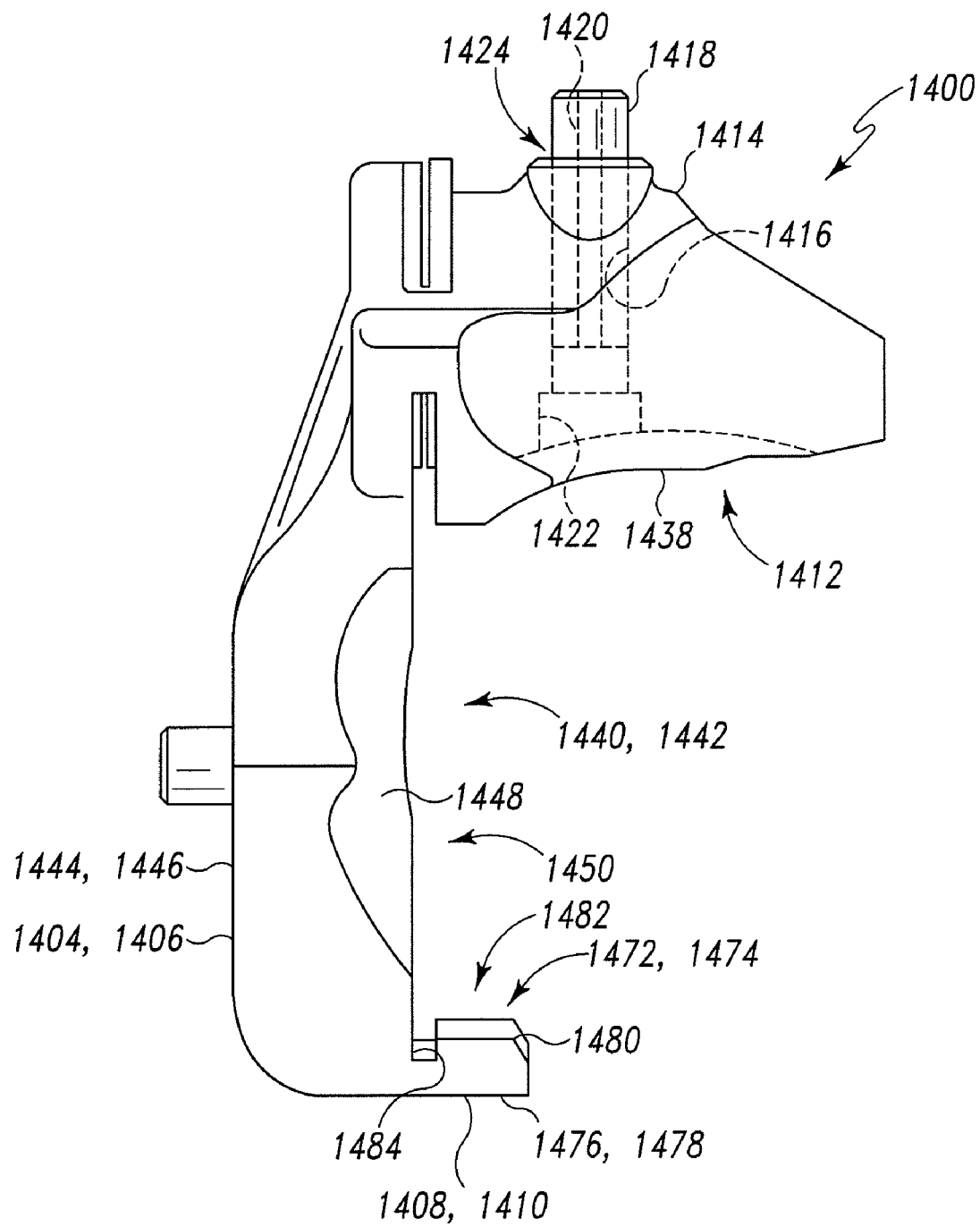
FIG. 60 is a side elevation view of the customized patient-specific orthopaedic surgical instrument of FIG. 58.

Referring now to FIGS. 58-60, in another embodiment, the customized patient-specific orthopaedic surgical instrument may be embodied as a femoral cutting block 1400. The cutting block 1400 is configured to be coupled to a femur of a patient similar to the cutting block 100 described above. The cutting block 1400 includes a body 1402 configured to be coupled to the anterior side of the patient's femur and two arms or tabs 1404, 1406, which extend away from the body 1402 in a posteriorly direction. The tabs 1404, 1406 are configured to wrap around a distal end of the femur as discussed in more detail below. Each of the tabs 1404, 1406 includes an inwardly-curving or otherwise superiorly extending lip 1408, 1410, respectively, which references the posterior condyles of the femur. Similar to the cutting block 1300, the cutting block 1400 may be formed from any suitable material. For example, the cutting block 1400 may be formed from a material such as a plastic or resin material. In one particular embodiment, the cutting block 1400 is formed from Vero resin using a rapid prototype fabrication process. However, the cutting block 1400 may be formed from other materials in other embodiments. For example, in another particular embodiment, the cutting block 1400 is formed from a polyimide thermoplastic resin, such as a Ultem resin, which is commercially available from Saudi Basic Industries Corporation Innovative Plastics of Riyhadh, Saudi Arabia.

The body 1402 includes a bone-contacting or bone-facing surface 1412 and an outer surface 1414 opposite the bone-facing surface 1412. The outer surface 1414 includes a number of guide holes or passageways 1416 defined therethrough. A guide pin bushing 1418 is received in each guide hole 1416. The guide pin bushings 1418 include an internal passageway 1420 sized to receive a respective guide pin to secure the block 1400 to the patient's femur. As shown in FIG. 60, the guide passageways 1416 extends from the outer surface 1414 to the bone-facing surface 1412 and is counterbored on the bone-facing surface 1412. That is, the passageway 1416 has an opening 1422 on the bone facing surface 1412 having a diameter greater than the diameter of an opening 1424 on the outer surface 1414.

The cutting guide 1400 includes a cutting guide 1430 secured to the body 1402. In one particular embodiment, the cutting guide 1430 is overmolded to the body 1402. The cutting guide 1430 includes a cutting guide slot 1432. The cutting guide 1430 may be formed from the same material as the body 1402 or from a different material. In one particular embodiment, the cutting guide 1430 is formed from a metallic material such as stainless steel. The body 1402 also includes a window or opening 1434 defined therethough. The opening 1434 allows a surgeon to visualize the positioning of the block 1400 on the patient's femur by viewing portions of the femur through the opening 1434. Additionally, the opening 1434 may reduce the amount of air pockets or other perfections created during the fabrication of the block 1400. In the illustrative embodiment, the opening 1434 extends from the cutting guide 1400 to a point more superior than the superior-most point 1436 of the guide pin bushings 1418. However, in other embodiments, the cutting block 1400 may include windows or openings formed in the body 1402 having other shapes and sizes.

The bone-facing surface 1412 of the body 1402 includes a negative contour 1438 configured to receive a portion of the anterior side of the patient's femur having a corresponding contour. As discussed above, the customized patient-specific negative contour 1438 of the bone-contacting surface 1412 allows the positioning of the cutting block 1400 on the patient's femur in a unique pre-determined location and orientation.

The tabs 1404, 1406 include a bone-contacting or bone-facing surface 1440, 1442, respectively, and an outer surface 1444, 1446, respectively, opposite the bone-facing surface 1440, 1442. The bone-facing surface 1440 of the tab 1404 includes a negative contour 1448 configured to receive a portion of the distal side of the patient's femur having a respective corresponding contour. Similarly, the bone-facing surface 1442 of the tab 1406 includes a negative contour 1450 configured to receive a portion of the distal side of the patient's femur having a respective corresponding contour.

As discussed above, the arms or tabs 1404, 1406 extend posteriorly from the body 1400 to define a U-shaped opening 1405 therebetween. The tabs 1404, 1406 may extend from the body 1400 the same distance or a different distance. For example, as shown in FIG. 59, the tab 1404 extends from the body 1400 a distance 1452 and the tab 1406 extends from the body 1400 a distance 1454, which is less than the distance 1452. Each of the tabs 1404, 1406 includes a respective guide hole or passageway 1460 defined therethrough. A guide pin bushing 1462 is received in each guide hole 1460. The guide pin bushings 1462 include an internal passageway 1464 sized to receive a respective guide pin to further secure the block 1400 to the patient's femur. Similar to the guide passageways 1416, the guide passageways 1460 may be counterbored on the bone-facing surface 1440, 1442 of the tabs 1404, 1406.

The lips 1408, 1410 of the tabs 1404, 1406 also include a bone-contacting or bone-facing surface 1472, 1474, respectively, and an outer surface 1476, 1478, respectively, opposite the bone-facing surface 1472, 1474. The bone-facing surface 1472 of the lip 1408 includes a negative contour 1480 configured to receive a portion of the posterior side of the patient's femur having a respective corresponding contour. Similarly, the bone-facing surface 1474 of the lip 1410 includes a negative contour 1482 configured to receive a portion of the distal side of the patient's femur having a respective corresponding contour. Each the lips 1408, 1410 includes a lateral slot 1484 that forms a saw relieve slot and is configured to provide an amount of clearance for the bone saw blade used to remove a portion of the patient's bone. That is, during the performance of the orthopaedic surgical procedure, a distal end of the bone saw blade may be received in the slot 1484.

In some embodiments, the negative contours 1438, 1448, 1450, 1480, 1482 of the bone-contacting surfaces 1412, 1440, 1442, 1472, 1474 of the cutting block 1400 may or may not match the corresponding contour surface of the patient's bone. That is, as discussed above, the negative contours 1438, 1448, 1450, 1480, 1482 may be scaled or otherwise resized (e.g., enlarged) to compensate for the patient's cartilage or lack thereof.

In use, the femoral cutting block 1400 is coupled to the distal end of the patient's femur. Again, because the bone-contacting surfaces 1412, 1440, 1442, 1472, 1474 of the cutting block 1400 include the negative contours 1438, 1448, 1450, 1480, 1482, the block 1400 may be coupled to the patient's femur in a pre-planned, unique position. When so coupled, the tabs 1404, 1406 wrap around the distal end of the patient's femur and the lips 1408, 1410 of the tabs 1404, 1406 wrap around the posterior side of the patient's femur. Additionally, when the block 1400 is coupled to the patient's femur, a portion of the anterior side of the femur is received in the negative contour 1438 of the body 1402, a portion of the distal side of the patient's femur is received in the negative contours 1448, 1450 of the tabs 1404, 1406, and a portion of the posterior side of the femur is received in the negative contours 1480, 1482 of the lips 1408, 1410. As such, the anterior, distal, and posterior surfaces of the patient femur are referenced by the femoral cutting block 1400.

Figure 61:
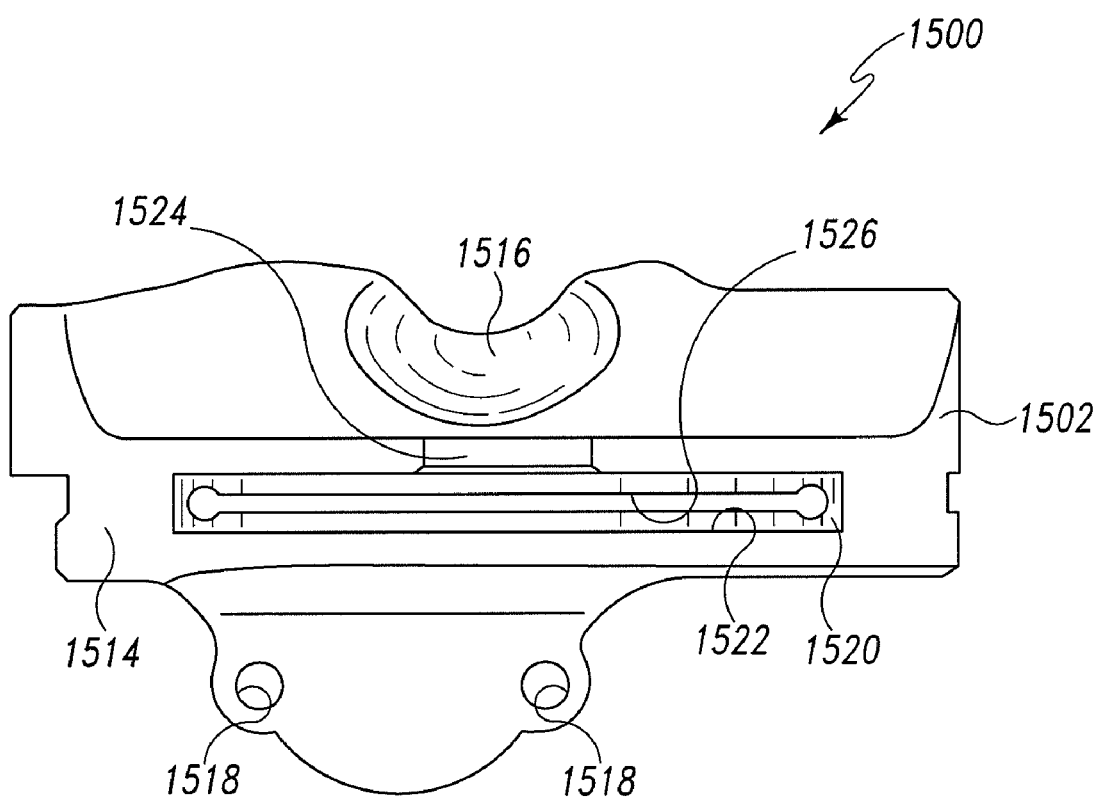
FIG. 61 is an anterior elevation view of another embodiment of a customized patient-specific orthopaedic surgical instrument.
Figure 62:
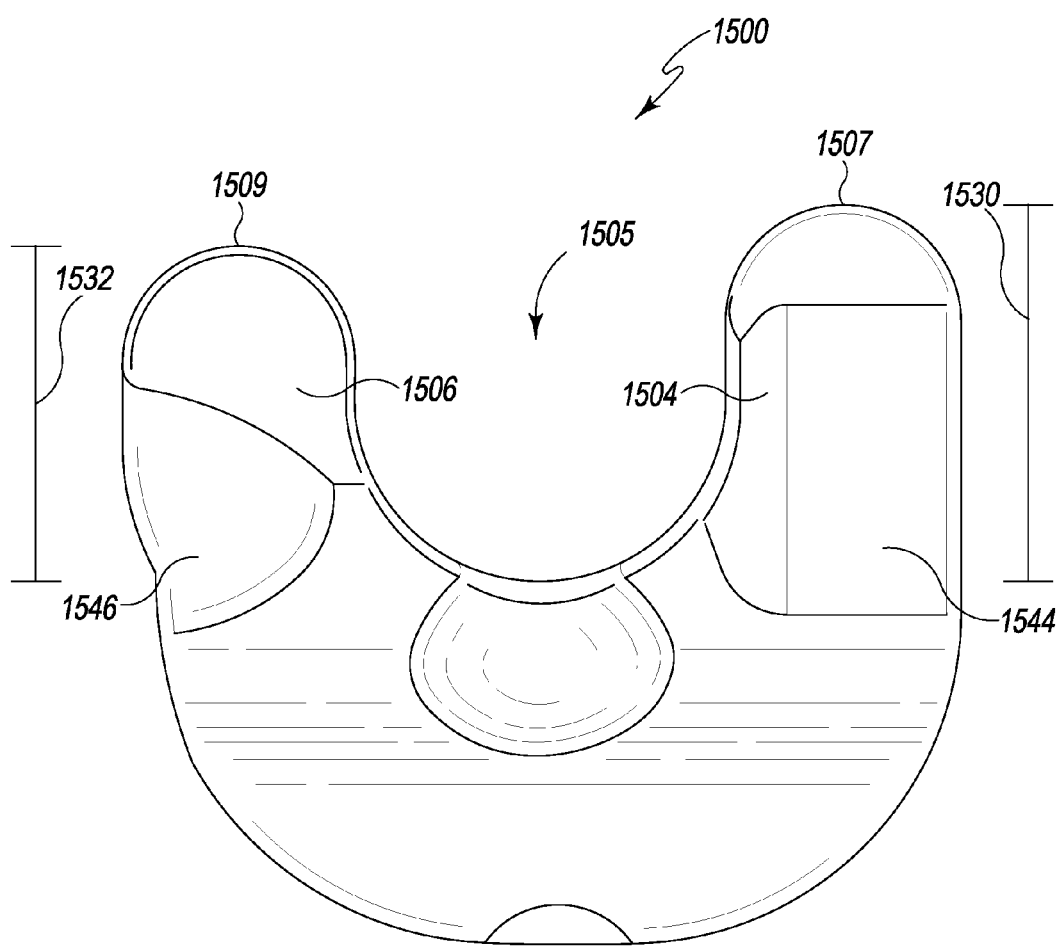
FIG. 62 is a top plan view of the customized patient-specific orthopaedic surgical instrument of FIG. 61.
Figure 63:
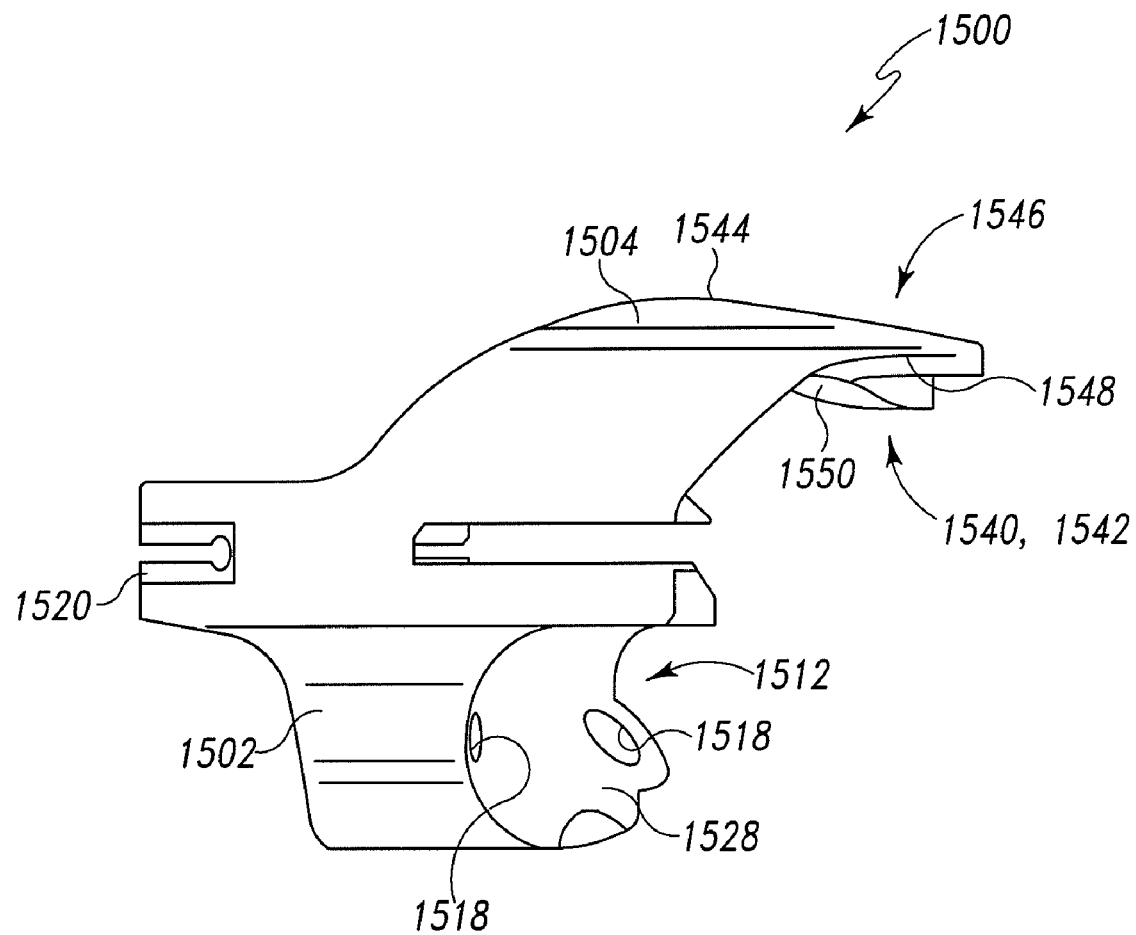
FIG. 63 is a side elevation view of the customized patient-specific orthopaedic surgical instrument of FIG. 61.

Referring now to FIGS. 61-63, in another embodiment, the customized patient-specific orthopaedic surgical instrument may be embodied as a tibial cutting block 1500. The cutting block 1500 is configured to be coupled to a tibia of a patient similar to the cutting block 300 described above. The cutting block 1500 includes a body 1502 configured to be coupled to the anterior side of the patient's tibia and two arms or tabs 1504, 1506, which extend away from the body 1502 in a posteriorly direction. The tabs 1504, 1506 are configured to wrap over a proximal end of the tibia as discussed in more detail below. The cutting block 1500 may be formed from any suitable material. For example, the cutting block 1500 may be formed from a material such as a plastic or resin material. In one particular embodiment, the cutting block 1500 is formed from Vero resin using a rapid prototype fabrication process. However, the cutting block 1500 may be formed from other materials in other embodiments. For example, in another particular embodiment, the cutting block 1500 is formed from a polyimide thermoplastic resin, such as a Ultem resin, which is commercially available from Saudi Basic Industries Corporation Innovative Plastics of Riyhadh, Saudi Arabia.

The body 1502 includes a bone-contacting or bone-facing surface 1512 and an outer surface 1514 opposite the bone-facing surface 1512. The outer surface 1514 includes a depression or recessed area 1516, which provides an indication to a surgeon where to apply pressure to the body 1502 when coupling the cutting block 1500 to the patient's tibia. Additionally, a number of guide pin holes or passageways 1518 are defined through the body 1502 and have a diameter sized to receive respective guide pins to secure the block 1500 to the patient's tibia. In some embodiments, one or more of the guide pin holes 1518 may be oblique or otherwise angled with respect to the remaining guide pin holes 1518 to further secure the block 1500 to the patient's bone.

The body 1502 includes a modular cutting guide 1520. That is, the body 1502 includes a cutting guide receiver slot 1522 in which the cutting guide 1520 is received. A latch 1524 or other locking device secures the cutting guide 1520 in place in the cutting guide receiver slot 1522. As such, one of a number of different cutting guides 1520 having a cutting guide slot 1526 defined in various offset positions may be coupled to the body 1502 to allow a surgeon to selectively determine the amount of bone of the patient's bone is removed during the bone cutting procedure. For example, a cutting guide 1520 having a cutting guide slot 1526 offset by +2 millimeters, with respect to a neutral reference cutting guide 1520, may be used if the surgeon desires to remove a greater amount of the patient's bone. The cutting guide 1520 may be formed from the same material as the body 1502 or from a different material. In one particular embodiment, the cutting guide 1520 is formed form a metallic material such as stainless steel.

The bone-facing surface 1512 of the body 1502 includes a negative contour 1528 configured to receive a portion of the anterior side of the patient's tibia having a corresponding contour. As discussed above, the customized patient-specific negative contour 1528 of the bone-contacting surface 1512 allows the positioning of the cutting block 1500 on the patient's tibia in a unique pre-determined location and orientation.

As discussed above, the arms or tabs 1504, 1506 extend posteriorly from the body 1502 to define a U-shaped opening 1505 therebetween. The tabs 1504, 1506 may extend from the body 1502 the same distance or a different distance. For example, as shown in FIG. 62, the tab 1504 extends from the body 1502 a distance 1530 and the tab 1506 extends from the body 1502 a distance 1532, which is greater than the distance 1530. The tabs 1504, 1506 taper in the anterior-posterior direction. That is, the thickness of the tabs 1504, 1506 at an anterior end of the tabs 1504, 1506 is greater than the thickness of the tabs 1504, 1506 at a respective posterior end 1507, 1509. The tapering of the tabs 1504, 1506 allow the tabs 1504, 1506 to be inserted within the joint gap defined between the patient's femur and tibia.

The tabs 1504, 1506 include a bone-contacting or bone-facing surface 1540, 1542, respectively, and an outer surface 1544, 1546, respectively, opposite the bone-facing surface 1540, 1542. The bone-facing surface 1540 of the tab 1504 includes a negative contour 1548 configured to receive a portion of the distal side of the patient's tibia having a respective corresponding contour. Similarly, the bone-facing surface 1542 of the tab 1506 includes a negative contour 1550 configured to receive a portion of the distal side of the patient's tibia having a respective corresponding contour.

In some embodiments, the negative contours 1528, 1548, 1550 of the bone-contacting surfaces 1512, 1540, 1542 of the cutting block 1500 may or may not match the corresponding contour surface of the patient's bone. That is, as discussed above, the negative contours 1528, 1548, 1550 may be scaled or otherwise resized (e.g., enlarged) to compensate for the patient's cartilage or lack thereof.

In use, the tibial cutting block 1500 is coupled to the proximal end of the patient's tibia. Again, because the bone-contacting surfaces 1512, 1540, 1542 of the cutting block 1500 include the negative contours 1528, 1548, 1550, the block 1500 may be coupled to the patient's tibia in a pre-planned, unique position. When so coupled, the tabs 1504, 1506 wrap around the proximal end of the patient's tibia. Additionally, when the block 1500 is coupled to the patient's femur, a portion of the anterior side of the tibia is received in the negative contour 1528 of the body 1502 and a portion of the proximal side of the patient's tibia is received in the negative contours 1548, 1550 of the tabs 1504, 1506. As such, the anterior and proximal surfaces of the patient tibia are referenced by the tibial cutting block 1500.

Figure 64:
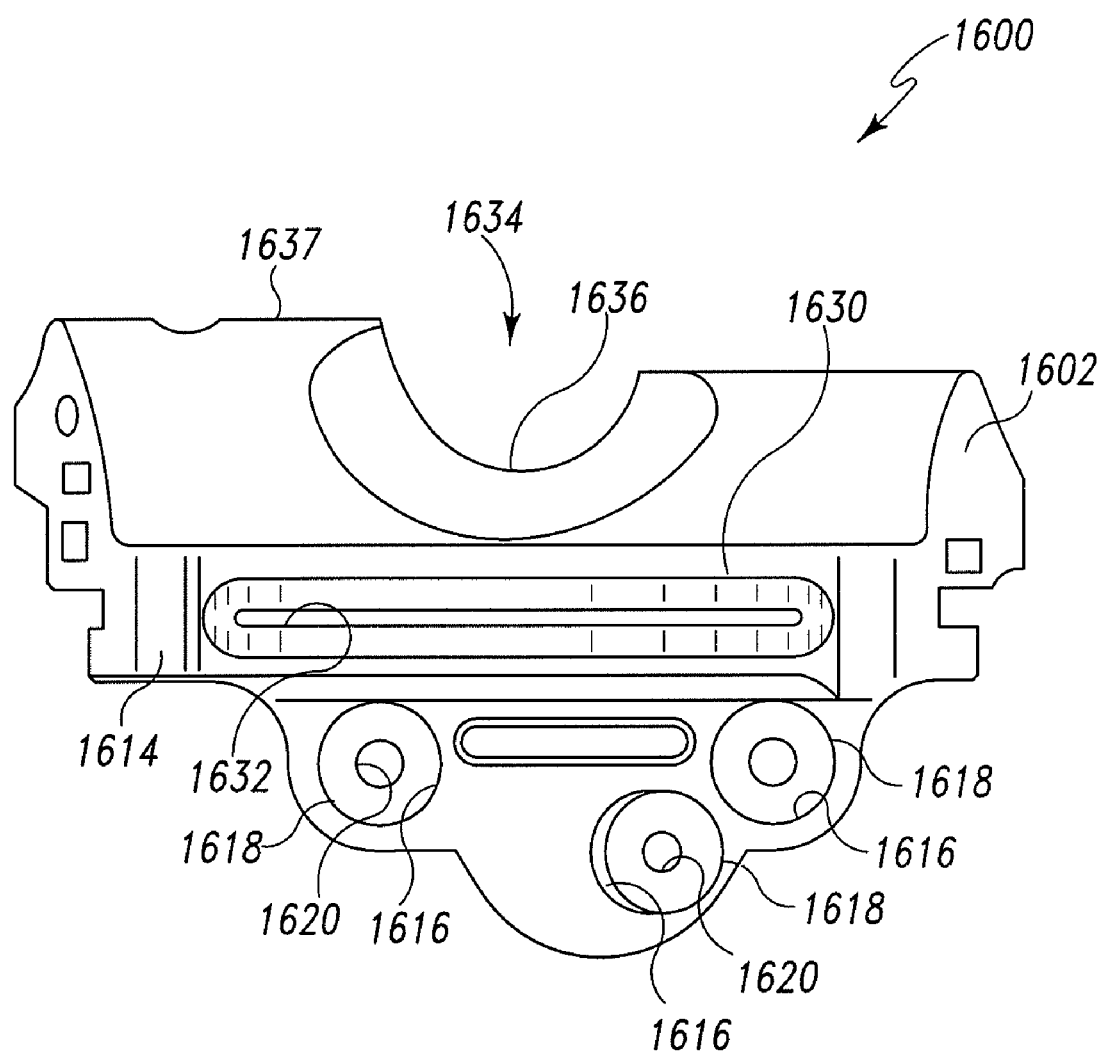
FIG. 64 is an anterior elevation view of another embodiment of a customized patient-specific orthopaedic surgical instrument.
Figure 65:
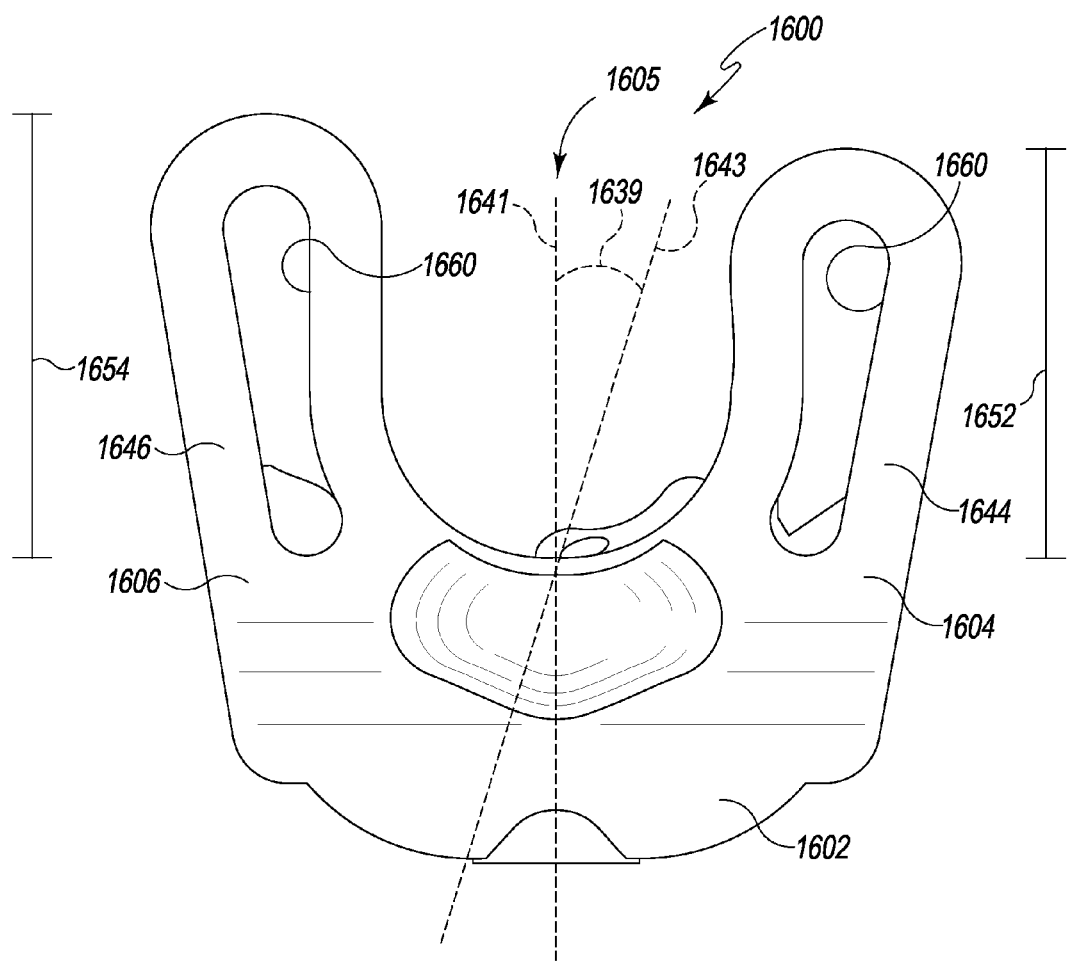
FIG. 65 is a top plan view of the customized patient-specific orthopaedic surgical instrument of FIG. 64.
Figure 66:
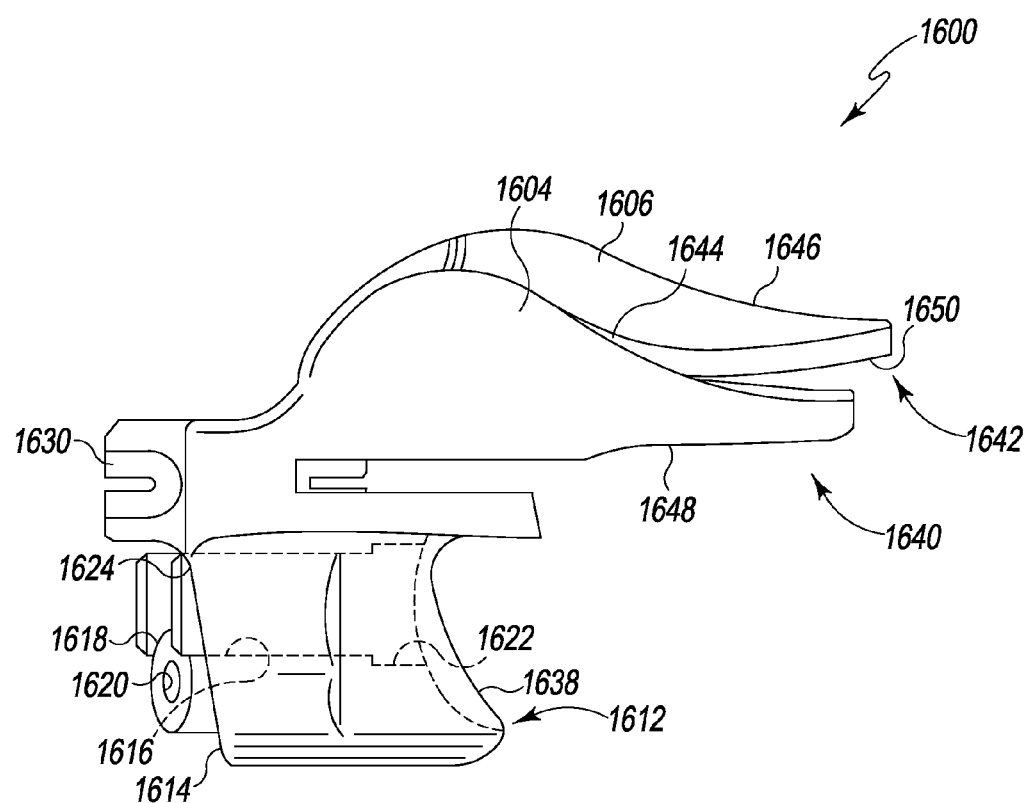
FIG. 66 is a side elevation view of the customized patient-specific orthopaedic surgical instrument of FIG. 64.

Referring now to FIGS. 64-66, in another embodiment, the customized patient-specific orthopaedic surgical instrument may be embodied as a tibial cutting block 1600. The cutting block 1600 is configured to be coupled to a tibia of a patient similar to the cutting block 1500 described above. The cutting block 1600 includes a body 1602 configured to be coupled to the anterior side of the patient's tibia and two arms or tabs 1604, 1606, which extend away from the body 1602 in a posteriorly direction. The tabs 1604, 1606 are configured to wrap around a proximal end of the tibia as discussed in more detail below. Similar to the cutting block 1500, the cutting block 1600 may be formed from any suitable material. For example, the cutting block 1600 may be formed from a plastic or resin material. In one particular embodiment, the cutting block 1600 is formed from Vero resin using a rapid prototype fabrication process. However, the cutting block 1600 may be formed from other materials in other embodiments. For example, in another particular embodiment, the cutting block 1600 is formed from a polyimide thermoplastic resin, such as a Ultem resin, which is commercially available from Saudi Basic Industries Corporation Innovative Plastics of Riyhadh, Saudi Arabia.

The body 1602 includes a bone-contacting or bone-facing surface 1612 and an outer surface 1614 opposite the bone-facing surface 1612. The outer surface 1614 includes a number of guide holes or passageways 1616 defined therethrough. A guide pin bushing 1618 is received in each guide hole 1616. The guide pin bushings 1618 include an internal passageway 1620 sized to receive a respective guide pin to secure the block 1600 to the patient's tibia. As shown in FIG. 66, the guide passageways 1616 extends from the outer surface 1614 to the bone-facing surface 1612 and is counterbored on the bone-facing surface 1612. That is, the passageway 1616 has an opening 1622 on the bone facing surface 1612 having a diameter greater than the diameter of an opening 1624 on the outer surface 1614

The cutting guide 1600 includes a cutting guide 1630 secured to the body 1602. In one particular embodiment, the cutting guide 1630 is overmolded to the body 1602. The cutting guide 1630 includes a cutting guide slot 1632. The cutting guide 1630 may be formed from the same material as the body 1602 or from a different material. In one particular embodiment, the cutting guide 1630 is formed from a metallic material such as stainless steel. The body 1602 also includes a window or opening 1634 to allow a surgeon to visualize the positioning of the block 1600 on the patient's tibia by viewing portions of the tibia through the opening 1634. In the illustrative embodiment, the window 1634 is embodied as a notch 1636 defined on a superior end surface 1637 of the body 1602 of the cutting guide 1600. However, in other embodiments, the cutting block 1600 may include windows or openings formed in the body 1602 having other shapes and sizes.

The bone-facing surface 1612 of the body 1602 includes a negative contour 1638 configured to receive a portion of the anterior side of the patient's tibia having a corresponding contour and a portion of the medial side of the patient's tibia. That is, the negative contour 1638 is selected such that cutting block 1600 is configured to be coupled to the patient's tibia on an anterior-medial side. For example, as illustrated in FIG. 65, when the cutting block 1600 is secured to a patient's tibia, an angle 1639 is defined between a vertically-extending, bisecting plane 1641 of the body 1602 of the block 1600 and a bisecting sagittal plane 1643 of the patient's tibia. The magnitude of the angle 1639 may be selected based on, for example, the gender or age of the patient. In one particular embodiment, the angle is in the range of about 10 degrees to about 30 degrees. In another particular embodiment, the angle is about 20 degrees. As discussed above, the customized patient-specific negative contour 1638 of the bone-contacting surface 1612 allows the positioning of the cutting block 1600 on the patient's tibia in a unique pre-determined location and orientation.

The tabs 1604, 1606 include a bone-contacting or bone-facing surface 1640, 1642, respectively, and an outer surface 1644, 1646, respectively, opposite the bone-facing surface 1640, 1642. The bone-facing surface 1640 of the tab 1604 includes a negative contour 1648 configured to receive a portion of the proximal side of the patient's tibia having a respective corresponding contour. Similarly, the bone-facing surface 1642 of the tab 1606 includes a negative contour 1650 configured to receive a portion of the proximal side of the patient's tibia having a respective corresponding contour.

As discussed above, the arms or tabs 1604, 1606 extend posteriorly from the body 1600 to define a U-shaped opening 1605 therebetween. The tabs 1604, 1606 may extend from the body 1600 the same distance or a different distance. For example, as shown in FIG. 65, the tab 1604 extends from the body 1600 a distance 1652 and the tab 1606 extends from the body 1600 a distance 1654, which is greater than the distance 1652. Each of the tabs 1604, 1606 includes a respective elongated opening or window 1660 defined therethrough. Similar to the window 1634 described above, the windows 1660 allow a surgeon to visualize the positioning of the block 1600 on the patient's tibia by viewing portions of the proximal end tibia through the opening 1660.

In some embodiments, the negative contours 1638, 1648, 1650 of the bone-contacting surfaces 1612, 1640, 1642 of the cutting block 1400 may or may not match the corresponding contour surface of the patient's bone. That is, as discussed above, the negative contours 1638, 1648, 1650 may be scaled or otherwise resized (e.g., enlarged) to compensate for the patient's cartilage or lack thereof.

In use, the tibial cutting block 1600 is coupled to the proximal end of the patient's tibia. Again, because the bone-contacting surfaces 1612, 1640, 1642 of the cutting block 1600 include the negative contours 1638, 1648, 1650, the block 1600 may be coupled to the patient's tibia in a pre-planned, unique position. When so coupled, the tabs 1604, 1606 wrap around the proximal end of the patient's tibia. Additionally, when the block 1600 is coupled to the patient's tibia, a portion of the anterior side of the tibia is received in the negative contour 1638 of the body 1602 and a portion of the proximal side of the patient's tibia is received in the negative contours 1648, 1650 of the tabs 1604, 1606.

Figure 67:
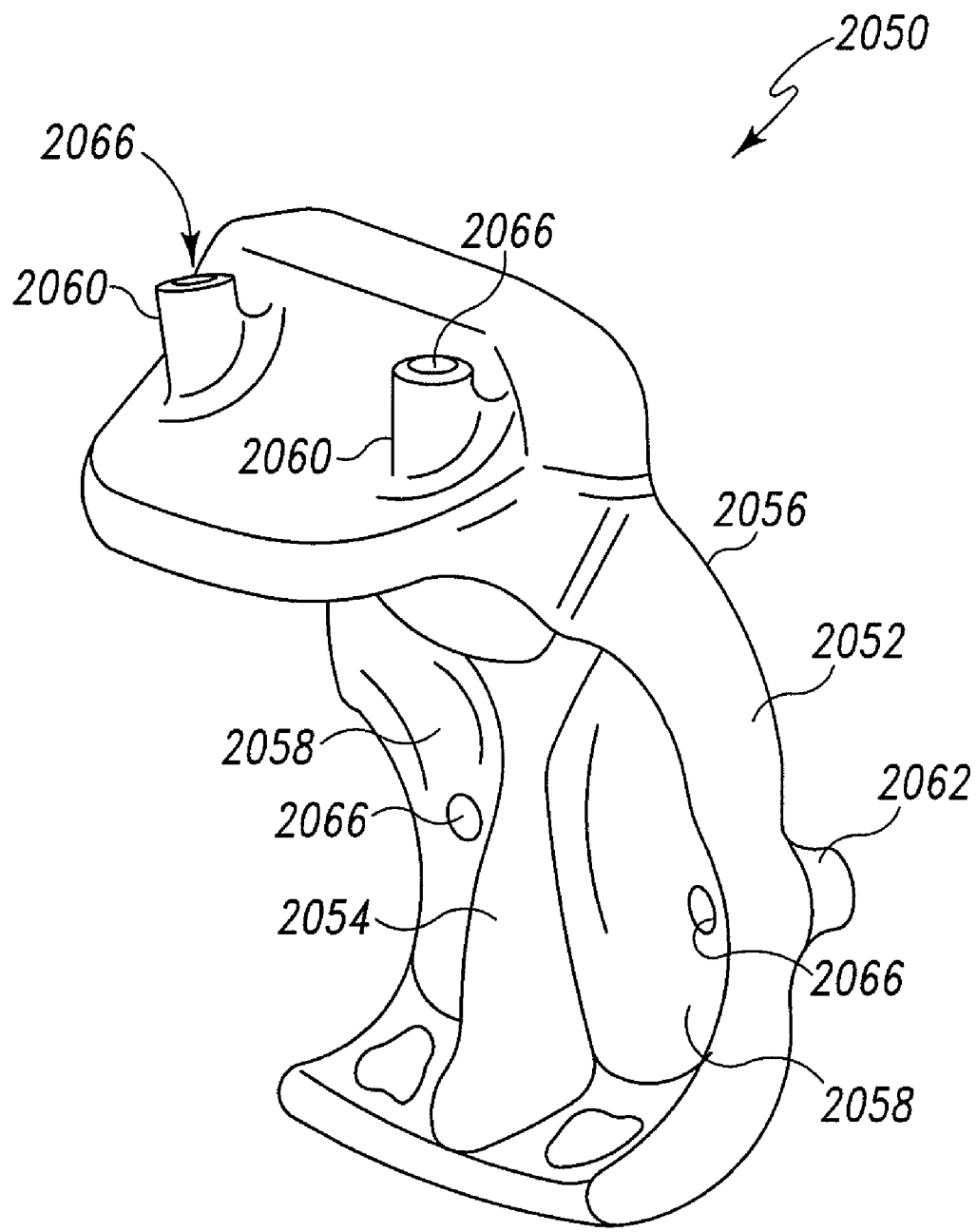
FIG. 67 is a perspective view of one embodiment of a customized patient-specific orthopaedic surgical instrument.

Referring now to FIG. 67, in one embodiment, the customized patient-specific orthopaedic surgical instrument may be embodied as a drill guide instrument 2050. The drill guide instrument 2050 includes a body 2052 having a bone-contacting or bone-facing surface 2054 and an outer surface 2056. The bone-contacting surface 2054 includes a negative contour 2058 configured to receive a portion of the patient's bone having a corresponding contour. As discussed above, the negative contour 2058 allows the positioning of the drill guide instrument 2050 on the patient's bone in a unique pre-determined location and orientation. Illustratively, the drill guide instrument 2050 is configured for use with the femur of a patient, but in other embodiments, the drill guide instrument 2050 may be configured for use with other bones of the patient such as the tibia. The body 2052 of the drill guide instrument 2050 includes a number of drill guides 2060, 2062, each having a drill guide passageway 2066 defined therethrough. Illustratively, the drill guides 2060 and corresponding drill guide passageways 2066 are positioned on the body 2052 of the instrument 2050 to facilitate the positioning of guide pins for a patient-universal distal femur cutting block while the drill guide 2062 and corresponding drill guide passageways 2066 are positioned on the body 2052 to facilitate the positioning of guide pins for a patient-universal 4-in-1 femur cutting block. However, in other embodiments, the drill guide instrument 2050 may have a greater or lesser number of drill guide positioned in other locations on the body 2052.

Figure 68:
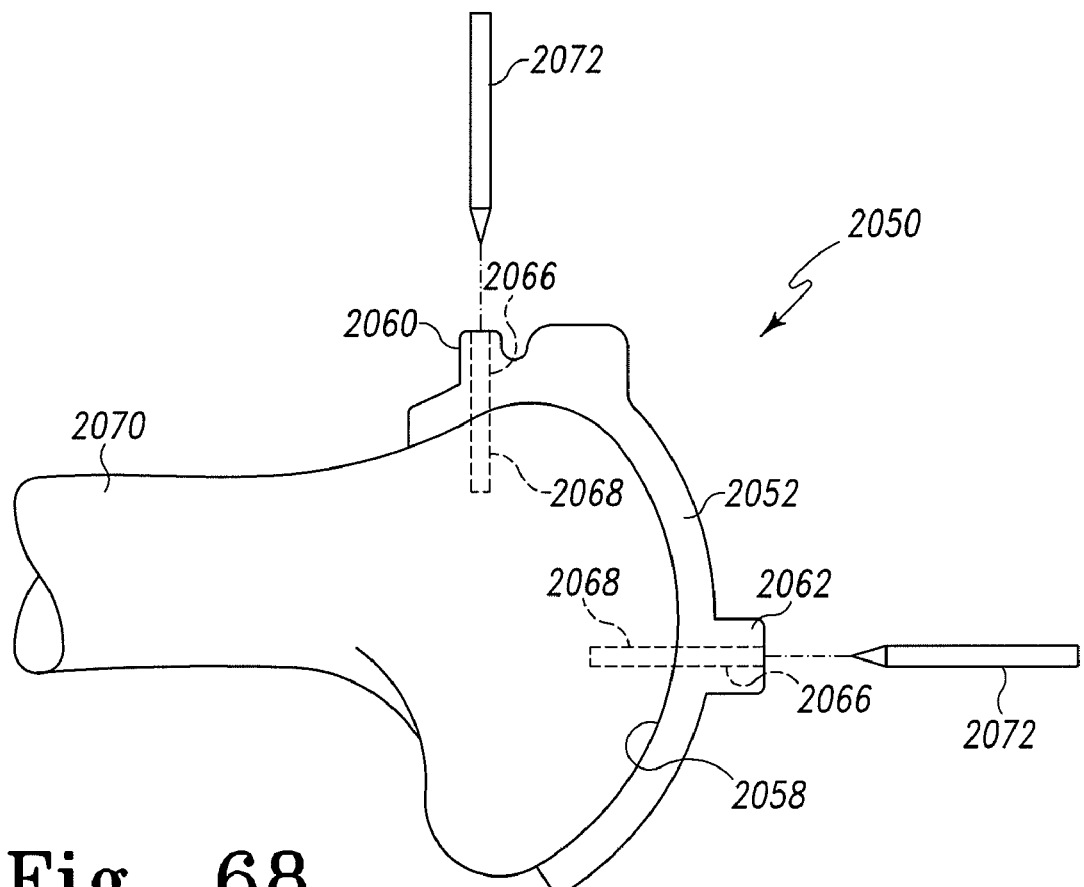
FIG. 68 is a side elevation view of the customized patient-specific orthopaedic surgical instrument of FIG. 67 coupled to a bone of a patient.

In use, the illustrative drill guide instrument 2050 is configured to be coupled to the distal end of a femur 2070 of a patient as illustrated in FIG. 68. Again, because the drill guide instrument 2050 includes the negative contour 2058, the drill guide instrument 2050 may be coupled to the femur 2070 in a pre-planned, unique position such that the drill guides 2060, 2062 are positioned in a desired location relative to the femur 2070. As such, because the positioning of the drill guide instrument 2050 has been predefined based on the negative contour 2058, an orthopaedic surgeon may couple the drill guide instrument 2050 to the femur 2070 without the need of estimating the correct location.

After the drill guide instrument 2050 is coupled to the distal end of the femur 2070, the orthopaedic surgeon may use the drill guides 2060, 2062 to drill a number of holes or passageways 2068 in the femur 2070. After the passageways 2068 have been drilled into the femur 2070, a number of guide pins 2072 may be inserted or threaded into the passageways 2068. The drill guide instrument 2050 may be left in place during the insertion of the guide pins 2072 or may be removed prior thereto. The guide pins 2072 are inserted into the femur 2070 such that a portion of each pin 2072 extends outwardly from the femur 2070.

Figure 69:
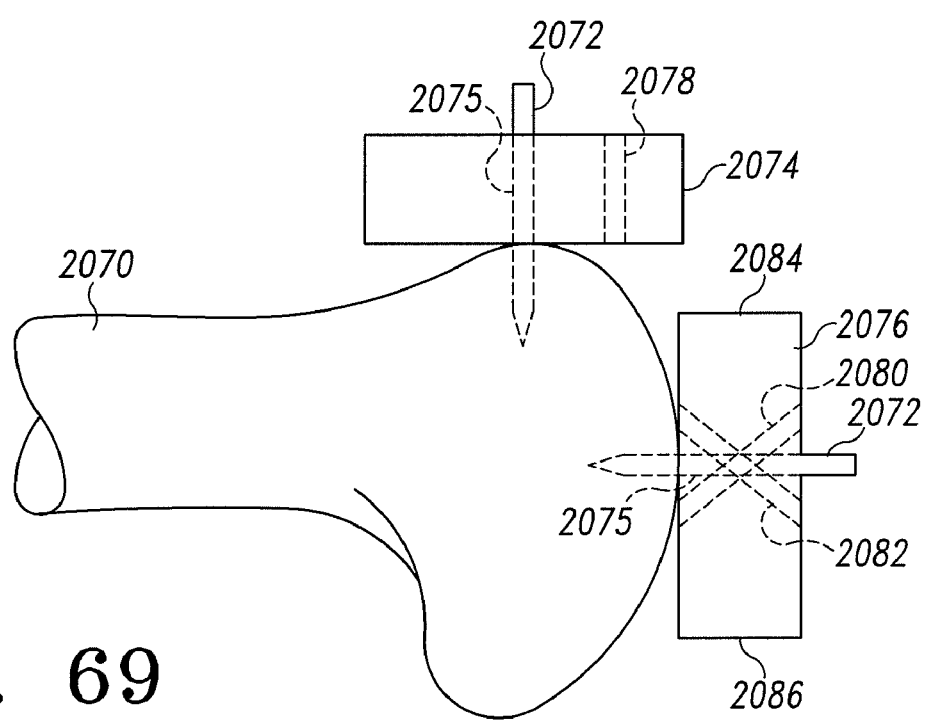
FIG. 69 is a side elevation view of a pair of universal bone-cutting blocks coupled to the bone of the patient of FIG. 68.

After the guide pins 2072 have been inserted into the femur 2070, a number patient-universal or standard bone cutting blocks may be coupled to the femur 2070 using the guide pins 2072. For example, as illustrated in FIG. 69, a patient-universal distal cutting block 2074 and a patient-universal 4-in-1 femur-cutting block 2076 may be coupled to the femur 2070. Each of the blocks 2074, 2076 include a guide pin passageway 2075 configured to receive the portion of the corresponding guide pin that extends outwardly from the femur 2070. Additionally, each of the blocks 2074, 2076 include one or more cutting guides. For example, the block 2074 includes a captured cutting guide 2078. The block 2076 includes a pair of angled, captured cutting guides 2080, 2082. In addition, the block 2076 includes a pair of non-captured cutting guides 2084, 2086, which define the ends of the block 2076. In use, each of the cutting guides 2078, 2080, 2082, 2084, 2086 may be used to guide a bone saw blade or other cutting device. To do so, the bone saw blade may be inserted into the captured guides 2078, 2080, 2082 or abutted against the non-captured guides 2084, 2086 to facilitate the cutting of the femur 2070. It should be appreciated that because the position of the guide pins 2072 are pre-determined due to the configuration of the drill guide instrument 2050, any bone cuts made using the patient-universal cutting blocks 2074, 2076 correspond to the predetermined bone cutting planes (see process step 24 of algorithm 10 described above in regard to FIG. 1).

Figure 70:
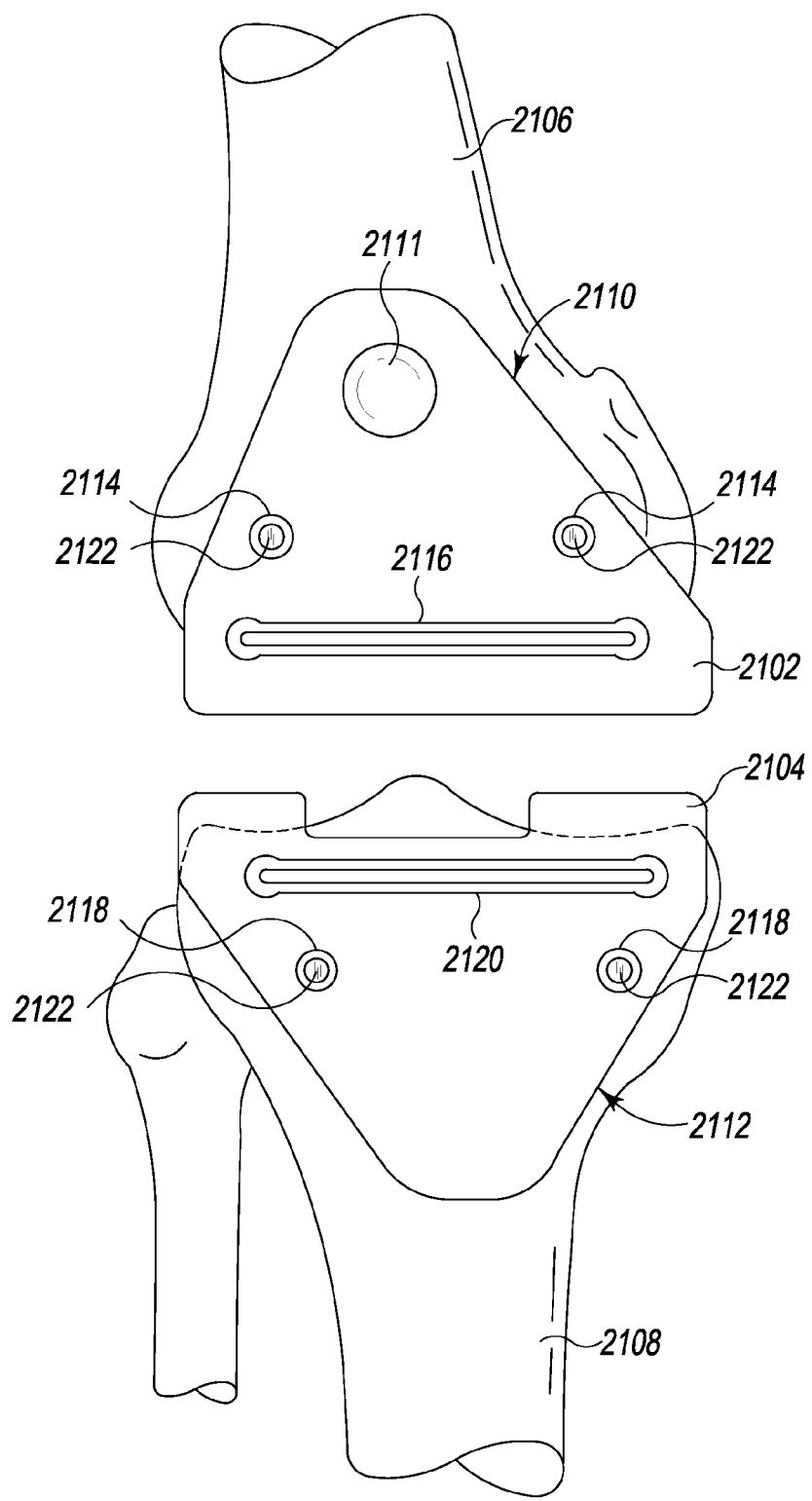
FIG. 70 is a front elevation view of another embodiment of a customized patient-specific orthopaedic surgical instrument coupled to the bony anatomy of a patient.
Figure 71:
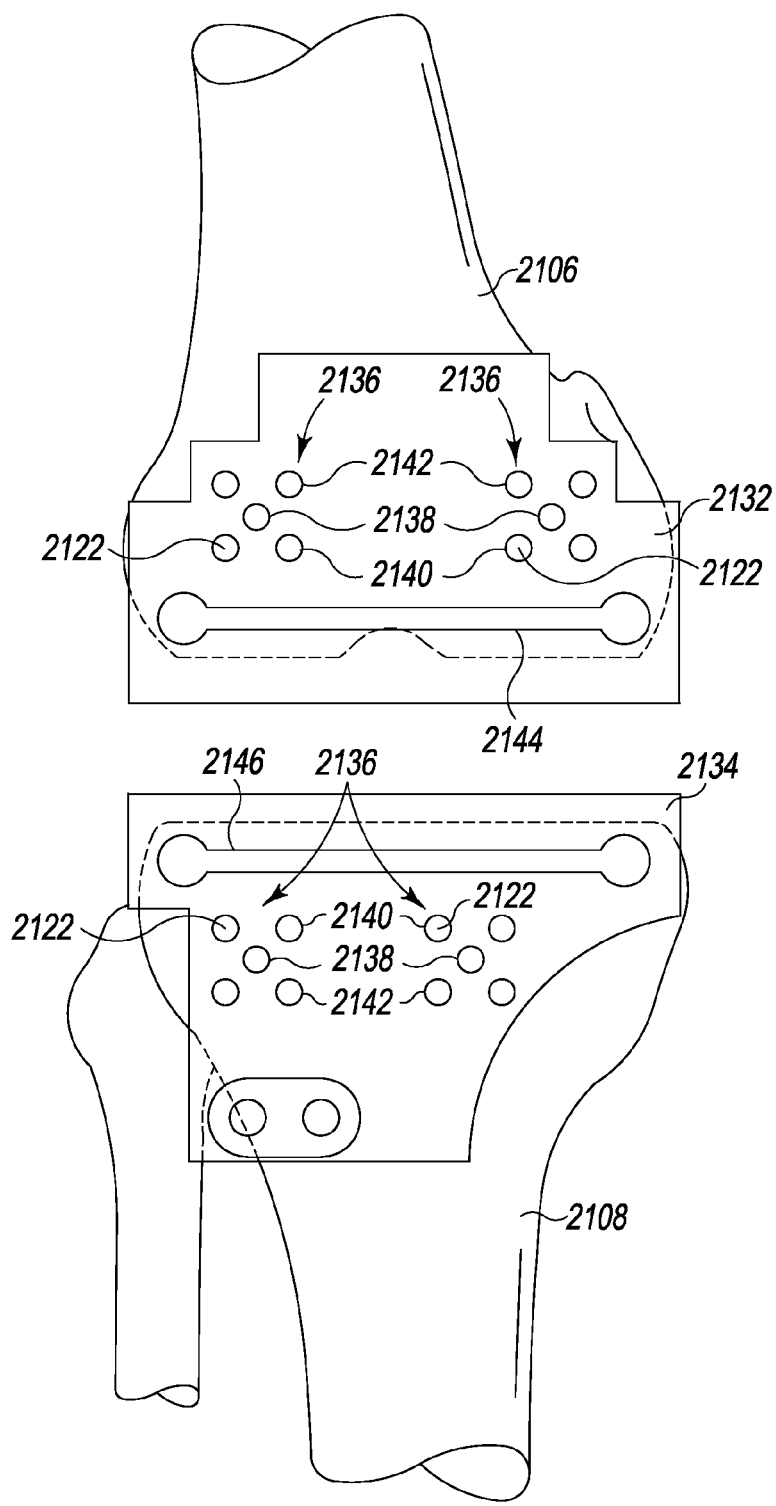
FIG. 71 is a front elevation view of a pair of re-cut bone-cutting blocks coupled to the bony anatomy of the patient of FIG. 70.

Referring now to FIGS. 70 and 71, in another embodiment, the customized patient-specific orthopaedic surgical instrument may be embodied as a pair of bone-cutting blocks 2102, 2104. The bone-cutting block 2102 is a femoral cutting block and is configured to be coupled to a femur 2106 of the patient. The bone-cutting block 2104 is a tibial cutting block and is configured to be coupled to a tibia 2108 of the patient. The bone-cutting block 2102 includes a bone-contacting or bone-facing surface 2110 having a negative contour (not shown) matching a portion of the contour of the femur 2106. Similarly, the bone-cutting block 2104 includes a bone-contacting or bone-facing surface 2112 having a negative contour (not shown) matching a portion of the contour of the tibia 2108. As discussed above, the negative contours of the blocks 2102, 2104 allow the positioning of the patient-specific cutting blocks 2102, 2104 on the patient's respective bone in a unique pre-determined location and orientation.

The femoral cutting block 2102 includes a pair of pin guides 2114. In use, the pin guides 2114 are used as drill guides to establish guide pin holes in the femur 2106. The cutting block 2102 also includes a cutting guide 2116. Illustratively, the cutting guide 2116 is a captured cutting guide, but may be embodied as a non-captured or open cutting guide in other embodiments. Similarly, the tibial cutting block 2104 includes a pair of pin guides 2118 and a cutting guide 2120. As discussed above, the cutting guides 2116, 2120 are used to guide a bone saw blade or other cutting device.

In some embodiments, the bone-contacting surface 2110 of the bone-cutting block 2102 may also include a thumb or pressure recess 2111, which is positioned on the block 2102 to correspond to a fossa of the patient's bone 2106. In use, the thumb recess 2111 may be used by the surgeon to properly seat the cutting block 2102 on the patient's bone 2106

In use, the cutting blocks 2102, 2104 are configured to be coupled to patient's femur 2106 and tibia 2108, respectively. Again, because each of the blocks 2102, 2104 include the respective negative contours, the blocks 2102, 2104 may be coupled to the respective bone 2106, 2108 in a pre-planned, unique position such that the pin guides 2114, 2118 and cutting guides 2116, 2120 are positioned in a desired location relative to the respective bone 2106, 2108. After the blocks 2102, 2104 have been coupled to the respective bone 2106, 2108, the orthopaedic surgeon may drill guide pin holes into the bones 2106, 2108 using the pin guides 2114, 2118 as drill guides. Guide pins 2122 may then be inserted into each pin guide 2114, 2118 to secure the corresponding patient-specific cutting block 2102, 2104 to the respective bone 2106, 2108. After the cutting blocks 2102, 2104 have been secured to the femur 2106 and tibia 2108 of the patient, the orthopaedic surgeon may resect the femur 2106 and the tibia 2108 using the cutting guides 2116, 2120 with a bone saw or other cutting device. To do so, the surgeon may insert a bone saw blade of the bone saw into the cutting guide 2116, 2120. It should be appreciated that because the position of the cutting guides 2116, 2120 are pre-determined due to the configuration of the respective bone cutting blocks 2102, 2104, any bone cuts made using the patient-specific cutting blocks 2102, 2104 correspond to the predetermined bone cutting planes (see process step 24 of algorithm 10 described above in regard to FIG. 1).

In some instances, the orthopaedic surgeon may determine that additional bone must be removed from the femur and/or tibia subsequent to the first resection using the patient-specific cutting blocks 2102, 2104. In such cases, the orthopaedic surgeon may use a pair of patient-universal re-cut blocks 2132, 2134 as shown in FIG. 71. The patient-universal recut blocks 2132, 2134 may be coupled to the femur 2106 and the tibia 2108 of the patient, respectively, using the guide pins 2122. That is, the location of the pin guides 2114, 2118 on the respective patient-specific cutting blocks 2102, 2104 is selected such that the guide pins 2122, once inserted into the patient's bone, may be used with patient-universal or standard re-cut blocks. As such, new guide pins for the re-cut blocks 2132, 2134 are not needed. Each of the re-cut blocks 2132, 2134 include a grouping of guide pin holes 2136 configured to receive the guide pins 2122. Illustratively, each grouping of the guide pin holes 2136 includes a neutral guide pin hole 2138, a plus two millimeter guide pin hole 2140, and a minus two millimeter guide pin hole 2142. However, guide pin holes corresponding to other resection amounts may be used in other embodiments. Additionally, as illustrated in FIG. 71, the guide pin holes 2136 include pairings of holes that may be used to adjust the angle of the resection cut. Each of the re-cut blocks 2132, 2134 also include a captured cutting guide 2144, 2146. However, in other embodiments, the re-cut blocks 2132, 2134 may include non-captured or open cutting guides in addition to or in place of the guides 2144, 2146.

Figure 72:
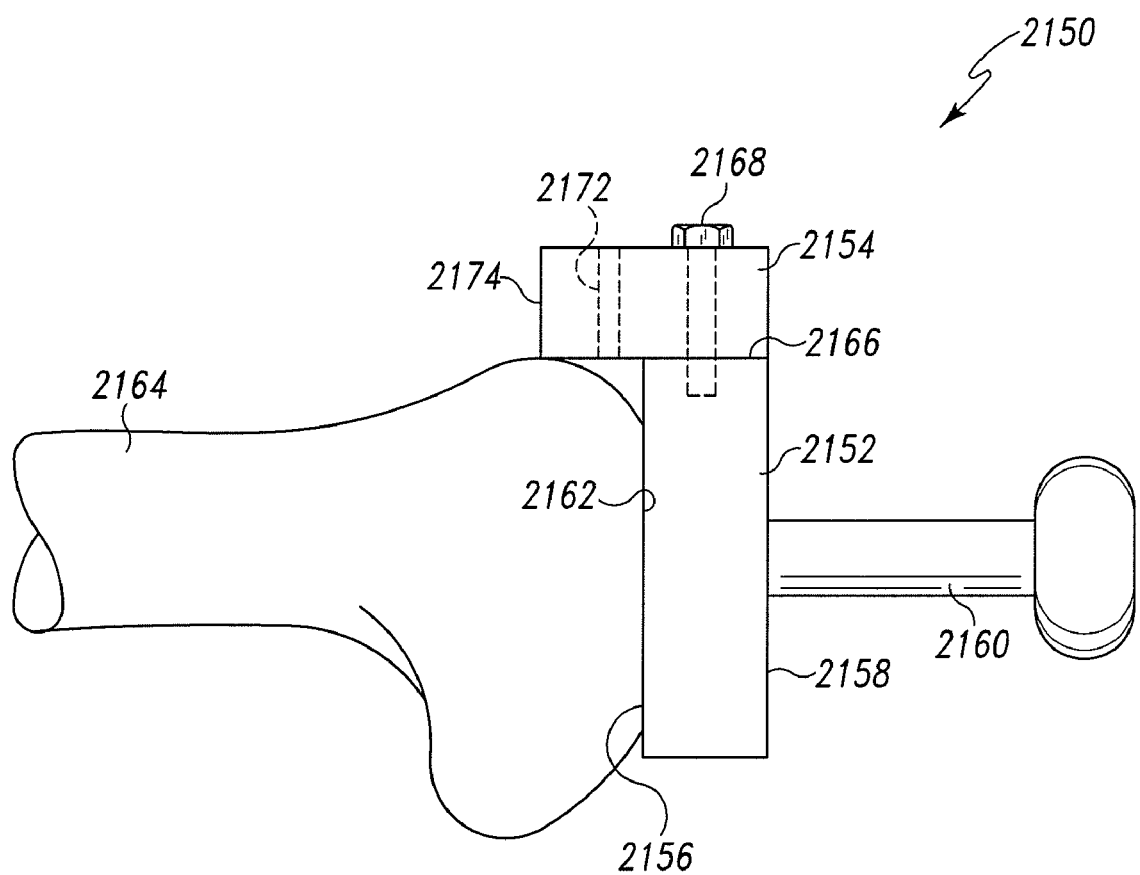
FIG. 72 is a side elevation view of another embodiment of a re-cut bone-cutting block.
Figure 73:
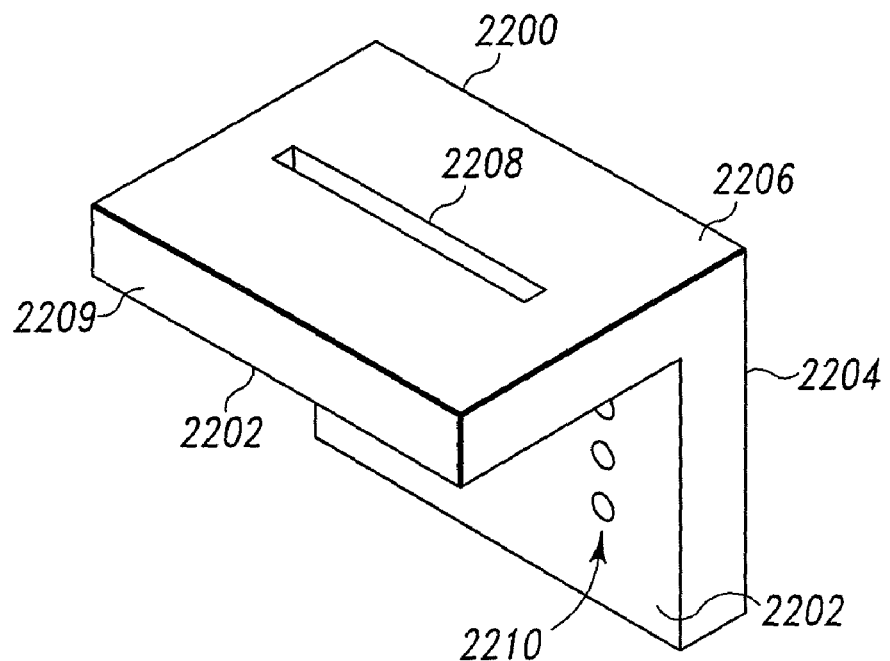
FIG. 73 is a top perspective view of another embodiment of a re-cut cutting block.

Referring now to FIG. 72, in one embodiment, a patient-universal re-cut instrument 2150 includes a base 2152 and a cutting block 2154 removably coupled to the base 2152. The base 2152 includes a substantially planar bone-contacting or bone-facing surface 2156 and an outer surface 2158. A handle 2160 extends outwardly from the outer surface 2158 to facilitate the positioning of the instrument 2150. The bone-contacting surface 2156 is configured to contact the resected surface 2162 of a bone 2164 of the patient as illustrated in FIG. 72.

The cutting block 2154 is secured to an end 2166 of the base 2152 via a securing device 2168 such as a bolt, thumb-screw, or other securing device capable of removably coupling the block 2154 to the base 2152. The cutting block 2154 includes a captured cutting guide 2172, but may also include a non-captured cutting guide 2174 in some embodiments. In such embodiments, the non-captured cutting guide 2174 may define an end side of the cutting block 2154. The cutting guide 2172 may be defined in the cutting block 2154 such that any amount of bone may be resected. For example, in one illustrative embodiment, the cutting guide 2172 is defined in the cutting block 2154 such that two millimeters of bone is removed during each resectioning of the bone 2164. In other embodiments, the cutting block 2154 may be configured to remove other amounts of bone. In addition, because the cutting block 2154 is removable from the base 2152, cutting blocks having cutting guides configured to facilitate the removal of various amounts of bone may be selectively coupled to the base 2152. As such, a selection of cutting blocks configured to remove various amounts of bone during resectioning may be used with a single base 2152.

Figure 74:
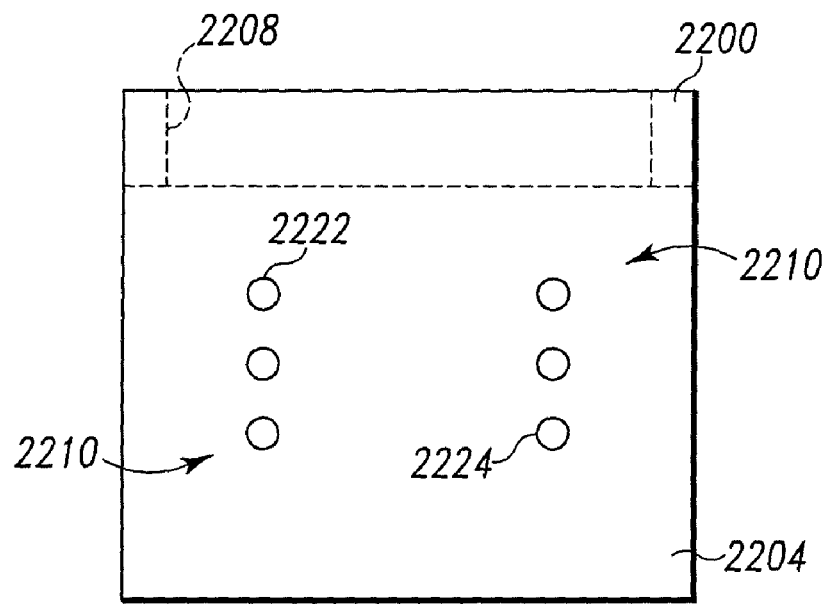
FIG. 74 is an end elevation view of the re-cut bone-cutting block of FIG. 73.
Figure 75:
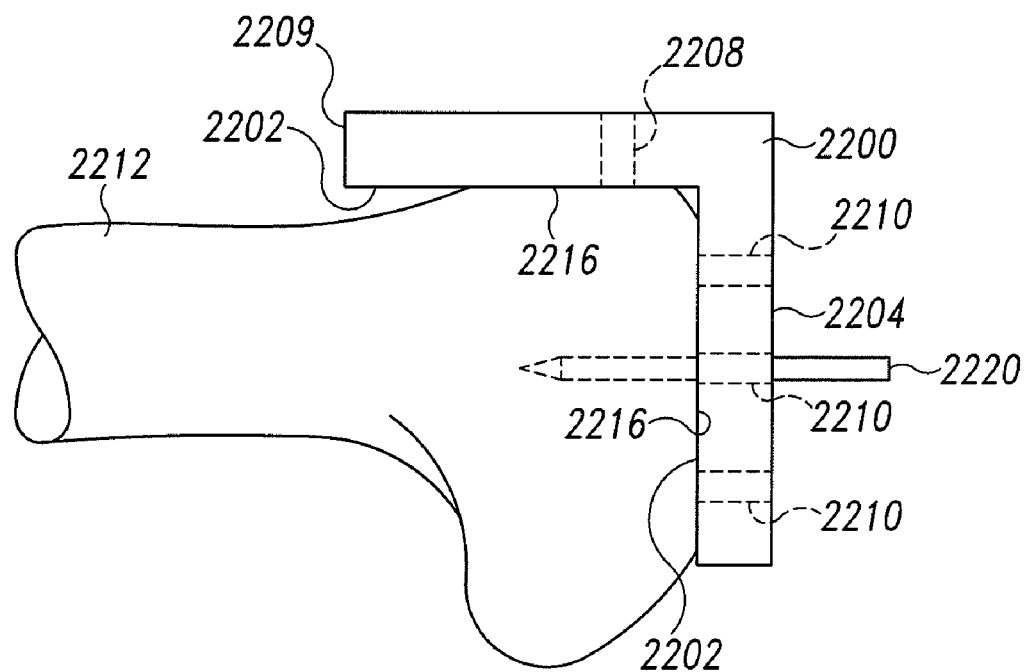
FIG. 75 is a side elevation view of the re-cut bone-cutting block of FIG. 73 coupled to a bone of a patient.
Figure 76:
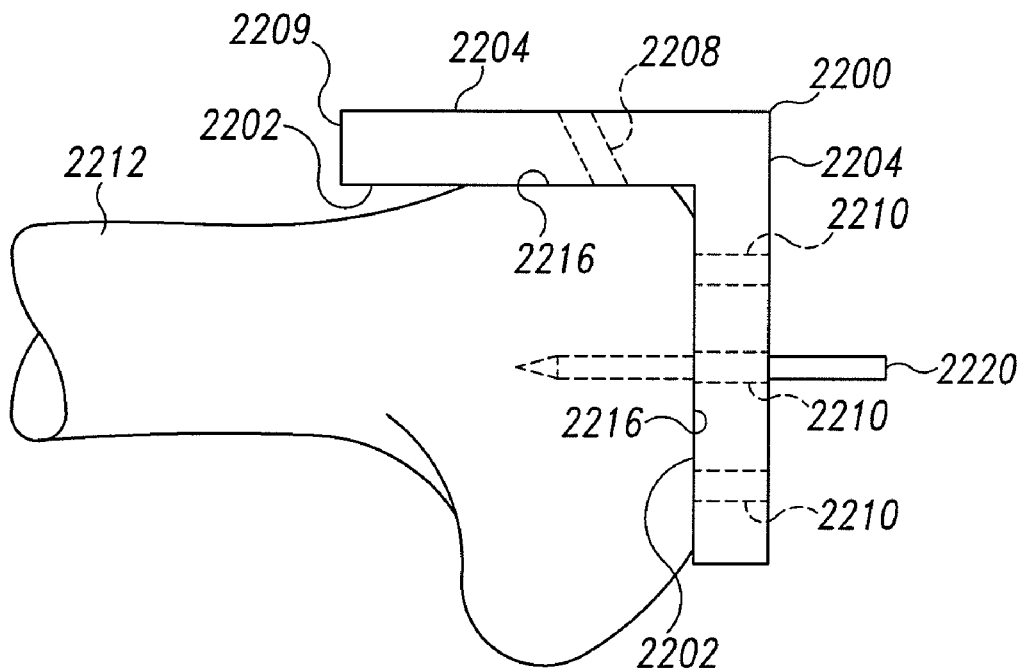
FIG. 76 is a side elevation view of another embodiment of the re-cut bone-cutting block of FIG. 73 coupled to a bone of a patient.
Figure 77:
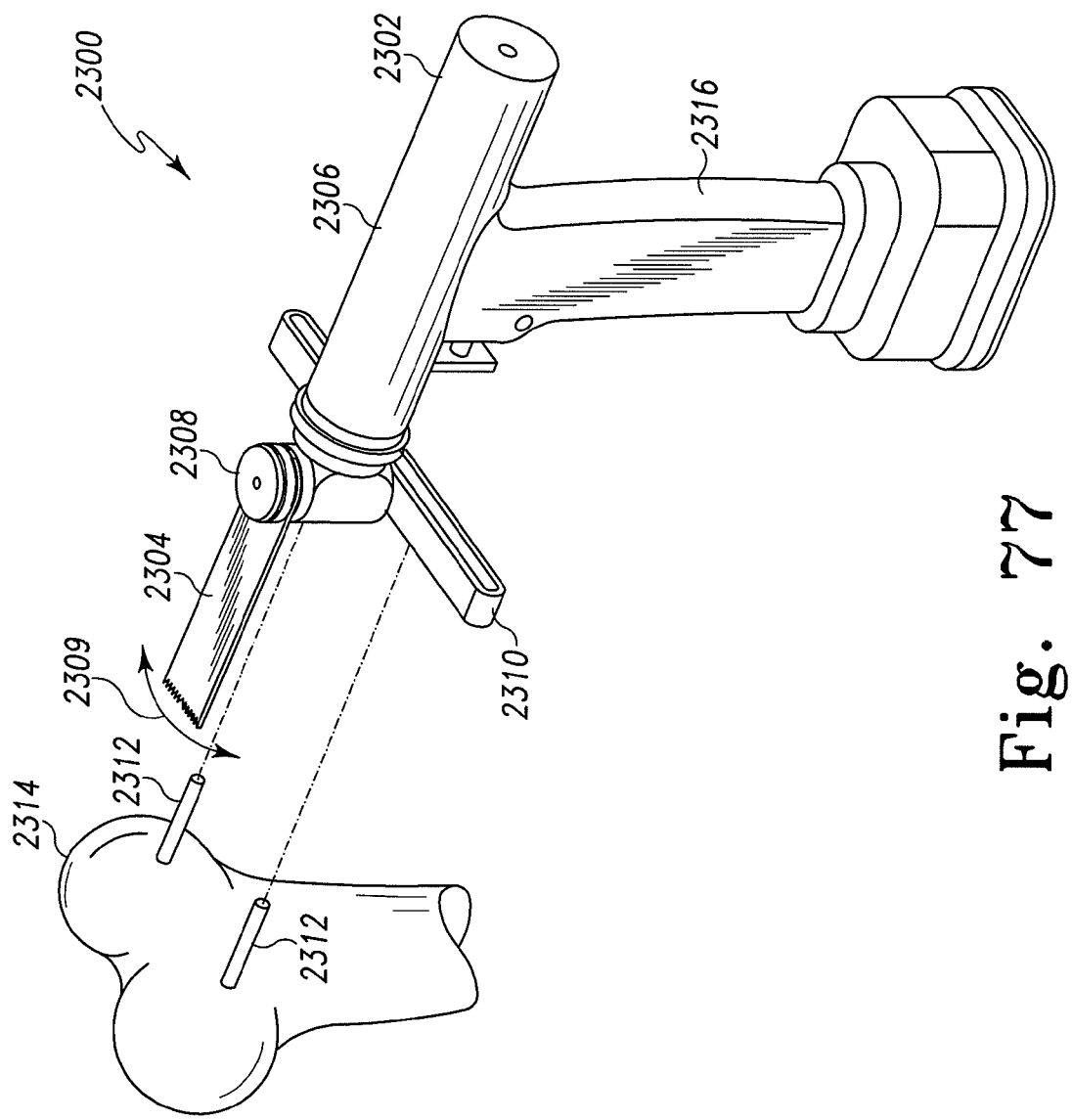
FIG. 77 is a perspective view of one embodiment of an orthopaedic surgical instrument.

Referring now to FIGS. 73-76, in another embodiment, a patient-universal re-cut instrument or block 2200 includes a planar bone-contacting or bone-facing surface 2202, a lower outer surface 2204, and an upper outer surface 2206. The bone-contacting surface 2202 is configured to contact the resected surface 2216 of a bone 2212 of the patient as illustrated in FIGS. 75 and 76. Illustratively, the re-cut block 2200 is configured for use with a femur of the patient, but may be configured for use with the tibia or other bone of the patient in other embodiments. The illustrative re-cut instrument 2200 has a substantially "L"-shape, but may have other shapes in other embodiments configured to be coupled to the end of a resected bone.

The re-cut instrument 2200 includes a captured cutting guide 2208 defined in the upper outer surface 2206, but may also include a non-captured cutting guide 2209 in some embodiments. In such embodiments, the non-captured cutting guide 2209 may define an end side of the re-cut block 2200. The cutting guide 2208 may be defined in the re-cut block 2200 such that any amount of bone may be resected. For example, in one illustrative embodiment, the cutting guide 2208 is defined in the re-cut block 2200 such that two millimeters of bone is removed during each resectioning of the bone 2212. In other embodiments, the re-cut block 2200 may be configured to remove other amounts of bone.

The re-cut instrument 2200 also includes a number of guide pin holes 2210 as illustrated in FIG. 74. The guide pin holes 2210 are defined in the lower outer surface 2204 of the instrument 2200 such that the instrument 2200 may be coupled to the bone 2212 of the patient in a neutral or angled position. That is, as illustrated in FIGS. 75 and 76, the re-cut block 2200 is configured to be coupled to the bone 2212 of the patient using the guide pins 2220, which were secured to the bone 2212 of the patient using a customized patient-specific orthopaedic surgical instrument such as one of the bone-cutting blocks 2102, 2104 described above in regard to FIGS. 70 and 71.

After the initial cut of the bone has been made using the customized patient orthopaedic surgical instrument, the recut instrument 2200 may be coupled to the bone 2212 using the guide pins 2220. As discussed above, the re-cut block 2200 may be coupled to the bone 2212 in a neutral orientation or in an angled orientation to facilitate straight or angled cuts, respectively. For example, if an angled cut is desired, the re-cut instrument 2200 may be coupled to the bone 2212 such that the guide pins 2220 are received in guide pin holes 2222, 2224, which are offset relative to each other (see FIG. 74). As such, the cutting guide 2208 is oriented in an angled position relative to the bone 2212 of the patient. In some embodiments as illustrated in FIG. 76, the cutting guide 2208 may be defined in the re-cut instrument at an angle to provide additional angulation to the bone cut. In use, an orthopedic surgeon may be supplied with a variety of re-cut blocks 2200, each configured to remove different amounts of bone and/or cut the bone at various angles. For example, the re-cut blocks 2200 may be shipped to the orthopaedic surgeon along with the customized patient-specific orthopaedic surgical instrument as discussed above in regard to process steps 30, 32 of algorithm 10.

Referring now to FIGS. 77-80, in one embodiment, an orthopaedic surgical tool usable with various customized patient-specific orthopaedic surgical instruments is embodied as a bone saw tool 2300. The bone saw tool 2300 includes a bone saw 2302 and a bone saw blade 2304. The bone saw 2300 includes a housing 2306 having a bone saw chuck 2308 configured to receive the bone saw blade 2304 positioned on one end of the housing 2306. A handle 2316 extends downwardly from the housing 2306. A user may couple the bone saw blade 2304 to the bone saw 2302 by inserting the bone saw blade 2304 into the chuck 2308 and operating the chuck 2308 to secure the bone saw blade 2304 to the bone saw 2302. In use, the illustrative bone saw blade chuck 2308 moves the saw blade 2304 in a cutting motion. For example, in some embodiments, the bone saw blade chuck 2308 oscillates the bone saw blade 2304 along a cutting arc 2309. However, in other embodiments, the bone saw blade 2304 may be oscillated or otherwise moved in any direction and along any cutting path depending on the particular application and type of bone saw used.

The bone saw 2302 also includes a guide 2310 coupled to the bottom of the housing 2306. The guide 2310 is configured as a body having one or more holes to receive one or more guide pins 2312 that have been coupled to a bone 2314 of a patient. In the illustrative embodiment described herein, the guide 2310 is embodied as an elongated body having a slot defined therein for receiving the guide pins 2312. The guide pins 2312 may be coupled to the bone 2314 using a customized patient-specific orthopaedic surgical instrument such as the drill guide instrument 2050 illustrated in and described above in regard to FIGS. 67-69. As such, the guide pins 2312 are coupled to the bone 2314 in a pre-determined position due to the configuration of the customized patient-specific orthopaedic surgical instrument such that any bone cuts made with the bone saw 2302 correspond to the predetermined bone cutting planes (see process step 24 of algorithm 10 described above in regard to FIG. 1).

As discussed above, the guide 2310 is configured to receive the guide pins 2312. The guide 2310 is elongated and oriented orthogonally with respect to the guide pins 2312 such that the pins 2312 may be received in the guide 2310. In use, the bone saw 2302 may be moved in a medial-lateral direction with respect to the patient's bone 2314 until one of the guide pins 2312 contacts an inner side wall of the guide 2310.

Figure 78:
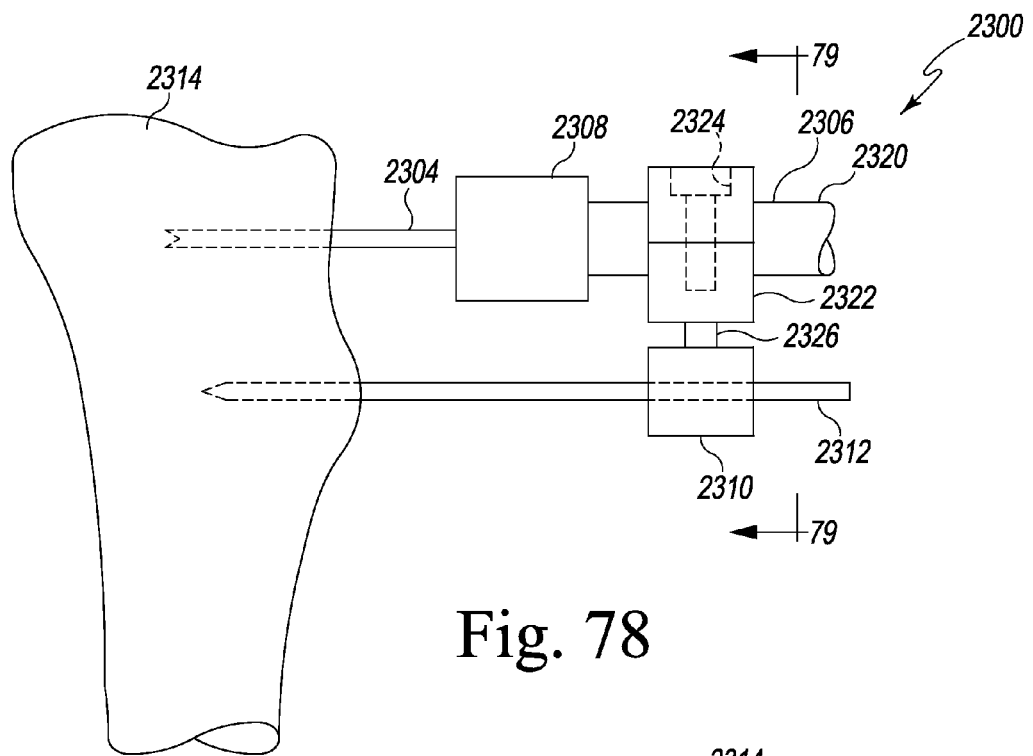
FIG. 78 is a partial side elevation view of the orthopaedic surgical instrument of FIG. 77.

In other embodiments, the guide 2310 may be secured to the bone saw 2302 via use of other devices. For example, as illustrated in FIG. 78, the housing 2306 of the bone saw 2302 may include a shaft 2320 in some embodiments. In such embodiments, the guide 2310 may be secured to the shaft 2320 via a clamp 2322. The guide 2310 may be removably coupled to the shaft 2320 in some embodiments. For example, the clamp 2322 may include a securing device such as a bolt 2324, which may be removed to release or remove the guide 2310 from the bone saw 2302.

Figure 79:
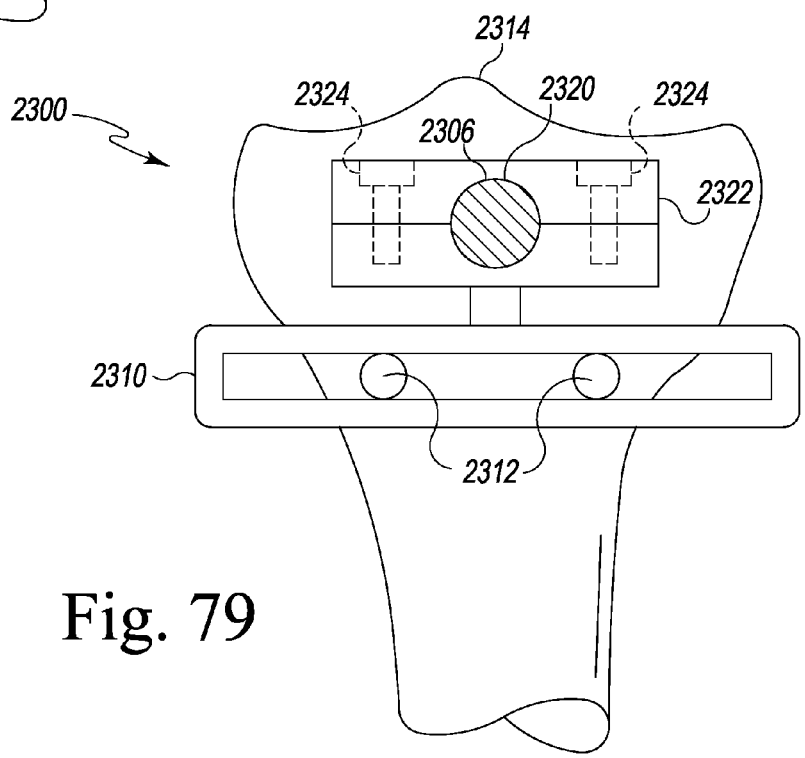
FIG. 79 is a cross-sectional view of the orthopaedic surgical instrument of FIG. 78.

As shown in FIGS. 78 and 79, the guide pins 2312 are received in the guide 2310 in use. In some embodiments, the guide 2310 may be configured to swivel or turn with respect to the bone saw 2302. That is, the guide 2310 may be coupled to the clamp 2322 via a swiveling post 2326. As such, during use, the bone saw 2302 may be moved in a medial-lateral direction and swivel with respect to the guide pins 2312.

Figure 80:
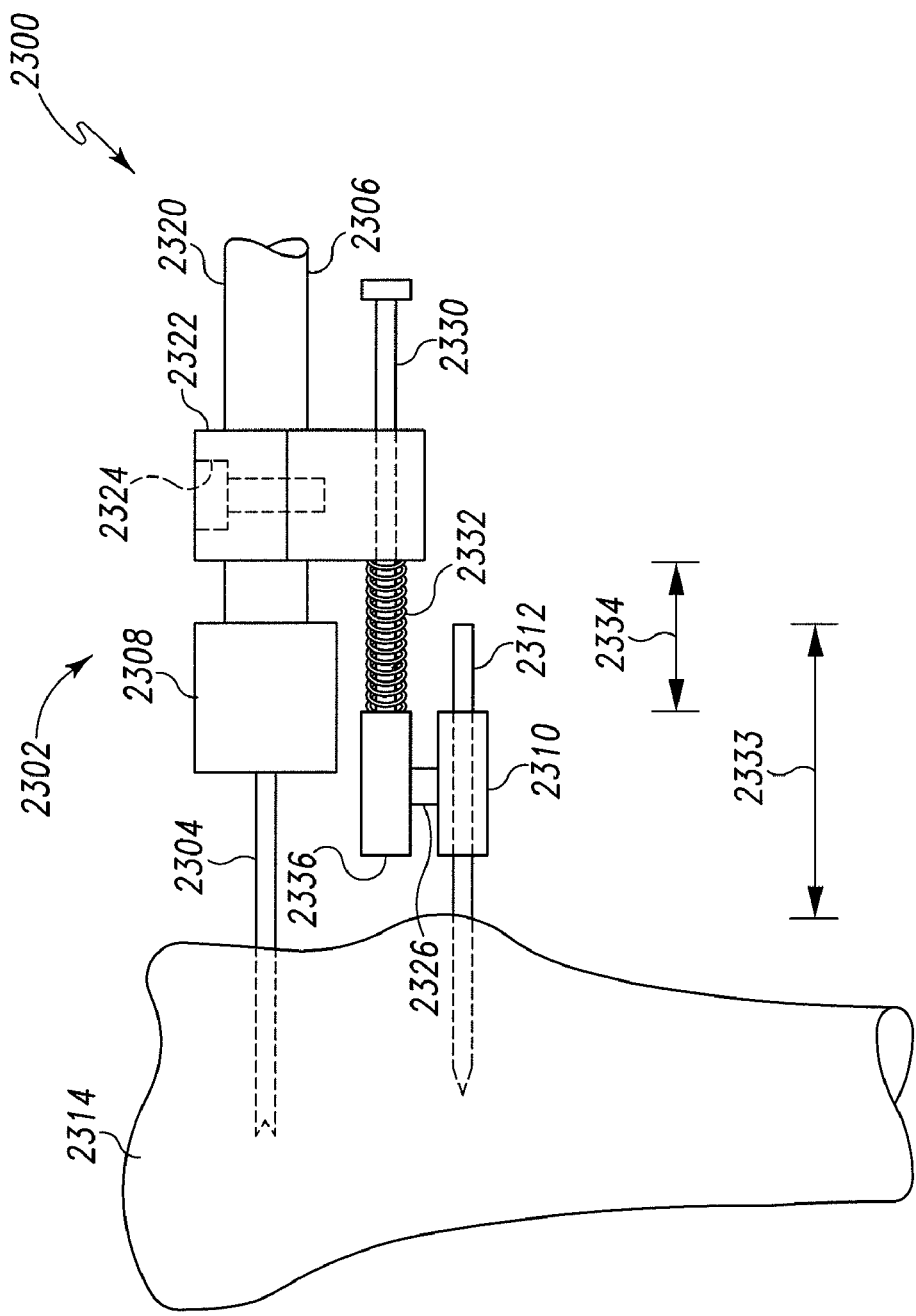
FIG. 80 is a partial side elevation view of another embodiment of the orthopaedic surgical instrument of FIG. 78.

In some embodiments, the distance 2333 at which the guide pins 2312 extend from the bone 2312 may vary. For example, in some embodiments, the guide pins 2312 may extend from the bone 2314 a short distance. In such embodiments, the guide 2310 of the bone saw 2302 may be configured to move inwardly and outwardly with respect to the bone saw 2302 to accommodate guide pins 2312 of various lengths. For example, as illustrated in FIG. 80, the guide 2310 may be coupled to a base 2336, which is coupled to the clamp 2322 via a rod 2330. The rod 2330 extends through a spring 2332 positioned between the base of the guide 2310 and the clamp 2324. The spring 2332 biases the rod 2330 in an extended position relative to the clamp 2324. However, if the guide pins 2312 extend from the bone 2314 a short distance 2333, the guide 2310 may be pressed against the side of the bone 2314 during use to cause the spring 2332 to be compressed to a length 2334. In response to compression of the spring, the guide 2310 is retracted inwardly with respect to the bone saw 2302. In some embodiments, the guide 2310 may be coupled to the base 2336 via a swiveling post 2326. In such embodiments the guide 2310 is configured to swivel or turn with respect to the bone saw 2302.

Figure 81:
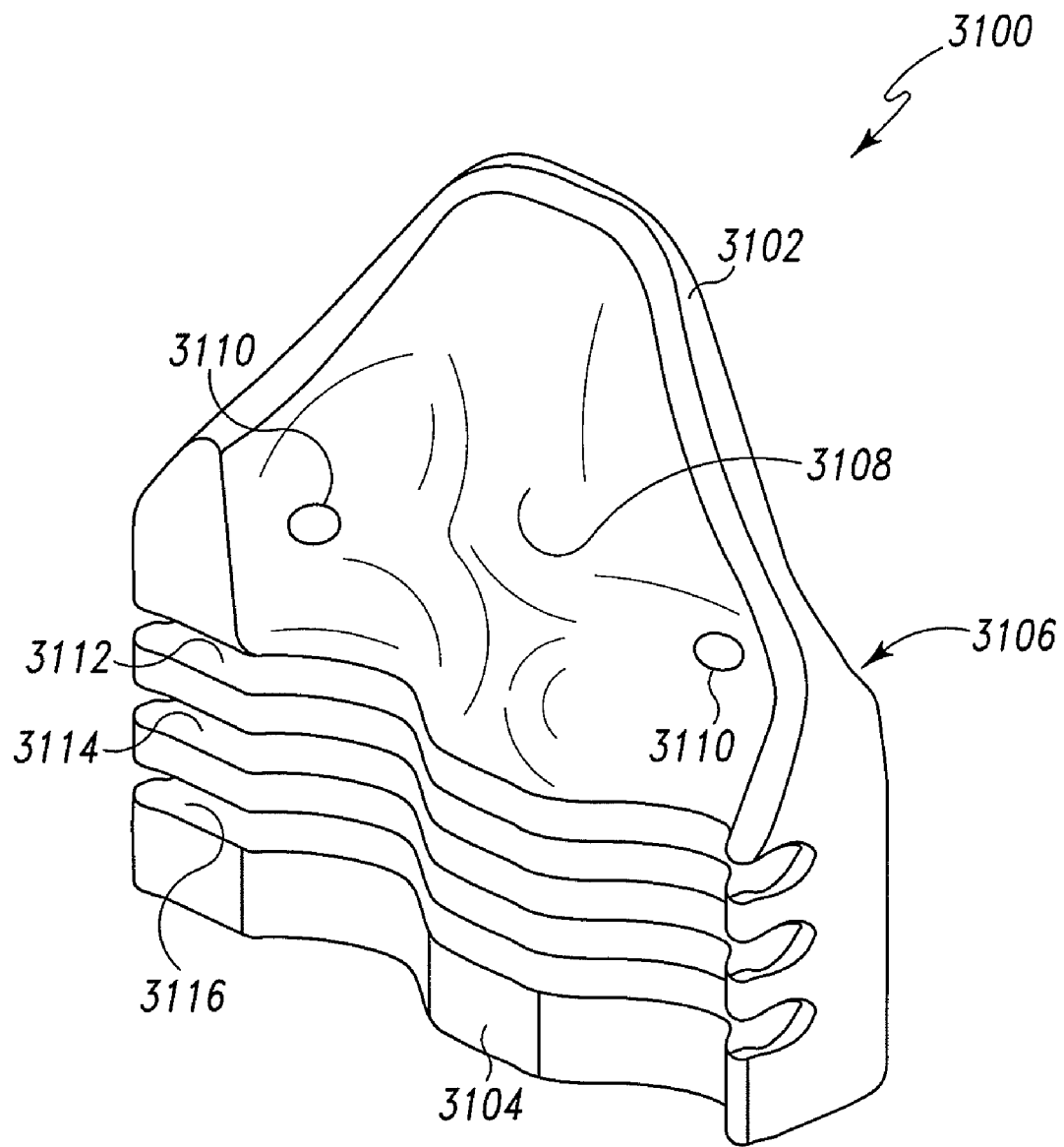
FIG. 81 is a perspective view of one embodiment of a customized patient-specific orthopaedic surgical instrument.

Referring now to FIG. 81, in one embodiment, the customized patient-specific orthopaedic surgical instrument may be embodied as a cutting block 3100. The cutting block 3100 is configured to be coupled to a bone, such as femur or tibia, of a patient. The cutting block 3100 includes a body 3102 having a bone-contacting or bone-facing surface 3104 and an outer surface 3106. The bone-contacting surface 3104 includes a negative contour 3108 configured to receive a portion of the patient's bone having a corresponding contour. As discussed above, the negative contour 3108 of the bone-contacting surface 3104 allows the positioning of the cutting block 3100 on the patient's bone in a unique pre-determined location and orientation.

The cutting block 3100 also includes a number of pin guides 3110. In use, the pin guides 3110 are used as drill guides to establish guide pin holes in the bone of the patient for securing a number of guide pins (not shown) to the bone. The cutting block 3100 may then be coupled and secured to the patient's bone via the guide pins.

The cutting block 3100 also includes a first cutting guide 3112, a second cutting guide 3114, and a third cutting guide 3116. Each of the cutting guides 3112, 3114, 3116 are spaced apart from each other a predetermined distance. For example, in one particular embodiment, each of the cutting guides 3112, 3114, 3116 are spaced apart a distance of about two millimeters, but may be spaced apart from each other distances in other embodiments. In some embodiments, the second cutting guide 3114 is embodied as the neutral or zero offset cutting guide. That is, because the position of the cutting guide 3114 is pre-determined due to the configuration of the cutting block 3100, any bone cuts made using the patient-specific cutting block 3100 correspond to the predetermined bone cutting planes (see process step 24 of algorithm 10 described above in regard to FIG. 1). As such, the cutting guide 3112 is spaced apart from the cutting guide 3114 and usable to remove a greater amount of the patient's bone (e.g., two millimeters more) relative to the cutting guide 3114. Similarly, the cutting guide 3116 is spaced apart from the cutting guide 3114 and usable by the surgeon to remove a lesser amount of the patient's bone (e.g., two millimeters less) relative to the cutting guide 3114.

Figure 82:
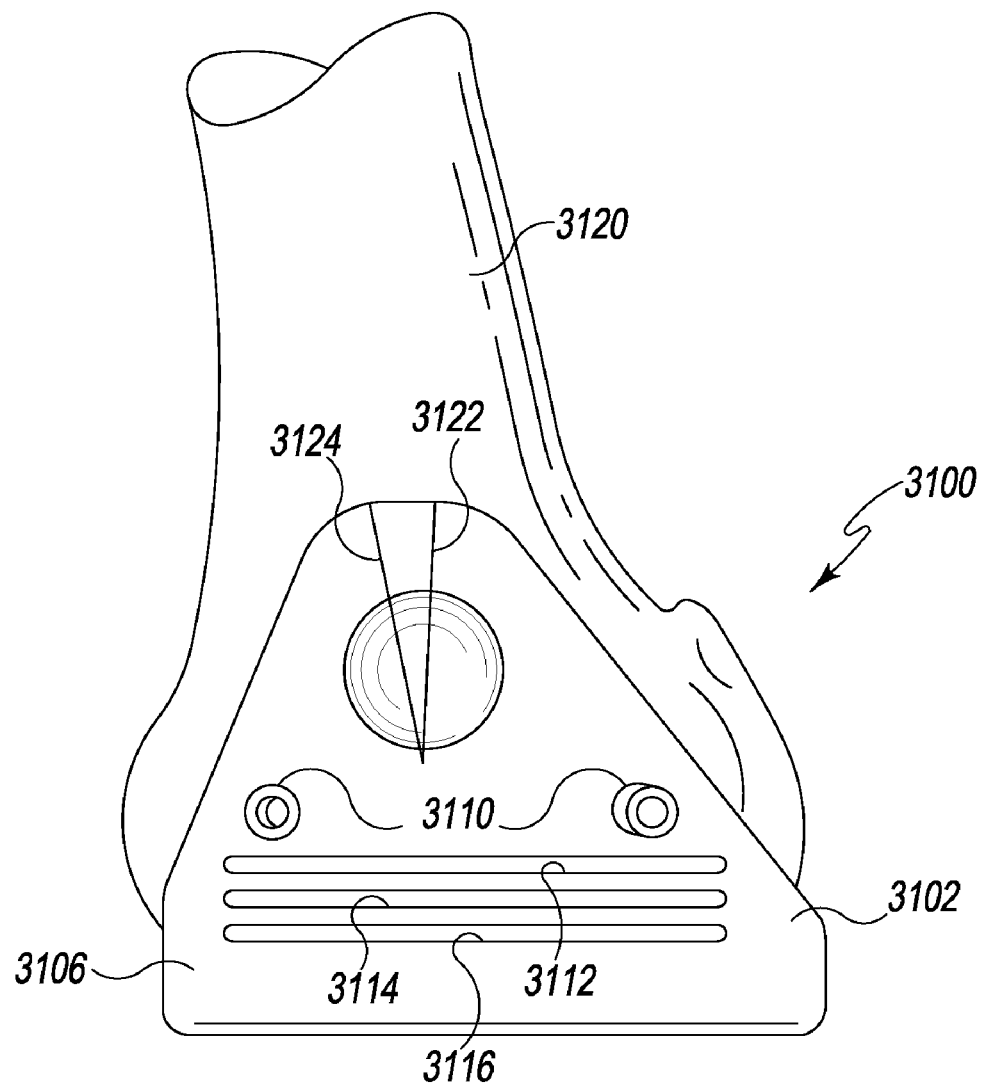
FIG. 82 is an anterior elevation view of the customized patient-specific orthopaedic surgical instrument of FIG. 81 secured to a bone of a patient.

In use, the cutting block 3100 is configured to be coupled to a patient's bone 3120, such as the femur or tibia as illustrated in FIG. 82. Again, because the bone-contacting surface 3104 of the cutting block 3100 includes the negative contour 3108, the block 3100 may be coupled to the bone 3120 in a pre-planned, unique position. The cutting block 3100 may be secured to the bone 3120 via use of a number of guide pins (not shown) received in the pin guides 3110 and the bone 3120. In some embodiments, the cutting block 3100 may include a mechanical alignment line or indicator 3122 and/or an anatomical alignment line or indicator 3124.

After the cutting block 3100 has been secured to the patient's bone 3120, the orthopaedic surgeon may perform the bone resectioning. As discussed above, the surgeon may use the cutting guide 3114 to resect the pre-planned amount of bone. That is, the bone cut made using the cutting guide 3114 corresponds to the cutting plane determined during the fabrication of the cutting block 3100 (see process step 24 of algorithm 10 described above in regard to FIG. 1). However, the orthopaedic surgeon may make an intra-operative decision based on analysis of the bony anatomy of the patient and/or soft tissue complex to remove more or less of the patient's bone with respect to the pre-planned amount (i.e., the amount removed if the surgeon uses the cutting guide 3114). For example, the orthopaedic surgeon may use the cutting guide 3112 to remove more of the patient's bone or the cutting guide 3116 to remove less of the patient's bone. As such, it should appreciated that the cutting block 3100 provides an amount of intra-operative adjustability to the orthopaedic surgeon.

Figure 83:
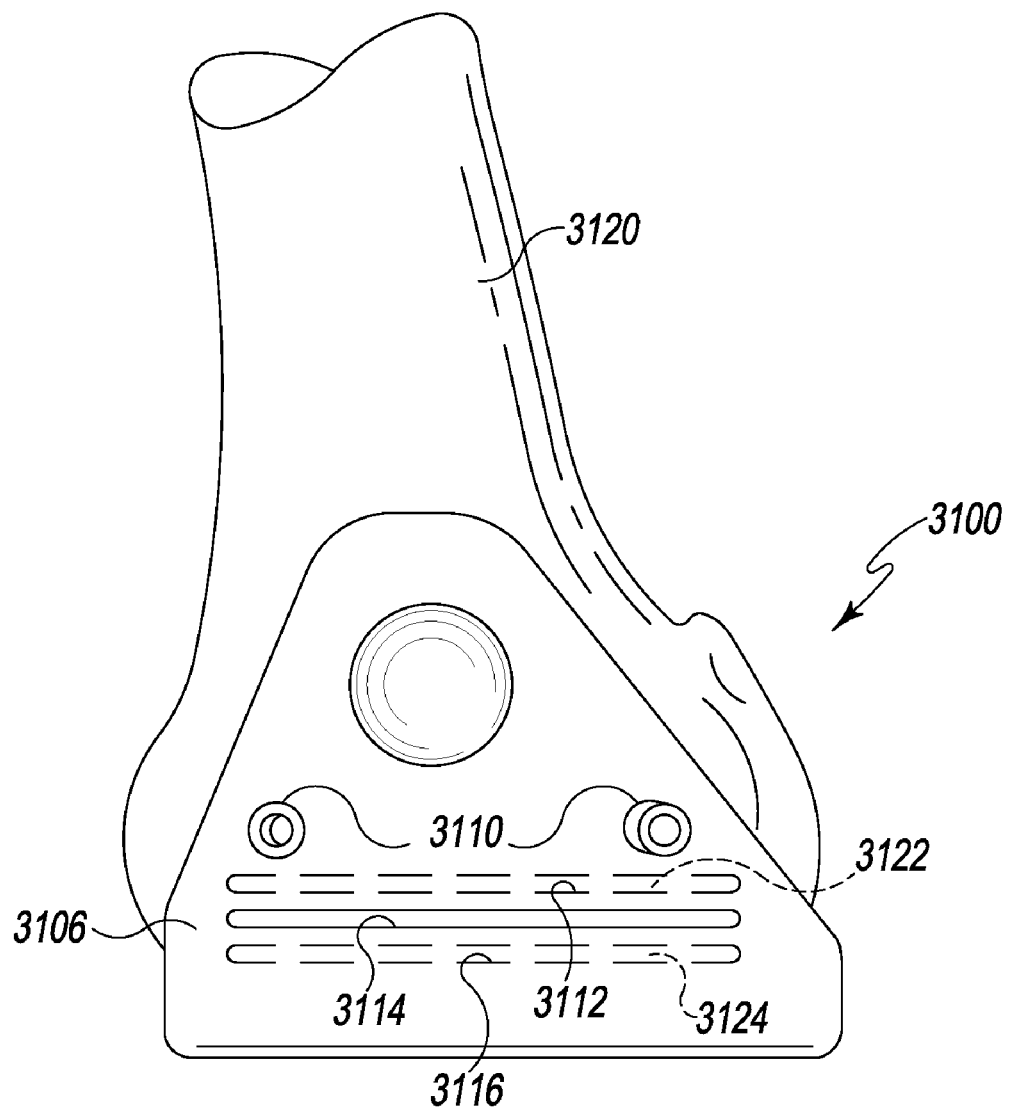
FIG. 83 is an anterior elevation view of another embodiment of a customized patient-specific orthopaedic surgical instrument secured to a bone of a patient.

Referring now to FIG. 83, in some embodiments, the cutting block 3100 may include a breakaway tab 3122 covering the cutting guide 3112 and a breakaway tab 3124 covering the cutting guide 3116. The breakaway tabs 3122, 3124 may be formed from a transparent material in some embodiments. The orthopaedic surgeon may estimate the amount of bone that will be removed when using each cutting guide 3112, 3116 by looking through the transparent breakaway tabs 3122, 3124. In use, if the surgeon decides to use one of the cutting guides 3112, 3116, the surgeon may remove the respective breakaway tab 3122, 3124 and resect the patient's bone 3120 using the corresponding cutting guide 3112, 3116.

Figure 84:
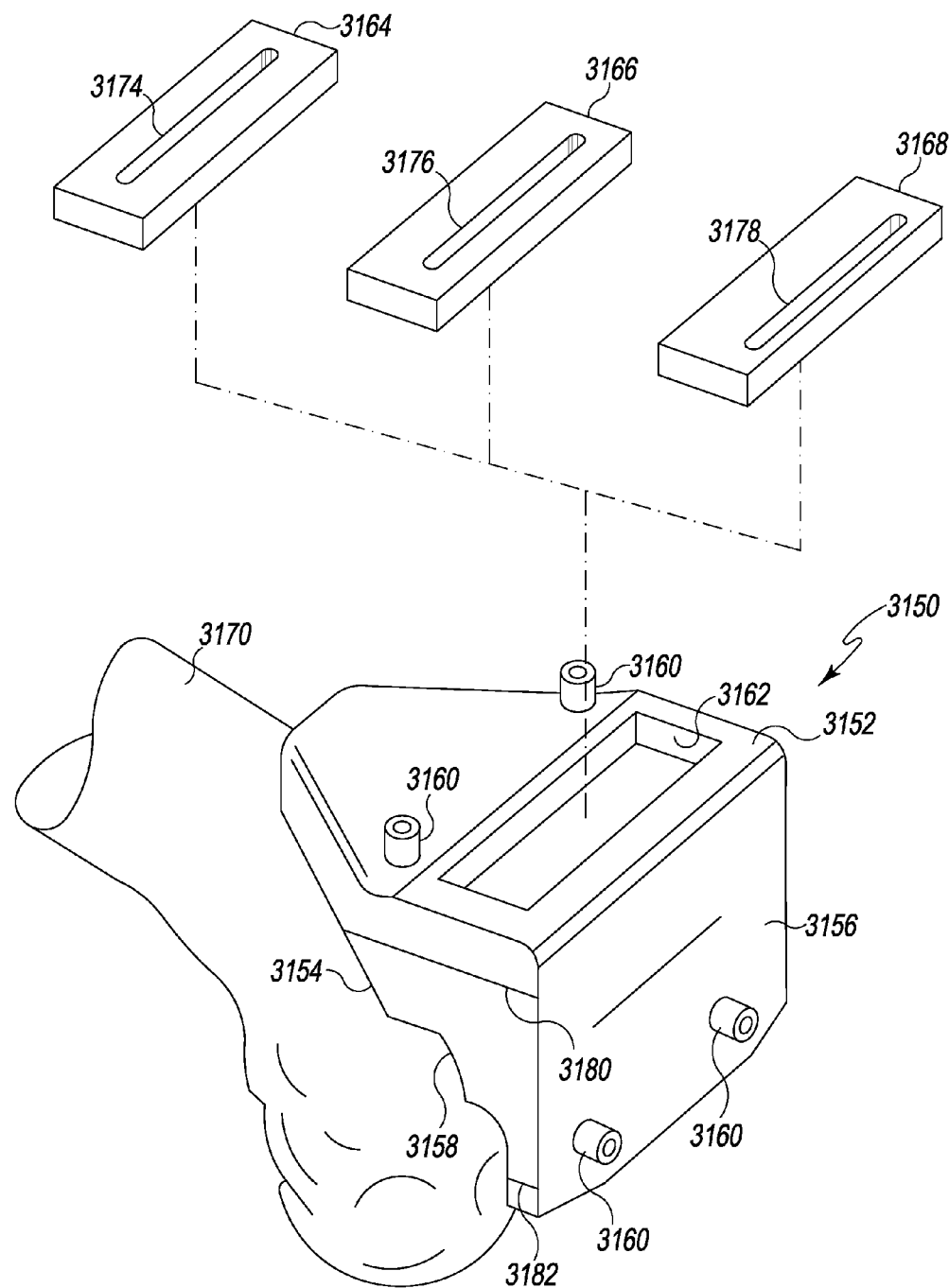
FIG. 84 is an exploded perspective view of another embodiment of a customized patient-specific orthopaedic surgical instrument secured to a bone of a patient.
Figure 85:
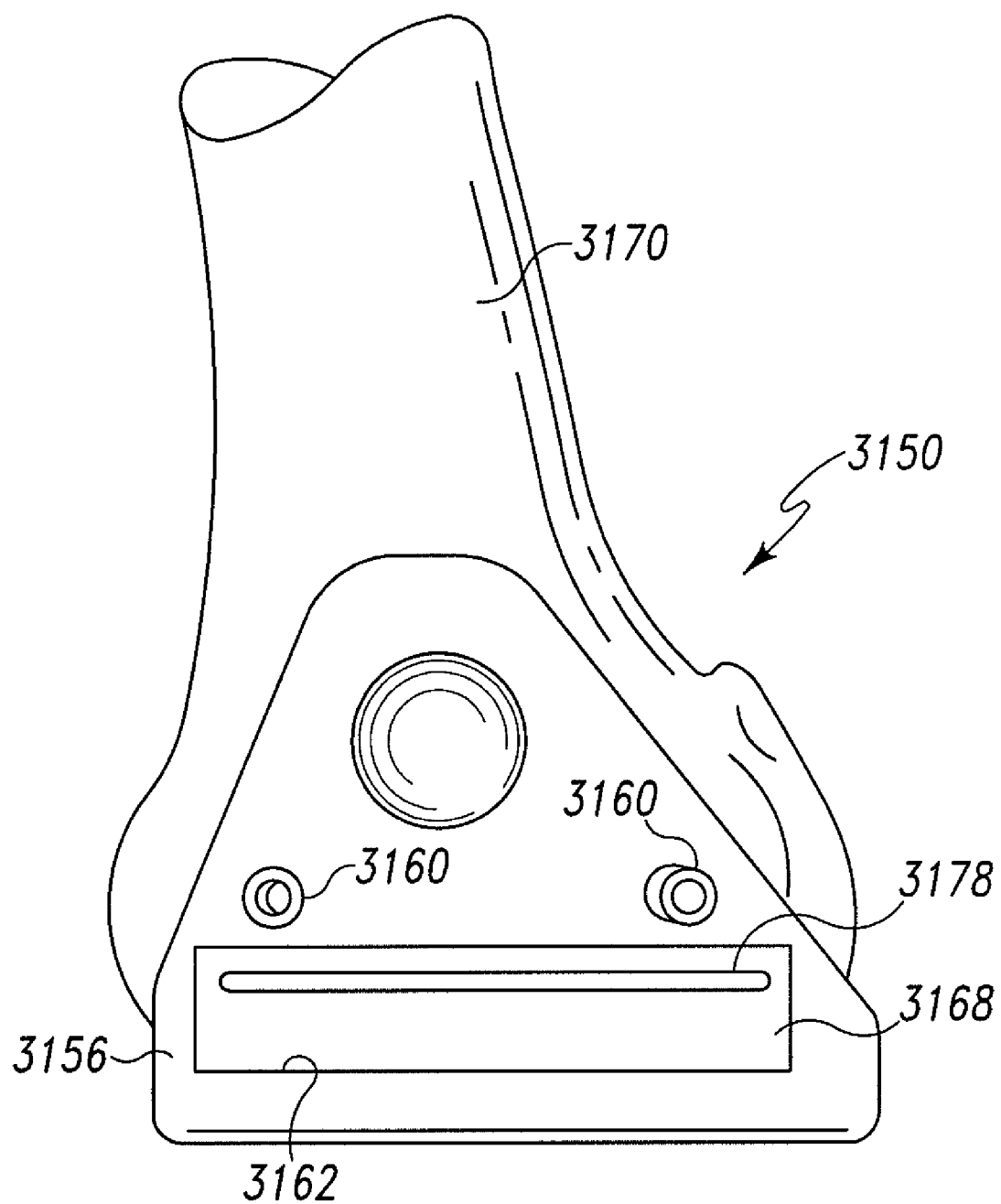
FIG. 85 is an anterior elevation view of one embodiment of the customized patient-specific orthopaedic surgical instrument of FIG. 84 secured to a bone of a patient.
Figure 86:
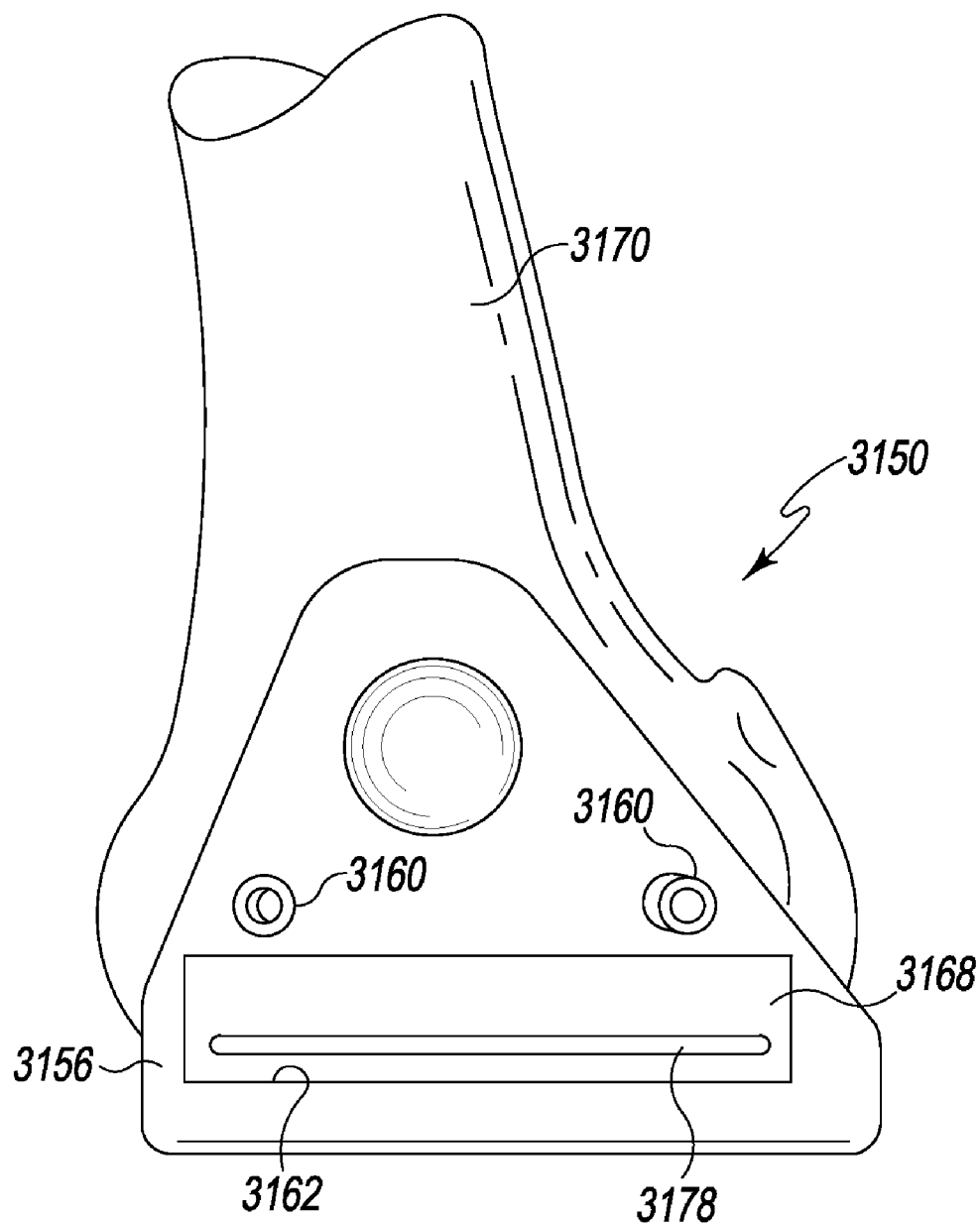
FIG. 86 is an anterior elevation view of another embodiment of the customized patient-specific orthopaedic surgical instrument of FIG. 84 secured to a bone of a patient.

Referring now to FIGS. 84-86, in one embodiment, the customized patient-specific orthopaedic surgical instrument may be embodied as a cutting block 3150. The cutting block 3150 is configured to be coupled to a bone, such as femur or tibia, of a patient. The cutting block 3150 includes a body 3152 having a bone-contacting or bone-facing surface 3154 and an outer surface 3156. The bone-contacting surface 3154 includes a negative contour 3158 configured to receive a portion of the patient's bone having a corresponding contour. As discussed above, the negative contour 3158 of the bone-contacting surface 3154 allows the positioning of the cutting block 3150 on the patient's bone in a unique, pre-determined location and orientation. In some embodiments, the cutting block 3150 may also include an anterior resection line or indicator 3180 and/or a posterior resection line 3182.

The cutting block 3150 also includes a number of pin guides 3160. In use, the pin guides 3160 are used as drill guides to establish guide pin holes in the bone of the patient for securing a number of guide pins (not shown) to the bone. The cutting block 3150 may then be coupled and secured to the patient's bone via the guide pins.

The cutting block 3150 also includes an aperture 3162 defined in the outer surface 3156 of the body 3152. The aperture 3162 is configured to receive one of a number of cutting guide inserts 3164, 3166, 3168. The illustrative aperture 3162 is rectangular in shape, but may have other shapes in other embodiments configured to receive the inserts 3164, 3166, 3168. The cutting guide inserts 3164, 3166, 3168 are similarly configured to be received in the aperture 3162. As such, the illustrative inserts 3164, 3166, 3168 are embodied as rectangular blocks, but may have other configurations in other embodiments.

Each of the inserts 3164, 3166, 3168 includes a cutting guide 3174, 3176, 3178, respectively, defined therethrough. The cutting guides 3174, 3176, 3178 are defined in a different location in each of the inserts 3164, 3166, 3168 with respect to each other. For examples, as shown in FIG. 84, the cutting guide 3174 of the cutting guide insert 3164 is located in a neutral, central, or non-offset position relative to the insert 3164. However, the cutting guide 3176 of the cutting guide insert 3166 is offset from the center of the cutting guide insert 3166. Additionally, the cutting guide 3178 of the cutting guide insert 3168 is offset from the center of the cutting guide insert 3168 an amount greater than the cutting guide 3176 of the insert 3166. The cutting guides 3176, 3178 may be offset by any amount. In one particular embodiment, the cutting guide 3176 is offset from the center of the cutting guide insert 3166 by about two millimeters and the cutting guide 3178 is offset from the center of the cutting guide insert 3168 by about four millimeters. Additionally, any number of cutting guide inserts having a variety of offset cutting guides may be used in other embodiments.

In use, the cutting block 3150 is configured to be coupled to a patient's bone 3170, such as the femur or tibia. Again, because the bone-contacting surface 3154 of the cutting block 3150 includes negative contour 3158, the block 3150 may be coupled to the bone 3170 in a pre-planned, unique position. The cutting block 3150 may be secured to the bone 3170 via use of a number of guide pins (not shown) received in the pin guides 3160 and the bone 3170. Any one of the cutting guide inserts 3164, 3166, 3168 may be inserted into the aperture 3162 of the cutting block 3150. For example, the cutting guide insert 3164 having a non-offset cutting guide 3174 may be inserted into the aperture 3162 to resect the pre-planned amount of bone. That is, the bone cut made using the cutting guide 3164 corresponds to the cutting plane determined during the fabrication of the cutting block 3150 (see process step 24 of algorithm 10 described above in regard to FIG. 1).

However, the orthopaedic surgeon may make an intra-operative decision based on analysis of the bony anatomy of the patient and/or soft tissue complex to remove more or less of the patient's bone with respect to the pre-planned amount (i.e., the amount removed if the surgeon uses the cutting guide insert 3164). For example, the orthopaedic surgeon may use the cutting guide insert 3166 to remove more (or less) of the patient's bone or the cutting guide insert 3168 to remove even more (or even less) of the patient's bone.

Each cutting guide insert 3166, 3168 having an offset cutting guide 3176, 3178 may be inserted into the aperture 3162 in one of two configurations such that the cutting guide insert 3166, 3168 is configured to remove more or less of the patient's bone 3170 relative to the non-offset cutting guide insert 3164. For example, as illustrated in FIG. 85, the cutting guide insert 3168 may be inserted into the aperture 3162 in a first orientation such that any bone resectioning performed using the cutting block 3150 will remove more bone (e.g., about four millimeters more) relative to the non-offset cutting guide insert 3164. Alternatively, as illustrated in FIG. 86, the cutting guide insert 3168 may be removed from the aperture 3162 and re-inserted in a second orientation such that any bone resectioning performed using the cutting block will remove less bone (e.g., about four millimeters less) relative to the non-offset cutting guide insert 3164. Accordingly, the orthopaedic surgeon may resect up to about four millimeters less or more bone relative to the non-offset cutting guide insert 3164 in some embodiments. As such, it should be appreciated that the cutting block 3150 provides an amount of intra-operative adjustability to the orthopaedic surgeon. In some embodiments, the orthopaedic surgeon may be provided with the cutting block 3150 and a selection of various cutting guide inserts to provide a wide range of adjustability.

Figure 87:
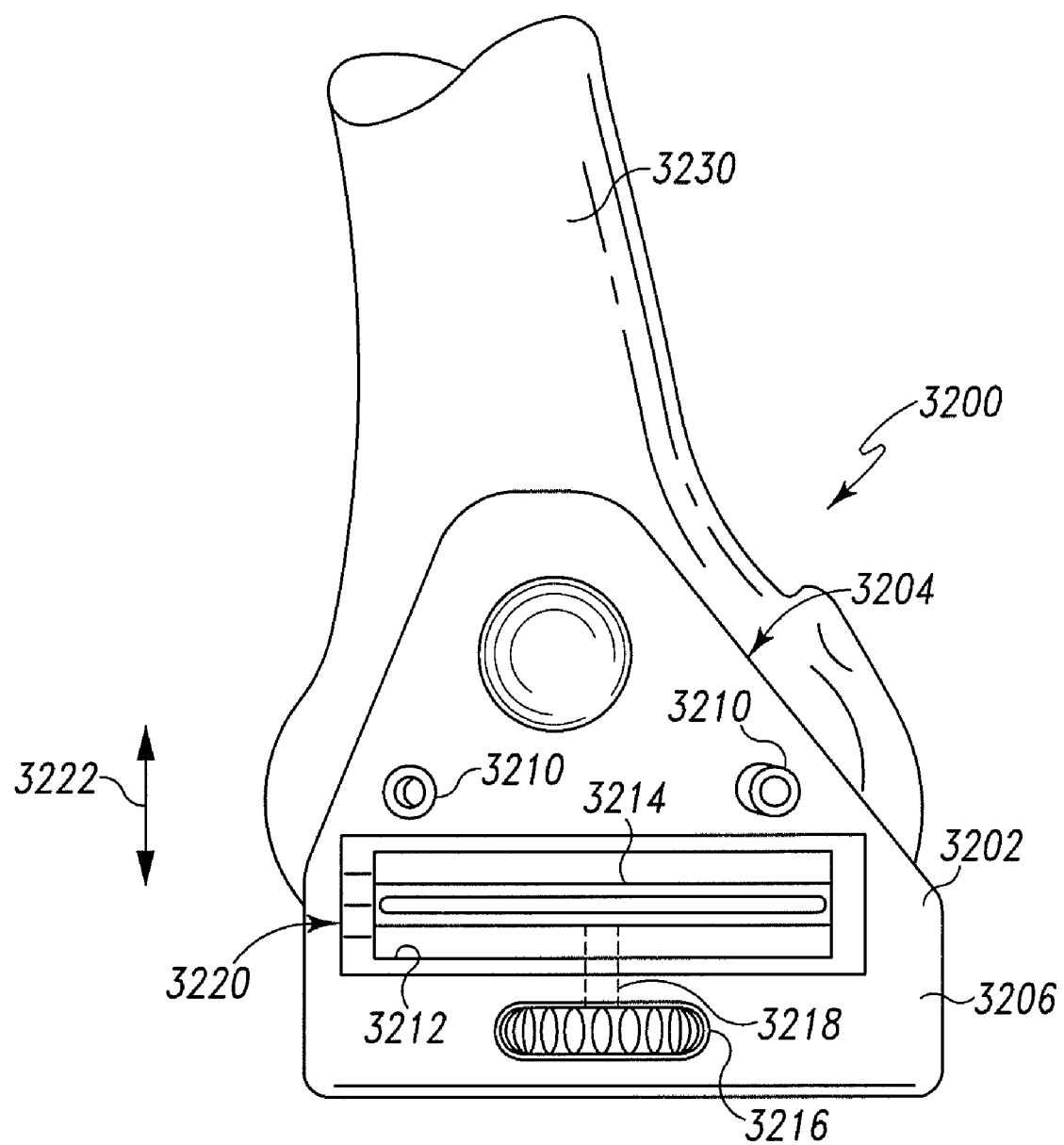
FIG. 87 is an anterior elevation view of another embodiment of a customized patient-specific orthopaedic surgical instrument secured to a bone of a patient.

Referring now to FIG. 87, in one embodiment, the customized patient-specific orthopaedic surgical instrument may be embodied as a cutting block 3200. The cutting block 3200 is configured to be coupled to a bone, such as femur or tibia, of a patient. The cutting block 3200 includes a body 3202 having a bone-contacting or bone-facing surface 3204 and an outer surface 3206. The bone-contacting surface 3204 includes a negative contour (not shown) configured to receive a portion of the patient's bone having a corresponding contour. As discussed above, the negative contour of the bone-contacting surface 3204 allows the positioning of the cutting block 3200 on the patient's bone in a unique pre-determined location and orientation.

The cutting block 3200 also includes a number of pin guides 3210. In use, the pin guides 3210 are used as drill guides to establish guide pin holes in the bone of the patient for securing a number of guide pins (not shown) to the bone. The cutting block 3200 may then be coupled and secured to the patient's bone via the guide pins.

The cutting block 3200 also includes an aperture 3212 defined in the outer surface 3206 of the body 3202. An adjustable cutting guide 3214 is positioned in the aperture 3212. The adjustable cutting guide 3214 is operably coupled to a thumbwheel, dial, or other positioning device 3216 via a mechanical linkage 3218. In some embodiments, the cutting block 3200 may include indicia 3220 located toward the side of the aperture 3212 and configured to provide a visual indication of the position of the adjustable cutting guide 3214.

In use, the cutting block 3200 is configured to be coupled to a patient's bone 3230, such as the femur or tibia. Again, because the bone-contacting surface 3204 of the cutting block 3200 includes the negative contour, the block 3200 may be coupled to the bone 3230 in a pre-planned, unique position. The cutting block 3200 may be secured to the bone 3230 via use of a number of guide pins (not shown) received in the pin guides 3210 and the bone 3230. After the cutting block 3200 has been secured to the patient's bone 3230, the orthopaedic surgeon may resect the bone 3230. The amount of resection may be adjusted by the surgeon intra-operatively via the thumbwheel 3216. That is, the orthopaedic surgeon may adjust the position of the adjustable cutting guide 3214 in the aperture 3212, as indicated by the direction arrow 3222, by operating the thumbwheel 3216. For example, the surgeon may adjust the cutting guide 3214 to remove more or less of the patient's bone 3230. The surgeon may monitor the position of the cutting guide 3214 based on the indicia 3220.

Figure 88:
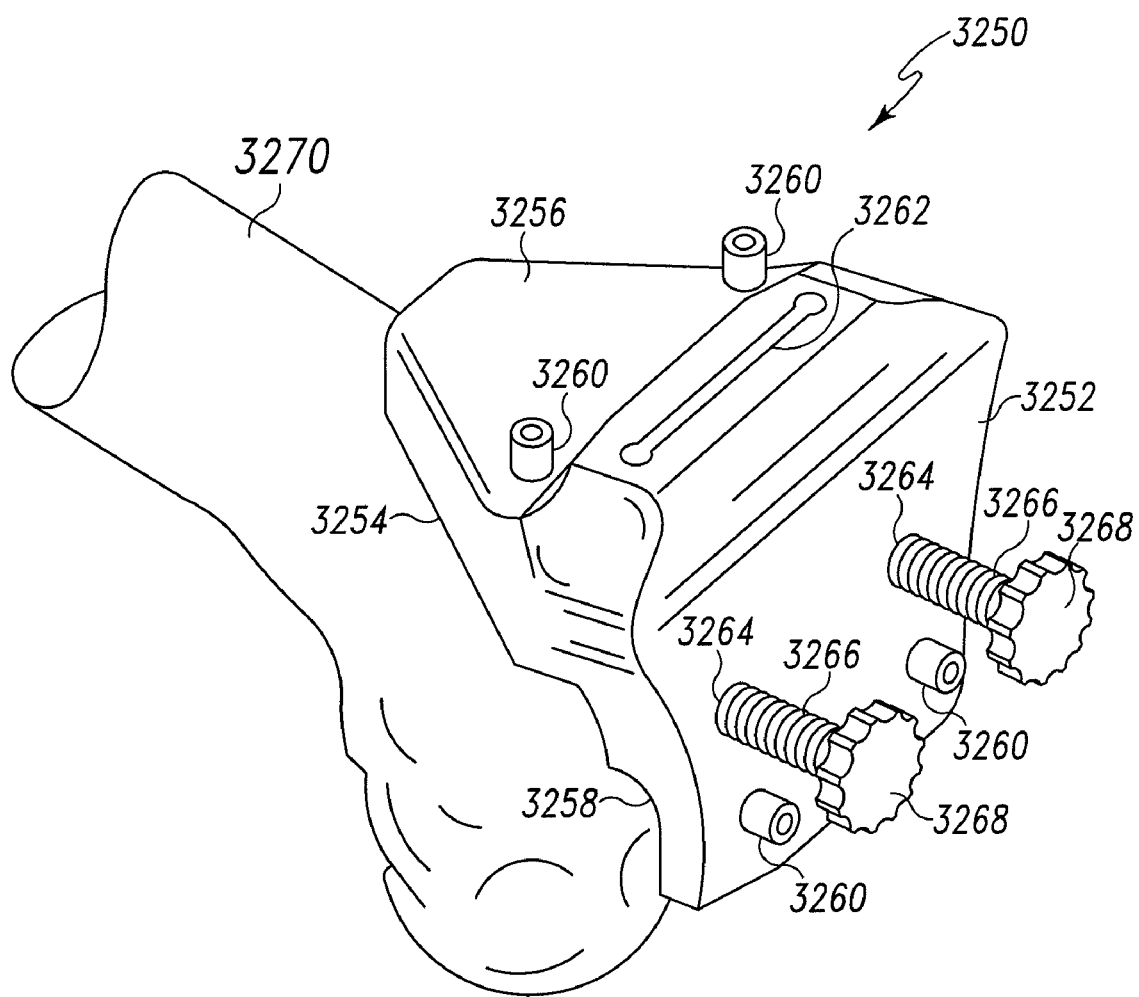
FIG. 88 is a perspective view of another embodiment of a customized patient-specific orthopaedic surgical instrument secured to a bone of a patient.

Referring now to FIG. 88, in another embodiment, the customized patient-specific orthopaedic surgical instrument may be embodied as a cutting block 3250. The cutting block 3250 is configured to be coupled to a bone, such as femur or tibia, of a patient. The cutting block 3250 includes a body 3252 having a bone-contacting or bone-facing surface 3254 and an outer surface 3256. The bone-contacting surface 3254 includes a negative contour 3258 configured to receive a portion of the patient's bone having a corresponding contour. As discussed above, the negative contour 3258 of the bone-contacting surface 3254 allows the positioning of the cutting block 3250 on the patient's bone in a unique pre-determined location and orientation.

The cutting block 3250 also includes a number of pin guides 3260. In use, the pin guides 3260 are used as drill guides to establish guide pin holes in the bone of the patient for securing a number of guide pins (not shown) to the bone. The cutting block 3250 may then be coupled and secured to the patient's bone via the guide pins. The cutting block 3250 also includes a cutting guide 3262. Illustratively, the cutting guide 3262 is a captured cutting guide, but may be embodied as a non-captured or open cutting guide in other embodiments.

The cutting block 3250 also includes a pair of threaded apertures 3264 defined in an end wall of the body 3252. A pair of threaded bolts 3266 are received in the apertures 3264. The threaded bolts 3266 each include a handle 3268 usable to adjust the position of the respective bolt 3266 with respect to the body 3252 of the cutting block 3250. That is, each bolt 3266 may be separately threaded into or out of the block 3250. The threaded apertures 3264 extend through the block such that the ends of the bolts 3266 opposite the handles 3268 may contact the bone 3270 of the patient when threaded into the body 3252 a sufficient amount.

In use, the cutting block 3250 is configured to be coupled to a patient's bone 3270, such as the femur or tibia. Again, because the bone-contacting surface 3254 of the cutting block 3250 includes the negative contour 3258, the block 3250 may be coupled to the bone 3270 in a pre-planned, unique position. The cutting block 3250 may be secured to the bone 3270 via use of a number of guide pins (not shown) received in the pin guides 3260 and the bone 3270. After the cutting block 3250 has been secured to the patient's bone 3270, the orthopaedic surgeon may make an intra-operative decision based on analysis of the bony anatomy of the patient and/or soft tissue complex to adjust the position of the cutting block 3250 relative to the bone 3270. To do so, the surgeon may operate one or both of the threaded bolts 3266 to move the block closer to or away from the end of the bone 3270 and/or change the angulation of the block 3250 relative to the bone 3270. That is, the orthopaedic surgeon may thread in or out both bolts 3266 to move the block 3250 closer to or farther away from the bone 3270, respectively. Additionally or alternatively, the orthopaedic surgeon may thread in or out only one of the bolts 3266 to alter the valgus/varus angulation of the cutting block 3250 relative to the patient's bone 3270. As such, it should appreciated that the cutting block 3250 provides an amount of intra-operative adjustability to the orthopaedic surgeon. It should also be appreciated that in some embodiments other methods of adjustability may be used in addition to the bolts 3266 to provide the surgeon with even more intra-operative adjustability.

Figure 89:
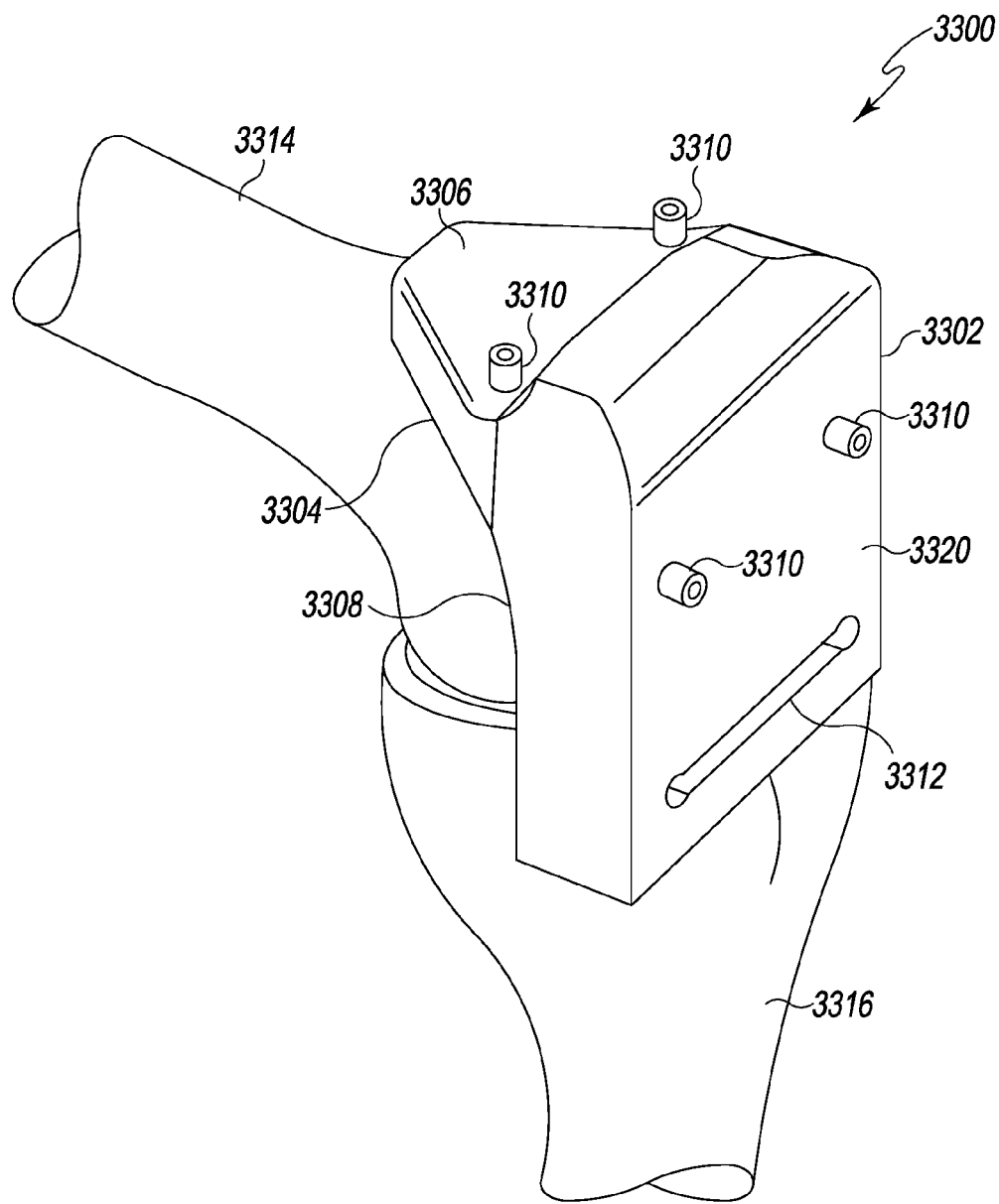
FIG. 89 is a perspective view of another embodiment of a customized patient-specific orthopaedic surgical instrument secured to a bone of a patient.

Referring now to FIG. 89, in another embodiment, the customized patient-specific orthopaedic surgical instrument may be embodied as a cutting block 3300. The cutting block 3300 is configured to be coupled to a femur 3314 of the patient to perform resectioning on a tibia 3316 of the patient. The cutting block 3300 includes a body 3302 having a bone-contacting or bone-facing surface 3304 and an outer surface

3306. The bone-contacting surface 3304 includes a negative contour 3308 configured to receive a portion of the patient's femur 3314 having a corresponding contour. As discussed above, the negative contour 3308 of the bone-contacting surface 3304 allows the positioning of the cutting block 3300 on the patient's femur 3314 in a unique pre-determined location and orientation.

The cutting block 3300 also includes a number of pin guides 3310. In use, the pin guides 3310 are used as drill guides to establish guide pin holes in the bone of the patient for securing a number of guide pins (not shown) to the bone. The cutting block 3300 may then be coupled and secured to the patient's bone via the guide pins.

The cutting block 3300 includes an extended distal wall 3320 that extends downwardly over the tibia 3316. A tibial cutting guide 3312 is defined in the extended distal wall 3320. Illustratively, the tibial cutting guide 3312 is a captured cutting guide, but may be embodied as a non-captured or open cutting guide in other embodiments. In use, the cutting block 3300 is configured to be coupled to a patient's femur 3314 to perform a cut on the patient's tibia 3316 while the patient's knee is in flexion. Again, because the bone-contacting surface 3304 of the cutting block 3300 includes the negative contour 3308, the block 3300 may be coupled to the femur 3314 in a pre-planned, unique position. The cutting block 3300 may be secured to the femur 3314 via use of a number of guide pins (not shown) received in the pin guides 3310 and the femur 314. Because the cutting block 3300 is secured to the femur 3314, the stability of the block 3300 while performing the tibial cuts may be improved.

Figure 90:
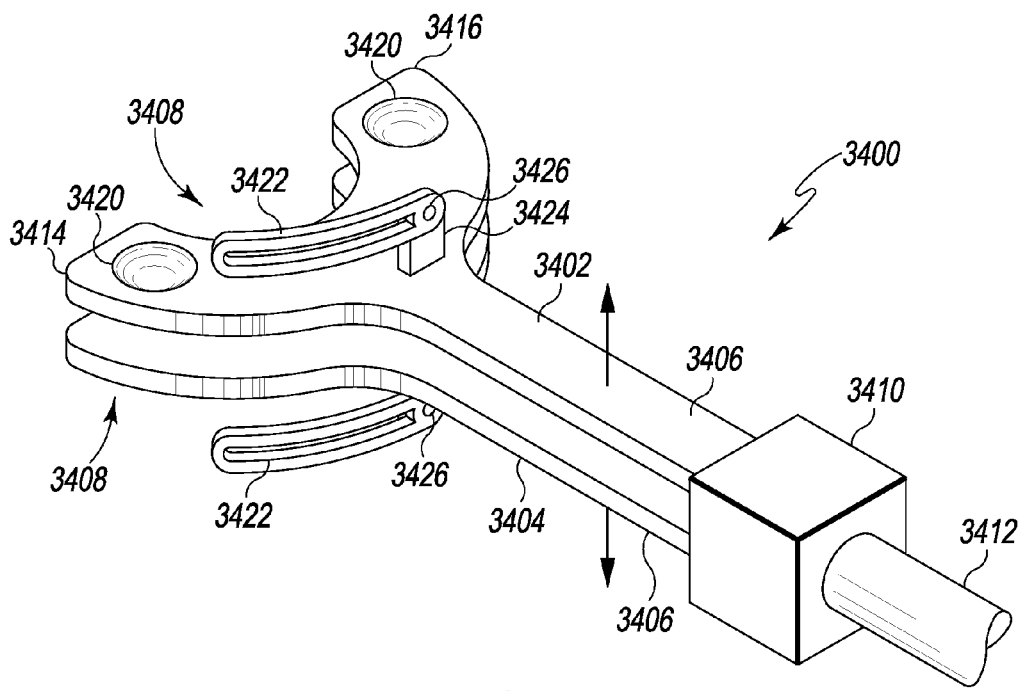
FIG. 90 a perspective view of another embodiment of a customized patient-specific orthopaedic surgical instrument.
Figure 91:
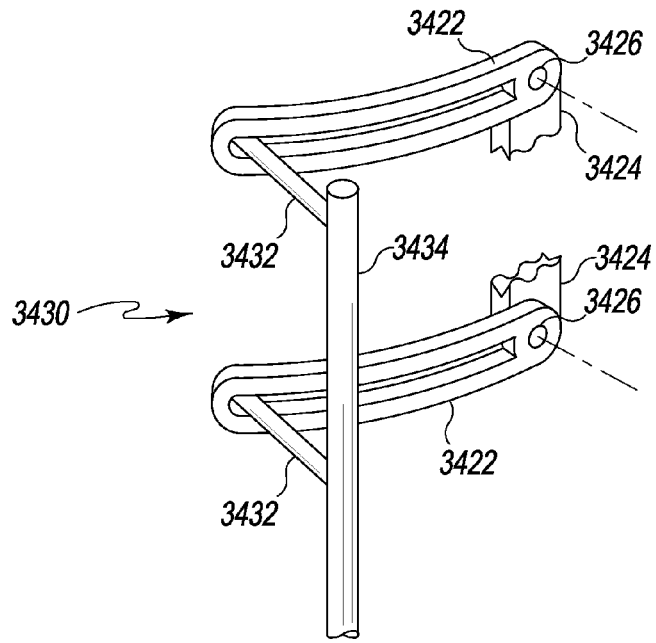
FIG. 91 is a perspective view of a tool for use with the customized patient-specific orthopaedic surgical instrument of FIG. 90.
Figure 92:
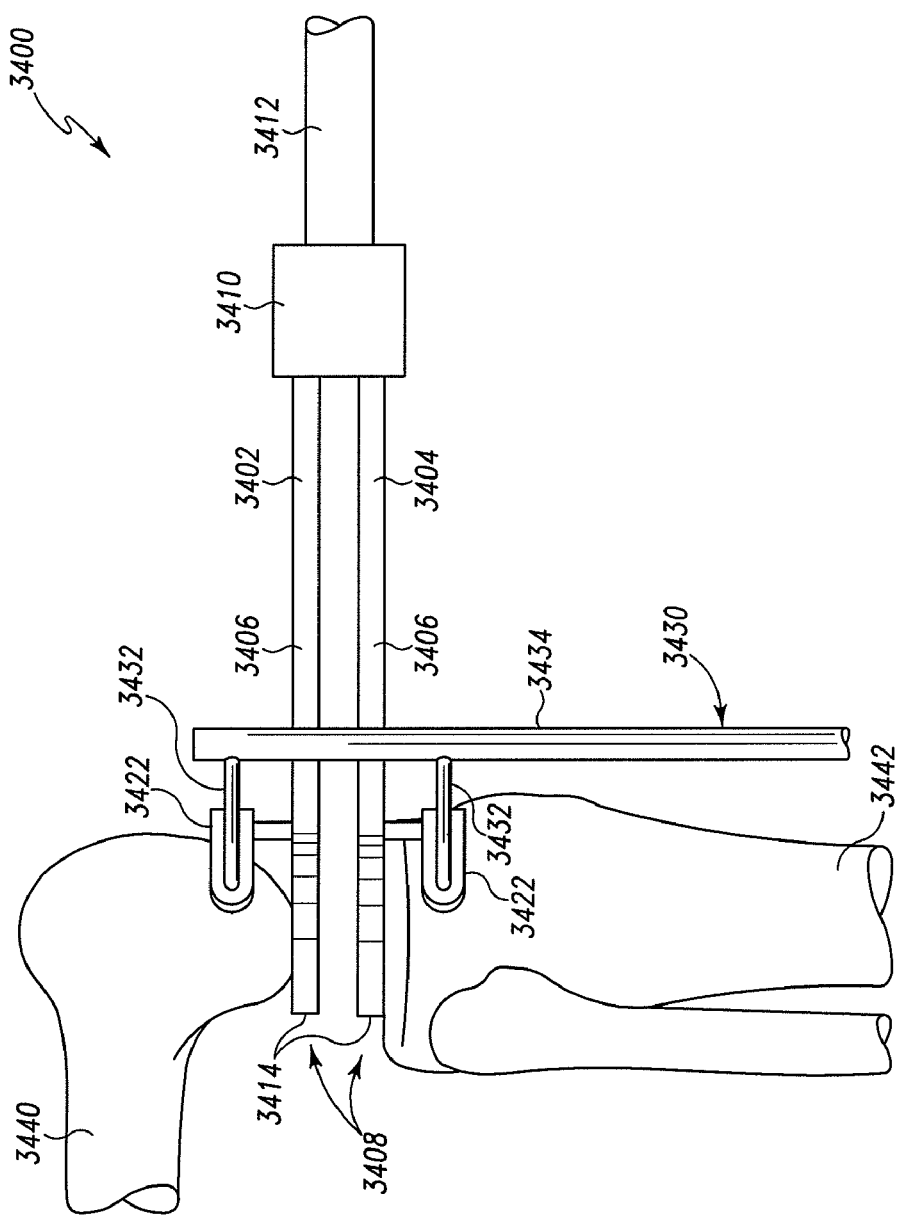
FIG. 92 is a side elevation view of the customized patient-specific orthopaedic surgical instrument of FIG. 90.

Referring now to FIGS. 90-92, in another embodiment, a customized patient-specific orthopaedic surgical instrument 3400 includes a pair of paddles 3402, 3404. The paddles 3402, 3404 are substantially identical and include an elongated shaft 3406 and a bone plate 3408. The elongated shafts 3406 are operably coupled to a hub 3410. A handle 3412 is also secured to the hub 3410 to facilitate positioning of the orthopaedic surgical instrument 3400. In some embodiments, the hub 3410 includes mechanical linkage for independently or conjointly moving each paddle 3402, 3404 toward each other or away from each other as desired. For example, the hub 3410 may include a thumb dial usable to adjust the position of the paddles 3402, 3404. In another embodiment, the hub 3410 includes a biasing member, such as a spring, positioned between the paddles 3402, 3404. In such embodiments, the biasing member biases the paddles 3402, 3404 away from each other.

Each of the bone plates 3408 includes two curved arms 3414, 3416 that wrap inwardly toward each other to form a substantially "U"-shape. Each arm 3414, 3416 includes a condyle recess 3420 configured to receive a portion of the condyle of the femur or tibia of the patient. Additionally, each paddle 3402, 3404 of the orthopaedic surgical instrument 3400 includes a cutting guide 3422 secured to the respective bone plate 3408 via a bracket 3424. The cutting guides 3422 are pivotably coupled to the bracket 3424 via a pivot hinge 3426.

Each cutting guide 3422 is independently or conjointly adjustable relative to the respective bone plate 3408. That is, each cutting guide 3422 may be pivoted to one of a number of positions relative to the respective bracket 3424. In some embodiments, an adjustment tool 3430 may be used to simultaneously position each cutting guide 3422 as shown in FIG. 91. The adjustment tool 3430 includes an elongated handle 3434 and two guide bars 3432 extending outwardly from the handle 3434. The guide bars 3432 are sized and positioned relative to each other such that each guide bar 3432 is receivable in the guide slot of the respective cutting guide 3422. After the adjustment tool 3430 is so positioned, the tool 3430 may be used to adjust both cutting guides 3422 simultaneously by moving the tool 3430 up or down.

In some embodiments, the orthopaedic surgical instrument 3400 may be patient-universal. However, in other embodiments, the orthopaedic surgical instrument 3400 may be customized for a particular patient. In such embodiments, the orthopaedic surgical instrument 3400 may be customized to the particular patient based on the positioning of the condyle recesses 3416 on the bone plates 3408 and the positioning of the cutting guides 3422 (e.g., via the height of the bracket 3424).

In use, the orthopaedic surgical instrument 3400 is configured to be inserted between the patient's femur 3440 and tibia 3442 as illustrated in FIG. 92. The condyles of the patient's femur 3440 and the tibia 3442 are received in the condyle recesses 3420 of the respective bone plate 3408. After the instrument 3400 has been inserted between the bones 3440, 3442, the paddles 3402, 3404 may be adjusted. For example, the paddles 3402, 3404 may be moved toward or away from each other as required by the patient's joint and surrounding soft tissue. After the paddles 3402, 3404 have been positioned in the desired location, each of the cutting guides 3422 may be positioned. To do so, the orthopaedic surgeon may separately position each cutting guide 3422. Alternatively, the orthopaedic surgeon may use the adjustment tool 3430 to simultaneously position each cutting guide 3422. It should be appreciated that the proximal cutting guide 3422 may be used by the orthopedic surgeon to perform femur resectioning and the distal cutting guide 3422 may be used by the surgeon to perform tibia resectioning. As such, the orthopaedic surgical tool 3400 provides an amount of adjustability to the surgeon.

Figure 93:
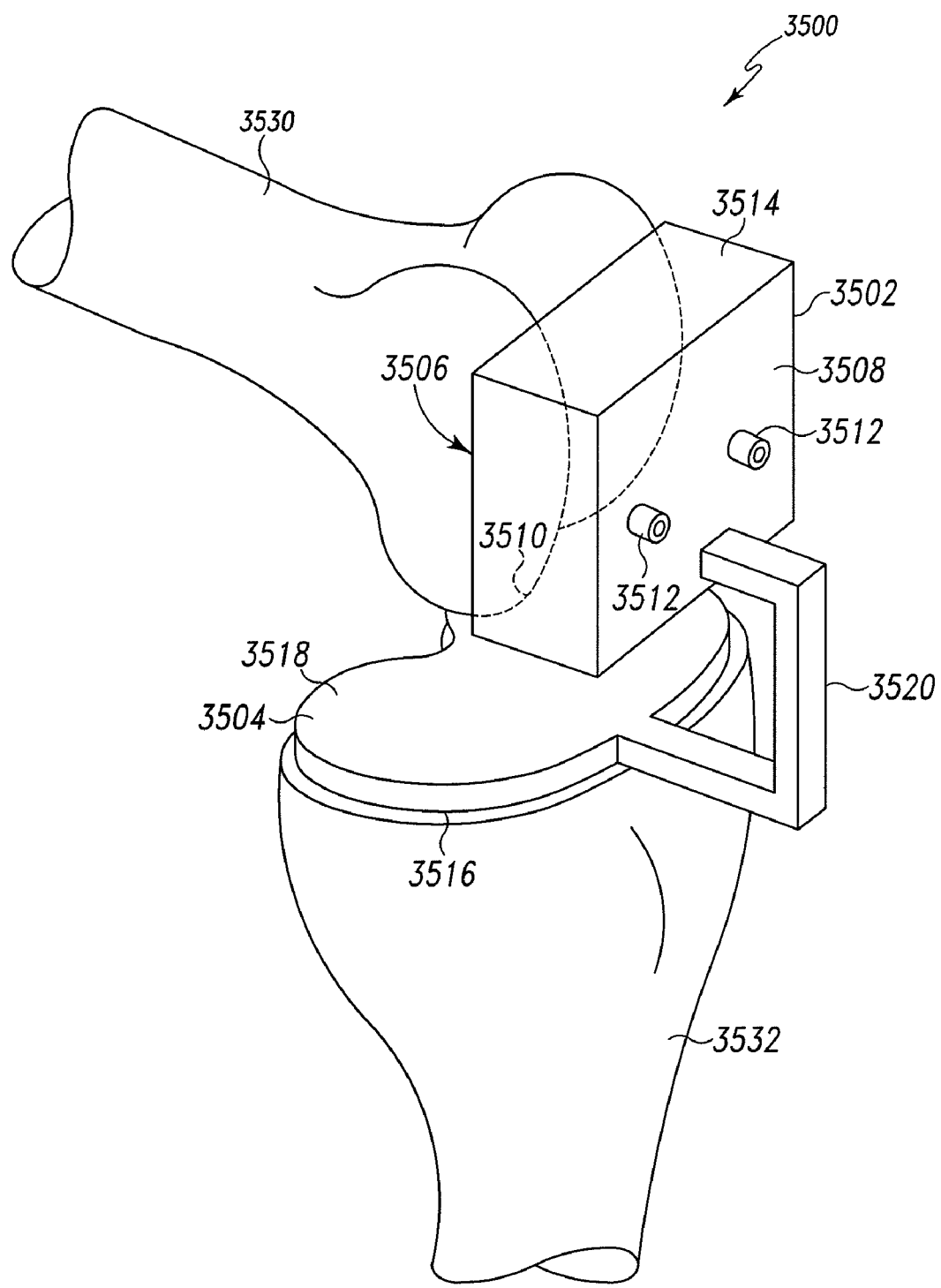
FIG. 93 is a perspective view of another embodiment of a customized patient-specific orthopaedic surgical instrument.

Referring now to FIG. 93, in another embodiment, the customized patient-specific orthopaedic surgical instrument 3500 includes a femoral cutting block 3502 and a tibial platform 3504. The femoral cutting block 3502 includes a bone-contacting or bone-facing surface 3506 and an outer surface 3508. The bone-contacting surface 3506 includes a negative contour 3510 configured to receive a portion of the patient's femur 3530 having a corresponding contour. As discussed above, the negative contour 3510 of the bone-contacting surface 3506 allows the positioning of the cutting block 3502 on the patient's femur 3530 in a unique pre-determined location and orientation.

The femoral cutting block 3502 also includes a number of pin guides 3512. In use, the pin guides 3512 are used as drill guides to establish guide pin holes in the femur 3530 of the patient for securing a number of guide pins (not shown) to the femur 3530. The cutting block 3502 may then be coupled and secured to the patient's femur 3530 via the guide pins. The cutting block 3502 also includes a cutting guide 3514. Illustratively, the cutting guide 3514 is a non-captured or open cutting guide, which is defined by an upper wall surface of the block 3502. However, in other embodiments, the cutting guide 3514 may be embodied as a closed cutting guide.

The tibial platform 3504 includes a bone-contacting or bone-facing surface 3516 and an upper surface 3518. In some embodiments, similar to the bone-contacting surface 3506 of the cutting block 3502, the bone-contacting surface 3516 includes a negative contour (not shown) configured to receive a portion of the patient's tibia 3532 having a corresponding contour. In such embodiments, as discussed above, the negative contour of the bone-contacting surface 3516 allows the positioning of the tibial platform 3504 on the patient's tibia 3532 in a unique pre-determined location and orientation. However, in other embodiments, the bone-contacting surface 3516 may be substantially planar and configured to be positioned on a resected tibia 3532 having a planar top surface.

The tibial platform 3504 is connected to the femoral cutting block 3502 via a rod 3520. As illustrated in FIG. 93, the rod 3520 extends away from the platform 3504 and the cutting block 3502 to provide additional room around the patient's knee joint for the orthopaedic surgeon.

Figure 94:
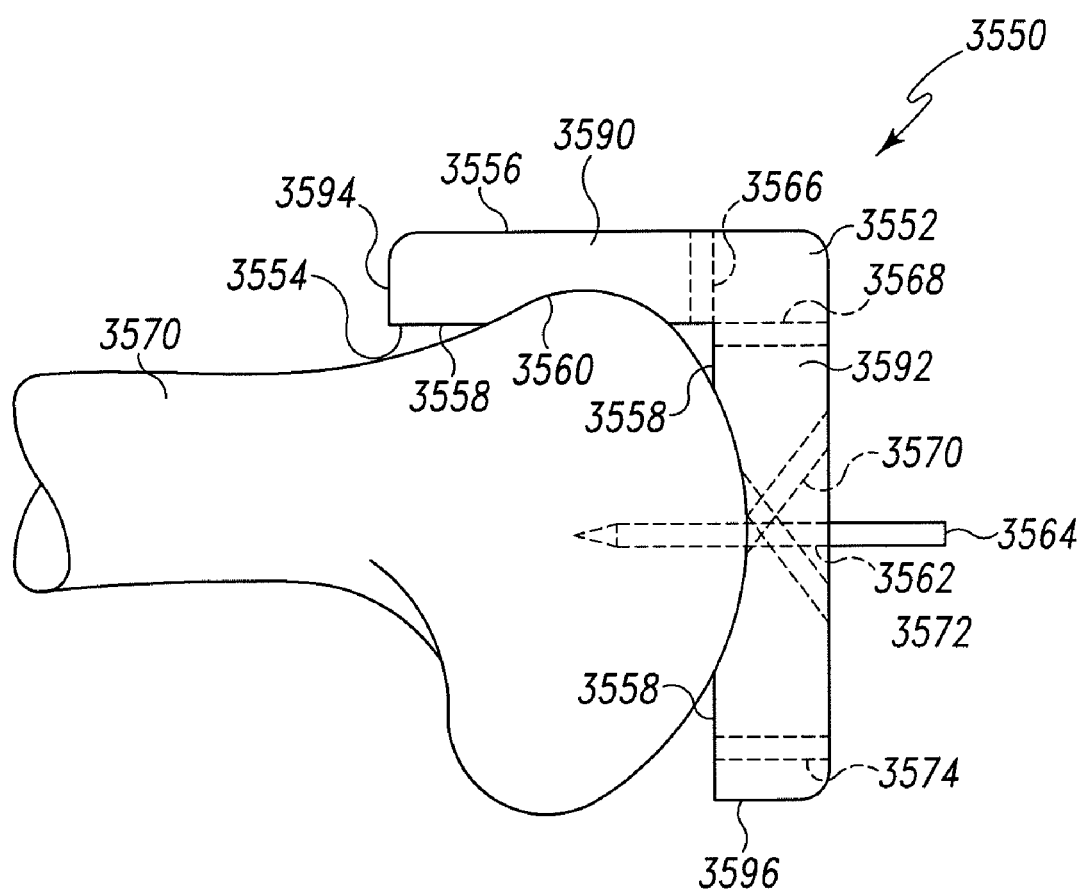
FIG. 94 is a side elevation view of another embodiment of a customized patient-specific orthopaedic surgical instrument secured to a bone of a patient.
Figure 95:
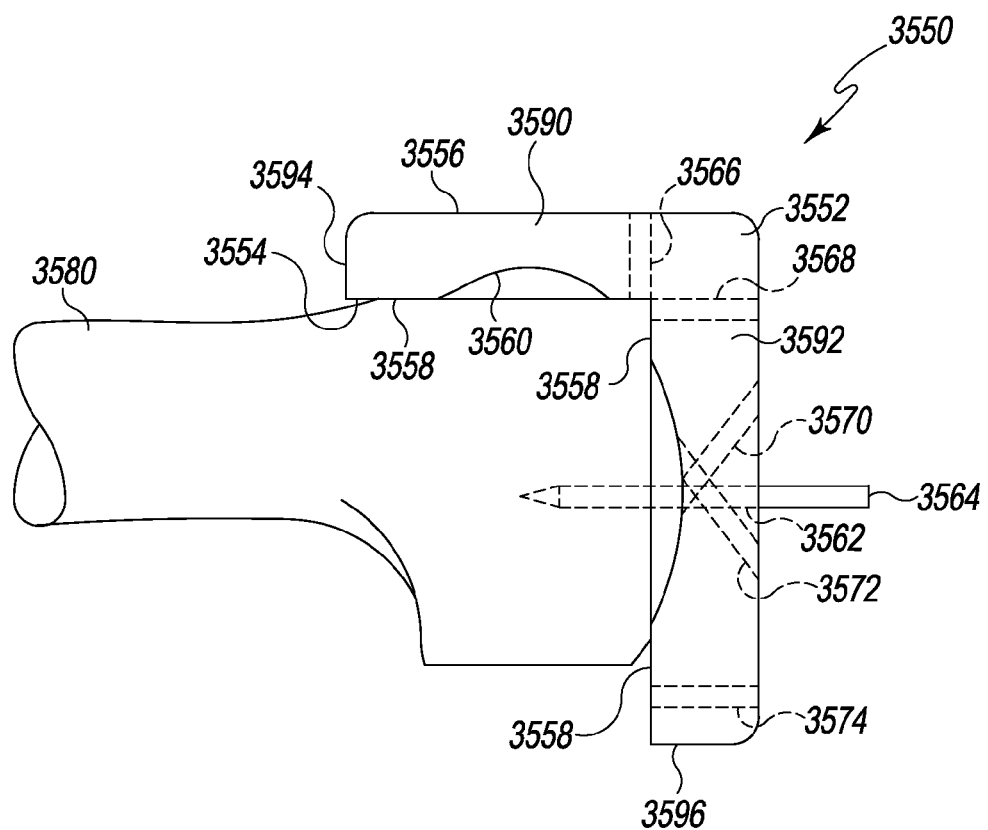
FIG. 95 is a side elevation view of the customized patient-specific orthopaedic surgical instrument of FIG. 94 after a bone resection procedure.

Referring now to FIGS. 94 and 95, in another embodiment, the customized patient-specific orthopaedic surgical instrument may be embodied as a 5-in-1 cutting block 3550. The cutting block 3550 is configured to be coupled to a bone, such as femur or tibia, of a patient. The cutting block 3550 includes a generally L-shaped body 3552 having an anterior plate 3590 and a distal plate 3592. Both of the plates 3590, 3590 have a bone-contacting or bone-facing surface 3554 and an outer surface 3556. The bone-contacting surface 3554 includes a number of planar bottom or flat surfaces 3558 and a negative contour 3560 configured to receive a portion of the patient's bone having a corresponding contour. As discussed above, the negative contour 3560 of the bone-contacting surface 3554 allows the positioning of the cutting block 3550 on the patient's bone in a unique pre-determined location and orientation. In the case of the anterior plate 3590, one of the flat surfaces 3558 extends distally in a direction away from a proximal-most edge 3594 of the anterior plate 3590 and transitions to an anterior negative contour 3560 that extends distally away from the flat surface 3558. The anterior negative contour 3560 in turn transitions to another of the flat surfaces 3558 which extends distally away from the anterior negative contour 3560 toward the distal plate 3592. In the case of the distal plate 3592, one of the flat surfaces 3558 extends posteriorly in a direction away from the anterior plate 3590 and transitions to an distal negative contour 3560 that extends posteriorly away from the flat surface 3558. The distal negative contour 3560 in turn transitions to another of the flat surfaces 3558 which extends posteriorly away from the distal negative contour 3560 toward a posterior-most edge 3596 of the distal plate 3592.

The cutting block 3550 also includes a number of pin guides 3562. In use, the pin guides 3562 are used as drill guides to establish guide pinholes in the bone of the patient for securing a number of guide pins 3564 to the bone. The cutting block 3550 may then be coupled and secured to the patient's bone via the guide pins 3564.

The cutting block 3550 also includes five captured cutting guides 3566, 3568, 3570, 3572, 3574. The illustrative cutting guide 3566 is a distal cutting guide, the cutting guide 3568 is an anterior cutting guide, and the cutting guide 3574 is a posterior cutting guide. The cutting guides 3570, 3572 are angled cutting guides. It should be appreciated that the cutting guides 3566, 3568, 3570, 3572, 3574 allow the orthopaedic surgeon to perform up to five different bone cuts using the same cutting block 3550.

In use, the cutting block 3550 is configured to be coupled to a patient's bone 3550, such as the femur or tibia. Again, because the bone-contacting surface 3554 of the cutting block 3550 includes negative contour 3560, the block 3550 may be coupled to the bone 3580 in a pre-planned, unique position. The cutting block 3550 may be secured to the bone 3580 via use of a number of guide pins 3564 received in the pin guides 3562 and the bone 3580. After the cutting block 3550 has been secured to the patient's bone 3580 as illustrated in FIG. 94, the orthopaedic surgeon may use the block 3550 to perform any one of a number of resections of the bone 3580 using one or more of the cutting guides 3566, 3568, 3570, 3572, 3574.

Additionally, the cutting block 3550 may be used to perform a number of re-cuts of the patient's bone. For example, as illustrated in FIG. 95, after the initial resectioning procedure, the orthopaedic surgeon may determine that additional bone must be removed from the patient's bone 3580. If so, the surgeon may re-secure the cutting block 3550 to the patient's resected bone 3580. In such a configuration, the planar bottom surfaces 3558 of the bone-contacting surface 3554 contact or confront the planar resected surfaces of the patient's bone. As such, the planar bottom surfaces 3558 allow the cutting block 3550 to remain stable on the resected bone 3580 even though the block 3550 includes the negative contours 3560 defined in the bone-contacting surface 3554. It should be appreciated that the cutting block 3550 may be used to perform any number of resectioning cuts as described above. As such, the cutting block 3550 provides an amount of intra-operative adjustability to the orthopaedic surgeon.

In other embodiments, adjustability of the positioning and cutting planes of the customized patient-specific orthopaedic surgical instrument may be implemented using other methods. For example, in some embodiments, more than a single customized patient-specific orthopaedic surgical instrument is designed and fabricated in process steps 24-30 of the algorithm 10 described above in regard to FIG. 1. That is, rather than a single patient-specific orthopaedic surgical instrument, two or more patient-specific instruments may be designed, fabricated, and shipped to the orthopaedic surgeon. Each instrument may be configured to generate different cutting planes. For example, one instrument may be used to perform a resection that is two millimeters greater or lesser than the standard instrument. In this way, the orthopaedic surgeon may decide pre- or intra-operatively which particular instrument to use based on intra-operative analysis of the patient's joint and/or soft tissue complex.

Additionally, in some orthopaedic surgical procedures, the surgeon may remove the posterior cruciate ligament (PCL). In such embodiments, the flexion gap of the patient's joint may be increased. As such, the customized patient-specific orthopaedic instrument may be fabricated to adjust for the increased flexion gap. For example, a cutting block configured to remove an additional amount of bone may be fabricated.

Further, in some embodiments, the femoral lugs of each orthopaedic implant are positioned in the same location across the different sizes of implants. As such, the downsizing or adjustment of sizes for the orthopaedic implants may be done without the need of additional drilling, guide pin attachment, and/or the like.

Figure 96:
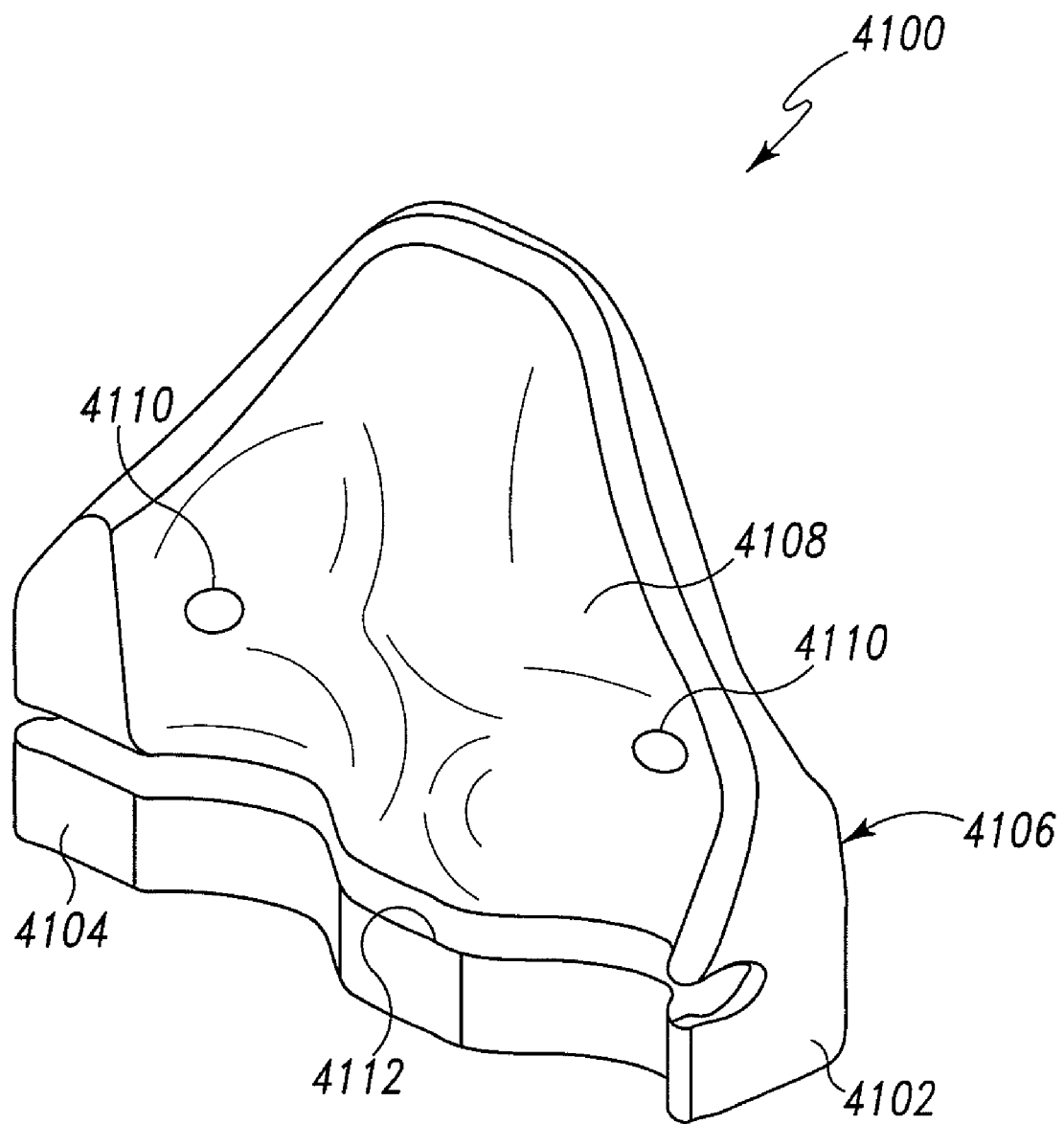
FIG. 96 is a perspective view of one embodiment of a customized patient-specific orthopaedic surgical instrument.

Referring now to FIG. 96, in one embodiment, the customized patient-specific orthopaedic surgical instrument may be embodied as a cutting block 4100. The cutting block 4100 is configured to be coupled to a bone, such as femur or tibia, of a patient. The cutting block 4100 includes a body 4102 having a bone-contacting or bone-facing surface 4104 and an outer surface 4106. The bone-contacting surface 4104 includes a negative contour 4108 configured to receive a portion of the patient's bone having a corresponding contour. As discussed above, the negative contour 4108 of the bone-contacting surface 4104 allows the positioning of the cutting block 4100 on the patient's bone in a unique pre-determined location and orientation.

The cutting block 4100 also includes a number of pin guides 4110. In use, the pin guides 4110 are used as drill guides to establish guide pin holes in the bone of the patient for securing a number of guide pins (not shown) to the bone. The cutting block 4100 may then be coupled to the patient's bone via the guide pins. The cutting block 4100 also includes a cutting guide 4112. Illustratively, the cutting guide 4112 is embodied as a captured cutting guide, but may be embodied as a non-captured or open cutting guide in other embodiments. It should be appreciated that because the position of the cutting guide 4112 is pre-determined due to the configuration of the cutting block 4100, any bone cuts made using the patient-specific cutting block 4100 correspond to the predetermined bone cutting planes (see process step 24 of algorithm 10 described above in regard to FIG. 1).

Figure 97:
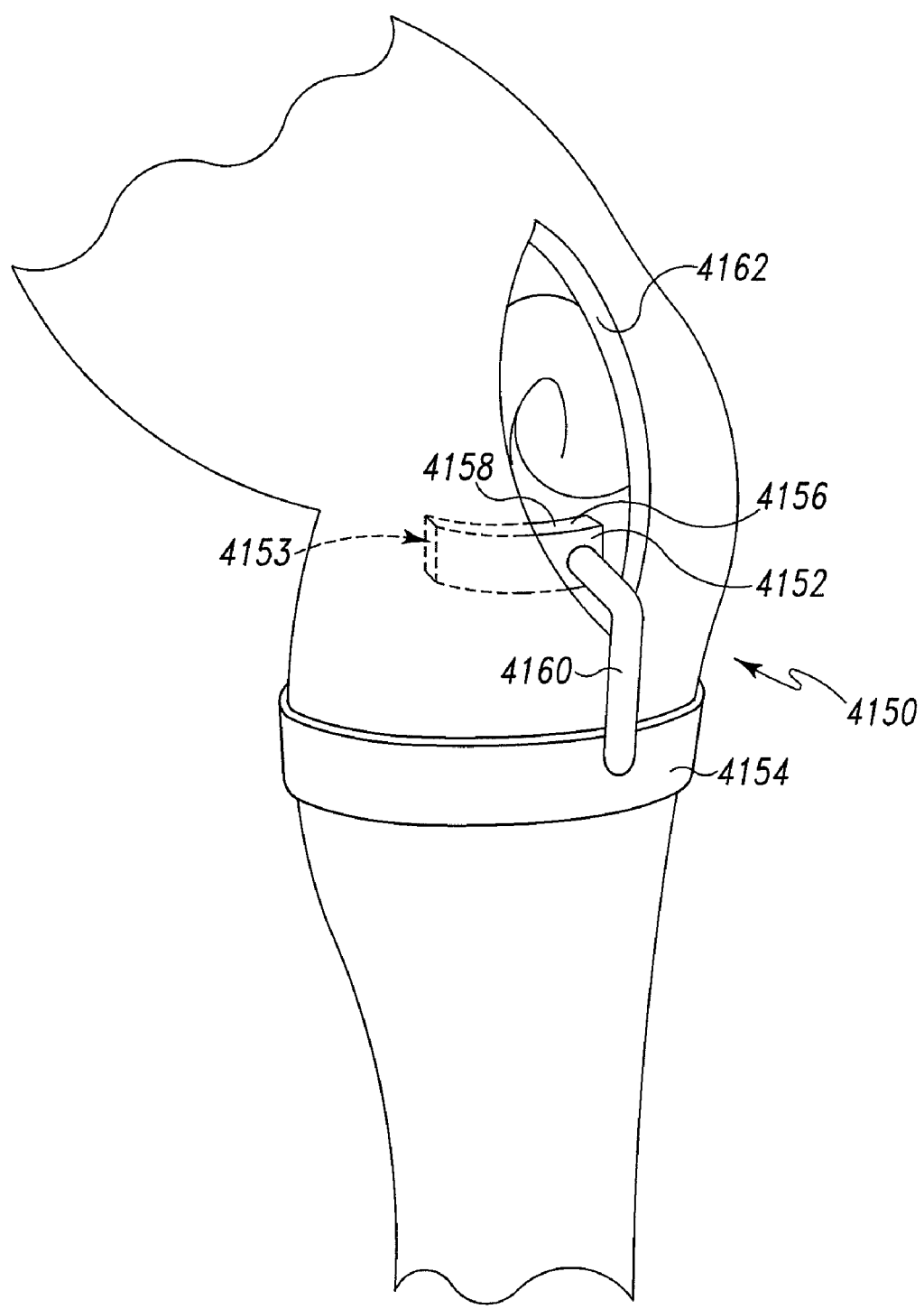
FIG. 97 is a perspective view of another embodiment of a customized patient-specific orthopaedic surgical instrument secured to a leg of a patient.

Referring now to FIG. 97, in another embodiment, a customized patient-specific orthopaedic surgical instrument 4150 includes a cutting block 4152 and a leg clamp 4154. The cutting block 4152 is illustratively configured to be coupled to the patient's tibia, but may be configured to be coupled to another bone of the patient, such as the femur, in other embodiments. The cutting block 4152 is customized to the particular patient and, similar to the cutting block 4100 described above in regard to FIG. 96, includes a bone-contacting or bone-facing surface 4153 having a negative contour (not shown) configured to receive a portion of the patient's bone having a corresponding contour. As discussed above, the negative contour of the bone-contacting surface 4153 allows the positioning of the cutting block 4150 on the patient's bone in a unique pre-determined location and orientation.

The illustrative cutting block 4152 includes a non-captured cutting guide 4158. That is, a top surface 4156 of the cutting block 4152 is used as the cutting guide and is aligned such that the cutting plane established using the cutting block 4152 corresponds to the cutting plane determined in process step 24 of the algorithm 10 described above in regard to FIG. 1. Additionally, the illustrative cutting block 4152 is positioned such that the block 4152 extends around the medial side of the patient's bone a distance greater than the distance that the block 4152 extends around the lateral side of the patient's bone. However, in other embodiments, the block 4152 may be aligned in a different manner. The cutting block 4152 may or may not be secured to the patient's bone. For example, in one embodiment, the cutting block 4152 is secured to the patient's bone via a number of guide pins similar to the cutting block 4100 described above in regard to FIG. 96.

The cutting block 4152 is coupled to the leg clamp 4154 via a rod 4160, which extends out of the incision site 4162 of the patient's leg. The rod 4160 is configured such that the clamp 4154 may be secured to the patient's leg. The clamp 4154 may be made from any suitable material and, in one particular embodiment, is disposable. For example, the clamp 4154 may be formed from a plastic material and secured to the patient's leg via use of a securing device such as a hook-and-loop device. Additionally, in some embodiments, the clamp 4154 is adjustable to fit a number of different leg sizes. However, in other embodiments, the clamp 4154 may be patient-specific and designed to fit the leg of the particular patient.

In use, the cutting block 4152 of the customized patient-specific orthopaedic surgical instrument 4150 is inserted into the incision site 4162 and, in some embodiments, secured to the patient's bone via a number of guide pins. The clamp 4154 is secured to the patient's leg using the securing device, such as a hook-and-loop mechanism. It should be appreciated that because the cutting block 4152 is secured to the patient's leg via the clamp 4154, the stability of the block 4152 may be increased.

Figure 98:
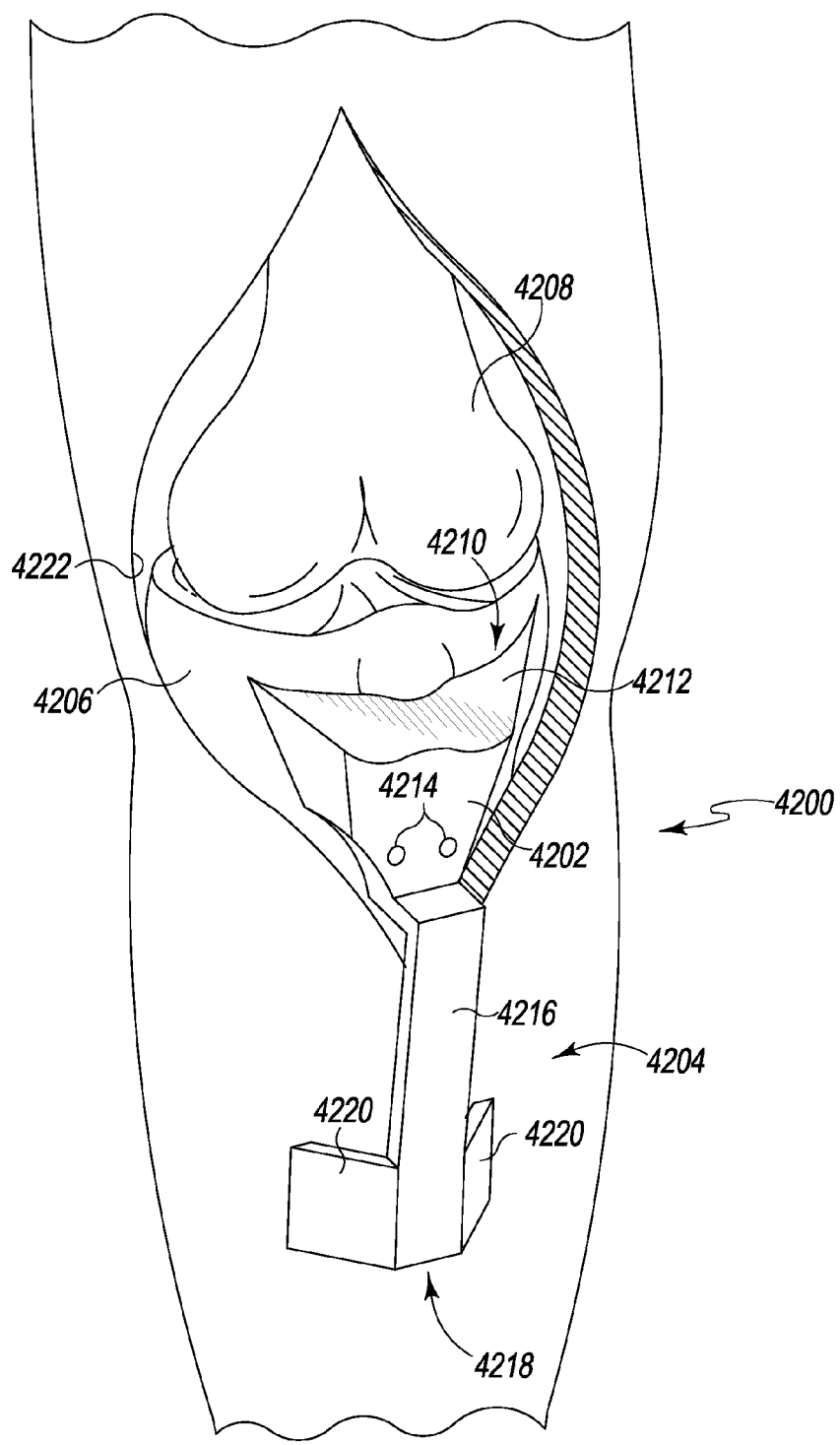
FIG. 98 is a perspective view of another embodiment of a customized patient-specific orthopaedic surgical instrument secured to a leg of a patient.

Referring now to FIG. 98, in another embodiment, a customized patient-specific orthopaedic surgical instrument 4200 includes a cutting block 4202 and a brace 4204. Similar to the cutting block 4150 described above in regard to FIG. 97, the cutting block 4202 is illustratively configured to be coupled to the patient's tibia 4206, but may be configured to be coupled to another bone of the patient, such as the femur 4208, in other embodiments. The cutting block 4202 is customized to the particular patient and, similar to the cutting block 4100 described above in regard to FIG. 96, includes a bone-contacting or bone-facing surface 4210 having a negative contour (not shown) configured to receive a portion of the patient's bone having a corresponding contour. As discussed above, the negative contour of the bone-contacting surface 4210 allows the positioning of the cutting block 4202 on the patient's bone in a unique pre-determined location and orientation.

The illustrative cutting block 4202 includes an non-captured cutting guide 4212 similar to the cutting block 4152 described above. That is, a top surface of the cutting block 4202 is used as the cutting guide and is aligned such that the cutting plane established using the cutting block 4202 corresponds to the cutting plane determined in process step 24 of the algorithm 10 described above in regard to FIG. 1. The cutting block 4202 includes a number of pin guides 4214, which facilitate the coupling of the cutting block 4202 to the tibia 4206 via a number of guide pins.

The brace 4204 of the instrument 4200 includes an arm 4216, which extends from the cutting block 4202 and out of the incision site 4222 of the patient's leg. The brace 4204 also includes a bone support 4218 coupled to the arm 4216. The bone support 4218 includes two inwardly extending flanges 4220. The bone support 4218 is configured to receive or otherwise be supported by the apex of the patient's tibia 4206 to provide an amount of stability to the cutting block 4202. As such, the arm 4216 may extend from the cutting block 4202 any suitable distance such that the bone support 4218 is positioned to engage the tibial apex.

Figure 99:
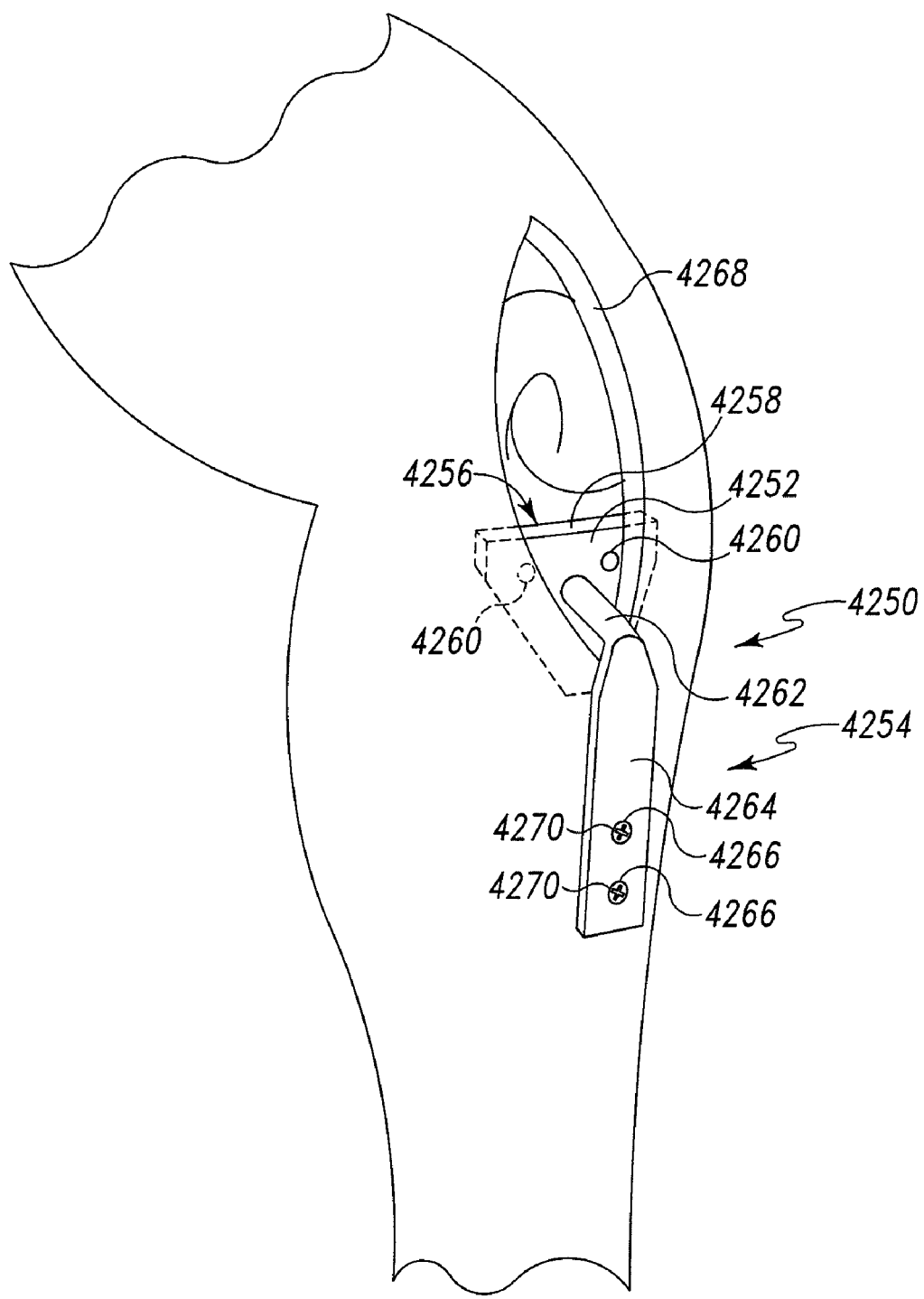
FIG. 99 is a perspective view of another embodiment of a customized patient-specific orthopaedic surgical instrument secured to a leg of a patient.

Referring now to FIG. 99, in another embodiment, a customized patient-specific orthopaedic surgical instrument 4250 includes a cutting block 4252 and a brace 4254. Similar to the cutting block 4200 described above in regard to FIG. 98, the cutting block 4252 is illustratively configured to be coupled to the patient's tibia, but may be configured to be coupled to another bone of the patient, such as the femur, in other embodiments. The cutting block 4252 is customized to the particular patient and, similar to the cutting block 4100 described above in regard to FIG. 96, includes a bone-contacting or bone-facing surface 4256 having a negative contour (not shown) configured to receive a portion of the patient's bone having a corresponding contour. As discussed above, the negative contour of the bone-contacting surface allows the positioning of the cutting block 4252 on the patient's bone in a unique pre-determined location and orientation.

The illustrative cutting block 4250 includes a non-captured cutting guide 4258 similar to the cutting block 4202 described above. That is, a top surface of the cutting block 4250 is used as the cutting guide and is aligned such that the cutting plane established using the cutting block 4252 corresponds to the cutting plane determined in process step 24 of the algorithm 10 described above in regard to FIG. 1. The cutting block 4252 also includes a number of pin guides 4260, which facilitate the coupling of the cutting block 4202 to the tibia via a number of guide pins.

The brace 4254 of the instrument 4250 includes an arm 4262, which extends from the cutting block 4252 and out of the incision site 4268 of the patient's leg. The brace 4254 also includes a flat flange 4264 coupled to the arm 4262. The flange 4264 is positioned to be substantially parallel to the patient's tibia and includes a number of apertures 4266 defined therethrough. The flange 4264 is secured to the patient's tibia via a number of percutaneous pins or screws 4270 that are received in the aperture 4266. It should be appreciated that because the flange 4264 is secured to the patient's bone, the stability of the cutting block 4252 may be increased.

Figure 100:
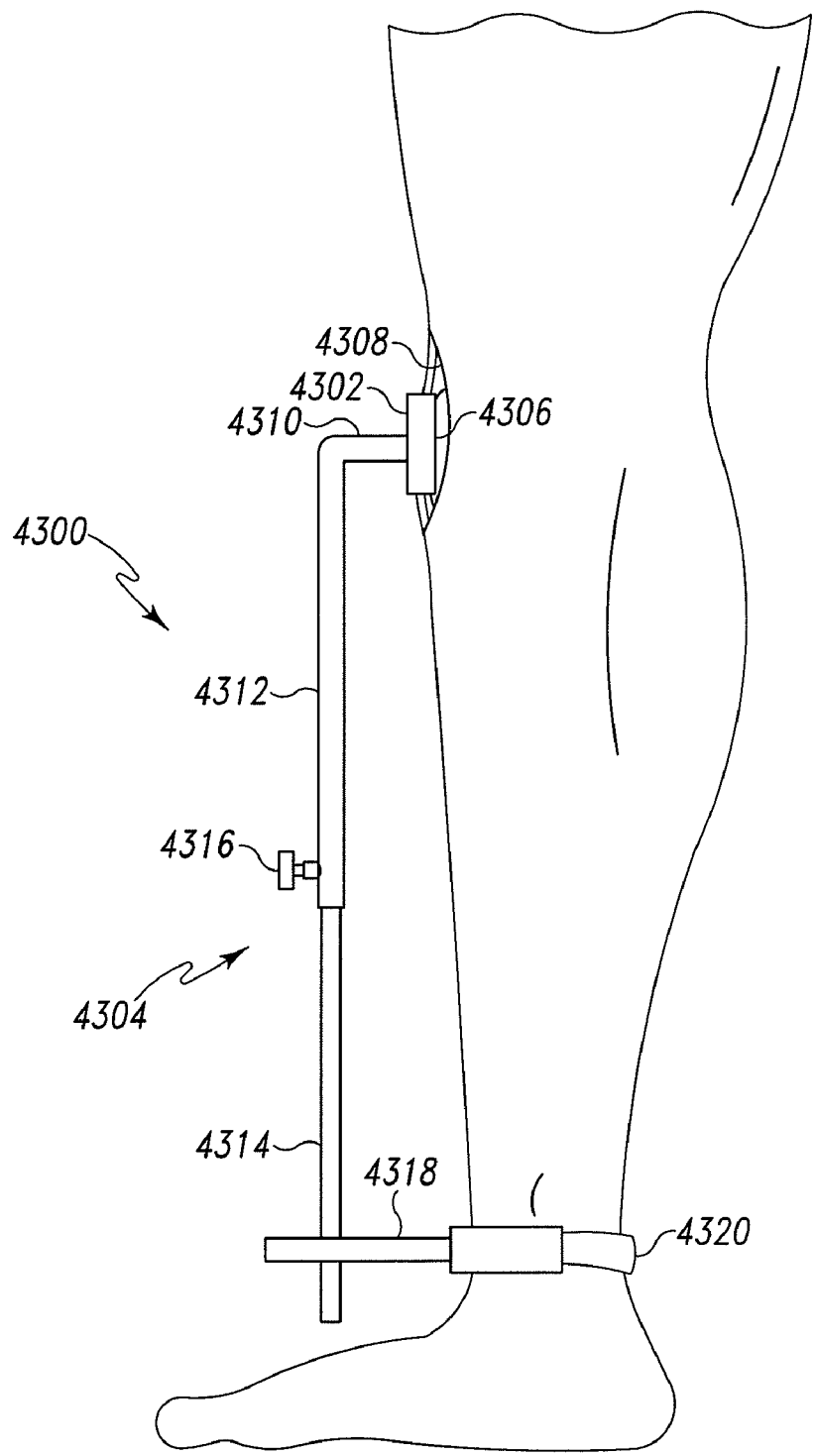
FIG. 100 is a perspective view of another embodiment of a customized patient-specific orthopaedic surgical instrument secured to a leg of a patient.

Referring now to FIG. 100, in another embodiment, a customized patient-specific orthopaedic surgical instrument 4300 includes a patient-specific cutting block 4302 and an alignment rod 4304. The cutting block 4302 is configured to be coupled to a bone of the patient such as, for example the patient's tibia or femur. Similar to the cutting blocks 4152, 4202, 4252 described above, the cutting block 4302 is customized to the particular patient and includes a bone-contacting or bone-facing surface 4306 having a negative contour (not shown) configured to receive a portion of the patient's bone having a corresponding contour. As discussed above, the negative contour of the bone-contacting surface 4306 allows the positioning of the cutting block 4302 on the patient's bone in a unique pre-determined location and orientation.

In some embodiments, the cutting block 4302 may include a captured cutting guide. Additionally or alternatively, the cutting block 4302 may include a non-captured cutting guide. The cutting block 4302 may or may not be configured to be secured to the patient's bone. For example, in some embodiments, the cutting block may include a number of pin guides to facilitate the securing of the cutting block 4302 to the patient's bone via a number of guide pins (not shown).

The cutting block 4302 is coupled to the alignment rod 4304 via a horizontal bar 4310, which extends out of the incision site 4308. In the illustrative embodiment, the horizontal bar 4310 is integral to the alignment rod 4304. The alignment rod 4304 includes an upper rod 4312 and a lower rod 4314 having a diameter smaller than the diameter of the upper rod 4312. In the illustrative embodiment, the lower rod 4314 is a telescoping rod and is configured to be retracted into and extended from the upper rod 4312 such that the overall length of the alignment rod 4314 is adjustable. In other embodiments, the upper rod 4312 may be a telescoping rod and configured to be retracted into and extended from the lower rod 4314. In the illustrative embodiment, the position of the lower rod 4314 relative to the upper rod 4312 may be fixed via use of a securing device 4316. The securing device 4316 may be embodied as a thumbscrew or other securing device capable of securing the lower rod 4314 in a fixed position relative to the upper rod 4312.

The alignment rod 4304 also includes an ankle brace 4318 configured to be secured to the ankle of the patient. The ankle brace extends from the lower rod 4314 in a substantially orthogonal orientation and includes a rear strap or clamp 4320. The rear strap 4320 is configured to secure the patient's ankle to the ankle brace 4318. In some embodiments, the rear strap 4320 is removable from the ankle brace 4318 to allow the patient's ankle to be received therein.

In use, the cutting block 4302 may be coupled to the patient's bone via the guide pins. The lower rod 4314 may be extended from or retracted into the upper rod 4312 to adjust the overall length of the alignment rod 4304 to the length of the patient's leg. After the alignment rod has been adjusted, the ankle brace 4318 may be secured to the patient's ankle. It should be appreciated that in use the alignment rod 4304 may be positioned to target the center of the patient's ankle to align the cutting block 4302 accordingly.

Figure 101:
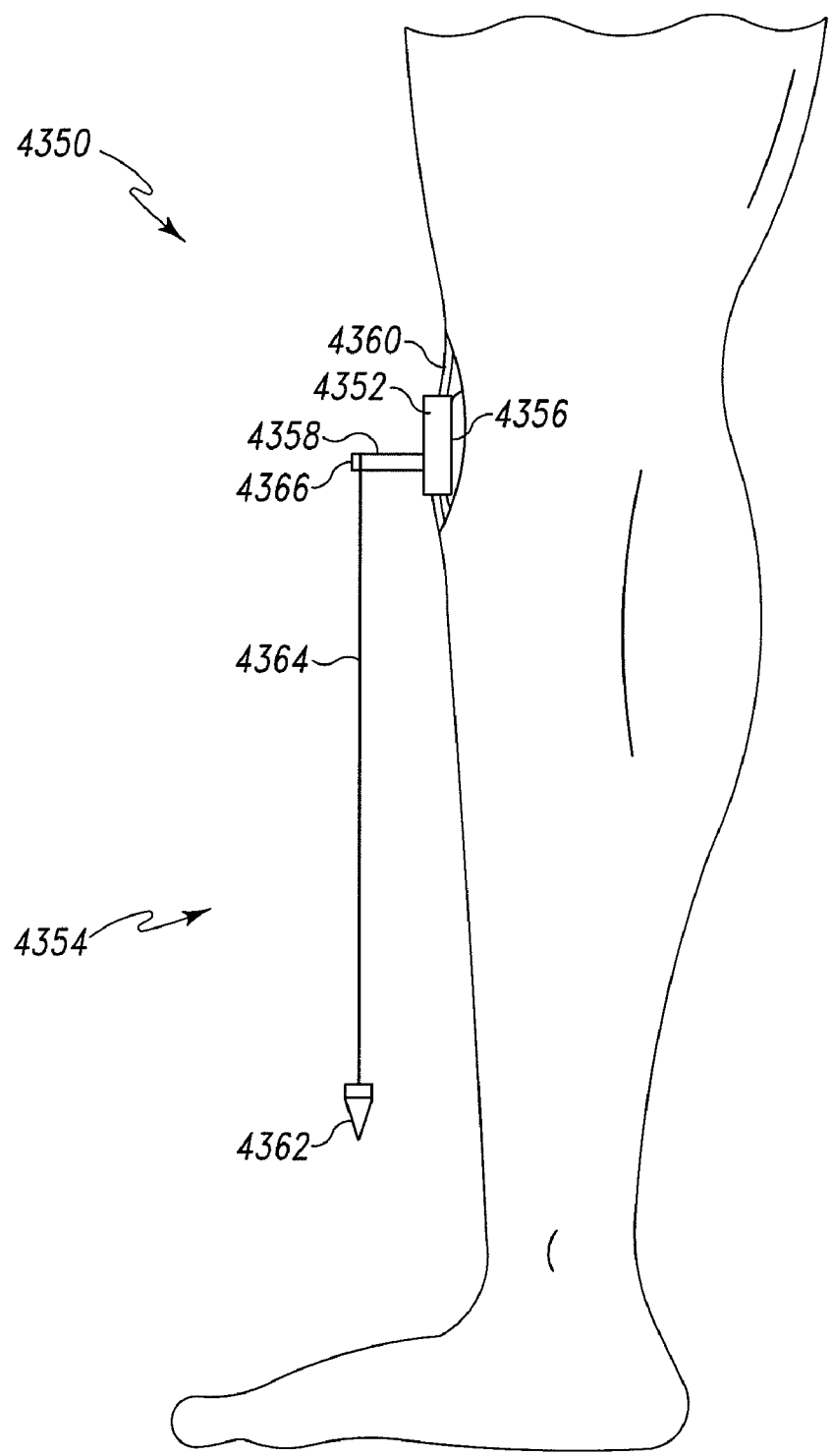
FIG. 101 is a perspective view of another embodiment of a customized patient-specific orthopaedic surgical instrument secured to a leg of a patient.

Referring now to FIG. 101, in another embodiment, a customized patient-specific orthopaedic surgical instrument 4350 includes a patient-specific cutting block 4352 and an alignment device 4354. The cutting block 4352 is configured to be coupled to a bone of the patient such as, for example the patient's tibia or femur. Similar to the cutting blocks 4152, 4202, 4252 described above, the cutting block 4352 is customized to the particular patient and includes a bone-contacting surface 4356 having a negative contour (not shown) configured to receive a portion of the patient's bone having a corresponding contour. As discussed above, the negative contour of the bone-contacting surface 4356 allows the positioning of the cutting block 4352 on the patient's bone in a unique pre-determined location and orientation.

In some embodiments, the cutting block 4352 may include a captured cutting guide. Additionally or alternatively, the cutting block 4352 may include a non-captured cutting guide. The cutting block 4352 may or may not be configured to be secured to the patient's bone. For example, in some embodiments, the cutting block may include a number of pin guides to facilitate the securing of the cutting block 4352 to the patient's bone via a number of guide pins (not shown).

As shown in FIG. 101, the instrument 4350 includes an extension rod 4358 coupled to the cutting block 4352 and extending out of the incision site 4360. Illustratively, the extension rod 4358 is substantially straight. The alignment device 4354 is secured to an end 4366 of the extension rod 4358. The alignment device 4354 includes a tensioner 4362, such as a weight, coupled to the end 4366 via a cord 4364. In other embodiments, the orthopaedic surgeon may apply a downward force on the cord 4364 in place of the tensioner 4362.

In use, the cutting block 4352 may be coupled to the patient's bone via the guide pins. In so doing, the position of the cord 4364 and the tensioner 4362 relative to the patient's leg may be used to align the cutting block 4352 accordingly. Once so aligned, the cord 4364 and tensioner 4362 may be removed from the cutting block 4352 if so desired.

Figure 102:
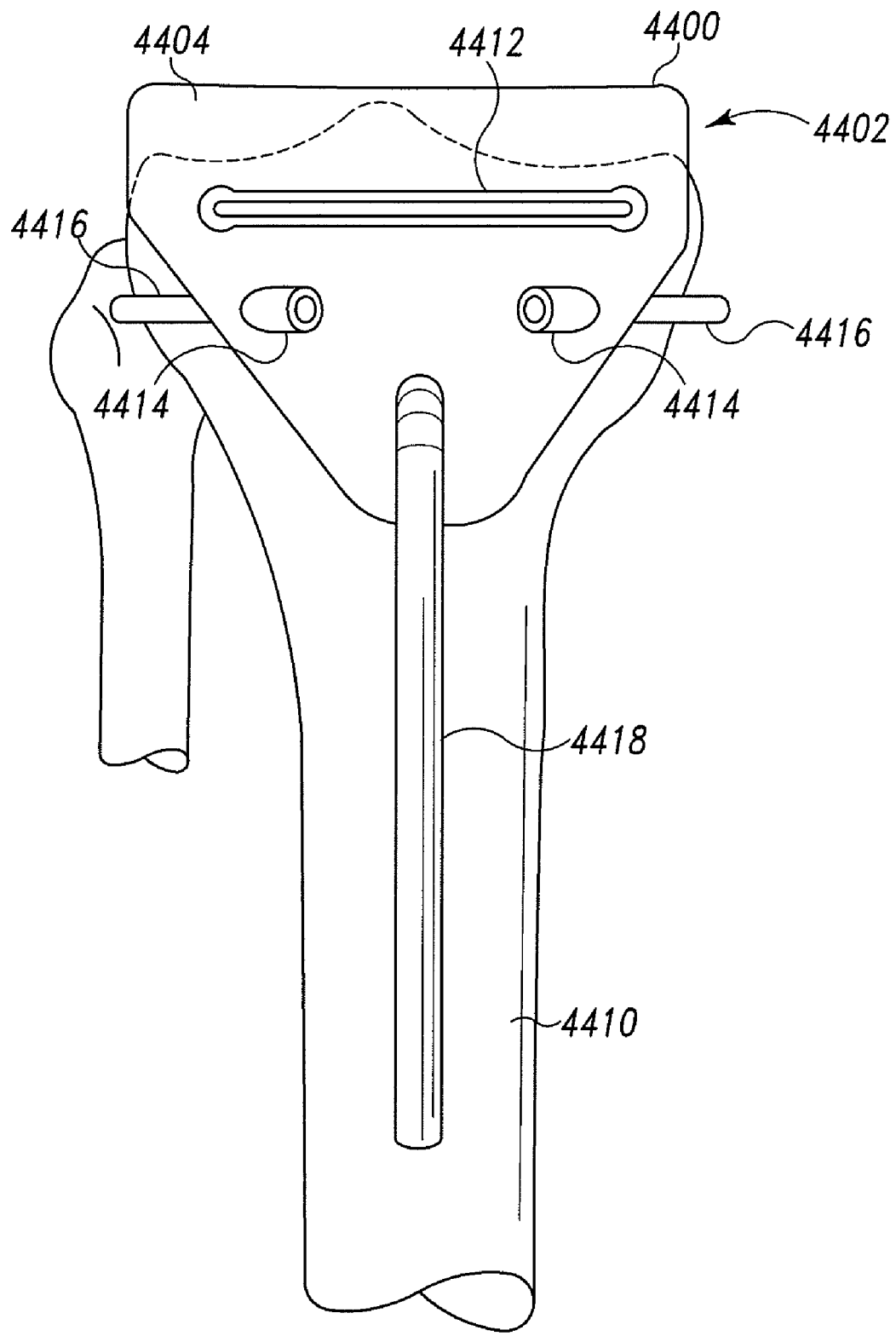
FIG. 102 is a perspective view of another embodiment of a customized patient-specific orthopaedic surgical instrument secured to a bone of a patient.
Figure 103:
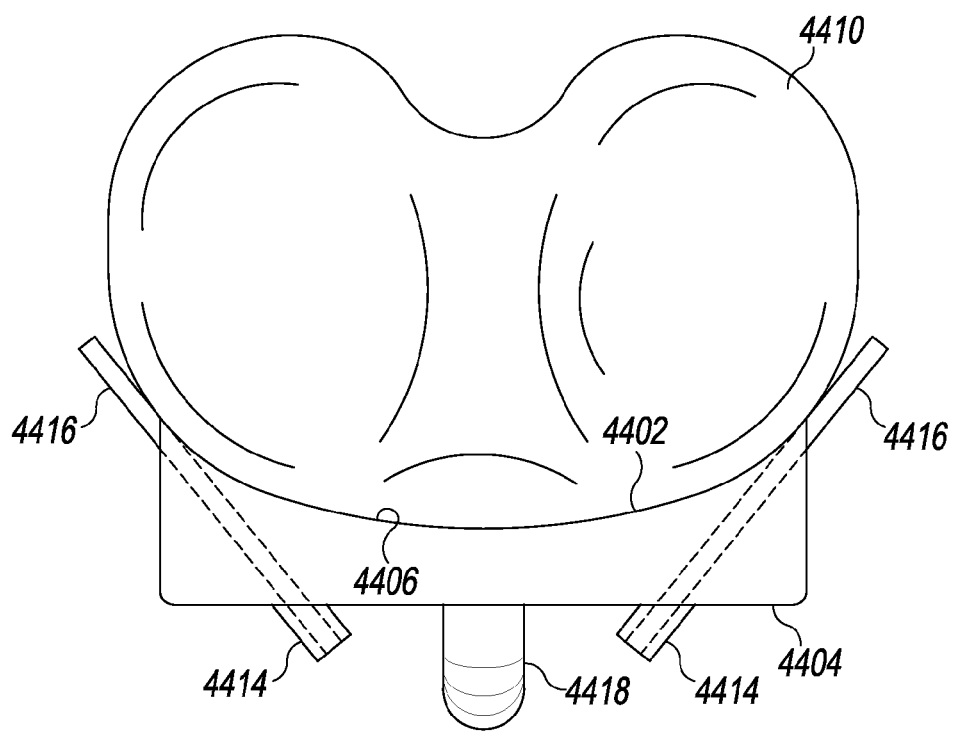
FIG. 103 is a top plan view of the customized patient-specific orthopaedic surgical instrument of FIG. 102.

Referring now to FIGS. 102 and 103, in another embodiment, the customized patient-specific orthopaedic surgical instrument may be embodied as a cutting block 4400. The cutting block 4400 is configured to be coupled to a bone 4410 of the patient. The cutting block 4400 is illustratively a tibial cutting block, but may be configured for use with other bones, such as the femur, in other embodiments. The cutting block 4400 includes a bone-contacting or bone-facing surface 4402 and an outer surface 4404. The bone-contacting surface 4402 includes a negative contour 4406 (see FIG. 103) configured to receive a portion of the patient's bone having a corresponding contour. As discussed above, the negative contour 4406 of the bone-contacting surface 4402 allows the positioning of the cutting block 4400 on the patient's bone 4410 in a unique pre-determined location and orientation.

The cutting block 4400 includes a cutting guide 4412. Illustratively, the cutting guide 4412 is a captured cutting guide, but may be embodied as a non-captured or open cutting guide in other embodiments. It should be appreciated that because the position of the cutting guide 4412 is pre-determined due to the configuration of the cutting block 4400, any bone cuts made using the patient-specific cutting block 4400 correspond to the predetermined bone cutting planes (see process step 24 of algorithm 10 described above in regard to FIG. 1).

The cutting block 4400 also includes a number of pin guides 4414. The pin guides 4414 are angled relative to the outer surface 4404 of the block 4400. The location and angulation of the pin guides 4414 is customized to the particular patient such that when the cutting block is coupled to the patient's bone 4410, a number of guide pins 4416 may be inserted into the pin guides 4414. When so position, a portion of each guide pin 4416 extends from the bone-contacting surface 4402. The guide pins 4416 are so positioned such that guide pins contact the surface of the bone 4410. For example, in one particular embodiment, the pin guides 4414 are configured such that the bone 4410 of the patient is wedged between the guide pins 4416 when the pins 4416 are inserted into the guides 4414. It should be appreciated that is use the contact between the guide pins 4416 and the patient's bone may increase the stability of the cutting block 4400.

In some embodiments, the cutting block 4400 may also include other pin guides (not shown) to facilitate the coupling of the cutting block 4400 to the patient's bone 4410. That is, a number of guide pins may be inserted into the additional guides to secure the cutting block 4400 to the tibia 4410 as discussed above. Additionally, in some embodiments, the cutting block 4400 may include an alignment rod 4418 extending downwardly therefrom. In use, an orthopaedic surgeon may use the alignment rod 4418 to reference the orientation of the cutting block 4400 relative to the patient's bone 4410. For example, the alignment rod 4418 may be used to reference the anterior/posterior angulation of the cutting block 4400.

Figure 104:
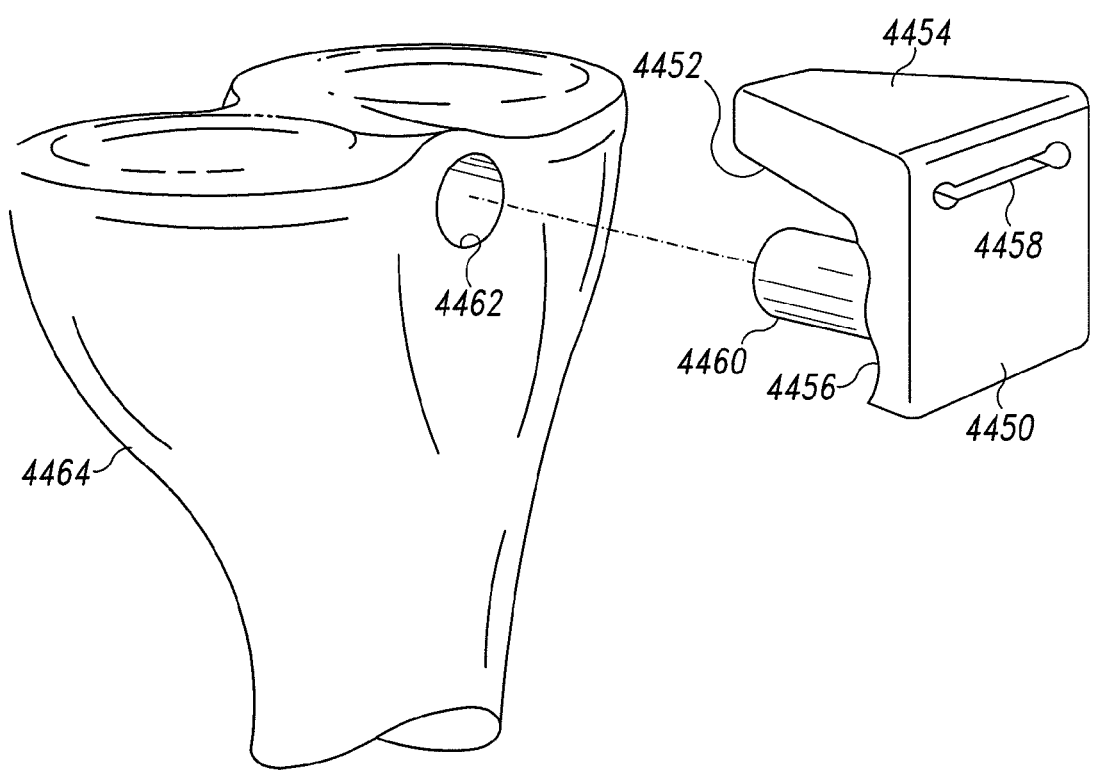
FIG. 104 is a perspective view of another embodiment of a customized patient-specific orthopaedic surgical instrument.

Referring now to FIG. 104, in another embodiment, the customized patient-specific orthopaedic surgical instrument may be embodied as a cutting block 4450. The cutting block 4450 is configured to be coupled to a bone 4464 of the patient. The cutting block 4450 is illustratively a tibial cutting block, but may be configured for use with other bones, such as the femur, in other embodiments. The cutting block 4450 includes a bone-contacting or bone-facing surface 4452 and an outer surface 4454. The bone-contacting surface 4452 includes a negative contour 4456 configured to receive a portion of the patient's bone having a corresponding contour. As discussed above, the negative contour 4456 of the bone-contacting surface 4452 allows the positioning of the cutting block 4450 on the patient's bone 4464 in a unique pre-determined location and orientation.

The cutting block 4450 includes a cutting guide 4468. Illustratively, the cutting guide 4468 is a captured cutting guide, but may be embodied as a non-captured or open cutting guide in other embodiments. It should be appreciated that because the position of the cutting guide 4468 is pre-determined due to the configuration of the cutting block 4450, any bone cuts made using the patient-specific cutting block 4450 correspond to the predetermined bone cutting planes (see process step 24 of algorithm 10 described above in regard to FIG. 1). In some embodiments, the cutting block 4450 may also include a number of pin guides (not shown). As discussed above, the pin guides may be used to facilitate the coupling of the cutting block 4450 to the patient's bone 4464 via use of a number of corresponding guide pins (not shown).

The cutting block 4450 also includes a post 4460 extending from the bone-contacting surface 4456. The post 4460 is configured to be received in an aperture 4462 formed in the patient's bone 4464. The aperture 4462 may be defined in the patient's tibia or bone 4464 via use of an orthopaedic drill or the like. The position of the aperture 4462 may be customized to the particular patient. Additionally, the position of the aperture 4462 may be standardized relative to the particular type of bone being resected. After the aperture 4462 is formed, a number of various orthopaedic instruments may use the aperture 4462 as a common guide or guide point. For example, in use, the illustrative cutting block 4450 is configured to be coupled to the patient's tibia 4464 such that the post 4460 is received in the aperture 4462. In some embodiments, as discussed above, the cutting block 4450 may also be secured to the bone 4464 via a number of guide pins. The patient's bone 4464 may then be resected. It should be appreciated that when the post 4460 is received in the aperture 4462, the stability of the cutting block 4450 may be increased.

Figure 105:
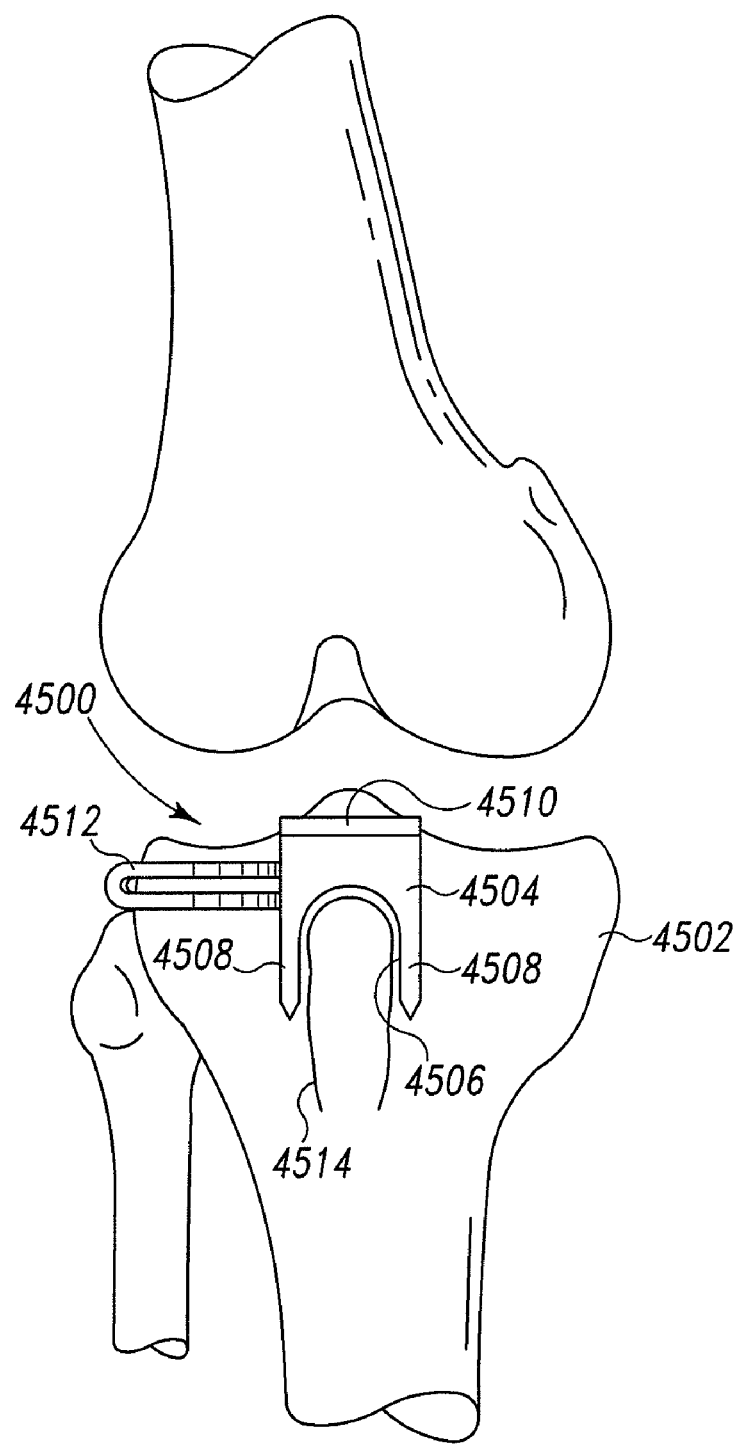
FIG. 105 is an anterior elevation view of another embodiment of a customized patient-specific orthopaedic surgical instrument secured to a bone of a patient.
Figure 106:
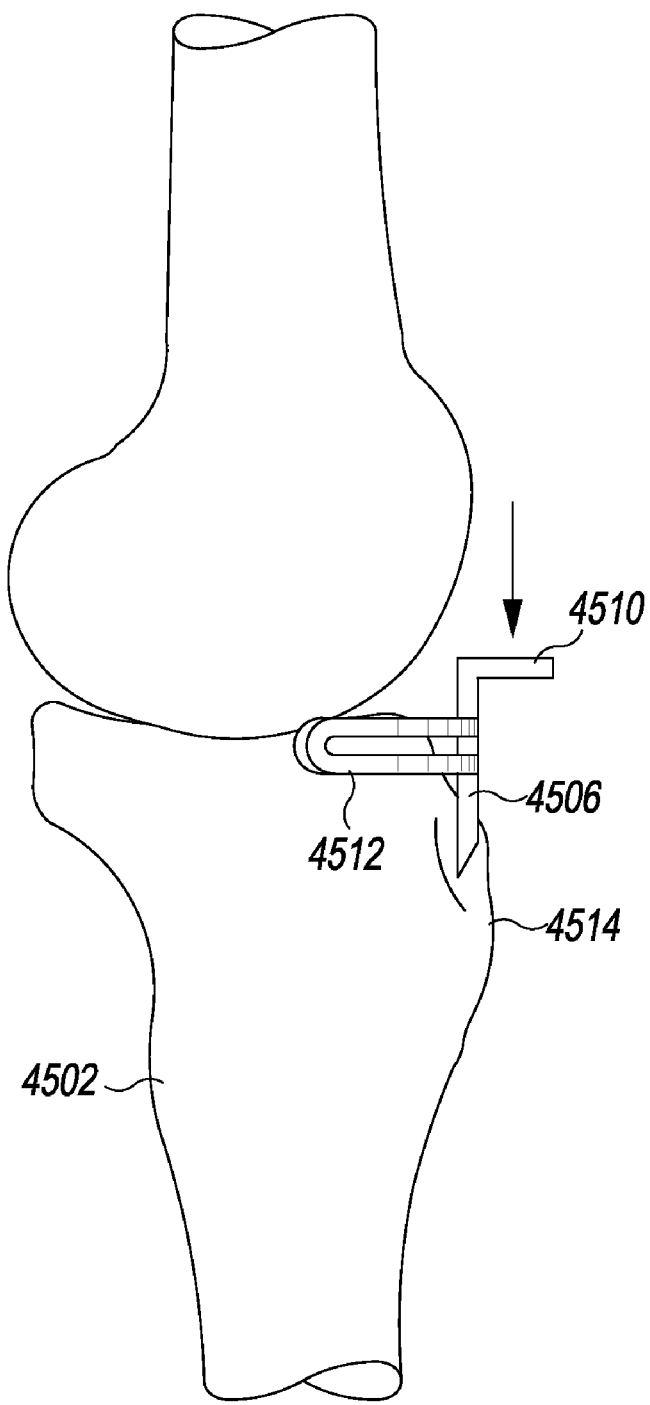
FIG. 106 is a side elevation view of the customized patient-specific orthopaedic surgical instrument of FIG. 105.

Referring now to FIGS. 105 and 106, in another embodiment, the customized patient-specific orthopaedic surgical instrument may be embodied as a tibial cutting block 4500. The tibial cutting block 4500 is configured to be coupled to a tibia 4502 of the patient. The tibial cutting block 4500 includes a body 4504 having a tubercle-receiving clamp 4506. The clamp 4506 includes two arms 4508 that extend downwardly from the body 4504. The cutting block 4500 also includes a flange 4510 defined at an end of the body 4504 opposite the clamp 4506.

The cutting block 4500 also includes a captured cutting guide 4512. The cutting guide 4512 extends from a side of the body 4504. Illustratively, the cutting guide 4512 is curved such that the guide 4512 wraps around a portion of the tibia 4502. The clamp 4506 is customized to the particular patient's bony anatomy such that the position of the cutting guide 4512 relative to the tibia 4502 is predetermined. It should be appreciated that because the position of the cutting guide 4512 is predetermined, any bone cuts made using the patient-specific cutting block 4500 correspond to the predetermined bone cutting planes (see process step 24 of algorithm 10 described above in regard to FIG. 1). In some embodiments, the cutting block 4500 may also include a number of pin guides (not shown). As discussed above, the pin guides may be used to facilitate the coupling of the cutting block 4500 to the patient's bone 4502 via use of a number of corresponding guide pins (not shown).

In use, as shown in FIG. 106, the cutting block 4500 is secured to the patient's tibia 4502 by impacting the cutting block 4500 onto the bone 4502 such that the tibial tubercle 4514 of the patient's tibia 4502 is received in the clamp 4506. To do so, an orthopaedic hammer or other impacting device may be used to apply an amount of downward force on the flange 4510 of the block 4500. The cutting block 4500 is secured to the patient's bone 4502 via the clamp 4506.

Figure 107:
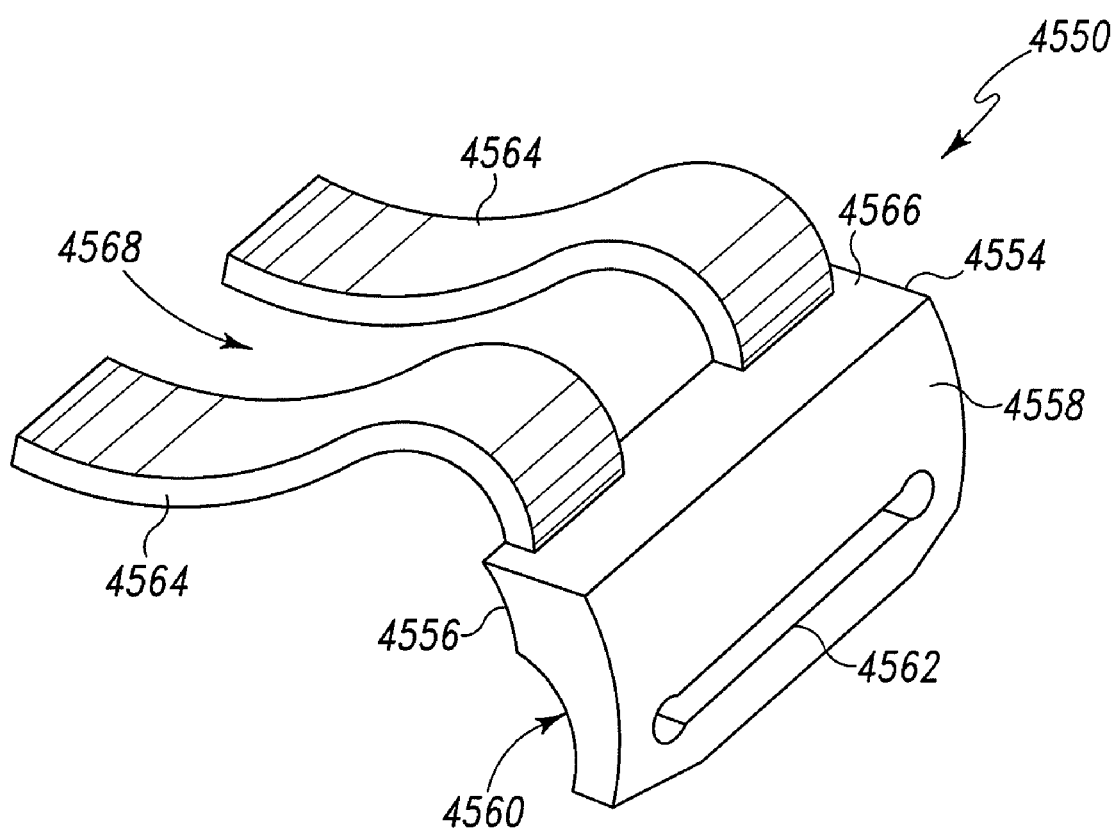
FIG. 107 is a perspective view of another embodiment of a customized patient-specific orthopaedic surgical instrument.
Figure 108:
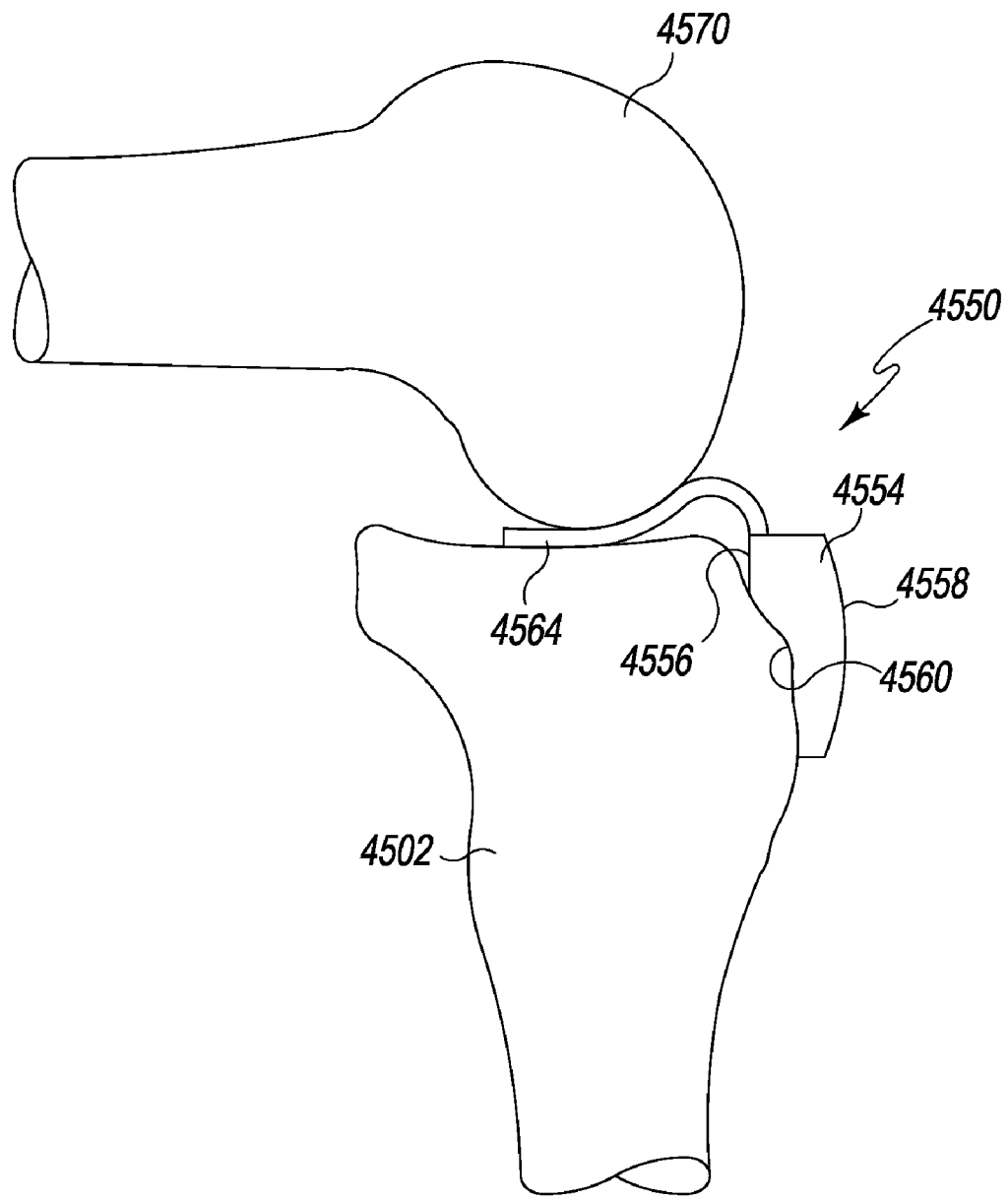
FIG. 108 is a side elevation view of the customized patient-specific orthopaedic surgical instrument of FIG. 107 secured to a bone of a patient.

Referring now to FIGS. 107 and 108, in another embodiment, the customized patient-specific orthopaedic surgical instrument may be embodied as a tibial cutting block 4550. The tibial cutting block 4550 is configured to be coupled to a tibia 4502 of the patient. The tibial cutting block 4550 includes a body 4554 having a bone-contacting or bone-facing surface 4556 and an outer surface 4558. The bone-contacting surface 4556 includes a negative contour 4560 configured to receive a portion of the patient's bone having a corresponding contour. As discussed above, the negative contour 4560 of the bone-contacting surface 4556 allows the positioning of the cutting block 4550 on the patient's bone 4502 in a unique pre-determined location and orientation.

The cutting block 4550 includes a cutting guide 4562. Illustratively, the cutting guide 4562 is a captured cutting guide, but may be embodied as a non-captured or open cutting guide in other embodiments. It should be appreciated that because the position of the cutting guide 4562 is pre-determined due to the configuration of the cutting block 4550, any bone cuts made using the patient-specific cutting block 4550 correspond to the predetermined bone cutting planes (see process step 24 of algorithm 10 described above in regard to FIG. 1). In some embodiments, the cutting block 4550 may also include a number of pin guides (not shown). As discussed above, the pin guides may be used to facilitate the coupling of the cutting block 4550 to the patient's bone 4502 via use of a number of corresponding guide pins (not shown).

The cutting block 4550 also includes a pair of tabs 4564 that extend from an upper side 4566 of the body 4564 of the cutting block 4550. The tabs 4564 are spaced apart to define an open area 4568 therebetween. Additionally, the tabs 4564 are curved when viewed in the medial/lateral plane. In use, the cutting block 4550 is coupled to the patient's tibia 4502 such that the tabs 4564 are received between the tibia 4502 and the posterior condyles of the patient's femur 4570 when the patient's knee is in flexion. In such a position, the tabs 4564 are secured in place by the joint force between the femur 4570 and the tibia 4502. In should be appreciated that by securing the tabs 4564 between the femur 4570 and the tibia 4502, the stability of the cutting block 4550 may be improved. Additionally, in some embodiments, the cutting block 4550 may be secured to the tibia 4502 via use of guide pins for further stability.

Figure 109:
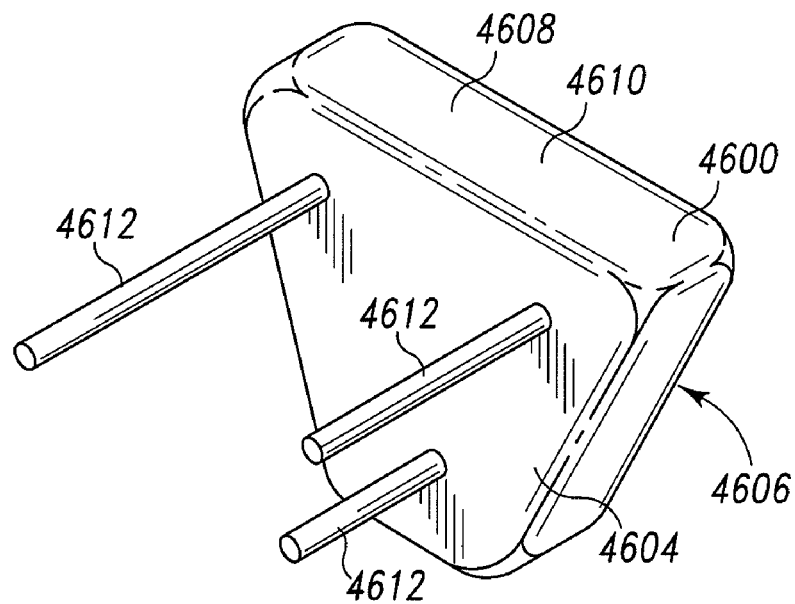
FIG. 109 is a perspective view of another embodiment of a customized patient-specific orthopaedic surgical instrument.
Figure 110:
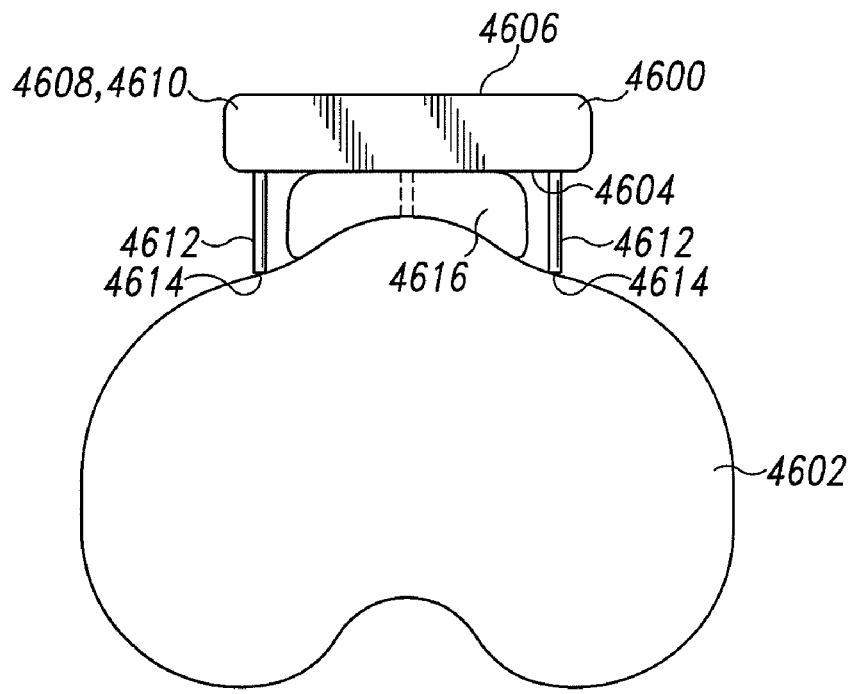
FIG. 110 is a top plan view of the customized patient-specific orthopaedic surgical instrument of FIG. 109 secured to a bone of a patient.

Referring now to FIGS. 109 and 110, in another embodiment, the customized patient-specific orthopaedic surgical instrument may be embodied as a cutting block 4600. The cutting block 4600 is configured to be coupled to a bone 4602 of the patient. For example, the cutting block 4600 may be configured to be coupled to a tibia, femur, or other bone of the patient. The cutting block 4600 includes a bone-facing surface 4604 and an outer surface 4606. The illustrative cutting block 4600 includes a non-captured cutting guide 4608, but may include a captured cutting guide in other embodiments. The non-captured cutting guide 4608 is defined by a side surface 4610 of the cutting block 4600. In use, an orthopaedic surgeon may use the surface 4610 as a guide for the cutting blade of a bone saw or the like.

The cutting block 4600 also includes a number of guide pins 4612. The guide pins 4612 extend from the bone-facing surface 4604 of the block 4600. Each of the guide pins 4612 extend from the bone-facing surface 4604 a particular length. The length of each guide pin 4612 is determined based on the particular bony anatomy of the patient. That is, the length of the guide pins 4612 is selected such that the cutting block 4600 is patient-specific. Additionally, length of the guide pins 4612 allows the positioning of the cutting block 4600 in a pre-determined location and orientation relative to the bone 4602.

In use, the cutting block 4600 is coupled to the patient's bone 4602 as illustrated in FIG. 110. Again, the guide pins 4612 are designed to have a length such that the end 4614 of each pin 4612 contacts the surface of the bone 4602. In some embodiments, an amount of form-fitting, hardening material 4616 may be positioned between the cutting block 4600 and the patient's bone 4602 to further stabilize the cutting block 4600. The material 4616 may be embodied as any type of form-fitting material such as, for example, dental plaster, configured to hardened after a set-up period. In some embodiments, the material 4616 is positioned in a formable container such as a bag or the like.

Figure 111:
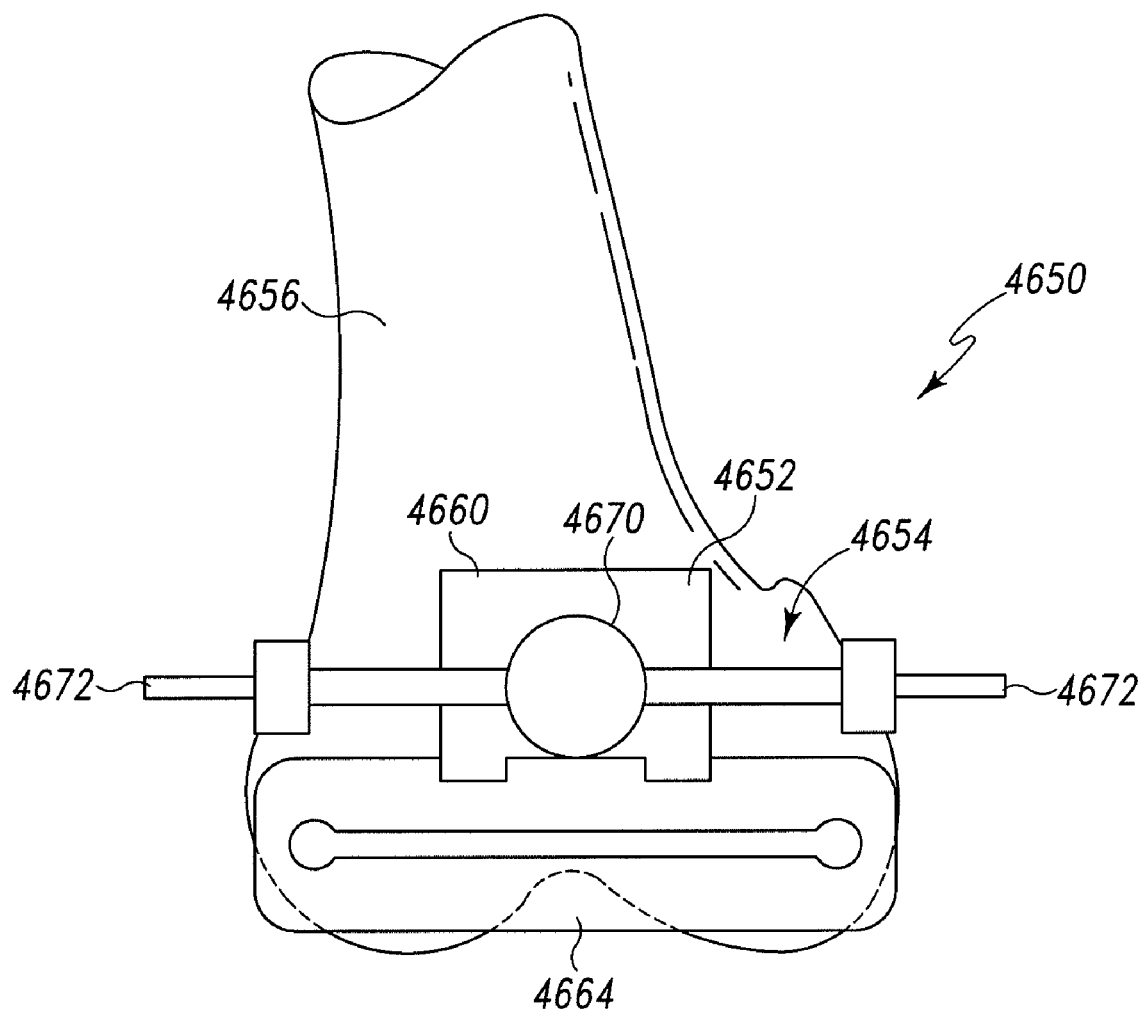
FIG. 111 is an anterior elevation view of another embodiment of a customized patient-specific orthopaedic surgical instrument secured to a bone of a patient.
Figure 112:
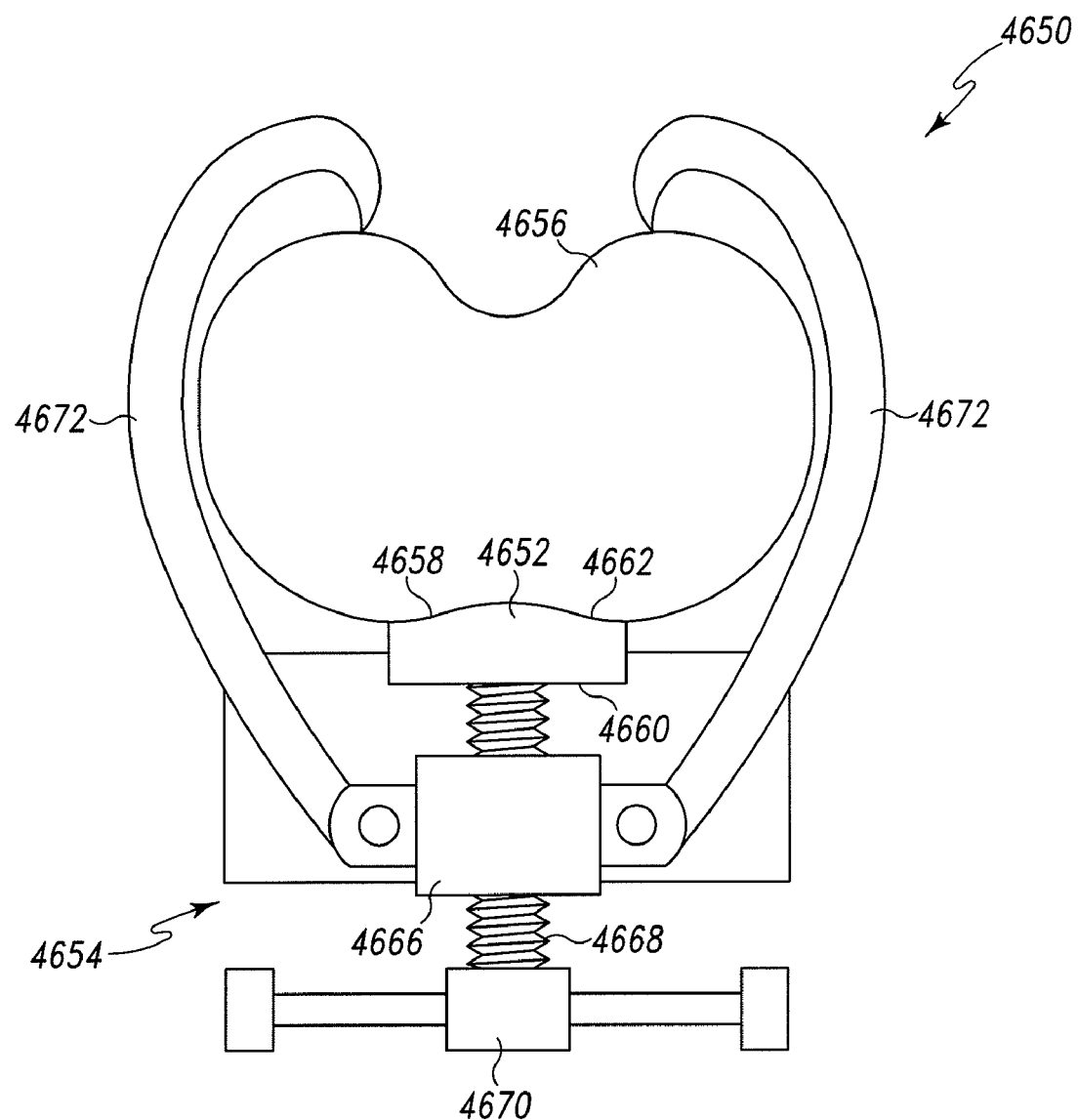
FIG. 112 is a top elevation proximal-to-distal view of the customized patient-specific orthopaedic surgical instrument of FIG. 111.

Referring now to FIGS. 111 and 112, in another embodiment, a customized patient-specific orthopaedic surgical instrument 4650 includes a cutting block 4652 and a clamp 4654 coupled to the block 4652. The cutting block 4652 is configured to be coupled to a bone 4656 of the patient, such as the tibia or femur. The cutting block 4652 includes a bone-contacting or bone-facing surface 4658 and an outer surface 4660 (see FIG. 112). The bone-contacting surface 4658 includes a negative contour 4662 configured to receive a portion of the patient's bone 4656 having a corresponding contour. As discussed above, the negative contour 4662 of the bone-contacting surface 4658 allows the positioning of the cutting block 4652 on the patient's bone 4656 in a unique pre-determined location and orientation.

The cutting block 4652 also includes a cutting guide 4664. Illustratively, the cutting guide 4664 is a captured cutting guide, but may be embodied as a non-captured or open cutting guide in other embodiments. It should be appreciated that because the position of the cutting guide 4664 is pre-determined due to the configuration of the cutting block 4652, any bone cuts made using the patient-specific cutting block 4652 correspond to the predetermined bone cutting planes (see process step 24 of algorithm 10 described above in regard to FIG. 1).

The clamp 4654 includes a base 4666 received on a threaded rod 4668. The base 4666 of the clamp 4654 is coupled to the cutting block 4652 via the threaded rod 4668. A handle 4670 is secured to the threaded rod 4668 at an end opposite the block 4652. The clamp 4654 also includes a pair of hooks or arms 4672 coupled to the base 4666. The hooks 4672 are configured to pivot with respect to the base 4666.

In use, the cutting block 4652 is configured to be coupled to the bone 4656 of the patient. The cutting block 4652 is secured to the bone 4656 via the clamp 4654. To do so, the hooks 4672 are positioned around the bone 4656 as illustrated in FIG. 112. The handle 4670 may then be operated (i.e., twisted in the appropriate direction) to cause the base 4666 of the clamp 4654 to be moved away from the cutting block 4652. As the base 4666 of the clamp 4654 is moved away from the block 4652, the hooks 4672 contact the bone 4656. As such, the cutting block 4652 may be secured to the bone 4656 by tightening the clamp 4654 in the above-described manner. Although described as being positioned around the bone 4656, the clamp 4654 may be configured to be positioned around the outside of the patient's leg. That is, in some embodiments, the hooks 4672 of the clamp 4654 may be positioned around the skin of the patient's leg. In such embodiments, the hooks 4672 engage the patient's skin when the clamp 4654 is tightened.

Figure 113:
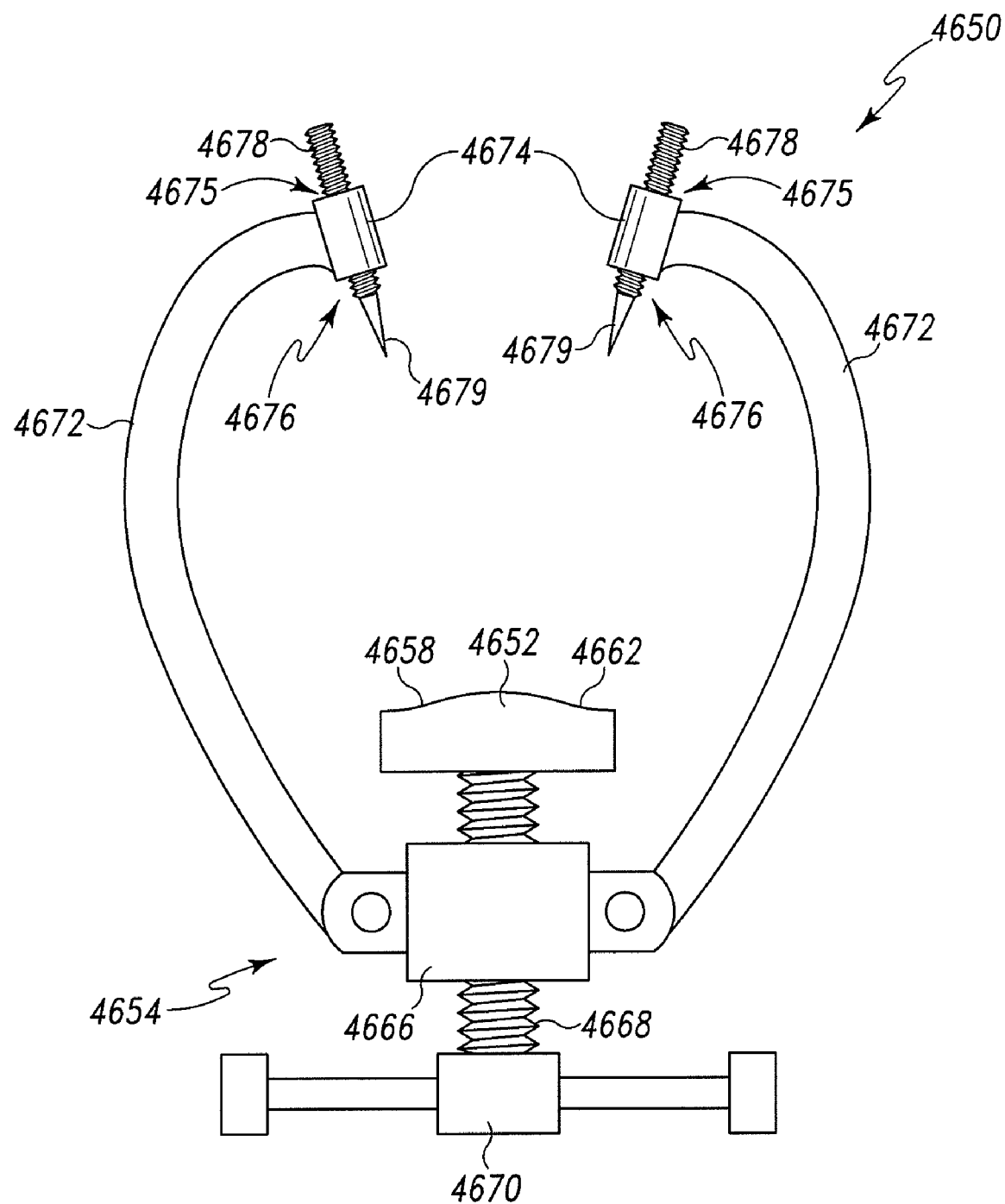
FIG. 113 is a top elevation view of another embodiment of the customized patient-specific orthopaedic surgical instrument of FIG. 111.

The hooks 4672 may have any one of a number of different configurations in other embodiments. For example, as illustrated in FIG. 113, each of the hooks 4672 may include a post 4674 defined at the end 4676 of the hook 4672. Each post 4674 includes a threaded aperture 4675 defined therethrough. A threaded pin 4678 is received in each threaded aperture 4675. Each threaded pin 4678 includes a pointed end 4679 configured to contact the patient's bone 4656 or skin during use. The position of the threaded pin 4678 relative to the hook 4672 may be adjusted by threading the pin 4678 into or out of the threaded aperture 4675. As such, the hooks 4672 may be positioned around the patient's bone 4656 or skin, depending on the embodiment, and the pins 4678 may be threaded into a position such that the pins 4678 engage the bone 4656 or skin to secure the clamp 4654 to the patient's leg.

Figure 114:
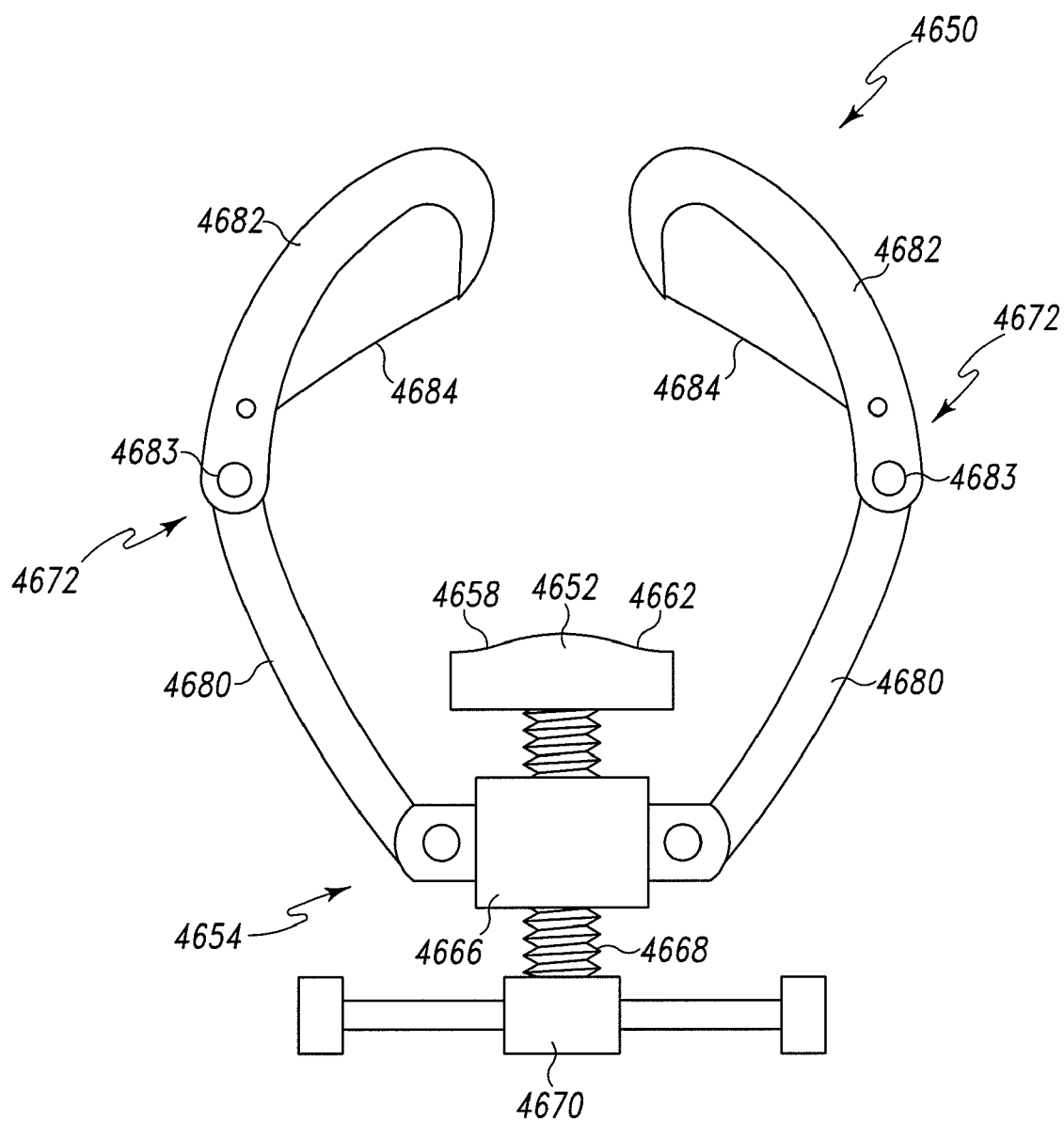
FIG. 114 is a top elevation view of another embodiment of the customized patient-specific orthopaedic surgical instrument of FIG. 111.

Referring to FIG. 114, in another embodiment, each of the hooks 4672 of the clamp 4654 include a linkage arm 4680 and a pivotable hook 4682. The linkage arms 4680 are coupled to the base 4666 and are configured to pivot with respect thereto. The hooks 4682 are coupled to the respective linkage arms 4680 via a hinge 4683. The hooks 4682 are configured to pivot with respect to the respective linkage arms 4680. In some embodiments, the pivotable hooks 4682 may include a biasing member 4684 secured to the tip of the hook 4682 and extending to the base of the hook 4682. The biasing member 4684 may be formed from a metallic material in some embodiments. The biasing member 4684 is configured to bend or otherwise deform when the clamp 4654 is coupled to patient's bone 4656 or leg to reduce the likely hood that the clamp 4654 damages the bone 4656 or skin tissue of the patient.

Figure 115:
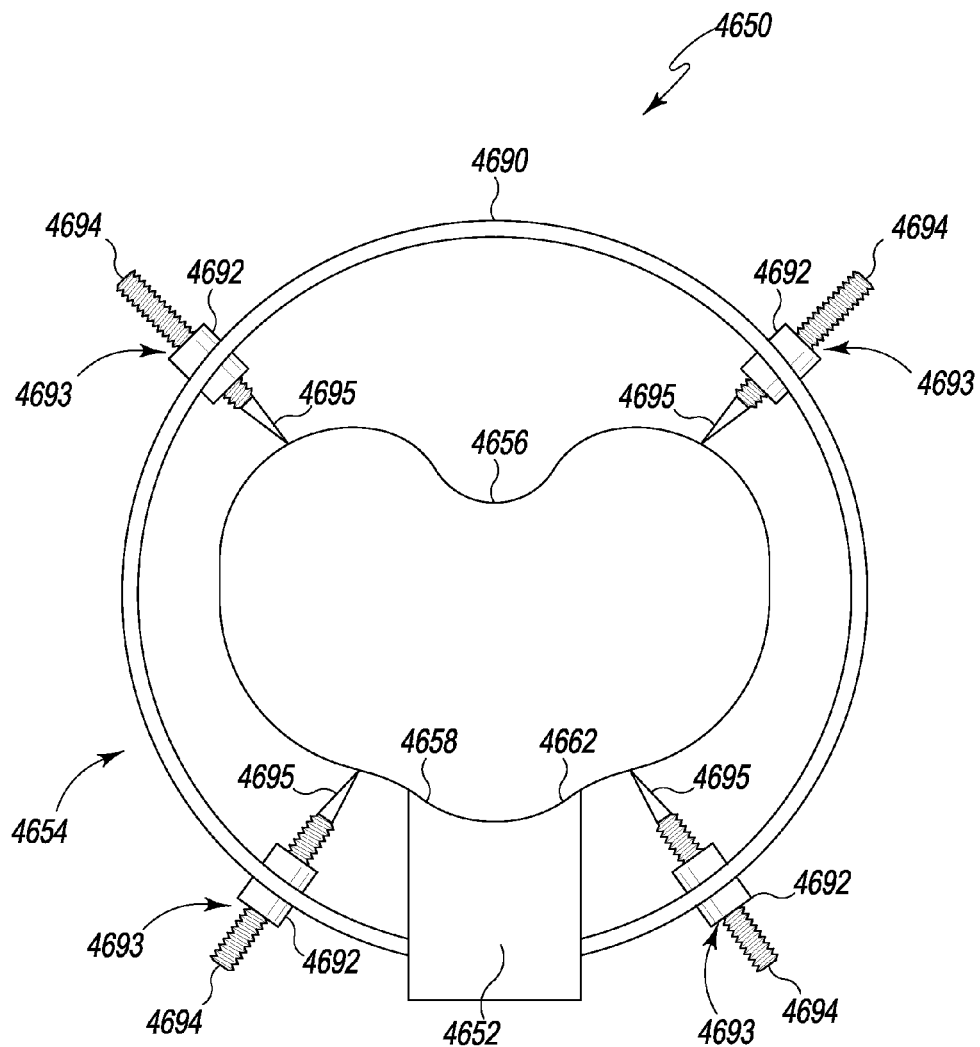
FIG. 115 is a top elevation view of another embodiment of the customized patient-specific orthopaedic surgical instrument of FIG. 111.

Referring to FIG. 115, in some embodiments, the clamp 4654 may be embodied as a halo clamp 4690. The halo clamp 4690 is configured to be positioned around the patient's bone 4656. The halo clamp 4690 includes a number of posts 4692, each having a threaded aperture 4693 defined therethrough. A threaded pin 4694 is received in each threaded aperture 4693 and includes a pointed end 4695. The pointed ends 4695 of the pins 4694 are configured to contact the patient's bone 4656 when the halo clamp 4690 is coupled to the bone 4656. The position of the threaded pins 4694 relative to the halo clamp 4690 may be adjusted by threading the pins 4694 into or out of the threaded apertures 4693.

In use, the halo clamp 4690 is configured to be positioned around the patient's bone 4656 and secured thereto via the threaded pins 4694. To do so, the threaded pins 4694 may be threaded into the respective posts 4692 until each pin contacts the bone 4656 of the patient with enough force to secure the halo clamp 4690 thereto. In one particular embodiment, the halo clamp 4690 is configured such that the center of mass of the bone 4656 is located at or near the center of the halo clamp 4690. That is, the customized patient-specific orthopaedic surgical instrument 4650 is designed such that the cutting block 4652 is configured to be positioned in the desired position, as determined in the process steps 24, 26 of the algorithm 10 described above in regard to FIG. 1, when the halo clamp 4690 is coupled to the bone 4656 in such a position that the center of mass of the bone is at or near the center of the halo clamp 4690. The center of mass of the bone may be determined by, for example, analysis of the medical images generated in process step 12 of the algorithm 10.

Figure 116:
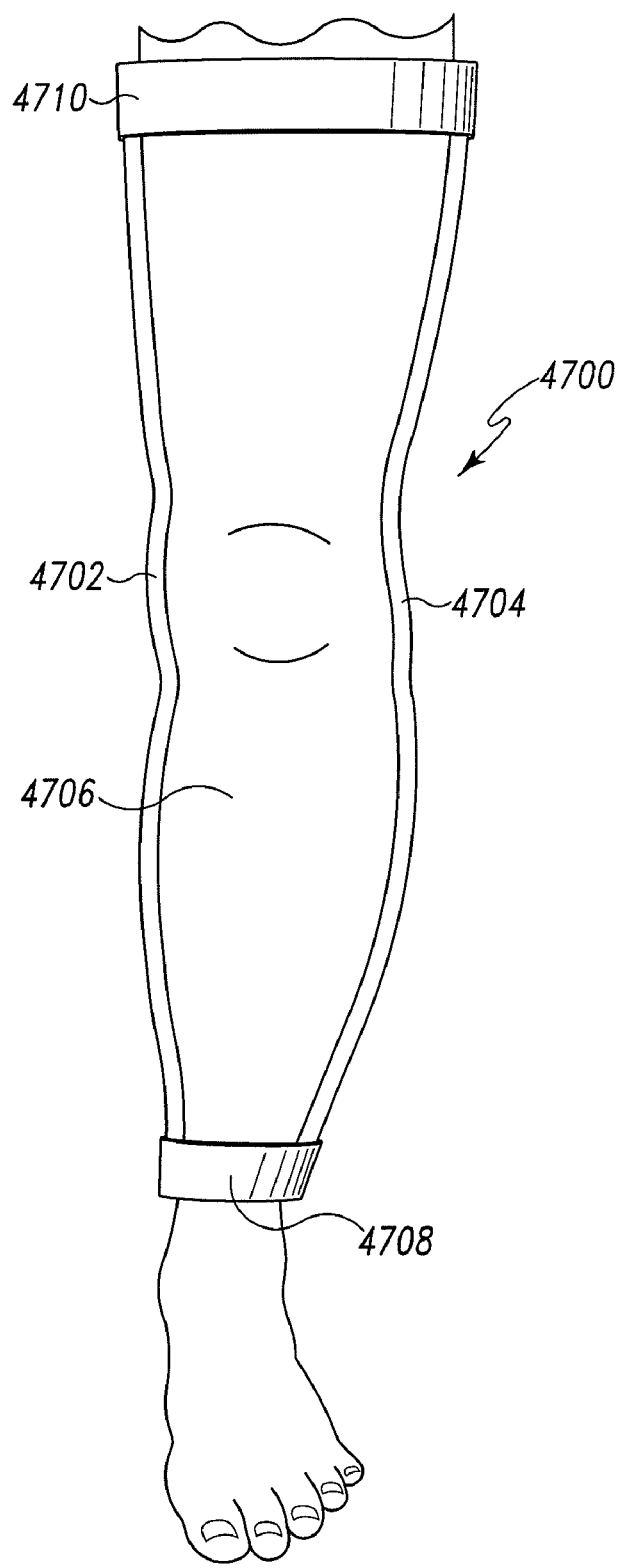
FIG. 116 is an anterior elevation view of one embodiment of a leg brace for securing a patient's leg.

Referring now to FIG. 116, in some embodiments, a leg brace 4700 may be coupled to a patient's leg 4706 during the generation of the medical images in the process step 12 of the algorithm 10 described above in regard to FIG. 1. The leg brace 4700 includes a medial support rod 4702 and a lateral support rod 4704. In some embodiments, the shape of the rods 4702, 4704 may be customized for the particular patient. That is, the rods 4702, 4704 may be shaped such that the rods 4702, 4704 define a negative contour configured to receive a corresponding contour of the patient's leg 4706. However, in other embodiments, the support rods 4702, 4704 may be universally shaped such that the leg brace 4700 is usable with a number of different patients. The leg brace 4700 includes an ankle clamp 4708 and a thigh clamp 4710. The ankle clamp 4708 is configured to be secured around the ankle area of the patient's leg 4706 and the thigh clamp 4710 is configured to be secured around the thigh area of the patient's leg 4706. In some embodiments, the clamps 4708, 4710 are adjustable to match the anatomy of different patients. The clamps 4708, 4710 may be formed from a plastic or fabric material. In use, the leg brace 4700 may be secured to the patient's leg 4706 to stabilize the patient's leg during the generation of the medical images such as during the performance of a computed tomography (CT) scan. By stabilizing the patient's leg, the medical images produced by the image generation process may be more accurate.

Figure 117:
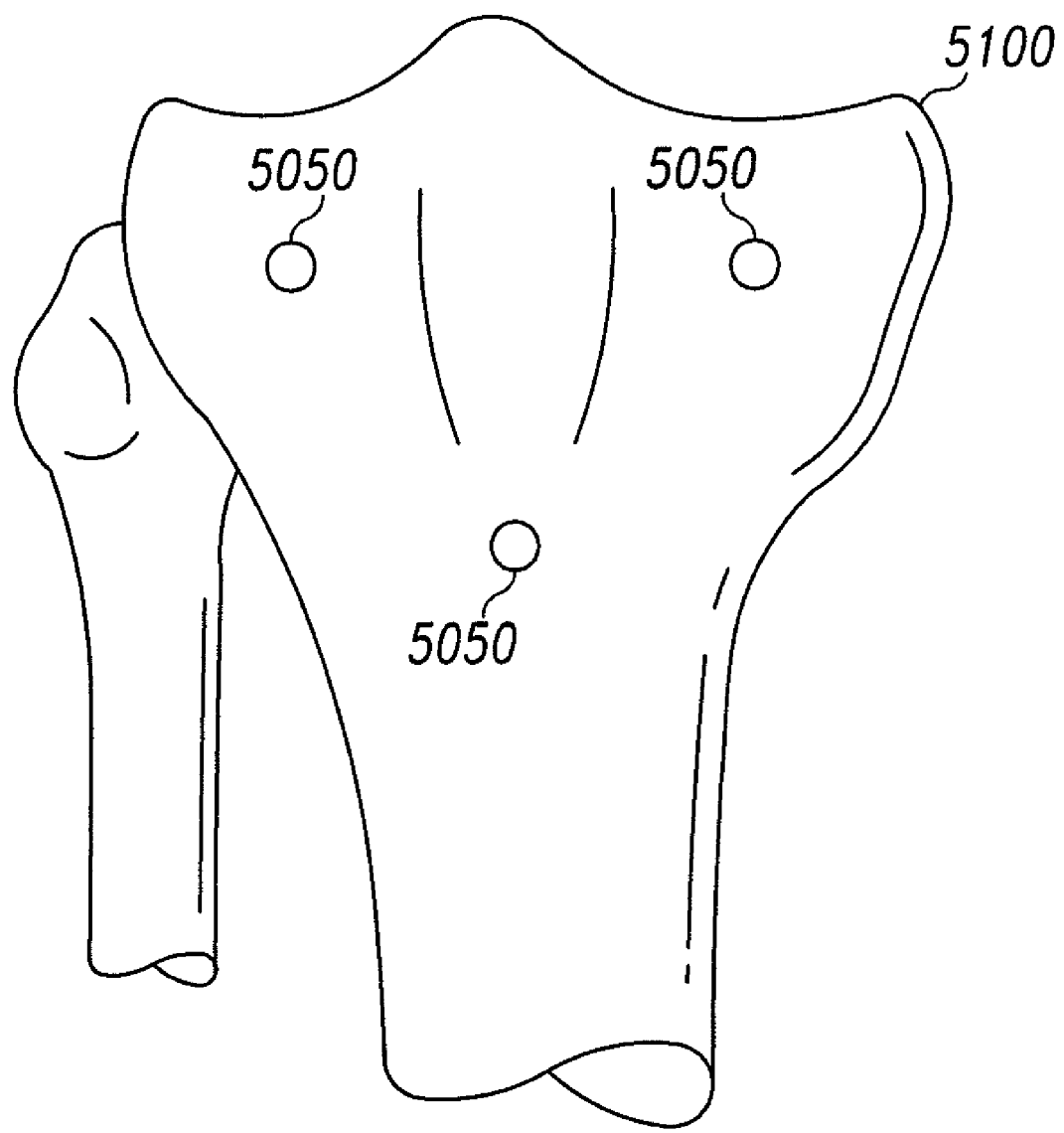
FIG. 117 is an anterior elevation view of a bone of a patient having a number of markers coupled thereto.

Referring now to FIG. 117, in some embodiments, a number of markers 5050 may be secured to the relevant bone 5100 of the patient prior to the generation of the medical images in process step 12. The markers 5050 may be embodied as pins, studs, or other devices securable to the bone 5100 of the patient in a pre-operative procedure. The markers 5050 may be secured to the bone 5100 via use of an orthopaedic drill in a manner similar to a guide pin, via use of a suitable adhesive such as bone cement, or the like. When so secured, a portion of each marker 5050 extends outwardly from the bone 5100. Alternatively, in other embodiments, the markers 5050 may be configured to be flush or substantially flush with the surface of the bone 5100. The markers 5050 may be formed from any material visible in the medical image such as a metallic material. The markers 5050 are secured to the bone 5100 in the general area to which the customized patient-specific orthopaedic surgical instrument is to be coupled. For example, in one embodiment, the markers 5050 identify particular landmark features of the patient's bone 5100. Additionally, the markers 5050 may be secured to the bone 5100 in any configuration and may be embodied as any number of individual markers.

In some embodiments, the negative contour of the customized patient-specific orthopaedic surgical instrument will include recesses designed to receive each of the markers 5050. In embodiments wherein the markers 5050 are substantially flush with the surface of the bone 5100, the customized patient-specific orthopaedic surgical instrument may include any number of windows or the like to visually align the instrument with the flush markers 5050. As such, the markers 5050 may increase the ease of positioning of the patient-specific surgical instrument to the bone 5100 of the patient, in particular in generally planar areas. After the orthopaedic surgical procedure has been performed by the surgeon in process step 32, the markers 5050 may be removed from the bone of the patient. Alternatively, in some embodiments, the markers 5050 are removed after the generation of the medical images.

Figure 118:
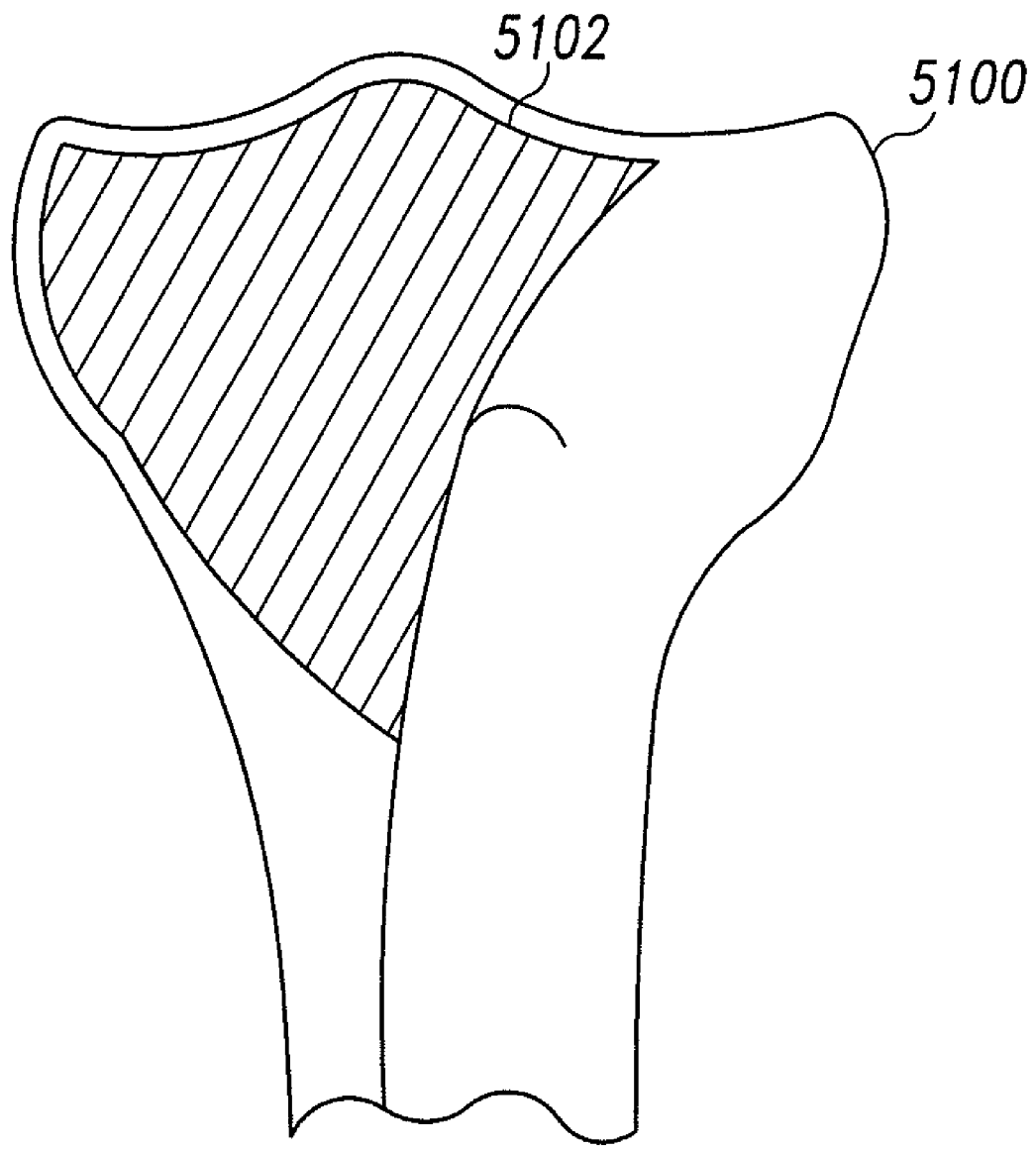
FIG. 118 is an anterior elevation view of another bone of a patient having a marking thereon.

Referring now to FIG. 118, in some embodiments, the orthopaedic surgeon may mark or otherwise indicate the general desired location of the customized patient-specific orthopaedic surgical instrument relative to the bone 5100. For example, the orthopaedic surgeon may highlight or otherwise define a marking 5102 of the desired area in the medical images generated in process step 12. The orthopaedic surgeon may generate such an indication or highlighting using a suitable software application or via hand-drawing on hard copies of the medical images, which are subsequently sent to the vendor. The particular shape, size, and location of the marking 5102 on the bone 5100 selected by the orthopaedic surgeon may be determined based on any criteria. For example, in some embodiments, the location of the marking 5102 may be determined based on the orthopaedic surgeon's preferences, the type and/or size of orthopaedic prosthesis to be used, the particular orthopaedic surgical procedure to be performed, and/or any other criteria selected by the orthopaedic surgeon.

Figure 119:
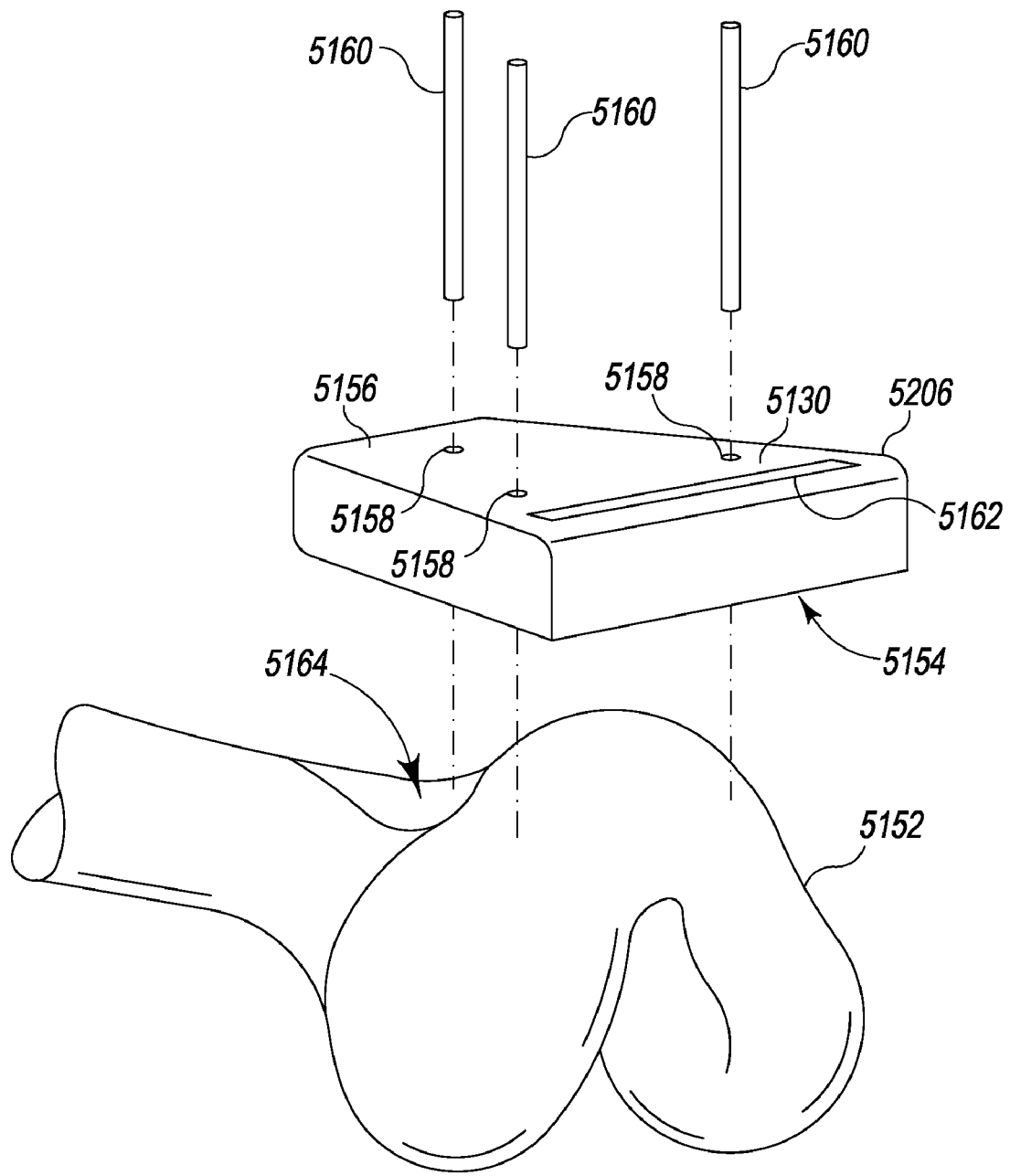
FIG. 119 is an exploded perspective view of a customized patient-specific orthopaedic surgical instrument for use with a bone of a patient.

Referring now to FIG. 119, in one embodiment, the customized patient-specific orthopaedic surgical instrument may be embodied as a femoral cutting block 5150. The femoral cutting block 5150 is configured to be coupled to a femur 5152 of the patient. The femoral cutting block 5150 includes a bone-contacting or bone-facing surface 5154 and an outer surface 5156. The bone-contacting surface 5154 includes a negative contour (not shown) configured to receive a portion of the patient's bone having a corresponding contour. As discussed above, the negative contour of the bone-contacting surface 5154 allows the positioning of the femoral cutting block 5150 on the patient's bone 5152 in a unique pre-determined location and orientation.

The femoral cutting block 5150 also includes a number of pin guides 5158. In use, the pin guides 5158 are used as drill guides to establish guide pin holes in the femur 5152 for securing a number of guide pins 5160 to the bone 5152. The cutting block 5150 also includes a cutting guide 5162. Illustratively, the cutting guide 5162 is a captured cutting guide, but may be embodied as a non-captured or open cutting guide in other embodiments. It should be appreciated that because the position of the cutting guide 5162 is pre-determined due to the configuration of the femoral cutting block 5150, any bone cuts made using the patient-specific femoral cutting block 5150 correspond to the predetermined bone cutting planes (see process step 24 of algorithm 10 described above in regard to FIG. 1).

In use, the femoral cutting block 5150 is configured to be coupled to the patient's femur 5152. Again, because the bone-contacting surface 5154 of the femoral cutting block 5150 includes negative contour, the block 5150 may be coupled to the femur 5152 in a pre-planned, unique position. In particular, the femoral cutting block 5150 is designed and configured to couple to the patient's femur 5152 such that the one or more of the guide pins 5160 are received in a corresponding fossa of the femur 5152. For example, as illustrated in FIG. 119, the femoral cutting block 5150 is configured such that one of the guide pins 5160 will be inserted into the femur 5152 through a fossa 5164 of the femur 5152. By securing the guide pin 5160 to the femur 5152 in the fossa 5164, the stability of the femoral cutting block 5150 on the femur 5152 may be improved. For example, in one particular embodiment, the femoral cutting block 5150 is designed such that the guide pin 5160 is substantially perpendicular to the surface of the femur 5152 defining the fossa 5164. In some embodiments, the femoral cutting block 5150 may be designed such that any number of the guide pins 5160 is received in a corresponding one or more fossas of the femur 5152 to further provide stability to the block 5150.

The femoral cutting block 5150 may be designed as described above during the generation of a model of the block 5150 in process step 26 of the algorithm 10 described above in regard to FIG. 1. To do so, a suitable software algorithm may be used to determine the location of the fossas of the relevant bone of the patient and design the cutting block 5150 such that the guide pins 5160 of the block 5150 are received in one or more of the fossas 5164.

Figure 120:
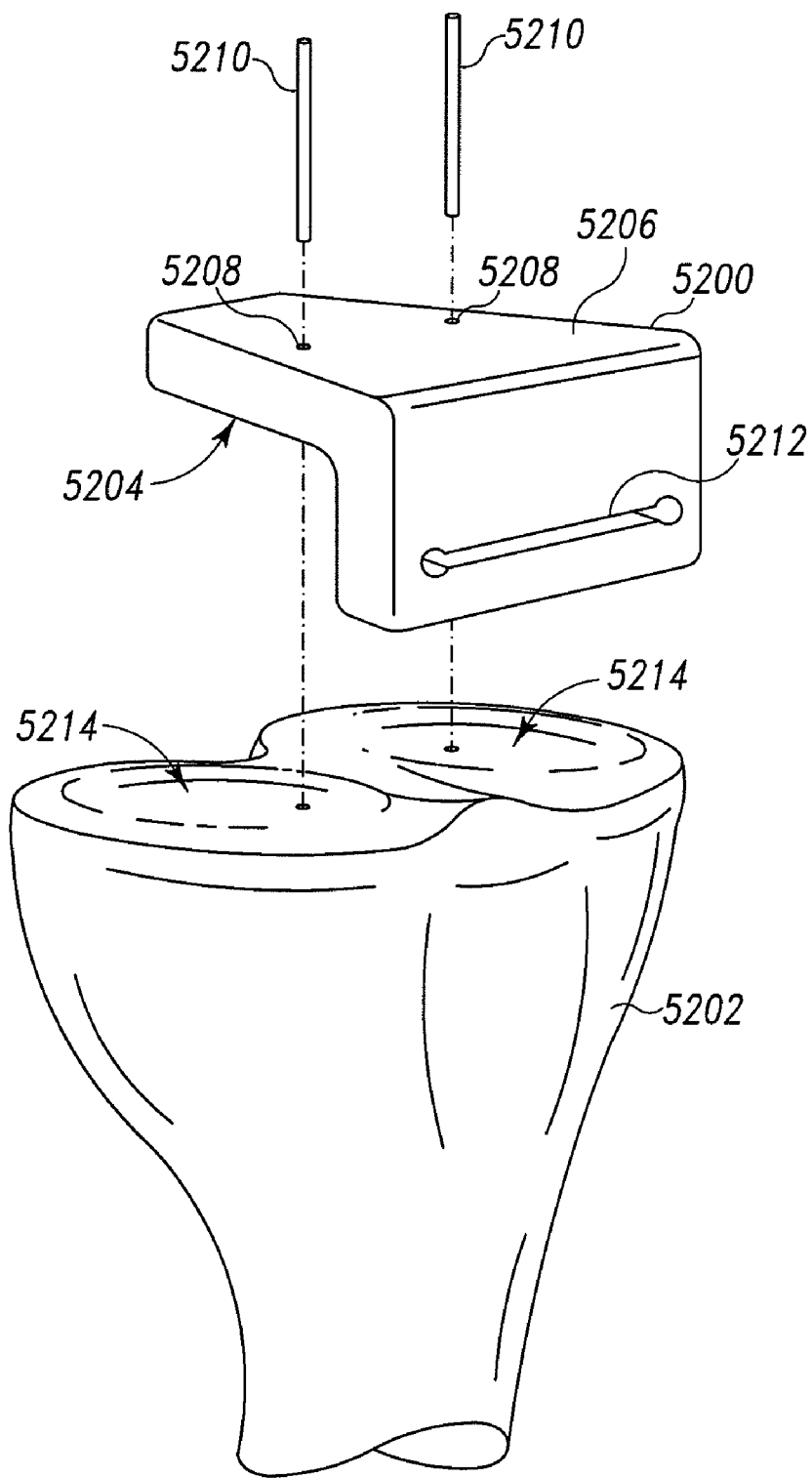
FIG. 120 is an exploded perspective view of another customized patient-specific orthopaedic surgical instrument for use with a bone of a patient.

Referring now to FIG. 120, in another embodiment, the customized patient-specific orthopaedic surgical instrument may be embodied as a tibial cutting block 5200. The tibial cutting block 5200 is configured to be coupled to a tibia 5202 of the patient. Similar to the femoral cutting block 5150, the tibial cutting block 5200 includes a bone-contacting or bone-facing surface 5204 and an outer surface 5206. The bone-contacting surface 5204 includes a negative contour (not shown) configured to receive a portion of the patient's bone having a corresponding contour. As discussed above, the negative contour of the bone-contacting surface 5204 allows the positioning of the tibial cutting block 5200 on the patient's bone 5202 in a unique pre-determined location and orientation.

The tibial cutting block 5200 also includes a number of pin guides 5208. In use, the pin guides 5208 are used as drill guides to establish guide pin holes in the tibia 5202 for securing a number of guide pins 5210 to the bone 5202. The cutting block 5200 also includes a cutting guide 5212. Illustratively, the cutting guide 5212 is a captured cutting guide, but may be embodied as a non-captured or open cutting guide in other embodiments. Again, it should be appreciated that because the position of the cutting guide 5212 is pre-determined due to the configuration of the tibial cutting block 5200, any bone cuts made using the patient-specific tibial cutting block 5200 correspond to the predetermined bone cutting planes (see process step 24 of algorithm 10 described above in regard to FIG. 1).

In use, the tibial cutting block 5200 is configured to be coupled to the patient's tibia 5202. Again, because the bone-contacting surface 5204 of the tibial cutting block 5200 includes negative contour, the block 5200 may be coupled to the tibia 5202 in a pre-planned, unique position. In particular, similar to the femoral cutting block 5150, the tibial cutting block 5200 is designed to couple to the patient's tibia 5202 such that the one or more of the guide pins 5210 are received in a corresponding fossa of the tibia 5202. For example, as illustrated in FIG. 120, the tibial cutting block 5200 is configured such that the guide pins 5210 will be inserted into the tibia 5202 through the medial and lateral condyles 5214 of the tibia 5202. By securing the guide pins 5210 to the tibia 5202 in the condyles 5214, the stability of the tibial cutting block 5200 on the tibia 5202 may be improved. For example, in one particular embodiment, the tibial cutting block 5200 is designed such that the guide pins 5210 are substantially perpendicular to the surface of the tibia 5202 defining the condoyles 5214. In some embodiments, the tibial cutting block 5200 may be designed such that any number of the guide pins 5200 is received in a corresponding one or more fossas or condyles of the tibia 5202 to further provide stability to the block 5150.

Again, similar to the femoral cutting block 5150, the tibial cutting block 5200 may be designed as described above during the generation of a model of the block 5200 in process step 26 of the algorithm 10 described above in regard to FIG. 1. To do so, a suitable software algorithm may be used to determine the location of the fossas of the relevant bone of the patient and design the cutting block such that the guide pins of the block are received in one or more of the fossas.

Figure 121:
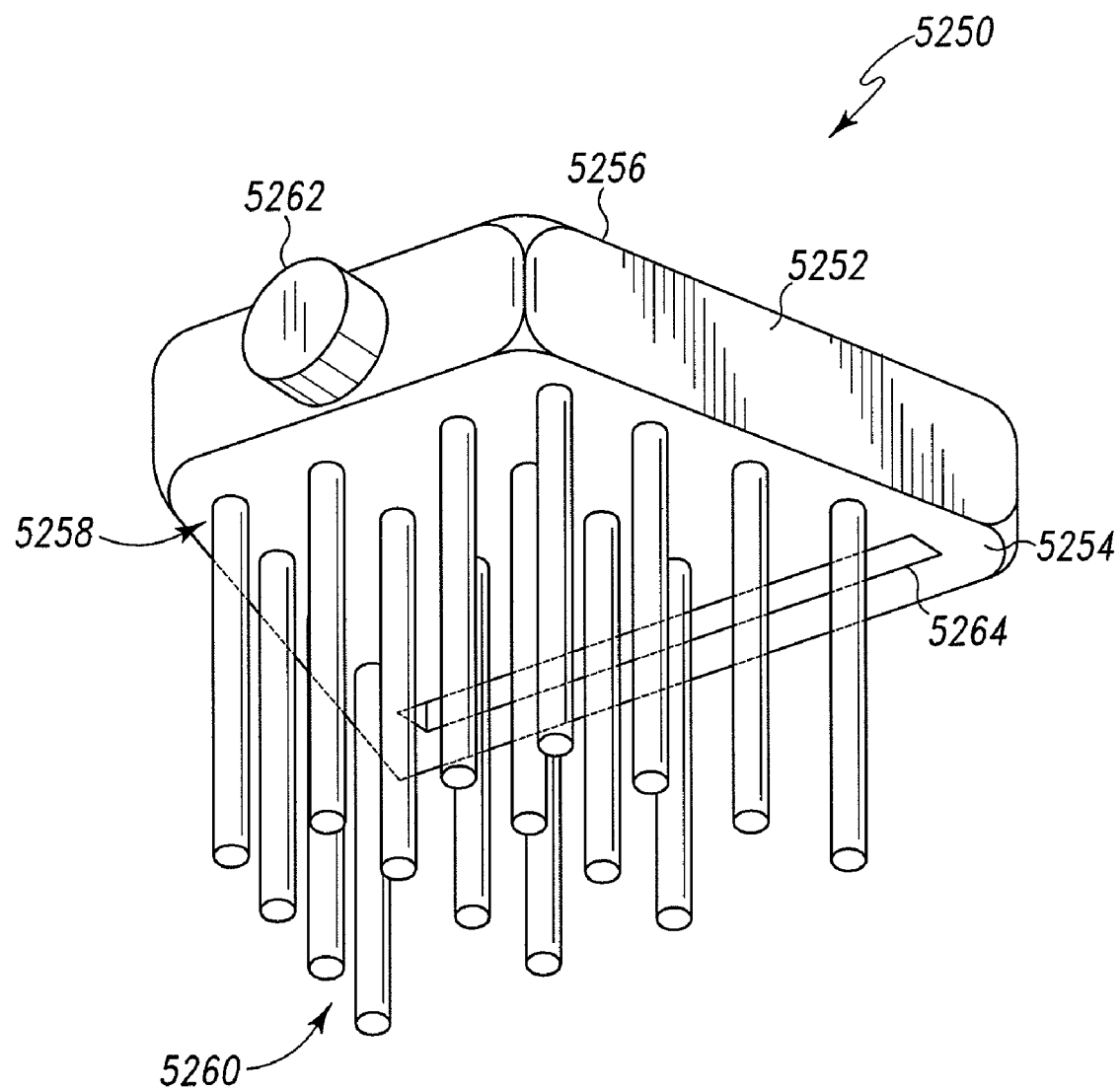
FIG. 121 is a bottom perspective view of another embodiment of a customized patient-specific orthopaedic surgical instrument.
Figure 122:
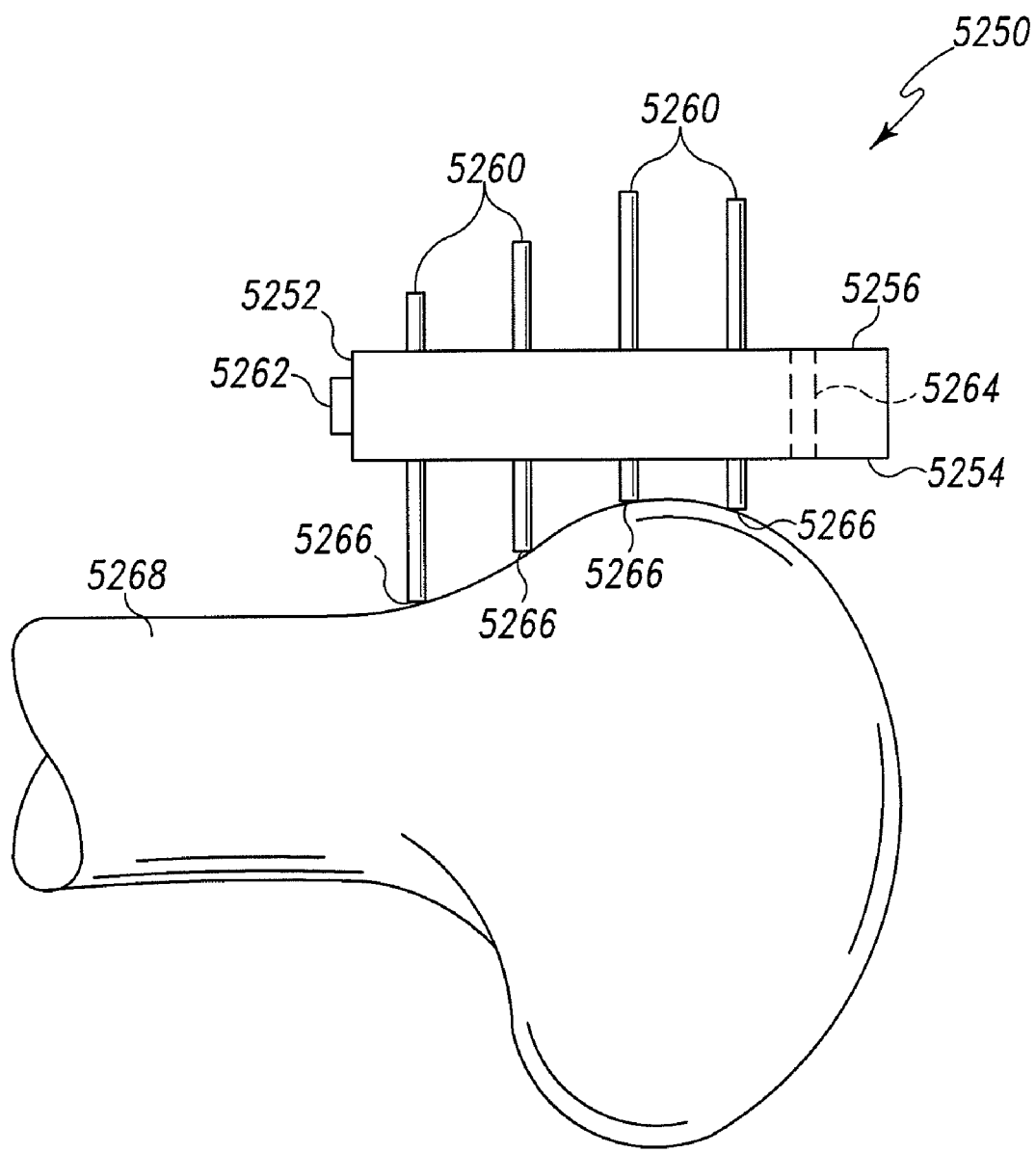
FIG. 122 is a side elevation view of the customized patient-specific orthopaedic surgical instrument of FIG. 121 coupled to a bone of a patient.
Figure 123:
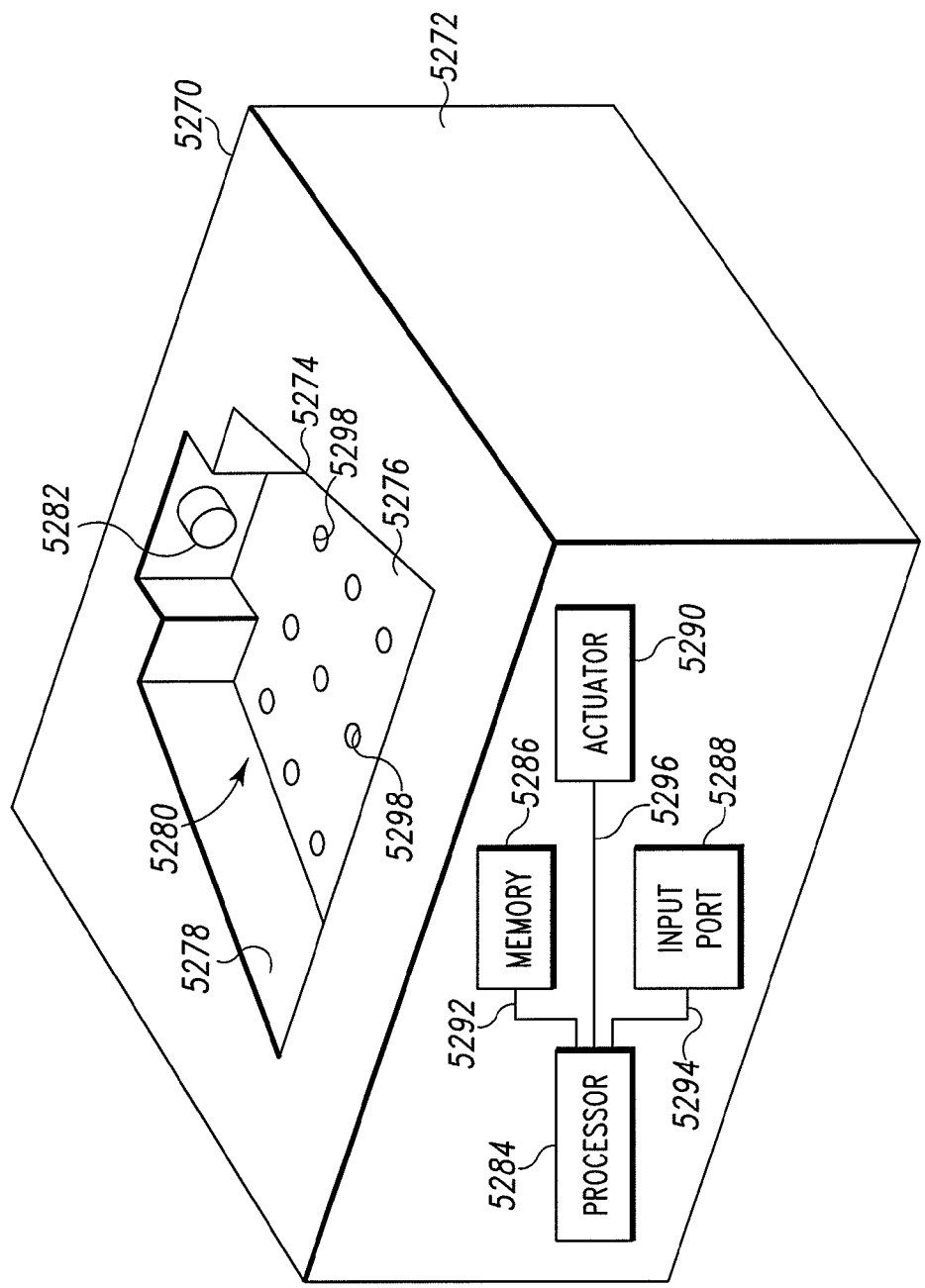
FIG. 123 is a perspective view of a programming device for use with the customized patient-specific orthopaedic surgical instrument of FIG. 121.

Referring now to FIGS. 121-123, in another embodiment, the customized patient-specific orthopaedic surgical instrument may be embodied as a cutting block 5250. The cutting block 5250 is illustratively embodied as a femoral cutting block, but may be embodied as cutting blocks for other bones, such as the tibia, in other embodiments. The cutting block 5250 includes a body 5252 having a bone-facing surface 5254 and an outer surface 5256. A number of guide pin holes 5258 are define in the body 5252 of the block 5250. A guide pin 5260 is received in each guide pin hole 5258 and configured to slide through the corresponding hole 5258 such that the guide pin 5260 is independently movable and positionable in any one of a number of positions relative to the body 5252. That is, each of the guide pins 5260 may be positioned such that a portion of the guide pin extends downwardly from the bone-facing surface 5254 and/or extends upwardly from the outer surface 5256 as shown in FIG. 122.

The cutting block 5250 also includes a cutting guide 5264. Illustratively, the cutting guide 5264 is a captured cutting guide, but may be embodied as a non-captured cutting guide in other embodiments. Again, it should be appreciated that because the position of the cutting guide 5264 is pre-determined due to the configuration of the cutting block 5250, any bone cuts made using the patient-specific cutting block 5250 correspond to the predetermined bone cutting planes (see process step 24 of algorithm 10 described above in regard to FIG. 1).

Additionally, the cutting block 5250 includes a securing device 5262 operable to individually lock each guide pin 5260 in a particular position relative to the cutting block 5250. That is, the guide pins 5260 may be locked in a separate position relative to the cutting block 5250 such that each guide pin 5260 extends downwardly from the bone-facing surface 5254 a selective equal or different distance. As such, the guide pins 5260 may be positioned such that the bone-contacting ends of the guide pins 5260 form a selective contour. For example, as illustrated in FIG. 122, the guide pins 5260 may be positioned, and subsequently locked into position via the securing device 5262, such that the bone-contacting ends 5266 of the guide pins 5260 form a negative contour that corresponds to a contour of a portion of a patients bone 5268. In such a position, a portion of each guide pin may extend from the bone-facing surface 5254 and/or the upper surface 5256. The securing device 5262 may use mechanical and/or magnetic devices to lock the guide pins 5260 in the desired position.

In use, an orthopaedic surgeon may selectively position the guide pins 5260 to form a negative contour that matches a portion of the patient's bone 5268 such that the cutting block 5250 may be positioned thereon in a unique pre-determined location and orientation. To do so, the surgeon may use a programming device 5270 as shown in FIG. 123. The programming device 5270 includes a housing 5272 having an aperture 5274 configured to receive the cutting block 5250. The aperture 5274 is defined by a bottom wall 5276 and a number of sidewalls 5278. The bottom wall 5276 includes a number of holes 5280 defined therein and positioned such that each of the guide pins 5260 of the block 5250 is received in a corresponding hole 5280 of the programming device 5270. The programming device 5270 includes a push rod 5298 or other adjustment device located in each hole 5280. The push rods 5298 are configured and operable to selectively position the corresponding guide pin 5260 by pushing the guide pin 5260 to the desired location relative to the block 5250. The programming device 5270 also includes a coupler 5282 configured to engage the securing device 5262 of the block 5250 when the block 5250 is positioned in the aperture 5274. The coupler 5282 is configured to operate the securing device 5262 to lock the guide pins 5260 in a desired position.

In one embodiment, the programming device 5270 includes a processor 5284, a memory device 5286, an input port 5288, and one or more actuators or motors 5290. The processor 5284 may be embodied as any type of processor including, for example, discrete processing circuitry (e.g., a collection of logic devices), general purpose integrated circuit(s), and/or application specific integrated circuit(s) (i.e., ASICs). The memory device 5286 may be embodied as any type of memory device and may include one or more memory types, such as, random access memory (i.e., RAM) and/or read-only memory (i.e., ROM). The input port 5288 may be embodied as any type of input port configured to receive a portable media device (not shown) such as, for example, a compact disk, a digital video disk, a Universal Serial Bus (USB) device, or other portable media device. As such, the input port 5288 may be embodied as any type of serial port, parallel port, flash drive port, or other data port capable of communicating with and storing data on the portable media device.

The processor 5284 is communicatively coupled to the memory device 5286 via a number of communication links 5292 and to the input port 5288 via a number of communication links 5294. The communication links 5292, 5294 may be embodied as any type of communication links capable of facilitating communication between the processor 5284 and the memory device 5286 and the input port 5288, respectively. For example, the communication links 5292, 5294 may be embodied as any number of cables, wires, fiber optic cables, wireless signals, and/or the like.

The actuators 5290 may be embodied as any type of prime movers, and associated control and power circuitry, capable of separately controlling the push rods 5298 to individually position the guide pins 5260 of the cutting block 5250. In addition, one or more of the actuators 5290 is configured to control the coupler 5282 to operate the securing device 5262 of the block 5250 to lock the guide pins 5260 in their respective position. The actuators 5290 are communicatively coupled to the processor 5284 via a number of communication links 5296. Similar to the communication links 5292, 5294, the communication links 5296 may be embodied as any type of communication links capable of facilitating communication between the processor 5284 and the actuators 5290. For example, the communication links 5296 may be embodied as any number of cables, wires, fiber optic cables, wireless signals, and/or the like.

In use, the processor 5284 of the programming device 5270 is configured to control the actuators 5290 to operate the push rods 5298 located in the holes 5280 of the housing 5272. The push rods 5298 individually position the guide pins 5260 of the cutting block 5250 in a predetermined position relative to the block 5250. In such a predetermined position, the ends 5266 of the guide pins 5260 form a negative contour configured to receive a predetermined portion of the patient's bone 5268 as shown in FIG. 122. After the guide pins 5260 have been positioned in the desired locations, the processor 5284 may be configured to control one or more actuators 5290 to operate the coupler 5282. In response, the coupler 5282 is configured to engage the securing device 5262 of the block 5250 to lock the guide pins 5260 in the predetermined locations.

The processor 5284 may be configured to perform the above-described actions based on a software algorithm stored in the memory device 5286. The software algorithm may be received via the input port 5288. For example, the software algorithm executed by the processor 5284 to position the guide pins 5260 of the cutting block 5250 in the desired, predetermined location may be stored on a compact disk or USB device, which is coupled to the input port 5288 to download the software algorithm to the programming device 5270. The software algorithm may be supplied by a vendor in some embodiments. For example, referring back the FIG. 1, the model of the customized patient-specific orthopaedic surgical instrument generated in process step 26 of algorithm 10 may be embodied as a software algorithm usable by the programming device 5270. The vendor may ship or otherwise transmit the software algorithm to the orthopaedic surgeon for downloading into the programming device 5270. In response, the programming device 5270 configures the guide pins 5260 of the cutting block 5250 for use on the bone 5268 of the patient. In this way, the cutting block 5250 is re-configurable to be a patient-specific cutting block intended for use on a particular patient.

Figure 124:
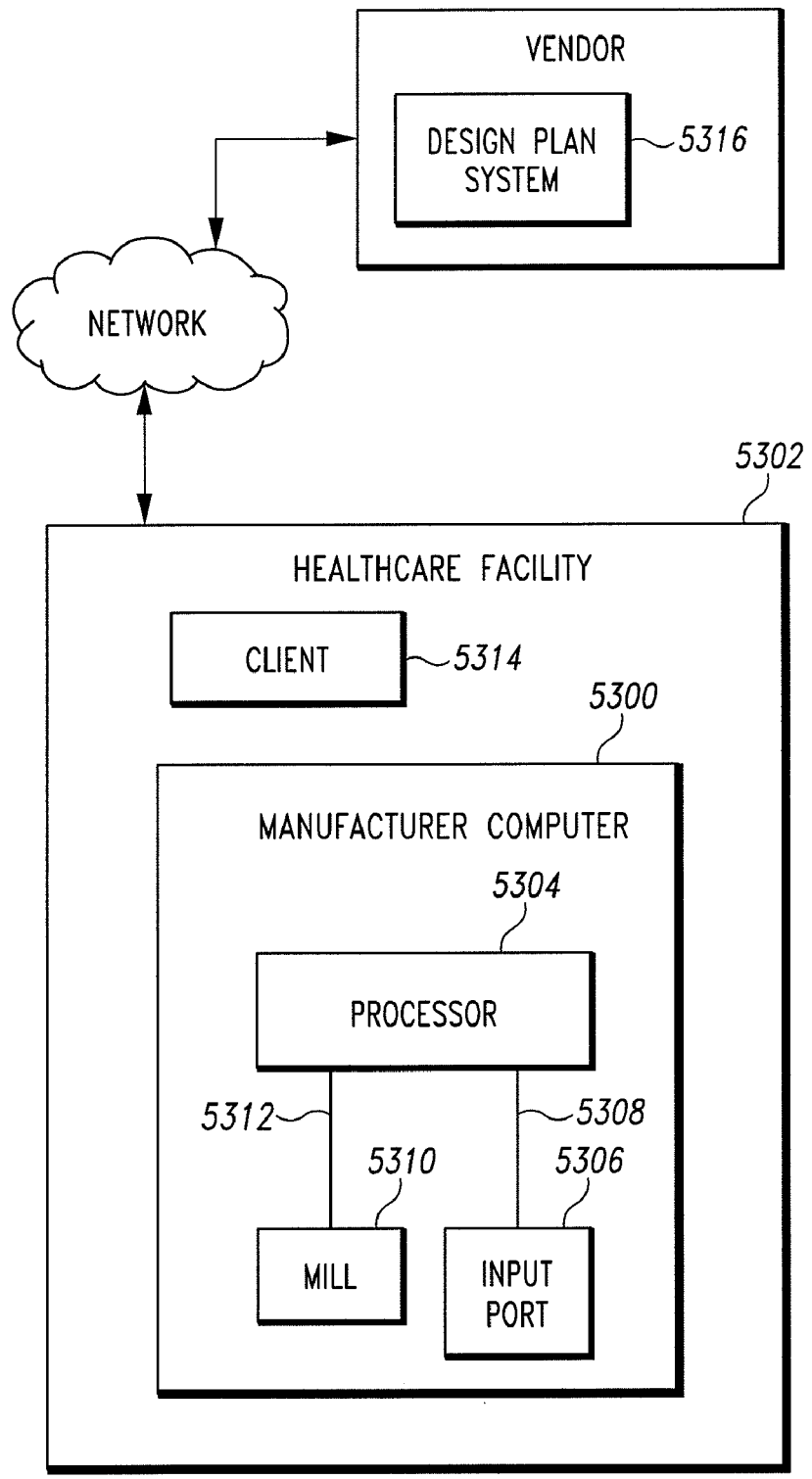
FIG. 124 is a simplified block diagram of a milling machine for fabrication of customized patient-specific orthopaedic surgical instruments.

Referring now to FIG. 124, in some embodiments, a milling machine 5300 is located at a healthcare facility 5302 to facilitate the fabrication of the customized patient-specific orthopaedic surgical instrument. The healthcare facility 5302 may be embodied as the healthcare facility, such as hospital or the like, wherein the orthopaedic surgical procedure is to be performed. Alternatively or additionally, the healthcare facility 5302 may be embodied as the office of the orthopaedic surgeon or other healthcare provider.

The milling machine 5300 includes a processor 5304, an input port 5306, and a mill 5310. The processor 5304 may be embodied as any type of processor including, for example, discrete processing circuitry (e.g., a collection of logic devices), general purpose integrated circuit(s), and/or application specific integrated circuit(s) (i.e., ASICs). The input port 5306 may be embodied as any type of input port configured to receive a portable media device (not shown) such as, for example, a compact disk, a digital video disk, a Universal Serial Bus (USB) device, or other portable media device. As such, the input port 5306 may be embodied as any type of serial port, parallel port, flash drive port, or other data port capable of communicating with and storing data on the portable media device. The processor 5304 is communicatively coupled to the input port 5306 via a number of communication links 5308. The communication links 5308 may be embodied as any type of communication links capable of facilitating communication between the processor 5304 and the input port 5306. For example, the communication links 5308 may be embodied as any number of cables, wires, fiber optic cables, wireless signals, and/or the like.

The milling machine 5300 also includes a mill 5310 communicatively coupled to the processor 5304 via a number of communication links 5312. Similar to communication links 5308, the communication links 5312 may be embodied as any type of communication links capable of facilitating communication between the processor 5304 and the mill 5310. For example, the communication links 5312 may be embodied as any number of cables, wires, fiber optic cables, wireless signals, and/or the like. The mill 5310 may be embodied as any type of mill and associated devices and circuitry capable of fabricating a customized patient-specific orthopaedic surgical instrument from suitable material such as plastic or metal.

In use, the processor 5304 is configured to control the mill 5310 to fabricate the customized patient-specific orthopaedic surgical instrument. The processor 5304 may be configured to control the mill 5310 based on a software algorithm received via the input port 5306. For example, the software algorithm executed by the processor 5304 to control the mill 5310 may be received from a compact disk or USB device, which is coupled to the input port. The software algorithm may be supplied by a vendor in some embodiments. For example, referring back the FIG. 1, the model of the customized patient-specific orthopaedic surgical instrument generated in process step 26 of algorithm 10 may be embodied as a software algorithm usable by the milling machine 5300. The vendor may ship or otherwise transmit the software algorithm to the orthopaedic surgeon for downloading into the milling machine 5300. In response, the milling machine 5300 is configured to fabricate the customized patient-specific orthopaedic surgical instrument based on the software algorithm instructions. In this way, the fabrication of the patient-specific instrument is performed locally, while the design of such instrument may be performed remotely with respect to the healthcare facility 5302.

One way to facilitate such remote fabrication of the customized patient-specific orthopaedic surgical instrument is via use of a network. In such a case, an instrument request including data relevant to a specific patient is generated by the surgeon or other healthcare provider. The instrument request may include data such as medical images that depict bones of the patient such as the femur and tibia. A client machine 5314 associated with the surgeon or healthcare provider (e.g., located at the healthcare facility) may be used to transmit the instrument request to the vendor.

The vendor may include a design plan system 5316. The design plan system 5316 may receive an instrument request for a design plan via the network from the client machine 5314 located at, for example, the healthcare facility 5302, generate a design plan that has been customized based upon information of the received request, and provide the healthcare facility 5302 with the custom design plan via the network. The design plan system 5316 may include one or more computing devices and associated software, middleware, and/or firmware that cooperate to perform the design plan customizations.

Once the design plan is sent to the healthcare facility 5302, it is transmitted to the milling machine 5300. The milling machine then uses the design plan to fabricate the customized patient-specific orthopaedic surgical instrument.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. A method of performing an orthopaedic surgical procedure on a bone of a patient, comprising:

positioning a customized patient-specific cutting block in contact with the bone of the patient, inserting a pair of guide pins into a pair of guide pin holes defined in the customized patient-specific cutting block, inserting a cutting blade of a bone saw into the customized patient-specific cutting block, making a first cut with the cutting blade in the bone of the patient with the customized patient-specific cutting block, removing the customized patient-specific cutting block from the bone of the patient without removing the guide pins from the bone of the patient, inserting the pair of guide pins into a pair of guide pin holes defined in a patient-universal re-cut block after removing the customized patient-specific cutting block from the bone, inserting the cutting blade into the patient-universal re-cut block, and making a second cut with the cutting blade in the bone of the patient with the patient-universal re-cut block.

2. The method of claim 1, wherein:

positioning the customized patient-specific cutting block in contact with the bone of the patient comprises positioning the customized patient-specific cutting block in contact with a femur of the patient, making the first cut in the bone of the patient with the customized patient-specific cutting block comprises making the first cut in the femur of the patient with the customized patient-specific cutting block, making the second cut in the bone of the patient with the patient-universal re-cut block comprises making the second cut in the femur of the patient with the patient-universal re-cut block, and the second cut is substantially parallel to the first cut.

3. The method of claim 1, wherein:

positioning the customized patient-specific cutting block in contact with the bone of the patient comprises positioning the customized patient-specific cutting block in contact with a femur of the patient, making the first cut in the bone of the patient with the customized patient-specific cutting block comprises making the first cut in the femur of the patient with the customized patient-specific cutting block, making the second cut in the bone of the patient with the patient-universal re-cut block comprises making the second cut in the femur of the patient with the patient-universal re-cut block, and the second cut is oriented in an angled position relative to the first cut.

4. The method of claim 1, wherein:

positioning the customized patient-specific cutting block in contact with the bone of the patient comprises positioning the customized patient-specific cutting block in contact with a tibia of the patient, making the first cut in the bone of the patient with the customized patient-specific cutting block comprises making the first cut in the tibia of the patient with the customized patient-specific cutting block, making the second cut in the bone of the patient with the patient-universal re-cut block comprises making the second cut in the tibia of the patient with the patient-universal re-cut block, and the second cut is substantially parallel to the first cut.

5. The method of claim 1, wherein:

positioning the customized patient-specific cutting block in contact with the bone of the patient comprises positioning the customized patient-specific cutting block in contact with a tibia of the patient, making the first cut in the bone of the patient with the customized patient-specific cutting block comprises making the first cut in the tibia of the patient with the customized patient-specific cutting block, making the second cut in the bone of the patient with the patient-universal re-cut block comprises making the second cut in the tibia of the patient with the patient-universal re-cut block, and the second cut is oriented in an angled position relative to the first cut.

6. The method of claim 1, wherein:

inserting the pair of guide pins into the pair of guide pin holes defined in the patient-universal re-cut block comprises inserting the pair of guide pins into the pair of guide pin holes defined in the patient-universal re-cut block such that a cutting guide of the patient-universal re-cut block is substantially parallel to the first cut, and making the second cut in the bone of the patient with the patient-universal re-cut block comprises making the second cut in the bone of the patient with the patient-universal re-cut block such that the second cut is substantially parallel to the first cut.

7. The method of claim 1, wherein:

inserting the pair of guide pins into the pair of guide pin holes defined in the patient-universal re-cut block comprises inserting the pair of guide pins into the pair of guide pin holes defined in the patient-universal re-cut block such that a cutting guide of the patient-universal re-cut block is oriented in an angled position relative to the first cut, and making the second cut in the bone of the patient with the patient-universal re-cut block comprises making the second cut in the bone of the patient with the patient-universal re-cut block such that the second cut is oriented in an angled position relative to the first cut.

8. The method of claim 1, wherein inserting the pair of guide pins into the pair of guide pin holes defined in the patient-universal re-cut block comprises:

determining an amount of additional bone to be removed from the bone of the patient subsequent to making the first cut in the bone of the patient with the customized patient-specific cutting block, selecting a pair of guide pin holes which corresponds to the amount of additional bone to be removed from the bone of the patient from a plurality of pairs of guide pin holes, and inserting the pair of guide pins into the selected pair of guide pin holes which corresponds to the amount of additional bone to be removed from the bone of the patient.

9. A method of performing an orthopaedic surgical procedure on a femur of a patient, comprising:

positioning a customized patient-specific cutting block in contact with the femur of the patient, inserting a pair of guide pins into a pair of guide pin holes defined in the customized patient-specific cutting block, inserting a cutting blade of a bone saw into the customized patient specific cutting block making a first cut with the cutting blade in the femur of the patient with the customized patient-specific cutting block, removing the customized patient-specific cutting block from the femur of the patient without removing the guide pins from the femur of the patient, determining an amount of additional bone to be removed from the femur of the patient subsequent to making the first cut in the femur of the patient with the customized patient-specific cutting block, selecting a pair of guide pin holes defined in a patient-universal re-cut block which corresponds to the amount of additional bone to be removed from the femur of the patient from a plurality of pairs of guide pin holes, inserting the pair of guide pins into the selected pair of guide pin holes which corresponds to the amount of additional bone to be removed from the femur of the patient after removing the customized patient-specific cutting block from the bone, inserting the cutting blade into the patient-universal re-cut block, and making a second cut with the cutting blade in the femur of the patient with the patient-universal re-cut block.

10. The method of claim 9, wherein:

inserting the pair of guide pins into the selected pair of guide pin holes which corresponds to the amount of additional bone to be removed from the femur of the patient comprises inserting the pair of guide pins into the selected pair of guide pin holes which corresponds to the amount of additional bone to be removed from the femur of the patient such that a cutting guide of the patient-universal re-cut block is substantially parallel to the first cut, and making the second cut in the femur of the patient with the patient-universal re-cut block comprises making the second cut in the femur of the patient with the patient-universal re-cut block such that the second cut is substantially parallel to the first cut.

11. The method of claim 9, wherein:

inserting the pair of guide pins into the selected pair of guide pin holes which corresponds to the amount of additional bone to be removed from the femur of the patient comprises inserting the pair of guide pins into the selected pair of guide pin holes which corresponds to the amount of additional bone to be removed from the femur of the patient such that a cutting guide of the patient-universal re-cut block is oriented in an angled position relative to the first cut, and making the second cut in the femur of the patient with the patient-universal re-cut block comprises making the second cut in the femur of the patient with the patient-universal re-cut block such that the second cut is oriented in an angled position relative to the first cut.

* * * * *